US008993317B2

(12) United States Patent
Merten et al.

(10) Patent No.: US 8,993,317 B2
(45) Date of Patent: Mar. 31, 2015

(54) BACULOVIRUS-BASED PRODUCTION OF BIOPHARMACEUTICALS FREE OF CONTAMINATING BACULOVIRAL VIRIONS

(75) Inventors: Otto-Wilhelm Merten, Crespieres (FR); Martin Marek, Malec (CZ); Monique Van Oers, Renkum (NL)

(73) Assignee: Genethon, Evry (FR)

( * ) Notice: Subject to any disclaimer, the term of this patent is extended or adjusted under 35 U.S.C. 154(b) by 46 days.

(21) Appl. No.: 13/390,806

(22) PCT Filed: Aug. 5, 2010

(86) PCT No.: PCT/EP2010/061456
§ 371 (c)(1),
(2), (4) Date: Feb. 16, 2012

(87) PCT Pub. No.: WO2011/020710
PCT Pub. Date: Feb. 24, 2011

(65) Prior Publication Data

US 2012/0149010 A1 Jun. 14, 2012

(30) Foreign Application Priority Data

Aug. 17, 2009 (EP) .................................... 09305761

(51) Int. Cl.

| | |
|---|---|
| ***C12N 15/866*** | (2006.01) |
| ***C12N 15/86*** | (2006.01) |
| ***C12N 7/00*** | (2006.01) |
| *C07K 1/00* | (2006.01) |

(52) U.S. Cl.
CPC *C12N 15/86* (2013.01); *C12N 7/00* (2013.01); *C12N 2710/14143* (2013.01); *C12N 2710/14152* (2013.01); *C12N 2750/14143* (2013.01); *C12N 2800/50* (2013.01)
USPC ...................................... 435/320.1; 435/69.1

(58) Field of Classification Search
CPC .................... C12N 15/86; C12N 2710/10343; A61K 2039/5256; C07K 14/005
See application file for complete search history.

(56) References Cited

U.S. PATENT DOCUMENTS

| | | | | |
|---|---|---|---|---|
| 6,387,670 | B1 * | 5/2002 | Leblois-Prehaud et al. | 435/173.3 |
| 2006/0166363 | A1 | 7/2006 | Zolotukhin et al. | |

FOREIGN PATENT DOCUMENTS

| | | |
|---|---|---|
| WO | WO 01/12829 | 2/2001 |

OTHER PUBLICATIONS

Wang et al. (Journal of Huazhong University of Science and technology, 2007, vol. 27 (3), pp. 269-273).*
Todd et al. (J. Viol. 1995, vol. 69 (2), pp. 968-974).*
Wang et al. J. Virol. 2010, vol. 84, No. 17, pp. 8821-8828.*
Urabe et al. J. Virol. 2006, vol. 80(4), pp. 1874-1885.*
Palombo et al. J. Virol, 1998, vol. 72 (6), pp. 5025-5034.*
Tang, X.-D. et al. "Characterization of a *Bombyx mori* nucleopolyhedrovirus with *Bmvp80* disruption" *Virus Research*, pp. 81-88, vol. 138.
Possee, R. D. et al. "Generation of Baculovirus Vectors for the High-Throughput Production of Proteins in Insect Cells" *Biotechnology and Bioengineering*, Dec. 15, 2008, pp. 1115-1122, vol. 101, No. 6.
Written Opinion in International Application No. PCT/EP2010/061456, Mar. 14, 2011, pp. 1-6.

* cited by examiner

*Primary Examiner* — Bao Li
(74) *Attorney, Agent, or Firm* — Saliwanchik, Lloyd & Eisenschenk

(57) ABSTRACT

The present invention relates to methods for the production of biopharmaceuticals implementing a baculovirus-based system. These methods advantageously allow the production of biopharmaceuticals with reduced or no contaminating baculoviral virions.

9 Claims, 16 Drawing Sheets

Fig 1

Figure 2:
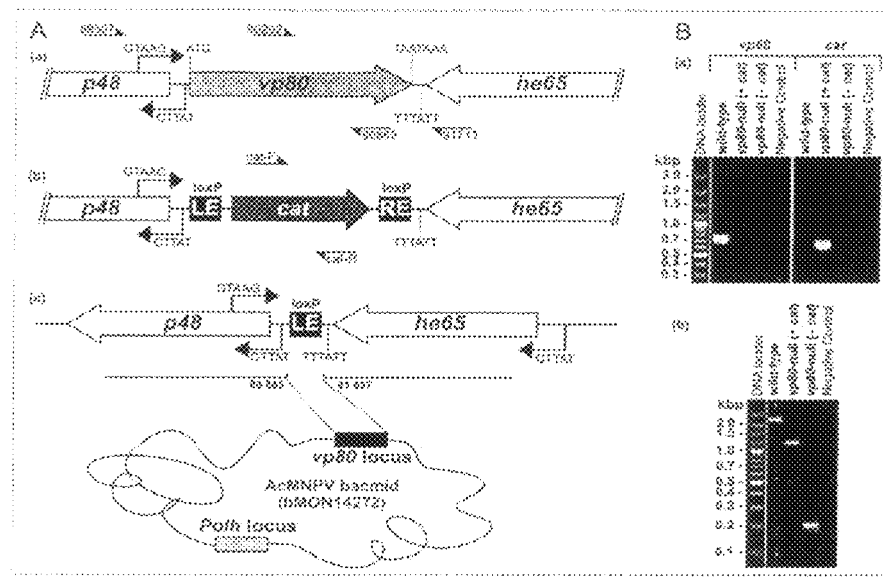

SEQUENCE LISTING

<160> NUMBER OF SEQ ID NOS: 56

<210> SEQ ID NO 1
<211> LENGTH: 133894
<212> TYPE: DNA
<213> ORGANISM: Autographa californica nucleopolyhedrovirus

<400> SEQUENCE: 1
gaattctacc cgtaaagcga gtttagtttt gaaaaacaaa tgacatcatt tgtataatga 60
catcatcccc tgattgtgtt ttacaagtag aattctatcc gtaaagcgag ttcagttttg 120
aaaacaaatg agtcatacct aaacacgtta ataatcttct gatatcagct tatgactcaa 180
gttatgagcc gtgtgcaaaa catgagataa gtttatgaca tcatccactg atcgtgcgtt 240
acaagtagaa ttctactcgt aaagccagtt cggttatgag ccgtgtgcaa aacatgacat 300
cagcttatga ctcatacttg attgtgtttt acgcgtagaa ttctactcgt aaagcgagtt 360
cggttatgag ccgtgtgcaa aacatgacat cagcttatga gtcataatta atcgtgcgtt 420
acaagtagaa ttctactcgt aaagcgagtt gaaggatcat atttagttgc gtttatgaga 480
taagattgaa agcacgtgta aaatgtttcc cgcgcgttgg cacaactatt tacaatgcgg 540
ccaagttata aaagattcta atctgatatg ttttaaaaca cctttgcggc ccgagttgtt 600
tgcgtacgtg actagcgaag aagatgtgtg gaccgcagaa cagatagtaa aacaaaaccc 660
tagtattgga gcaataatcg atttaaccaa cacgtctaaa tattatgatg gtgtgcattt 720
tttgcgggcg ggcctgttat acaaaaaaat tcaagtacct ggccagactt tgccgcctga 780
aagcatagtt caagaattta ttgacacggt aaaagaattt acagaaaagt gtcccggcat 840
gttggtgggc gtgcactgca cacacggtat taatcgcacc ggttacatgg tgtgcagata 900
tttaatgcac accctgggta ttgcgccgca ggaagccata gatagattcg aaaaagccag 960
aggtcacaaa attgaaagac aaaattacgt tcaagattta ttaatttaat taatattatt 1020
tgcattcttt aacaaatact ttatcctatt ttcaaattgt tgcgcttctt ccagcgaacc 1080

-continued

```
aaaactatgc ttcgcttgct ccgtttagct tgtagccgat cagtggcgtt gttccaatcg   1140
acggtaggat taggccggat attctccacc acaatgttgg caacgttgat gttacgttta   1200
tgcttttggt tttccacgta cgtcttttgg ccggtaatag ccgtaaacgt agtgccgtcg   1260
cgcgtcacgc acaacaccgg atgtttgcgc ttgtccgcgg ggtattgaac cgcgcgatcc   1320
gacaaatcca ccactttggc aactaaatcg gtgacctgcg cgtctttttt ctgcattatt   1380
tcgtctttct tttgcatggt ttcctggaag ccggtgtaca tgcggtttag atcagtcatg   1440
acgcgcgtga cctgcaaatc tttggcctcg atctgcttgt ccttgatggc aacgatgcgt   1500
tcaataaact cttgtttttt aacaagttcc tcggtttttt gcgccaccac cgcttgcagc   1560
gcgtttgtgt gctcggtgaa tgtcgcaatc agcttagtca ccaactgttt gctctcctcc   1620
tcccgttgtt tgatcgcggg atcgtacttg ccggtgcaga gcacttgagg aattacttct   1680
tctaaaagcc attcttgtaa ttctatggcg taaggcaatt tggacttcat aatcagctga   1740
atcacgccgg atttagtaat gagcactgta tgcggctgca aatacagcgg gtcgcccctt   1800
ttcacgacgc tgttagaggt agggccccca ttttggatgg tctgctcaaa taacgatttg   1860
tatttattgt ctacatgaac acgtatagct ttatcacaaa ctgtatattt taaactgtta   1920
gcgacgtcct tggccacgaa ccggacctgt tggtcgcgct ctagcacgta ccgcaggttg   1980
aacgtatctt ctccaaattt aaattctcca attttaacgc gagccatttt gatacacgtg   2040
tgtcgatttt gcaacaacta ttgtttttta acgcaaacta aacttattgt ggtaagcaat   2100
aattaaatat gggggaacat gcgccgctac aacactcgtc gttatgaacg cagacggcgc   2160
cggtctcggc gcaagcggct aaaacgtgtt gcgcgttcaa cgcggcaaac atcgcaaaag   2220
ccaatagtac agttttgatt tgcatattaa cggcgatttt ttaaattatc ttatttaata   2280
aatagttatg acgcctacaa ctccccgccc gcgttgactc gctgcacctc gagcagttcg   2340
ttgacgcctt cctccgtgtg gccgaacacg tcgagcgggt ggtcgatgac cagcggcgtg   2400
ccgcacgcga cgcacaagta tctgtacacc gaatgatcgt cgggcgaagg cacgtcggcc   2460
tccaagtggc aatattggca aattcgaaaa tatatacagt tgggttgttt gcgcatatct   2520
atcgtggcgt tgggcatgta cgtccgaacg ttgatttgca tgcaagccga aattaaatca   2580
ttgcgattag tgcgattaaa acgttgtaca tcctcgcttt taatcatgcc gtcgattaaa   2640
tcgcgcaatc gagtcaagtg atcaaagtgt ggaataatgt ttctttgta ttcccgagtc    2700
aagcgcagcg cgtattttaa caaactagcc atcttgtaag ttagtttcat ttaatgcaac   2760
tttatccaat aatatattat gtatcgcacg tcaagaatta acaatgcgcc cgttgtcgca   2820
tctcaacacg actatgatag agatcaaata aagcgcgaat taaatagctt gcgacgcaac   2880
gtgcacgatc tgtgcacgcg ttccggcacg agctttgatt gtaataagtt tttacgaagc   2940
gatgacatga cccccgtagt gacaacgatc acgcccaaaa gaactgccga ctacaaaatt   3000
accgagtatg tcggtgacgt taaaactatt aagccatcca atcgaccgtt agtcgaatca   3060
ggaccgctgg tgcgagaagc cgcgaagtat ggcgaatgca tcgtataacg tgtggagtcc   3120
gctcattaga gcgtcatgtt tagacaagaa agctacatat ttaattgatc ccgatgattt   3180
tattgataaa ttgaccctaa ctccatacac ggtattctac aatggcgggg ttttggtcaa   3240
aatttccgga ctgcgattgt acatgctgtt aacggctccg cccactatta atgaaattaa   3300
aaattccaat tttaaaaaac gcagcaagag aaacatttgt atgaaagaat gcgtagaagg   3360
aaagaaaaat gtcgtcgaca tgctgaacaa caagattaat atgcctccgt gtataaaaaa   3420
aatattgaac gatttgaaag aaaacaatgt accgcgcggc ggtatgtaca ggaagaggtt   3480
```

```
tatactaaac tgttacattg caaacgtggt ttcgtgtgcc aagtgtgaaa accgatgttt   3540
aatcaaggct ctgacgcatt tctacaacca cgactccaag tgtgtgggtg aagtcatgca   3600
tcttttaatc aaatcccaag atgtgtataa accaccaaac tgccaaaaaa tgaaaactgt   3660
cgacaagctc tgtccgtttg ctggcaactg caagggtctc aatcctattt gtaattattg   3720
aataataaaa caattataaa tgctaaattt gttttttatt aacgatacaa accaaacgca   3780
acaagaacat ttgtagtatt atctataatt gaaaacgcgt agttataatc gctgaggtaa   3840
tatttaaaat cattttcaaa tgattcacag ttaatttgcg acaatataat tttattttca   3900
cataaactag acgccttgtc gtcttcttct tcgtattcct tctctttttc atttttctcc   3960
tcataaaaat taacatagtt attatcgtat ccatatatgt atctatcgta tagagtaaat   4020
tttttgttgt cataaatata tatgtctttt ttaatggggt gtatagtacc gctgcgcata   4080
gtttttctgt aatttacaac agtgctattt tctggtagtt cttcggagtg tgttgcttta   4140
attattaaat ttatataatc aatgaatttg ggatcgtcgg ttttgtacaa tatgttgccg   4200
gcatagtacg cagcttcttc tagttcaatt acaccatttt ttagcagcac cggattaaca   4260
taactttcca aaatgttgta cgaaccgtta aacaaaaaca gttcacctcc cttttctata   4320
ctattgtctg cgagcagttg tttgttgtta aaaataacag ccattgtaat gagacgcaca   4380
aactaatatc acaaactgga aatgtctatc aatatatagt tgctgatatc atggagataa   4440
ttaaaatgat aaccatctcg caaataaata agtattttac tgttttcgta acagttttgt   4500
aataaaaaaa cctataaata tgccggatta ttcataccgt cccaccatcg ggcgtaccta   4560
cgtgtacgac aacaagtact acaaaaattt aggtgccgtt atcaagaacg ctaagcgcaa   4620
gaagcacttc gccgaacatg agatcgaaga ggctaccctc gacccccctag acaactacct   4680
agtggctgag gatcctttcc tgggacccgg caagaaccaa aaactcactc tcttcaagga   4740
aatccgtaat gttaaacccg acacgatgaa gcttgtcgtt ggatggaaag gaaaagagtt   4800
ctacagggaa acttggaccc gcttcatgga agacagcttc cccattgtta acgaccaaga   4860
agtgatggat gttttccttg ttgtcaacat gcgtcccact agacccaacc gttgttacaa   4920
attcctggcc caacacgctc tgcgttgcga ccccgactat gtacctcatg acgtgattag   4980
gatcgtcgag ccttcatggg tgggcagcaa caacgagtac cgcatcagcc tggctaagaa   5040
gggcggcggc tgcccaataa tgaaccttca ctctgagtac accaactcgt tcgaacagtt   5100
catcgatcgt gtcatctggg agaacttcta caagcccatc gtttacatcg gtaccgactc   5160
tgctgaagag gaggaaattc tccttgaagt ttccctggtg ttcaaagtaa aggagtttgc   5220
accagacgca cctctgttca ctggtccggc gtattaaaac acgatacatt gttattagta   5280
catttattaa gcgctagatt ctgtgcgttg ttgatttaca gacaattgtt gtacgtattt   5340
taataattca ttaaatttat aatctttagg gtggtatgtt agagcgaaaa tcaaatgatt   5400
ttcagcgtct ttatatctga atttaaatat taaatcctca atagatttgt aaaataggtt   5460
tcgattagtt tcaaacaagg gttgtttttc cgaaccgatg gctggactat ctaatggatt   5520
ttcgctcaac gccacaaaac ttgccaaatc ttgtagcagc aatctagctt tgtcgatatt   5580
cgtttgtgtt ttgttttgta ataaaggttc gacgtcgttc aaaatattat gcgcttttgt   5640
atttctttca tcactgtcgt tagtgtacaa ttgactcgac gtaaacacgt taaataaagc   5700
ttggacatat ttaacatcgg gcgtgttagc tttattaggc cgattatcgt cgtcgtccca   5760
accctcgtcg ttagaagttg cttccgaaga cgattttgcc atagccacac gacgcctatt   5820
```

-continued

```
aattgtgtcg gctaacacgt ccgcgatcaa atttgtagtt gagctttttg gaattatttc   5880
tgattgcggg cgtttttggg cgggtttcaa tctaactgtg cccgatttta attcagacaa   5940
cacgttagaa agcgatggtg caggcggtgg taacatttca gacggcaaat ctactaatgg   6000
cggcggtggt ggagctgatg ataaatctac catcggtgga ggcgcaggcg gggctggcgg   6060
cggaggcgga ggcggaggtg gtggcggtga tgcagacggc ggtttaggct caaatgtctc   6120
tttaggcaac acagtcggca cctcaactat tgtactggtt tcgggcgccg tttttggttt   6180
gaccggtctg agacgagtgc gatttttttc gtttctaata gcttccaaca attgttgtct   6240
gtcgtctaaa ggtgcagcgg gttgaggttc cgtcggcatt ggtggagcgg gcggcaattc   6300
agacatcgat ggtggtggtg gtggtggagg cgctggaatg ttaggcacgg gagaaggtgg   6360
tggcggcggt gccgccggta taatttgttc tggtttagtt tgttcgcgca cgattgtggg   6420
caccggcgca ggcgccgctg gctgcacaac ggaaggtcgt ctgcttcgag gcagcgcttg   6480
gggtggtggc aattcaatat tataattgga atacaaatcg taaaaatctg ctataagcat   6540
tgtaatttcg ctatcgttta ccgtgccgat atttaacaac cgctcaatgt aagcaattgt   6600
attgtaaaga gattgtctca agctcggatc ccgcacgccg ataacaagcc ttttcatttt   6660
tactacagca ttgtagtggc gagacacttc gctgtcgtcg acgtacatgt atgctttgtt   6720
gtcaaaaacg tcgttggcaa gctttaaaat atttaaaaga acatctctgt tcagcaccac   6780
tgtgttgtcg taaatgttgt ttttgataat ttgcgcttcc gcagtatcga cacgttcaaa   6840
aaattgatgc gcatcaattt tgttgttcct attattgaat aaataagatt gtacagattc   6900
atatctacga ttcgtcatgg ccaccacaaa tgctacgctg caaacgctgg tacaatttta   6960
cgaaaactgc aaaaacgtca aaactcggta taaaataatc aacgggcgct ttggcaaaat   7020
atctatttta tcgcacaagc ccactagcaa attgtatttg cagaaaacaa tttcggcgca   7080
caattttaac gctgacgaaa taaaagttca ccagttaatg agcgaccacc caaattttat   7140
aaaaatctat tttaatcacg gttccatcaa caaccaagtg atcgtgatgg actacattga   7200
ctgtcccgat ttatttgaaa cactacaaat taaaggcgag ctttcgtacc aacttgttag   7260
caatattatt agacagctgt gtgaagcgct caacgatttg cacaagcaca atttcataca   7320
caacgacata aaactcgaaa atgtcttata tttcgaagca cttgatcgcg tgtatgtttg   7380
cgattacgga ttgtgcaaac acgaaaactc acttagcgtg cacgacggca cgttggagta   7440
ttttagtccg gaaaaaattc gacacacaac tatgcacgtt tcgtttgact ggtacgccgt   7500
cggcgtgtta acatacaagt tgctaaccgg cggccgacac ccatttgaaa aaagcgaaga   7560
cgaaatgttg gacttgaata gcatgaagcg tcgtcagcaa tacaatgaca ttggcgtttt   7620
aaaacacgtt cgtaacgtta acgctcgtga ctttgtgtac tgcctaacaa gatacaacat   7680
agattgtaga ctcacaaatt acaaacaaat tataaaacat gagtttttgt cgtaaaaatg   7740
ccacttgttt tacgagtaga attctacgtg taacacacga tctaaaagat gatgtcattt   7800
tttatcaatg actcatttgt tttaaaacag acttgtttta cgagtagaat tctacgtgta   7860
aagcatgatc gtgagtggtg ttaataaaat cataaaaatt attgtaaatg tttattattt   7920
aaaaacgatt caaatatata ataaaaacaa tctacatcta tttcttcaca atccataaca   7980
cacaacaggt ccatcaatga gtttttgtct ttatccgaca tactatgtgc atgtaacaaa   8040
tcaaatacat cttttaaatt tttatacaca tctttacatt gtctaccaaa atctttaata   8100
accctataac aaggaaaaga cttttcttct tgcgtggttt tgccgcgcag atattgaaat   8160
aaaatgtgca tgcacgacaa cttgtgttta ctaaaatgct ccttgcctat accgcaaaac   8220
```

```
cggccataca tttcggcgat tacacgcgga caattgtacg attcgtctac gtgtaaacga   8280
tcatcataat cactcttgcg caaacgaata aattttttca ccgcttccga caaacgaggc   8340
accaattcgg cgggcacgct tcgatacatt attctgtgca cataagttac cacacaaaat   8400
ttattgtacc accatccgac aacgtcgtta ttagggttga acacgttggc gatgcgcagc   8460
agtttcccgt ttctcatgaa atattcaaag cggcccaaaa taatttgcaa gcaatccaac   8520
atgtcttgag aaatttctcg ttcaaaattg ttcaaagaga atatctgcca tccgttttga   8580
acgcgcacgc tgacgggaac caccgcatcg atttgctcca acacttcacg gacgttatcg   8640
tcgatgccca tcgtttcgct ggtgctgaac caatgggaaa ggctcttgat ggaatcgccc   8700
gcgtctatca tcttgaccgc ttcgtcaaag gtgcaactgc cgctcttcaa acgccgcata   8760
gcggtcacgt cccgctctat gcacgacata ccgtttacgt acgattctga taggtattcc   8820
tgaactatac ggtaatggtg atacgactcg ccatacacgt cgtgcacctc attgtattta   8880
gcataataat tgtaaattat taactttgca gcgagagaca tgttgtcagt aaagcggtgc   8940
taggctcaat aatactgatg tacaggcacg cgtgctattt atatataatt tcgcaaggag   9000
gggagctgtt atcggttgct attattaaag aatggccgtc tgtttttatc acaagcttgg   9060
cagcctcaac catgaagcgt cgtcattgta aattaaattc tctgcctcaa gaattatttg   9120
acaagattgt cgagtattta tctttatctg attactgcaa tttggtgctt gtctgtaaaa   9180
gaccttctag taaatataac gtgatatttg atagtactaa tcaccaacat ttgaaaggcg   9240
tgtacaaaaa gacagacgtg caaataacaa gctacaacga atacatcaac tgtatttgca   9300
acgaactgag acaagacgaa ttctatgcca aatcatcatg gattgcgagt atttgcggtc   9360
accagagagc gacaattttt agtgtaacaa ataaacaagt agaaatgaaa tatcatttgt   9420
ataatatagc aattgtggaa agtgaagatt gcaacggatt ttacccattt gagccaacgc   9480
gcgattgttt aatatgcaaa caaaaaaacc aatgtcctcg taattcattt attgtttcgt   9540
tgtgtaaata tttagaaaaa caaaatgtac aatcaaactt tatatattat ttatacgaaa   9600
taaatacata ataataacta ttatacatgt ttttatttta caatacttcc tgtataacct   9660
ctctaactac attaggagta caatccacgt caattacacg tttagctatt tttctaattt   9720
tgtaatgttt atcgtagagt tttttcgttaa tacattgaat agccaacaag ggatttgggt   9780
gcacaccgtc atagagtact tccatgtcgt cttcaaagcg catttttcgc ttgcgaaaat   9840
gccgctcttg gcccaaaaca aaagcgagtt tgatgcggtc gtcgatgcgt tccgaaaata   9900
cggccaaatg ctggtgtttg gtgatgtcgc gcggaaacgt caccgtgcca tttttgcttt   9960
ccgccacgac ggcggttttc aatttttcgg ccgactgcag catgttaagt ttggcgtcga  10020
gttcgtgcaa acgcaattca aactgctcaa acctgttgcc cacctcgttc ttgaacgtct  10080
cgtgggtgac cataaatttt tcgctgtttg cattcagttt ctttacatgt tttaaaacag  10140
attcaatctt gtcgcgcaaa tcatcacgct cgccttcagt ttgaatgtgc agcaacgcgt  10200
tgcttttgtt ggcaaaattt aaccgcatca aaatttccaa caacccgtgc ttggtcgcga  10260
acaatgcgcc caacgagttg agatcgcgtt tggatctctg tttgtgaaaa acaatttcgt  10320
ttaaatggta aacttgatcg ccgtcccaat tgcaatcaag tatgtcgtcg tgcgcaattt  10380
caagaccttt gcaaaaatct atcacattgt agcattttgc gttcgtgtcg ctgtgcacgt  10440
atctgtactt gaaactgtgc gtgttgcatt tgaatgagtc ccatttaacg atgtgcgacc  10500
attgttgggc gtttatgtgg tactttttgt agtcgtctgc attgaaccga tcttcggcgg  10560
```

-continued

```
cgatggcgtc gttgtcgttg tcaccggacc acatccacca gttccataac caggatagca  10620
ttgctttagc ttgtctagca attcctttgt tatacaacga gaaaatttcg ttcccttata  10680
attatagctg tacggtgcgc gtatttgttt gttaacgtta caaaaaatat ccctgtccac  10740
gtccggccaa tactgcaacg tgagcgcgtc caagtttgaa tcttgcatat gcggaacgta  10800
caaacgtacg gcctctctca cacaatgcgc aaaactgccc ggctgaatgt aatcactgtc  10860
caactttgca ggtttctcga aagccttgta ccgatgcacg cgaacatttt gagcggacgt  10920
gattttaaac ttgtcggtga attttaacca caaatgaaat ccacggttgc cggtatacat  10980
gactcttgac acgttctctt ccgtgtaaaa caacagaaac gccgtggcgc caatgtaaat  11040
tttcagcatt aaatcgtgtt cgtcaacata atttttgtaa tcggcgtcta cgacccattc  11100
cctgccgccg ccgtcgtcca acggtttgac gtgcacgtcg gacactttgt tttgcacaat  11160
ataactatac aattgtgcgg aggtatcaaa atatctgtcg gcgtgaatcc agcgcgcgtt  11220
gaccgtcatg aacgcgtact tgcggctgtc gttgtacgca atggcgtccc acatcatgtc  11280
gacgcgcttc tgcgtataat tgcacactaa catgttgccc tttgaacttg acctcgattg  11340
tgttaatttt tggctataaa aaggtcaccc tttaaaattt gttacataat caaattacca  11400
gtacagttat tcggtttgaa gcaaaatgac tattctctgc tggcttgcac tgctgtctac  11460
gcttactgct gtaaatgcgg ccaatatatt ggccgtgttt cctacgccag cttacagcca  11520
ccatatagtg tacaaagtgt atattgaagc ccttgccgaa aaatgtcaca acgttacggt  11580
cgtcaagccc aaactgtttg cgtattcaac taaaacttat tgcggtaata tcacggaaat  11640
taatgccgac atgtctgttg agcaatacaa aaaactagtg gcgaattcgg caatgtttag  11700
aaagcgcgga gtggtgtccg atacagacac ggtaaccgcc gctaactacc taggcttgat  11760
tgaaatgttc aaagaccagt ttgacaatat caacgtgcgc aatctcattg ccaacaacca  11820
gacgtttgat ttagtcgtcg tggaagcgtt tgccgattat gcgttggtgt ttggtcactt  11880
gtacgatccg gcgcccgtaa ttcaaatcgc gcctggctac ggtttggcgg aaaactttga  11940
cacggtcggc gccgtggcgc ggcaccccgt ccaccatcct aacatttggc gcagcaattt  12000
cgacgacacg gaggcaaacg tgatgacgga aatgcgtttg tataaagaat ttaaaatttt  12060
ggccaacatg tccaacgcgt tgctcaaaca acagtttgga cccaacacac cgacaattga  12120
aaaactacgc aacaaggtgc aattgctttt gctaaacctg catcccatat ttgacaacaa  12180
ccgacccgtg ccgcccagcg tgcagtatct tggcggagga atccatcttg taaagagcgc  12240
gccgttgacc aaattaagtc cggtcatcaa cgcgcaaatg aacaagtcaa aaagcggaac  12300
gatttacgta agttttgggt cgagcattga caccaaatcg tttgcaaacg agtttcttta  12360
catgttaatc aatacgttca aaacgttgga taattacacc atattatgga aaattgacga  12420
cgaagtagta aaaaacataa cgttgcccgc caacgtaatc acgcaaaatt ggtttaatca  12480
acgcgccgtg ctgcgtcata aaaaaatggc ggcgtttatt acgcaaggcg gactacaatc  12540
gagcgacgag gccttggaag ccgggatacc catggtgtgt ctgcccatga tgggcgacca  12600
gttttaccat gcgcacaaat tacagcaact cggcgtagcc cgcgccttgg acactgttac  12660
cgtttccagc gatcaactac tagtggcgat aaacgacgtg ttgtttaacg cgcctaccta  12720
caaaaaacac atggccgagt tatatgcgct catcaatcat gataaagcaa cgtttccgcc  12780
tctagataaa gccatcaaat tcacagaacg cgtaattcga tatagacatg acatcagtcg  12840
tcaattgtat tcattaaaaa caacagctgc caatgtaccg tattcaaatt actacatgta  12900
taaatctgtg ttttctattg taatgaatca cttaacacac ttttaattac gtcaataaat  12960
```

-continued

```
gttattcacc attatttacc tggtttttt gagaggggct ttgtgcgact gcgcacttcc  13020
agcctttata aacgctcacc aaccaaagca ggtcattatt gtgccaggac gttcaaaggc  13080
gaaacatcga aatggagtct gttcaaacgc gcttatgtgc cagtagcaat caatttgctc  13140
cgttcaaaaa gcgccagctt gccgtgccgg tcggttctgt gaacagtttg acacacacca  13200
tcacctccac caccgtcacc agcgtgattc caaaaaatta tcaagaaaaa cgtcagaaaa  13260
tatgccacat aatatcttcg ttgcgtaaca cgcacttgaa tttcaataag atacagtctg  13320
tacataaaaa gaaactgcgg catttgcaaa atttgctaag aaaaaagaac gaaattattg  13380
ccgagttggt tagaaaactt gaaagtgcac agaagaagac aacgcacaga aatattagta  13440
aaccagctca ttggaaatac tttggagtag tcagatgtga caacacaatt cgcacaatta  13500
ttggcaacga aaagtttgta aggagacgtt tggccgagct gtgcacattg tacaacgccg  13560
agtacgtgtt ttgccaagca cgcgccgatg gagacaaaga tcgacaggca ctagcgagtc  13620
tgctgacggc ggcgtttggt tcgcgagtca tagtttatga aaatagtcgc cggttcgagt  13680
ttataaatcc ggacgagatt gctagtggta aacgtttaat aattaaacat ttgcaagatg  13740
aatctcaaag tgatattaac gcctattaat ttgaaaggtg aggaagagcc caattgcgtt  13800
gagcgcatta ccataatgcc atgtatttta atagatactg agatctgttt aaatgtcaga  13860
tgccgttctc cttttgccaa attcaaagta ttgattattg tagatggctt tgatagcgct  13920
tatattcagg ctacctttg tagcattagc gatagtgtaa caattgttaa caaatctaac  13980
gaaaagcatg taacgtttga cgggtttgta aggccggacg atgaaggtac aacaatgcct  14040
tatgtcattg gaccattata ttctgtcgac gctgctgtcg ccgaccgtaa agtgaaggac  14100
gtggtggatt caattcaaaa ccaacagaca atgttaaaag tatttattaa cgaggctaat  14160
gtgtataaca aatggaatat gcttaaaggt ttaatttata ataataacaa tgaatctgtt  14220
ttagtaaaat aatgtagtaa aatttataaa ggtagataaa aattataata ttaataaaaa  14280
aaataatgtt actaaatggg ttcctgcgtt aaattatttt acgggtagac agctattaac  14340
tattttattt atttttaaat ttaaataaat gtattgttag aaaattgtgt tgttttatta  14400
gtataacgaa aaaatacatg acataaaccg cttccaattt tggtcacaca aactcttgtg  14460
tggatagttt acgtaatgag ttaaataggc gggcagttgt ccgctaaacg tgtcggtggt  14520
caagtagatg tgcattaatt tacgacaacc caaagcgggg ccgcttatgt caagtatttt  14580
tttcacaaaa ttggtaatgg tttcgttttg ttccttgtac aaacacatgt cggtgtgatc  14640
gttgacgcac gagttgtacg attccgccgg caggttggca aacaagcgct tgagatgctt  14700
gagtctgcgt tcaattttat aatcaaactt gttggtgaaa atgtctttca gcaagcacat  14760
taactggtcg ttcaaaacgc gctgcaacga cgacaccaac acatgatatt cgtttccaaa  14820
aagcgaaaaa tttttgatgc agcggtccgc gttgaagggt cgtttcataa tgcgcacgtt  14880
gacaaaaaac acgttgaaag acagcggggc tgtggttatt ttaacgccgt tgtcggtata  14940
ctcgtcgacg ccgtctgcgc ttgttatgtc aatttgtagc gcaaatctaa ccaaatcaaa  15000
ctcatcgttg tactgtgtct ttatgcattt tatatggcgg tttaagtgca agttgatttg  15060
gccgtttaat ctataggctc cgttttgata acatttcagc actaccaacg gatccgacat  15120
gtaaacttga cgcgttagca cgtccaattc agcgtaatgt tggtcgacgc atttttgtaa  15180
attagtttgc aggttgcaaa acatttttgc gcaaaagccg taatagtcaa aatctatgca  15240
ttttaatgcg cttctgtcgt cgtcaatatg gcatgtcacg gctgcgcctc cagttaacac  15300
```

```
gaataaaccg ccgttttcgc aaactacggc ttcgaaacaa tctttgataa atgccaactt  15360
tgctttagcc acaattttat cgcgcaggcg atcttcaata tcctttgtcg taatataagg  15420
taggacgcca agatttagtt gattcaacaa acgttccata atgaatagcg gcgacgcaac  15480
acgactacac tgttcaaatg cgcacgcaaa acaaaccctt gcaactttat ttgccaatcg  15540
taatcacagt agtttttacg agtacgccat cgcgtttgta agcacattgc tttttaaaaa  15600
taatttaaat ttaatgaccg cgtgcaattt gatcaactcg ttgatcaact ttgaactcaa  15660
catgtttggt aaaagtttat tgctaaatgg atttgttaat ttctgcattg ctaacagcga  15720
cggggttacg attcaacata aaatgttaac caacgtgtta agtttttgt tggaaaaata  15780
ttattaaaaa taaataaata aacttgttca gttctaatta ttgttttatt ttttataaaa  15840
taatacaatt ttatttatac attaatactt tggtatttat taatacaatt atttacaata  15900
ctttatttac actataatac tttatttaca ttagtactaa attaatacta aattacgcta  15960
atactaaatt aatactttat ataatcaaaa ataatacttt atataatact ttctaatcat  16020
cataaacggg taatagtttt ttctcttgaa atttacgctg caactcttcg ctaaaacaca  16080
tgggcggtgg agtgggagcg ggtggagtag gagtccttac gggtttgatg ggcgacagtt  16140
ctctggactt gcggaacagc ttgggcgaaa acgtcggcgt gcgccgacta atgatttctt  16200
catcgcacga ggcgtcgcac attgtgcacg cgtccggtga ggtacacaaa actttcttgg  16260
gcacgctgta caccggcttg ggcacgctat atgtgttgcc aaaactagaa ctcgttgtgg  16320
ttgccgaacg gagacgatgg gtgtgaagac ggcgatggct gtgaagacaa gtccgaaggc  16380
gcgataaaag atgaaagtgt ttctgaaacc gaagtggtgg tagaagtggt agaaggcggg  16440
tgcgttacgg caaccacgct gctgctattt ctgccttcgg agaccacttc cagcaatcta  16500
gagttactct ctcgttcttc gcggcgatag tcaatgtcgc aataatgttc ataagatgcc  16560
ttttcggctt cggcgcgcct tttcatgtat atgttgtgac gcatctcctt taactgcacg  16620
tacaaattcc agcattgcac agccagtatc gtaagcacgc ccattatgat tacgggataa  16680
ttttgattaa acacggtcgg ctcgtgatcg cttacaatcg ctcggcacat gatgcatttt  16740
ttgtaaatgt tcacatacac acagttttgg ctcaaggttt cggtatttgc gtagtcaatt  16800
tccagataca cgatagagtt ccagcacatt gattccaaat cgtagtgacg atataaaaca  16860
tctagcgccg gtagatgacc atttttgaac acgtagattt gaaacgcggc aaacagcatc  16920
caacacagcc cagtgatcac gtttaccata atacacgtga tagcgacgta aaagttttct  16980
ttcgcattga aatttacatt tgtgtttgaa gagctgctgc gatttttcgt ccacacgata  17040
atcttccata taaaataaaa catgtaaaat aatatccaca tgccgaacgc cagcattatc  17100
ggtatagata gattgataac cgattgcttt ccttcaattt ccagcaaaaa cgcgtatctg  17160
ctgtctatca ctcccattat agataacaca aacactatca gatatgctaa taataatgag  17220
gcattaagcc cgaattgtaa aactgcagtg attttattta acattttgaa tatttaattc  17280
aacaactaag taatggcaat atgtatcgag tactgatcgt gtttttcctg ttcgtgtttc  17340
tttatatagt gtaccagccc ttttatcagg catacttgca tatcggacat gcccaacaag  17400
attacaatga cacgttggac gataggatgg attacattga atccgtaatg cgtagaaggc  17460
actacgtgcc gattgaagcg ttgcccgcaa tcaggtttga tactaatctc ggcacgttgg  17520
ccggtgacac gattaaatgc atgtcggtgc ctttgtttgt tagtgacatt gacctgccga  17580
tgtttgattg tagtcagata tgcgataacc cgtctgcggc gtatttcttt gtcaacgaaa  17640
cggatgtgtt tgtggtcaac ggccacagac tgacggtggg cggatactgc tccactaata  17700
```

```
gtttgccccg caactgtaat cgcgagacga gcgtcatttt aatgagtctc aatcagtgga  17760
cgtgcatagc cgaggacccg cgttactatg cgggcacaga taacatgacg caactcgcag  17820
gcagacaaca ctttgaccgc attatgcccg gacagagtga taggaacgtc ctgtttgacc  17880
gattactagg ccgagaggtg aacgtgacca ctaacacgtt tcgccgcagc tgggacgagt  17940
tgctggagga cggcactagg cggttcgaaa tgcgctgcaa cgcccgagat aacaacaata  18000
atctcatgtt tgttaatccg cttaatcccc tcgagtgtct cccgaacgtg tgcactaacg  18060
ttagcaacgt gcacaccagt gttagacccg tatttgaaac gggagagtgt gactgcggcg  18120
acgaagcggt cacgcgtgtt acgcacattg tgccgggga caggacctct atgtgtgcca  18180
gcattataga tggcctggat aaaagtacgg catcatatag atatcgcgta gagtgcgtta  18240
atctgtacac ctctattcta aattattcta ataacaaatt gttatgtccc agtgacactt  18300
ttgatagtaa cacggacgca gcttttgcct ttgaagtgcc cggctcctac cctttatcgc  18360
gcaacggcat caacgagcca acttatcgct tttatcttga taccagatct cgagttaatt  18420
acaatgacgt cagagggcag ttatcttaat tgtgataaca caaacaataa gtcatttaaa  18480
tgttacgtca gtagttagta tataagccgt acatgttggc ttgcaaattc agtcaatatc  18540
aggcttttat catggacggt gtaaagctgc tagggacgtg cgcgctaata attttgttat  18600
cgacgacgag tacagttgtc gggcgtgacc gtatcacgtt tacgccgata gaagatagcg  18660
caggcctcat gtttgaacgc atgtacggct tgcgacatca tacagacgac agatttgtgt  18720
ttgtgaaaaa attcaatttt gtttcggtgc tgcaagagct caataatatc aaatctaaaa  18780
ttgaattata tgaagcgcaa gtttcaactt gcacaaacgt cagacaaata aaacagaaca  18840
gatcgagtat catcaaagct cgcattgaaa atcagctgca gtttttgacg caactaaaca  18900
aaaatctcat cacatactct gtggaaagca gcattttaag caacgacgtg ctggacaaca  18960
tcgatctgga atatgacgac agcggtgagt ttgacgttta cgacgaatac gaacagcctt  19020
cgcattggag caacatgact gtatccgacg cgcaagcttt gctccgaaac ccgcccaaag  19080
acagagtaat gtttttggac acggttacca ccagcgacgt gagcagcaaa tacgaagaat  19140
acataaactg cattgtgagc aaccgtaccg ttgaaaacga gtgcatgttt ttagccaaca  19200
tgatgaacgt gctcaacgac aaattggacg acgcagcagc tttggccaag atgctggagc  19260
gaatagtaaa acaaacgcga aagaacaaac tcaacatctc caacacggtt atagacgacg  19320
acacgctgct aacggaaatg aaaaaattaa cacaaacttt atacaaccaa aaccgcgtgt  19380
gggtagtgga ttttaacaag gacatgaata gttatttcga tttgtcgcaa gcgtataaat  19440
tgcatttata tgttgattta aacacggtca ttatgtttat taccatgcca ttgttaaaat  19500
ccaccgccgt ttcgtttaat ttgtatcgcg tcatgacggt gcctttttgc aggggcaaaa  19560
tgtgtctgct tatcatttcg ggcaatgaat actttgggat tacagacagc aaaaactatt  19620
atgtgcccgt atctgataac tttagacaag attgccaaga gtttacgggc tacaatgagt  19680
ttttgtgtcc cgaaactgag ccgattgcca ctatgaactc gaaagtgtgc gagattgaaa  19740
tgtttatggg tcgatatagc gacgacgtgg acaacatgtg cgacattagg gtggccaatt  19800
ataatcccaa aaaagcttac gtgaacactt taatagacta ccgaaaatgg ttgtacattt  19860
ttccaaacac gaccgtgtcc gtccactatt attgtcacga cgcgcttgta gaagttgata  19920
caaaagtttc gcccggcgtt ggtgttatgt tttcgactat ggcgcaaacg tgttcgatta  19980
gaataacgta tgatgtgacc ataactgtag attcgcgatt ttatgtcagc cattcaacta  20040
```

```
catactggcc taaaaagaaa tttaatttta acaactacat cgaccaaatg ttgcttgaaa  20100
aagcgaccac cagttttata ccgactgttg acaattttac ccggcccgtt ttattgcaac  20160
ttcctcataa atttcacatt aaagattaca catcgacgcc ccatcatttt ttccatcagt  20220
ctaaaattta caccaacagc gcggcgcccg acgaagactc gcaagacgac agtaatacca  20280
ccgtggttat tatcgctatt gtcgctgcaa tgatcctatt ctgtggatta ttgttatttt  20340
tgttttgctg tataaaaaaa cggtgtcatc aatcaaataa cgtggttgtg caatacaaaa  20400
ataacaatga atttgtcaca atttgcaata atttagaaga caatcgagca tacattaatt  20460
tacctaatga atacgatagc gatgatatgc caaaaccatt gtaccctta cttggcttta  20520
atgatgattt gttaaaagat gataaacctg tgttgtaccc tatgattata gaaagaataa  20580
aataaaacat gtataattga aataaatata ttatttaata aaatgttttt tatttatata  20640
ctattttcta ttacatattc caatgcacac aaatgtttaa tggctatcag ttttaatttt  20700
actaattcgt ctaaacaaaa attattcact tgctgttttt catccatttg acatatggcg  20760
tttataaata attcgctgtg ttttatgaac gaatcgtaaa ccgctgcctg ggccttcagc  20820
acggtcggcg cattgtattt ttgggtaaag tacgcaatat ttttagtcaa acacagagat  20880
tttaaatctt tttcatttat atccaagtcg gaacaatcgt atacaaaatc tagcttttca  20940
ctttcgggcg cgcccagata ctggtttacg agttcgagct gctccacttg gcctttgata  21000
tcggccgcta tgcacaacat tttgtcgatt gcagtttcat tgtttttaac ataataattt  21060
ttaacttttt tattttgcaa tttaatcaaa ctatttaaat tcgcttgacc tttcttacaa  21120
agcgcagtta atatgcaaga cattttgact tataataaaa aacaaaactt ttatatattc  21180
atttattgtt caataataac aaatattcca ggcttaaaag ctaacgaata gggcttttcg  21240
gtaattttct tattattcat gtccgtcatc tgcatctctt tgccgtactt gacgccgtca  21300
atggtgccca tcatgtacat tttaatctcc tccgaaggtc cgtctatttt gtccatttcg  21360
aacaatctat caaaatcttc aacgctcatt ctctgcatat caagaggaac gtttctgatc  21420
tttccggtgg cgtaaattga tccgttgttg tcacggttga ttatgtaaaa ccgacgaatc  21480
aacatgtcgc gctcgctagt tttgttctta tccggcaaat gaatgcacac gtttggttcc  21540
atcttcaaag gaaaatcgct ttgcaagtgt ttttgcaaaa tgttgccaaa tatattgttg  21600
tgtttgtgaa tgtctccgta ttgaatgcta aaaaactggc caaagttgct tttggcacgt  21660
tttatggttc caaagtcgga aaaccaaaat ccgcagggct tgccctgcac tcttggaccg  21720
atggtgtacg tagtcttgcc gttggccggc tccaacacca cgatattttt atcgggctcg  21780
ggatacaact tgtcttccca ttcgtgcaaa ctgttcaaat tagacagtcg acaaaattcg  21840
tttttcaaaa atctgccttc gaaacaacta caattcagta ttgaaaagtt gcctcgtttc  21900
acattaatcg ccatctgctc ctgccacaac atcttcgtca actcgtgtgg ctccaattga  21960
atggacgacg gcgtaaaata gcacattacg cccgtttcgt cgtgtttcac gttaaaagcg  22020
ccgctgttgt acggcaccag ctgctggtcc tcaccacctt ccgatctttc ccgcttcggc  22080
tggttgtcgt cgctgctcga atatccatcg ccaatcttgc gtttagttgc catgctaccg  22140
acgtgcgctg tctgctgtgg ttcaagtcta attgaagtgt ttcacagaat ataagatata  22200
taataaatat ggacgactct gttgccagca tgtgcgtaga caacgcgttt gcgtacacta  22260
ctgacgattt attgaaaaat attcctttta gtcattccaa atgcgcccct ttcaagctac  22320
aaaattacac cgttttgaag cggttgagca acgggtttat cgacaagtat gtggacgtgt  22380
gctctatcag cgagttgcaa aagtttaatt ttaagataga tcggctaacc aactacatat  22440
```

```
caaacatttt cgagtacgag tttgtagttt tagaacacga tttgtccaca gtgcacgtca  22500
ttaacgccga aacaaaaacc aaactgggcc atataaacgt gtcgctaaac caaaacgacg  22560
caaacgtgct cattttgacc gtaactttaa cgagctaaaa tgaacgagga cacgcccccg  22620
ttttatttta tcagcgtgtg tgacaacttt cgcgacaaca ccgccgaaca cgtattcgac  22680
atgttaatag aaagacatag ttcgtttgaa aattatccca ttgaaaacac ggcgtttatt  22740
aacagcttga tcgttaacgg gtttaaatac aatcaagttg acgatcacgt tgtgtgcgag  22800
tattgcgaag cagaaataaa aaattggtcc gaagacgagt gtattgaata tgcacacgta  22860
accttgtcgc cgtattgcgc gtatgctaac aagatcgccg agcgtgaatc gtttggcgac  22920
aacattacca tcaacgctgt actagtgaaa gaaggcaaac ccaagtgtgt gtacagatgc  22980
atgtccaatt tacagtcgcg tatggatacg tttgttaact tttggcctgc cgcattgcgt  23040
gacatgatta caaacattgc ggaagcggga cttttttaca cgggtcgcgg agacgaaact  23100
gtgtgtttct tttgcgactg ttgcgtacgt gattggcata ctaatgaaga cacctggcag  23160
cgacacgccg ccgaaaaccc gcaatgttat tttgtattgt cggtgaaagg taaagaattt  23220
tgtcaaaact caattactgt cactcacgtt gataaacgtg acgacgacaa tttaaacgaa  23280
aacgccgacg acattgagga aaaatatgaa tgcaaagtct gtctcgaacg ccaacgcgac  23340
gccgtgctta tgccgtgtcg gcatttttgc gtttgcgttc agtgttattt tggattagat  23400
caaaagtgtc cgacgtgtcg tcaggacgtc accgatttta taaaaatatt tgtggtgtaa  23460
taaaatggtg ttcaacgtgt actacaacgg ctattatgtg gaaaaaaaat tctccaagga  23520
gtttttaatt catattgcgc ctgatttgaa aaacagcgtc gactggaacg gcagcacgcg  23580
caaacagctg cgcgttctag acaagcgcgc ctacaggcag gtgttgcact gcaacggcag  23640
atactactgg cccgatggca caaagtttgt ctctcatccg tacaacaaat ctattcgcac  23700
gcacagcgca acagtcaaac ggaccgacag ctcgcatcga ttaaaaagcc acgtggtcga  23760
caaacgaccg cgccgctctt tagattctcc tcgcttggac ggatatgttt tggcatcgtc  23820
gcccatacca cacagcgact ggaatgaaga actaaagctg tacgcccaga gccacggcta  23880
cgacgactac gacgacaatt tagaagatgg cgaaatcgac gaacgtgact ctttaaaaag  23940
tttaaataat catctagacg acttgaatgt attagaaaaa caataaaaca tgtattaaaa  24000
ataataataa taaaactata ttttgtaata tataatgtat tttatttaaa aattgtctat  24060
tccgtagttg agaaagtttt gtcttgactt cataactctc ttctccatat tctgcagctc  24120
gtttacgttt tttgtgacgc ttttaatttt ctcaaaatgc tggctgtcaa tagttatttt  24180
ttgcttttgt ctattaattt cttccaattg agattttaaa tctcgctgag attgagatgc  24240
gttgtaattc cttgagaaca tcttgagaaa acatacagat gaggtaaaac agcatctttt  24300
atccaaatta ggagttaatt attattcatt tgtatcgcga ccatttgctc gtacacatct  24360
tccataaaat ggttattttt attgcgataa gtgttggcat tgacattttg caaatgtcgt  24420
aggttaaagg ggcaaatggg ctgcgtggcc gataaaagat tccagttcaa caatccctct  24480
tcgcccccgt ttaacttgaa aatggcgcta cacgtttcta cgctatcgtg ttcctgttga  24540
gtggcgcacg gttcgaccag tatcatcttg tgatatgcgg ttttgacatt catgtgcaac  24600
ggaataactt gcgggtcatc gcattcgtcg gaattaagct ttaaatggcg tccgtatgct  24660
ttccaaagtt tttcgtcgtc gaaccgcggc actgcttgca agtcgacgcg gggaaacggc  24720
gctctgtaca aaacgcctaa attcaaaaac tgattgcatt gttgcagctc tgtccaatcg  24780
```

-continued

```
acgcgatttt tgtaattttg aaacagcatc aggttgaacg ccgcgctggc gcgcacgttt  24840
gtaatcactg tgtaattgat cagcttgtgc caatactggg cattgaaatt ttcttcaaac  24900
tcatttctaa actctggatg cgcaaacatg tgtctaatgt agtacgcggg cggggcgttg  24960
aacgcagtcc atttgtcaat acacttccag tctgaatgta acgtgttcac caaaccggga  25020
tattcgtcaa acacgagcat gtgatccgac cacggtatgc tgtgggcgat caattttagt  25080
tcttgcacgc ggccttcgcg taagcaatac aaaatgagcg cgtcgctgat cttgacacag  25140
tcttgcatgt acgcggacaa attaacgttt tccatacagc tcacattgtt tattagcgcc  25200
gtgttcaagt gtttgtattt ggacacataa tcgtagttga tgtactgttt aatgggttct  25260
tgaaaccatt cttttagtag tatgtgactg gccactatgc gtttccaatt taatttgtgt  25320
gcgtattttt gctgcaccga caacgagagg ttattgtaat tttggatat ttcttccatg  25380
tccaacaagt ccccaaacgc gagtataaaa tcttgcgtca aaaatttttg ctcagacacc  25440
aacgaccaga tcaaatgtga tttaaacctg ttggcgattg ttatcgacaa cggcgaaatt  25500
gaaataattt tccaatccaa cttgttgcga aacacgtgaa taaaatcgac gcgtccgtaa  25560
cattcgcgcg atatgcgctt ccaaaacgtg tcatcttgca aattaagcaa atagacacga  25620
ttgttgggag atttgacggc caattcaatt atttttatat attctttttg ctttaaagcg  25680
cgttgtagca cttgggttgg agccatgtcg actgaagctc cacgctgttt gaagcaaggt  25740
gaccgttttg gtcggcatgt tcaaacgtcg attacatgtt tgctttgcat caaaatggcg  25800
taattaatta agaaacaaca tgaaagccat ctgcatcatt agcggcgatg ttcatggaaa  25860
aatttatttt caacaagaat cagcgaatca accgcttaaa attagcggct atttgttaaa  25920
tttgcctcga ggtttgcacg gctttcacgt gcacgaatat ggcgacacga gcaacggttg  25980
cacgtcggcc ggtgagcact ttaatcccac caatgaggac cacggcgctc ccgatgctga  26040
aattaggcat gttggcgact tgggcaacat aaaatcggct ggctacaatt cactgaccga  26100
agtaaacatg atggacaacg ttatgtctct atatggcccg cataatatta tcggaagaag  26160
tttggtcgtg cacacggaca aagacgattt gggccttacc gatcatccgt tgagcaaaac  26220
aaccggcaat tctggcggcc gtttgggatg cggaataatt gccatatgta aatgatgtca  26280
tcgttctaac tcgctttacg agtagaattc tacgtgtaaa acataatcaa gagatgatgt  26340
catttgtttt tcaaaactga actcaagaaa tgatgtcatt tgtttttcaa aactgaactg  26400
gctttacgag tagaattcta cttgtaacgc atgatcaagg gatgatgtca tttgtttttc  26460
aaaaccgaac tcgctttacg agtagaattc tacttgtaaa acataatcga aagatgatgt  26520
catttgtttt ttaaaattga actggcttta cgagtagaat tctacttgta aaacacaatc  26580
gagagatgat gtcatatttt gcacacggct ctaattaaac tcgctttacg agtaaaattc  26640
tacttgtaac gcatgatcaa gggatgatgt attggatgag tcatttgttt ttcaaaacta  26700
aactcgcttt acgagtagaa ttctacttgt aacgcacgcc caagggatga tgtcatttat  26760
ttgtgcaaag ctgatgtcat cttttgcaca cgattataaa cacaatcaaa taatgactca  26820
tttgtttttc aaaactgaac tcgctttacg agtagaattc tacttgtaaa acacaatcaa  26880
gcgatgatgt cattttaaaa atgatgtcat ttgtttttca aaactaaact cgctttacga  26940
gtagaattct acgtgtaaaa cacaatcaag ggatgatgtc atttactaaa ataaaataat  27000
tatttaaata aaaatgtttt tattgtaaaa tacacattga ttacacgtga catttacgat  27060
ggcgaacaat aatttcactt tttatattag gacacgacgt gtatatagga aagcttaagc  27120
gtttcaataa agccatggcg tacacgctaa gcttgcccag cttgcggctc tttgaaatct  27180
```

```
gtagttttcg gggagtaccg tcgttcttca gtgccacata cgtcaacttg cgatcgtaca  27240
ctttataata cgtgttgtag ttattttttt ccagaaattc cctcataaag caatccttgg  27300
ataaagtttt tgatccgtac agttggccac accggtccat gcacaggtac acacacgtga  27360
tggcgttttg aatgacgatg cgatttctgt caacggcaac gcgcttgaat atggtgtcga  27420
cgttgtccga ttcaatggtt ccgtaaacag ctccgtctgg atttactgcc aaaaactgcc  27480
ggttaataaa cagctggccg ggaatagacg tgcccgtgat gtgtgtcagc agagctgagc  27540
agtcagccat agaggctaga gctacaagtg ccagcaagcg atacatgatg aactttaagt  27600
ccccacagca aactggcgct tttatataaa aatttgggcc atttttggcg attagataat  27660
ttttgaagat tagataatat tgagattagt taataatttg tgtgattaga taacttttta  27720
gggtattgcg cattataaat caaggtcgag ttgtataaac tgctctggcg tgtaaaactg  27780
cagacttaag ttttttgcaa acactcggtc tgaatcgcta aaatctttct gaccggtggt  27840
tagattaatt cggccagccg cgtcgcccac ataaaaagat tgttccttgt caatatgcgt  27900
aaactgtttg gccatctcgc gccacattcc cgtgtcgggc tttcgatgct catccttgtt  27960
gggcgacaca taaaacgata tggcacgcc agtagctttt ttaatattct ctaatttata  28020
taataaatcg ctcgctttga ttttgccgga acctaaatgg gcttggttcg taaaaacaac  28080
taaatcgtag cctaattcgt acaaacgctt tagcttgtgt gcgcacggaa ggagctgcca  28140
gtcgtctggg tttttggaa atttggaccg tgtctttgag ctaattagcg tgccgtccaa  28200
atcaaaagcc gcaattttgg ttcttttagc gccgtcatga accgcgtacg catacaaatc  28260
gggctgctgt aacgtccaca tggtgaatgc atcttactca aagtccatca attcgtacgc  28320
gtttgtgtcc aggtcgggcg ttgaaaaatt gtagcttgcc attagatcgg atagcgattc  28380
aaattttgta agcgtttgta gcgcacgttt ggcatcttgt ttaaaattac acgacgacag  28440
acagtaaaaa tattcctcga taagcatgac tacacccata tcactgttta agtgctcgac  28500
gtagttgttg catgttatgt cgcgtgtgcc gcgatacgcg tgatttcggt gaaaatcaca  28560
ccacaaccag tcggcgtgcg tgtaacaaag tcgacagcga aacaatttat cgttttccaa  28620
aaaatttaaa tactcgacag ttttgcagct tagattccgc gtttgattca ccttaaaatc  28680
gtcgtcagcc tctataatct cgggcaacag cttgccttgt tgccccatcg tatcgatcac  28740
ctcccccaag tggcccggtg ttatattaag tcgtttaaaa tcatttattg cttcctgcac  28800
gtcggcctgg taatttttga ccacgggcgt ggaaatcaat tgccgttgaa gggaaataat  28860
tcgtggtgtg ggtatcggcc gcctgttgca caattccacc agcggtggag gcaagggcgc  28920
attcacagca accgttgtca tttataagta atagtgtaaa aatgcaaata ttcatcaaaa  28980
cattgacggg caaaaccatt accgccgaaa cggaacccgc agagacggtg gccgatctta  29040
agcaaaaaat tgccgataaa gaaggtgtgc ccgtagatca acaaagactt atctttgcgg  29100
gcaaacaact ggaagattcc aaaactatgg ccgattacaa tattcagaag gaatctactc  29160
ttcacatggt gttacgatta cgaggagggt attaataata acaataataa aaaccattaa  29220
atatacataa aagtttttta tttaatctga catatttgta tcttgtgtat tatcgctaac  29280
cattaaaagt gctggagcca cagtgttgcg gcgagtcttt atagaagatc gttgtttggc  29340
tggaactgag cttttccttt tcctgctgcc gctaatggga gtgggcacgt actctgtagt  29400
agacggtgca acgggcaact tgagcgctac cgtcttaaat ttggccatac ttttagtgat  29460
gaaatcgcgc gttaacactt cgtcgtaaat gttacttagc agaggcgcaa cattgtgatt  29520
```

-continued

```
aaatgtctcg tttaacaagc tgtaaaactc cgaataaagc ttatcgcgca tttcgcagct  29580
ctccttcaat tctgccaaat ttgcgttggt aagcaccaca gtctgtcttt ttttgctcgc  29640
tggaattgct gcgttctcgc ttgaagacga cgatgtcgat cggtcggcca ttttttttgcc  29700
cagcttttca gtgtgatcaa aaatgaacac aaaatctgcc aattcgggct tgtttttcac  29760
caaatcccac atggccgggc tactaggcca ctcgggctgc ttgatcttag tgtaccaact  29820
gttaaacaaa atgtatttat tgttgttaat cactttcttc ttgcgtttgg acattttgcg  29880
ttcgtcttgc atgacaggca ccacgttaag gatatagtta atgttctttc tttccaagaa  29940
atttacaata acggccagct ggtccatgtt ggatttgttg taagagctcg attccagttt  30000
attcaacagc ttttcatttt tgcacacggc cgcagtctcc ggagattgtt gctccggcac  30060
gtttaccatg tttgcttctt gtaaaccttt gaaacaaccc gtttgtattc ttgatgatat  30120
atttttttaa tgcccaacaa cctggcaatt cgtttgtgat gaagacacac cttacgcttc  30180
gaacatttgt cggtgattac tgtgaaatgg cctaaattag ctcttatata ttcttttata  30240
cgctcaaacg acacgatgtc caacatgtgc gcgcagacgt tttctgtgtt catcgtgtgc  30300
ttgagcgtgt tgatggcttc cctgaacagc gcttgtattt cgctgcgagt caagcagtcc  30360
gaatcacacc cgcctaagtg cgtgcaattt ttggggggca tcgttgtcta tctttttcag  30420
agtggcgtag aaaaagtcct gcaattgcct attatcaaaa cgcgccttga cgctgcgcac  30480
aaaatcaaaa aattcaatgt aattgctgta atcgtacgtg atcagttgtt tgtcgttcat  30540
ataattaaag tatttgttga gcggcacgat ggccaggctg cgcgctattt cgcaattgaa  30600
gcgtcgcggt tttaacatta tacggtagtc attgccaaac gtgcccggca acaacttcac  30660
ggtgtacgtg ttgggtttgg cgttcacgtt aatcaagttg ccgcgcacga cgcctacgta  30720
tatcaaatac ttgtaggtga cgccgtcatc tttccattgt aacgtaaatg gcaacttgta  30780
gatgaacgcg ctgtcaaaaa accggccagt ttcttccaca aactcgcgca cggctgtctc  30840
gtaaactttt gcgtcgcaac aatcgcgatg acctcgtggt atggaaattt tttctaaaaa  30900
agtgtcgttc atgtcggcgg cgggcgcgtt cgcgctccgg tacgcgcgac gggcacacag  30960
caggacagcc ttgtccggct cgattatcat aaacaatcct gcagcgtttc gcattttaca  31020
tatttgacac ttaaaaaatt gcgcacacga gcaccatcgt ttgataccta attgcaacta  31080
tttacaattt atcagtttac gttgaacccg ttttaatttt ttagatccgt ccttgttcag  31140
ttgcaagttg actaaatgac aaaatttttc ggttctgcaa aaccgccctt gtctgttcca  31200
cccgttgtat ttgaaaaaac tttttttcac gcggcgacaa ctgcttgtat aatattgccc  31260
aatgtaaaca tgcaaaattt tgttactctc gtcaaaacag cggttggcgt tccattccat  31320
aattttttta ttatttatca acgatggcca ttgtaaattg tcgtcattta tacgcatcat  31380
atgatttaac aaaagctttt cgtatagcgg aacttcaatt cccttggaac atttttcaaa  31440
cgataattta atttgtttct cggttggcag catttcatgc ttgattaaca atcgcctgac  31500
ttttatagcc acgtttatgt ctttgcacag caaatgtggg ttgtcgacaa tgtaatagtg  31560
caaagcattt gttacggcaa atgcgtagtt tgatttgacg acgccctttt tcttgacggg  31620
cattgcggct tttaaaatta cttgcaagca ttgtacgaat acctctttgt gtttaaacaa  31680
taatatggac aaacatcggc gaaacaattt gtaataatta tgaaatccca aattgcaggt  31740
tttaaacttc tttgttactt gttttataat aaataaaatt tgctgaccca tgtctgcgcc  31800
cacaacttta attaaccatt tgtgcgcata ttgattgtct cgttgttccc aaccggaaaa  31860
ttgattgatc tcgagccacc ggcattggtc gtttgatacc gtcgttaacg ccgacgctcc  31920
```

```
tgcctgtttg attacgggtt ctaaaagacg aaacagcagc gtaaatttgt ttttgcgtcg  31980
gtagtatttt ggcaggcaat aatcaaaaaa atccgtaagc aattctctgc atctattaat  32040
attcgttgcg tacgaatcga gtttttcaaa aattactttg tttgtatgaa aataacgttt  32100
gggcttctca caataataat cttcgttgta gaacagaaac ggtttgcgag aattggcacg  32160
tttgtccatg attggctcag tgtaacgatt gattcaaatc aaaattgaca acacgtttgc  32220
cgtaatgtgc accggttcgc acacgtttgc cgcgtatgta atccatgttt atttcgctgt  32280
cgcaattgat tacacgattg tgttgggcgg cgcgttttat tgaatttagg cgacgcgtcg  32340
acaactccaa aggattgtaa agcgcagatt tttccagagt aaacgagttt aagtggccac  32400
cgttgaacca ttccagagcc acgattgtgt acagcaaaaa gaatatttct ttgtcgacgt  32460
tttcaaacgc aaacttgttt tttaggcaat agtagtaaaa ttttaacgaa ttgtataaat  32520
aaaacataaa attgccattt ttaaagtaaa attctacatc cgtgacgaac aaaaggttta  32580
ctattttgtt ctccaacaag tgtgccaatt ttcttaagta caccattgaa tttttgtcgt  32640
cgtccatctc gatcaacaac acgtacggcg ttttggaatt taaaattatt ctaaaatttt  32700
cctgttgcaa cgattccaca gcgtccgacc aatatgacgc tgccacctct agacagatgt  32760
atttcttgga aaacacgtgt cgtttgataa cctcgctgat ggacgtgatc gattgtaaat  32820
acttttcaaa cgtcgcgtct tcccaaccac gcaccgaaac gggcgctgtc gtgtcgggct  32880
gatgtttgaa atccaaacca ctctgaatta acttggttgt gattcgtatg ctcaactgtt  32940
gacccaacgt gtagtgatct tcgtaggcgc gctcccacat cacgttacac acaaatttga  33000
cgagatcatc aacgtctttc tgttgcaaaa ttcgccgcaa acgcgccaca tcgcccttgt  33060
accaccgatc tcggcacaca agctgtagca tttttaaatc gtgatcgctc aagctattaa  33120
ttctggttag atttatatag tcgtcaatat cctcgggcgt ggtttgcgtc atgtctgtaa  33180
aacgtgcaaa atcaaacatt tttatgttgt agtcgaatct aacaaatcca tcggcgttca  33240
cttgcacttc gcgctttaca aaacgaggta gcgtgtaatc gaacccgttt aaatagattg  33300
cgtacaaaac cagcacttca tcttccagtt tgcacgcttg cggcaaaaat tgtgtggtgt  33360
gctccaaccg ggtgacaaac atgactatgg aaaataacgc ggaattcaac agacgactag  33420
agtacgtggg cacgatcgcc acaatgatga aacgaacatt gaacgtttta cgacagcagg  33480
gctattgcac gcaacaggat gcggattctt tgtgcgtgtc agacgacacg gcggcctggt  33540
tatgcggccg tttgccgacc tgcaattttg tatcgttccg cgtgcacatc gaccagtttg  33600
agcatccaaa tccggcgttg gaatatttta aatttgaaga aagtctggcg caacgccaac  33660
acgtgggccc gcgttacacg tacatgaatt acacgctttt taaaaacgtc gtggccctca  33720
aattggtcgt gtacacgcgc acgctacaag ctaacatgta cgcggacggg ttgccgtatt  33780
ttgtgcaaaa tttttcagaa acaagctaca aacatgttcg tgtgtatgtt agaaaacttg  33840
gtgcgataca agtagcgaca ttatcagttt acgaacaaat tattgaagat acaataaatg  33900
aactcgtcgt caatcacgtt gattagataa tgtccgtgtt aaatgtgata tcttagatta  33960
cgagcgcgca ataaccatag tttaatcgaa gagaatagcc gtcgccacaa tggataatta  34020
caaattgcaa ttgcaagaat tttttgacca agcgcccgac aacgacgatc ccaactttga  34080
acatcaaacg cccaatctat tggcgcatca gaaaaaaggc atacagtgga tgattaacag  34140
agaaaaaaac ggccggccca acggcggcgt gcttgccgac gacatgggac tcggcaaaac  34200
gctctctgtg ctaatgttaa tcgcaaaaaa caactctcta caattgaaaa ctctaatagt  34260
```

```
gtgtcctttg tctttaatca atcattgggt aaccgaaaac aagaagcatg atttaaattt  34320
taacatttta aagtattaca aatctttgga tgccgacacg gttgagcatt accacattgt  34380
ggtgaccacg tacgacgttt tattggcaca tttcaaattg atcaaacaaa ataaacagtc  34440
aagtctgttt tcaacccgct ggcatcgagt tgttctagat gaagcgcata ttatcaaaaa  34500
ctgcaagacg ggcgtgcaca acgccgcgtg cgctttgacc gcaacaaacc gatggtgcat  34560
taccggcaca ccgatccaca acaagcattg ggacatgtac tcgatgatta attttttgca  34620
atgtcgtcct tttaacaatc caagagtgtg gaaaatgtta aataaaaaca acgactctac  34680
aaatcgcata aaaagtatta ttaaaaaaat tgttttaaaa cgcgacaaat ctgaaatttc  34740
ttctaacatt cctaaacaca cggttgagta tgtacatgtt aattttaatg aagaagaaaa  34800
aacgttgtac gataaattaa agtgtgaatc ggaagaggcg tatgtgaagg ctgtggcagc  34860
gcgtgaaaac gaaaacgcac taagccgatt gcagcaaatg cagcacgtgt tatggctaat  34920
actgaaattg aggcaaatct gctgccaccc gtatttggcc atgcacggta aaaatatttt  34980
ggaaacaaac gactgtttta aaatggatta tatgagcagc aagtgcaaac gagtgctcga  35040
cttggtagac gacattttga acacaagcaa cgacaagata atattggttt cgcaatgggt  35100
ggaatattta aaaatatttg aaaacttttt taaacaaaaa aacattgcta cgttaatgta  35160
cacgggccaa ttaaaagtgg aagacaggat tttggccgag acgacattca atgatgctgc  35220
caatactcaa catcgaattt tgctgctttc cattaagtgc ggcggcgtcg ggttaaactt  35280
aataggcgga aaccacattg taatgttgga gcctcattgg aacccgcaaa ttgaattgca  35340
ggcgcaagac cgaatcagtc gtatgggaca aacaaaaaac acgtacgtgt acaagatgct  35400
aaatgtggaa gacaacagca tcgaaaaata cattaaacaa cgccaagaca aaaagattgc  35460
gtttgtcaac acggtctttg aagagactct gctcaattac gaagacatta aaaaattttt  35520
caacttgtag ctggtaagtc gtcatgaaca cccgatatgc tacttgctat gtttgcgacg  35580
agttggtgta cttgtttaag aaaacgttta gtaacatgtc cccttcggcc gctgcgtttt  35640
accaacggcg catggccatt gttaaaaacg gtatcgtgct gtgcccacgt tgttcgtcgg  35700
aactaaaaat tggcaacggc gtttcgattc caatttaccc ccaccgcgct caacaacatg  35760
cacgacggtc gcgttaagac gcaagcgctt cgagttttgg cccgctcgct acctccgctg  35820
tacgactcga ccgtcgatcg acacggctgc aaggtgttca cggtgcggcg ctacaacaga  35880
cgcgtaatcg actttgcggg cattcgcaac aaaacgctgg aaatcattaa aacggataga  35940
aacttgccgc tcaacacaga atgcaatgtg aaagttgtcg acagtgcatg catgcgttgc  36000
agaaaaagtt tcgcagttta ccccgccgtt acctatctgc attgcggaca ttcgtgtctg  36060
tgcaccgact gcgacgaaac ggtaaacgtg gacaacacgt gtcctaaatg taaaagcggc  36120
attagatata aattaaaata caaaactttg taacatgttg ccctacgaaa tggtgattgc  36180
cgtgttggtt tacttgtcgc cggcgcagat tctaaattta aaccttcctt ttgcatacca  36240
aaaaagtgtg ctgtttgcca gcaactctgc aaaagttaac gaacgcatca ggcggcgagc  36300
gcgtgacgac aacgacgacg acccctattt ttactacaaa cagttcataa agattaattt  36360
tttaactaaa aaaataataa atgtttataa taaaactgaa aagtgtatta gagcgacgtt  36420
tgatggtcgg tatgtggtta cacgcgacgt tttaatgtgc tttgtaaaca agagttatat  36480
gaagcaattg ctgcgcgagg ttgacactcg cattacacta cagcaacttg ttaaaatgta  36540
tagtccagaa tttggttttt atgtaaatag caaaattatg tttgtgttaa ctgaatcggt  36600
gttggcgtct atttgtttaa aacactcgtt cggcaaatgc gagtggttgg acaaaaaatat  36660
```

```
aaaaactgtg tgtttacaat taagaaaaat ttgtattaat aataagcaac attcgacatg  36720
tctatcgtat tgattattgt catagttgta atatttttaa tatgtttttt gtacctatca  36780
aatagcaata ataaaaatga tgccaataaa aacaatgctt ttattgatct caatcccttg  36840
ccgctcaatg ctacaaccgc tactactacc actgccgttg ctaccaccac taccaacaac  36900
aacaacagca tagtggcctt tcggcaaaac aacattcaag aactacaaaa ctttgaacga  36960
tggttcaaaa ataatctctc atattcgttt agccaaaaag ctgaaaaggt ggtaaatccc  37020
aatagaaatt ggaacgacaa cacggtattt gacaatttga gtccgtggac aagcgttccg  37080
gactttggta ccgtgtgcca cacgctcata gggtattgcg tacgctacaa caacaccagc  37140
gacacgttat accagaaccc tgaattggct tacaatctca ttaacgggct gcgcatcatt  37200
tgcagcaaac tgcccgatcc gccgccgcac caacaagcgc cctggggccc ggtcgccgat  37260
tggtaccatt tcacaatcac aatgcccgag gtgtttatga acattaccat tgtgctaaac  37320
gaaacgcagc attacgacga agctgcgtcc ctcacgcgtt actggctcgg cttgtatctg  37380
cccacggccg tcaactcgat gggctggcac cggacggcag gcaactcaat gcgcatgggt  37440
gtgccctaca cgtacagtca aatcttgcgc ggatattcat tggcgcaaat taggcaagag  37500
cagggaatac aagaaatcct aaacacgatc gcgtttccgt acgtgactca aggcaacggc  37560
ttgcacgtcg attcgatata catcgatcac attgacgtgc gcgcttacgg ctatttgata  37620
aattcatact ttacgtttgc ctattacacg tactattttg gagacgaggt aatcaacacg  37680
gtgggtttga cgagagccat cgaaaacgtg ggcagtcccg agggagttgt ggtgccaggc  37740
gtcatgtctc gaaacggcac gttgtactct aacgtgatag gcaactttat tacgtatccg  37800
ttggccgtcc attcggccga ttactccaaa gtgttgacca aactttcaaa aacatattac  37860
ggttcggttg tgggcgtaac gaataggttg gcttactacg aatccgatcc cacaaacaac  37920
attcaagcgc ccctgtggac catggcgcgg cgcatttgga atcggcgcgg cagaattatc  37980
aactataatg ccaacacggt gtcgtttgag tcgggtatta ttttgcaaag tttgaacgga  38040
atcatgcgca tcccgtcggg caccacgtcc acgcagtcgt tcagaccgac cattggccaa  38100
acggctatag ccaaaaccga cacggccggc gccattttgg tgtacgccaa gtttgcggaa  38160
atgaacaatt tgcaatttaa atcgtgcacg ttgttctacg atcacggcat gttccagcta  38220
tattacaaca ttggcgtgga accaaactcg ctcaacaaca caaacgggcg ggtgattgtg  38280
ctaagcagag acacgtcggt caacaccaac gatttgtcat ttgaagcgca aagaattaac  38340
aacaacaact cgtcggaagg caccacgttc aacggtgtgg tctgtcatcg cgttcctatc  38400
acaaacatca acgtgccttc tctgaccgtt cgaagtccca attctagcgt cgaactagtc  38460
gagcagataa ttagttttca aacaatgtac acggccacgg cttcggcctg ttacaaatta  38520
aacgtcgaag gtcattcgga ttccctgaga gcttttagag ttaattccga cgaaaacatt  38580
tatgtaaacg tgggcaacgg cgttaaagcc ctgtttaatt atccctgggt aatggtcaaa  38640
gaaaataaca aagtgtcttt catgtcggct aacgaagaca ctactatacc atttagcgtt  38700
ataatgaatt ccttcacctc tatcggcgaa ccagctttgc aatactctcc atcaaattgc  38760
tttgtgtatg gaaacggttt caaattgaac aacagcacgt ttgatttaca atttatttt  38820
gaaattgtgt aattatattt agggagaatg tgatattcaa aagactgact gttaacacaa  38880
aagactgata ttgttgttgt tacaaaatag ataataaaac aaaaaataaa ttaaatatta  38940
tttatttatt aaactgttta attttaatgc taacgcgtac aaatcacgct gttccgacgt  39000
```

-continued

```
ggacatggaa ttgcgcagaa aagtcttgat agtgtcgatt tcttcgccgt catccacttc  39060
catatatttg atttcttcct cgatttgcat ttccaagttt gcgtattctt gcaaataata  39120
atctagtcgt tgggcgacct cgccaatttt aaataataca ttatccgaca ccaaatgcca  39180
gcgagtgact gtgcgctcca tcatcctggc actttttaat gtgaatatta aaaggttgtt  39240
gcatatatat cgttaaacgt ttatgtttac tttcacgtta gctcgtttca ttgatgtaaa  39300
catttagttt tataacagcg tcggtaattt tattttttaa agtaaacaga ccaaaatcaa  39360
aggtgtcttc gacaggtacg attattttcc cattgacact gttttcgtgc acagatataa  39420
ttttatcacc gtttattatt ttgcccaaac acacgtactc gtttcttctc aagccaacta  39480
tttctaaaca attcactttt ctattatcgt gtacgcaatt aaaagtaaac gaagcgctac  39540
aattgtcgta ttctattaca attctgcggc atttataaaa tttattaatg ttgacgcaaa  39600
ttccatgcag cgcatccatt tcgtactgca aatgcggcgc aattaaaaaa tttcctcgtc  39660
gttgttaaca atcttgggcg ctaaaaagca cgccaacacg cccacgtctt taatgcaata  39720
ttccaatttg aacggcagtt cctcggacat gtatattgtc acggtgggcg ccaaaggagc  39780
ggctttagca aaatgacaca agtaatcgcc cgcaaaagtg tgcgttacgg tttgctttgc  39840
tttgagaacg gaaaagtttt cgttgtccgc gctcatctgc acgtccgccg agccaatgtc  39900
gccatttgct ctaaactgca gacccttctt ggaacacgac acaataatat cgtggtcgaa  39960
ttgcgtcatg tctttgcaca cctgcgcaaa ctcgacgctc gacatgtgga cgacgcaatc  40020
gtaatcgcta tccggaattc ccaaatgttc cacgtcgatg cacatcaact tgagcgtgta  40080
cgtgcagatt ctattgtcgt tgttgaacac gaacgccatc acatcgccct gatcttccgc  40140
tttcatcagt acagagctgc gctcgttaac gcatttgaca attttactta aactgtttat  40200
ggacacgttg agcggcacgt tgcggtcaca tctatatttt ttgaaaccct cggcgtgtag  40260
ttgcaacgac acgagcgcga catgcgaggt gtccataacc tgcatgctta cgcctcgatt  40320
atcacaatca aaagtagcgt gcggcagcag atccttaaaa gtttccacca gcctcttcaa  40380
aactgcgccg gttttaaatt ccgcttcgaa catttttagc agtgattcta attgcagctg  40440
ctctttgata caactaattt tacgacgacg atgcgagctt ttattcaacc gagcgtgcat  40500
gtttgcaatc gtgcaagcgt tatcaatttt tcattatcgt attgttgcac atcaacaggc  40560
tggacaccac gttgaactcg ccgcagtttt gcggcaagtt ggacccgccg cgcatccaat  40620
gcaaactttc cgacattctg ttgcctacga acgattgatt ctttgtccat tgatcgaagc  40680
gagtgccttc gactttttcg tgtccagtgt ggcttgtttt aataaattct ttgaaaatat  40740
tgtcgggtgt attattaaat agcatgtatg gtatgttgaa gatgggataa cgcttggcgt  40800
gcgggtcgtc atgatttcca ccgcgcacca catatttgcg ctcaatttta tcaaaattgg  40860
actggcgaga caaaaacgag acgggcgaca ggcatatttg ggcgtgcgta ccatcttcgg  40920
ccatccactc ggtcaggtct tcgctgcggt taaacacacc tttctgaccg tgaatgccac  40980
atatttttat tccttccaaa tcgttggtgg acgtgactat gactatttta agcataacgt  41040
tgtcgccgtt aaccaccatg ctggcgtcga gtttttcaat tttttgattt ttaatttgtc  41100
taaagtaaac gtacactttg taaacgttaa aattgccgtt ggtgcacgtt tcaattttgt  41160
accgtcggcc gtcgtacacc caattaatct ttgcgttgct caccaacaca ccggccatgt  41220
acagcacaag tccgtcgtct agcgcaacgt aatttttgtc gctactattc gtaaacttta  41280
ctaaacacga ctgcttgggg ccgaccacaa gcttgccctt caatttgttc actttgttgt  41340
tgtataaaca aatgggcagc gcaatgtgcg gaatgtacgg atcttcggcg gtcatgagtt  41400
```

```
tattgtctcg caccaacgtc cacaatttaa acattttatt gttgagcaaa atggacttgt  41460
ttaccgccac agagtagcca tttggtaaac ccgatacgca attttcctct ttgtactcaa  41520
acacgggcat ggcattcttt agattggtta gggacacaat caatttgggt acgggcgtgg  41580
tatgaaataa atgtataaaa ttacgataat aatactgctc caacttggac atgagcgatt  41640
tgacgtcatc gttttctacg atcgtacact gaataatggg attatagtat atagaatgtt  41700
tatagtggta ttcgtagggt gtcaacaata cgttaatgtc ggcttcgttg ttcacccgca  41760
actttttttt gatgcatatc attccttcgt gatgattaac gtaaagtatt ctgtctgtaa  41820
tcttcaattc gatgggcgcc atgtttcttt tcatagtgta cacgataaac gacgtgtttg  41880
atttaaaaca ttttaaattt gtgggtctat cattaaacgc gatcagcaac gagtcgtctt  41940
gaacgtcgtt gaggtcgtcc acgaacgcga ccagattgtg ttttagcaaa tattgaaatt  42000
tttgcgcaac catttcgtag tccacgttgg gcaaacatgc gttgcggcaa aggaaaaact  42060
ttttgcccgc cacggtcatt tcgccgtgaa aaaaactgcc aataaatttc acaaaatcct  42120
ttttttgctt caacattttc tggcgcatgc tgtcgttggt gattcgcgcc acctcgttgc  42180
cgacgcgata ttttaacacg ggcaacgaaa tttcaatatt gttattgctg ctgttgtcct  42240
gttgattggg aaagactttg cgttgcttgc taaaagtttt cgatacgcaa tatatgagac  42300
gcccgttgac tatacaatcg acaatctttt tcgactcttt gttgtacaag acgctttgaa  42360
ttttacgacg cttgttcgcc accgtgtacg cgtcgtcgtc ggccgtcttg tcgagaactc  42420
gttgatagtt ttgcaaaatt gtcgaagtta ataacagttc tatcaaatag gcgtgcttgt  42480
atacaatttt gttggccaaa ctgtctatag aatagtttat gtcgtgattc ataataattt  42540
ttatgtgttc cacgagttgt tgcttgtgaa gcgtgttgta ttcgaagaga aaatcgagcg  42600
gtttccattt gccgctgttg gccagatatg tttccagcac agaatttaaa tcttccgtca  42660
ctacgtaatc gctagcgtac acgtctcgag caaacaggac gtcgtcttgt ttgtcgtaaa  42720
ctagttggat tgcgcgattg atgtgcttct cttgatccac gttgccgtac aaaaacatgc  42780
gtttgcaatg tttggcgtat agcttgtcgt agaaattgtg caccaaaacg ttgttgttca  42840
tcattatgtt gggaaaactc aaaaatctgc cgtccagcat aaaagttccg ttaatattgt  42900
tgtttgcgtc gacatcgtcc gtttctctaa attgcttgtc taagcgcgtg ccgaatataa  42960
cgggcacaca tttatgcatt acgcaactga gctgttcatt aagagcgcaa cacaaataag  43020
acttgcgttc ttgaatagcg caaaaaagca tacgttcatt gctgtttgta gcgcaatcaa  43080
aagtatattt taatttgtat ttattttcaa ttctatcgta caactcgttg aaatcttgaa  43140
ccacgtccgt catcgtgaag cgattactgc gcactaatta tgtctaaacg tgttcgtgaa  43200
cggtcggttg tttcggatga aacggccaaa cgcattcgac aaaacgaaca ctgtcatgcc  43260
aaaaatgaat ctttttgggg gttttgcaac ttggaagaaa ttgattatta tcaatgttta  43320
aaaatgcaat acgttccgga ccaaaagttt gacaacgatt ttattttaac agtgtacaga  43380
atggccaacg tggtgacgaa acaagttaga ccgtataaca gtatcgacga aaagcaccat  43440
tacaacacgg tgcgtaacgt gttgatttta ataaaaaatg cgcgtttagt gcttagtaat  43500
agtgtcaaaa agcaatacta tgacgatgtg ttaaaattga aaaaaaatac agacttggaa  43560
tcgtacgatc cattgattac ggtctttttta caaattggcg aatctgtaaa tgaagaaata  43620
caaaaactca gaaaagcttt ggtcaatatt tttactaata aacccgacaa gtcggatata  43680
aacaacccag atgtagtttc gtatcaattt atttttggca gagtacaaaa attgtataac  43740
```

```
agggcaatta aacaaaaaac taaaactata attgtaaaac gtcctacaac tatgaacaga  43800
attcaaatag attggaaaac tctttccgaa gacgaacaaa aaatgactag acaagaaatt  43860
gccgaaaaaa ttgtaaagcc ttgttttgag caatttggca ctatattaca catatacgta  43920
tgtcctttaa aacacaaccg aattattgtc gagtatgcaa actcagagtc ggtacaaaaa  43980
gccatgactg taaatgacga cactcgattt acagttacag agttttccgt ggttcagtac  44040
tacaacgtgg ccaaaacaga aatggtgaac cagcgaattg acataataag caaggacatt  44100
gaggatttaa gaaacgcttt aaaatcttac acataaatta aaatatcgaa caaaggaaaa  44160
aaacaattgt aacaaaaata atttacatta aaatttacaa gttttttct agtgtcgtac  44220
ttttttacaa tgcgtctgtt gtccgtcgag cattgcaaac atattgtgga cggcgcaaaa  44280
tagcaaacaa aaggcacgtc cgcgctctcc cacgctattc taaaacgatg aatccatatt  44340
aatttttcat tgtcgccaaa cgtcgctccg ctgcctcctt ccaataacaa atactcagaa  44400
acacaaacat gtacaattgc tgtcgcggcg ttaattgtcg ctgtttttcc aaatagtcta  44460
ttatgggaaa caaacacttg tcacaacaca aatactcgtt aattgtcaca accgacaagc  44520
acatttggca aaatgcgtcg caatttttgt acggacgaga ttctatgcga agttcgttgt  44580
ccatgacgtc ttgggtccac tttttcaaca agacactttt atatttgtga tttgtacaac  44640
tttggtacgt gttagagtgt ttttgataag ctttgataag tttaaaactg ttggagtaag  44700
gccacgtcat tatgttctgc accttttgtt taaaagacag aaattactat atgttcaaac  44760
tatttaaaga ttattggcca acgtgcacga cagaatgcca gatatgtctt gagaaaattg  44820
acgataacgg gggcatagtg gcaatgcccg acactggcat gttaaacttg gaaaagatgt  44880
ttcacgaaca atgtattcag cgttggcgtc gcgaacatac tcgagatccc tttaatcgtg  44940
ttataaaata ttattttaac tttcccccaa aaacactaga ggagtgcaac gtgatgcttc  45000
gagaaactaa agggtctata ggcgatcacg aaattgatcg cgtttacaaa cgcgtttatc  45060
aacgcgttac acaggaagac gccctggaca ttgaactcga ttttaggcat ttttttaaaa  45120
tgcaatcatg acgaacgtat ggttcgcgac ggacgtcaac ctgatcaatt gtgtactgaa  45180
agataattta tttttgatag ataataatta cattatttta aatgtgttcg accaagaaac  45240
cgatcaagtt agacctctgt gcctcggtga aattaacgcc cttcaaaccg atgcggccgc  45300
ccaagccgat gcaatgctgg atacatcctc gacgagcgaa ttgcaaagta acgcgtccac  45360
gtaacaatta ttcagatccc gataacgaaa acgacatgtt gcacatgacc gtgttaaaca  45420
gcgtgttttt gaacgagcac gcgaaattgt attatcggca cttgttgcgc aacgatcaag  45480
ccgaggcgag aaaaacaatt ctcaacgccg acagcgtgta cgagtgcatg ttaattagac  45540
caattcgtac ggaacatttt agaagcgtcg acgaggctgg cgaacacaac atgagcgttt  45600
taaagatcat catcgatgcg gtcatcaagt acattggcaa actggccgac gacgagtaca  45660
ttttgatagc ggaccgcatg tatgtcgatt taatctattc cgaatttagg gccattattt  45720
tgcctcaaag cgcgtacatt atcaaaggag attacgcaga aagcgatagt gaaagcgggc  45780
aaagtgtcga cgtttgtaat gaactcgaat atccttggaa attaattacg gcgaacaatt  45840
gtattgtttc tacggacgag tcacgtcagt cgcaatacat ttatcgcact tttcttttgt  45900
acaatacagt cttgaccgca attcttaaac aaaacaatcc attcgacgta attgccgaaa  45960
atacttctat ttcaattata gtcaggaatt tgggcagctg tccaaacaat aaagatcggg  46020
taaagtgctg cgatcttaat tacggcggcg tcccgccggg acatgtcatg tgcccgccgc  46080
gtgagatcac caaaaaattt tttcattacg caaagtgggt tcgaaatccc aacaagtaca  46140
```

```
aacgatacag cgagttaatc gcgcgccaat cagaaaccgg cggcggatct gcgagtttac  46200
gcgaaaacgt aaacaaccag ctacacgctc gagatgtgtc tcaattacat ttattggatt  46260
gggaaaactt tatgggtgaa ttcagcagtt attttggtct gcacgcacac aacgtgtagc  46320
atcgccagta tttaacagct gacctatttg ttaaacaagc attcttatct caataattgg  46380
tccgacgtgg tgacaattgt atccacaatc atgaaaaaag tagcgcttgg aaaaattatc  46440
gaaaacacag tagaaagcaa atataaaagc aacagtgtgt cgtcgtcatt gtcaacgggc  46500
gccagtgcaa aattgagttt aagcgaatat tacaaaactt ttgaagcaaa taaagtgggc  46560
cagcacacta cgtacgacgt ggtcggcaag cgagattaca cgaaatttga caaattggtg  46620
aaaaaatatt gacatgctgc gatcaatcat gcgacgtttc aagagtacaa acaatctcag  46680
caaaaaaccc tccgattatt atgtagtgtt atgtccaaag tgttattttg tgacgtcggc  46740
cgaagtgagc gtggctgaat acatagaaat gcataaaaat tttaacacga aattcgccga  46800
tcggtgccct aacgatttta ttgtgaccaa ctctaaaagt tggaataatc atgaaaattg  46860
ttctgcccta ttttaccctc tgtgttaata aagtttgttg tttgtatttt gtggttttat  46920
ttatttacgc tagatattgg gtttaaggtt cttagaaata gagttgtatt ttccctacca  46980
aaagggattt gagcttcata taaatacaat attcgctcga caagcggttt atttcactcg  47040
gaggtattat atcaggcagt cgaacgtgcg cgatgaaaca tcccgtttac gctagatatt  47100
tggagtttga tgatgtagtg ttagatttga ctagtttaat atttttagag tttgataacg  47160
ctcaaaatga agagtacatt atttttatga atgtaaaaaa ggcgttttac aaaaactttc  47220
acattacttg tgatctgtcg cttgaaacgc tgaccgtgtt ggtgtacgaa aaagctcgcc  47280
taattgtgaa acaaatggag tttgagcagc cgccaaactt tgttaatttt atcagtttca  47340
acgcgaccga caacgacaac tccatgataa tagacttgtg ttccgacgcg cgcataatcg  47400
tggccaagaa gctgacgccc gacgaaacgt atcatcagcg cgtgtccgga tttttggatt  47460
ttcaaaaacg taactgcata cctcggcccc caatcgagtc ggacccaaaa gtgcgagacg  47520
ccttggatcg tgaactagaa ataaaactat acaagtagaa aaaaattaat ttattaatag  47580
ttgtaataat tatcttcgtc ctcatcttcg ctggtgtcat aatgcggtgg tgtgtttgtg  47640
ttttgtttta atcgtttgcg cgtcgacacc acttcgccga taggaaattt tttggatttc  47700
gcattaaatg ccctcttagc gacgcgccgt ttacgactac taaacatgtt gacgcgctcg  47760
tcgtcttcag tgtcataatc cgtgctagtg ttttcgttgt tattttctat gagacgatcg  47820
tttgatttag ttttcgtaga attgtccgcg ttatcgtcgc tttcgtcgat gtcgtcccta  47880
actatctcgt aggcggcttt gcgcggaatc caagattttg caatgtatct attttaacgt  47940
acttttcttc gagcgctttt ctagctttat gcatagcaat gtcttcgtcg ccgccgttca  48000
ttttatgata ctttgtaaac gtctcgacga ataacttttt ggcgcgagga ggcatttttt  48060
cattgtataa catatcggga atttgataca ttgtaattag aattaagcaa gttcgtcttc  48120
ggttgtactg tattcggttt ctgtatctgt agtggaatcc tctgtactag tagtagtgtc  48180
gctattgttg gcgtcaggcc ttggctgcca tttaccgtct atcaacatgt attttttcct  48240
aacagcacaa catgctagct tggtagctat ctgtgtcgac ttatattttt gtaaactacg  48300
atcgtagaat ttttcaaata tcctcttacc gttataggga aggttttgat aatatttagg  48360
caacatatca ataaaagaca atataaaaac tttgtgtttg tgttttattt atcacataaa  48420
atggacgtct ggcaagaatc acaaccaata ttagtgtttt ttttcttaca ttacgagatt  48480
```

```
caacttgata ctaaaattaa ttattaatta aattaaatta aattttgaag catttttttcg  48540
ctatcgtttt cagactcaaa attatcgacg ctatcgctat gaaaagcgta atatttgttg  48600
gctttgagat attctatatt ttgctcattt ttaacaataa acacgcgact cttttcgtcg  48660
cgtctcacca taacaccgtt tttacaaatg gaaatgtatt tgtaaaacgg caacagagcg  48720
tcgcgagttt ttttaagtaa cagcttttgc tccgctgtgg cggccacaaa tatttttacg  48780
ggcccgtcgt aattaatgtt taaattaaaa tttttaagtc gacgctcgcg cgacttggtt  48840
tgccattctt tagcgcgcgt cgcgtcacac agcttggcca caatgtggtt tttgtcaaac  48900
gaagattcta tgacgtgttt aaagtttagg tcgagtaaag cgcaaatctt ttttaaataa  48960
tagtttctaa tttttttatt attcagcctg ctgtcgtgaa taccgtatat ctcaacgctg  49020
tctgtgagat tgtcgtattc tagccttttt agtttttcgc tcatcgactt gatattgtcc  49080
gacacatttt cgtcgatttg cgttttgatc aacgacttga gcagagacac gttaatcaac  49140
tgttcaaatt gatccatatt aactatatca acccgatgcg tatatggtgc gtaaaatata  49200
ttttttaacc ctcttatact ttgcactctg cgttaatacg cgttcgtgta cagacgtaat  49260
catgttttct tttttggata aaactcctac tgagtttgac ctcatattag accctcacaa  49320
gttgcaaaac gtggcatttt ttaccaatga agaatttaaa gttattttaa aaaatttcat  49380
cacagattta aagaagaacc aaaaattaaa ttatttcaac agtttaatcg accaattaat  49440
caacgtgtac acagacgcgt cggtgaaaaa cacgcagccc gacgtgttgg ctaaaattat  49500
caaatcaact tgtgttatag tcacagattt gccgtccaac gtgtttctca aaaagttgaa  49560
gaccaacaag tttacagaca ctattaatta tttaattttg ccccacttta ttttgtggga  49620
tcacaatttt gttatatttt taaacaaagc tttcaattct aaacatgaaa acgatctggt  49680
tgacatttcg ggcgctctgc agaaaatcaa acttacacac ggtgtcatca aagatcagtt  49740
gcagagcaaa aacgggtacg cggtccaata cttgtacgcg acgtttctca acacggcctc  49800
gttctacgcc aacgtgcaat gtttaaatgg tgtcaacgaa attatgccgc cgcggagcag  49860
cgtaaagcgc tattatggac gtgatgtgga caacgtgcgt gcatggacca cgcgtcatcc  49920
caacattagc cagctgagta cgcaagtctc ggacgtccac attaacgagt catctaccga  49980
ctggaatgta aaagtgggtc tgggaatatt tcccggcgct aacacagact gcgacggtga  50040
caaaaaaatt attacatttt tacccaaacc taattcccta atcgactcgg aatgcctttt  50100
gtacggcgac cctcggttta atttcatttg ctttgacaaa aaccgtttgt cgtttgtgtc  50160
acaacaaatt tattatttgt acaaaaatat tgacgcaatg gaggcgttgt ttaaatctac  50220
accattggtt tacgcgctgt ggcaaaaaca taaacatgag cagtttgcac agaggctaga  50280
gatgttgttg cgtgattttt gcttaattgc cagttcaaac gctagttatt tactttttaa  50340
acagcttaca cagctcatag ctaacgaaga aatggtgtgc ggagatgaag aaatattcaa  50400
tttaggcggc caatttgtag acatgattaa aagcggtgct aaaggcagtc aaaatctgat  50460
taaaagcacg caacaatacc gacagacttt aaatacagat attgaaactg tgtcttcacg  50520
agccaccacc agtttaaata gttacatatc ttctcacaat aaggtaaaag tgtgtggcgc  50580
cgacatatat cataacacgg ttgtgttaca gagcgtgttt attaaaaata actatgtttg  50640
ttacaaaaac gacgaacgta caatcatgaa tatttgcgct ttgccctctg agtttctgtt  50700
tccagaacat ttgctcgaca tgttcattga atgataatat aaatagagcg catttgattg  50760
catgcaatca gtgttttatt aattttagag caacatgtac gataaattta tgatctatct  50820
tcacttgaat gggctgcacg gagaagcaaa atactacaaa tatttaatgt ctcaaatgga  50880
```

```
ttttgaaaat caagtagccg atgaaatcaa gcggttttgt gaaactcgtc tgaaaccggc  50940
aatcagttgc aacactttaa ctgcggaaag tctcaatacg ctcgtagaca gcgtagtctg  51000
caaaaatgga ctgttaaatc cttacgccaa agaagtacag tttgctttgc aatatctttt  51060
tgacgatgac gaaatatcca aacgagatca agatggcttt aaactatttt tattacataa  51120
ttatgacagg tgtgaaaata tggaagaata ttttttaatt aacaatttta gcatagcaga  51180
ctacgaattt gaagacatgt ttgaaattgt tcgtattgat tgtagagatc tgttattact  51240
tcttgctaaa tataatatgt aattaaaatt ttgtttgttt tattaaaatc ctggattaaa  51300
aaatgacgaa taatttgatt tgcgtgcacg ccaacaagat tcttcgtcat tatgatcaat  51360
gcgtgcatca agtttatgct tttgtaattg gcttctgacc actttagcca tttgagcgta  51420
tctgcattcg tcgtctagag tttcaaacac cagatcggcg caattataaa atccttcacc  51480
cacgggatct atgcgctgcc aacgcacata cattacaaat tgatttgacc tgtacggtat  51540
tactacgggt atagaataga ctagactgtt gtcacataat gaatcgcccg gatttggaat  51600
taaatttgaa tcgttaccac ctatgtattc taattcgttc caagttattg gattgcgacg  51660
atcccagttt gatttagtaa taaacacttc aaaataactg ggctcgtgta tggctgttgg  51720
acaaaaatga acattcatct gataaaccgg ttgatagcga tttaaatata gcgtatttgg  51780
cctccagttg ttaaaaggtt cgtccattcc gcttttatca ccaaacacag aattgcgatc  51840
gtttgaaccg gcaccgcaaa gtgtgtgcgg cacaaccctt tgtttgatta ggtcaaaatc  51900
gtcataatta ggaccggcca cagccgcgta ttccatatac tgttgaaaca tgtattgcgc  51960
tgtggaagcg gccgccccgg attctaaatc gagagctcga tatttataat agactgattt  52020
gtaagcattg cggcacgcgg cgtcgggaat gttatcgcca ttgtcgggcc aataaaagtt  52080
tccatcttta aaacatttat attgacgggc cgtcggcacg gacaaatagc cgtgagagcg  52140
cactgccggc gcgtgaatcg cagcaaacaa tgcaattaat aatgcaatca ttatgattat  52200
acttatagaa cactaatcgg aataataacc gctgtcgtaa tcttggtcaa aaacgttatg  52260
ttgaaacata ataacacctt acagtaacat acaataaaac aacatagtat cgtatataat  52320
tataaacttt attttttcat tttatacaaa caaaatttat acgtattgtt agcacattga  52380
gtgtcatttt cgctgtctga actatcacaa tcatcgtcat catcatcatc attgtcatcg  52440
tcgtcgtcac gtttgcgttt gacactgcat tttttttggt taattttcac taacactggt  52500
tcttttcgat cgtacaattg attctgcatg tacttttgca tgatcgcggt aaaacacttt  52560
gcaattttat ccttttgttc gtcgccaaat atttccagca actcgttcat aaatgtgcac  52620
aaaatgccca tgtgttttat ccagctgatt cgcattttca ctggatcgaa caaacgcaag  52680
gggtacgctt tttctgttac cttgccttcg atgtctatca aaaggtacgg gatacgatct  52740
ccgttgccgg gcacaaaatc cgtgcctttg ttaaccaaaa tttctctaca atgcctagcc  52800
accgtaatca cgcgtctttt gggtgacgga ccctcattat cgtcagttga tttgcgtttt  52860
ttgcccgggt tatcgttata ggtcatacta aagctgtagt cggtcaacga ttttgatttg  52920
gcaaactcat catagtattc ataaaaacta gtctgtaaac tttgcaaaca tttgtccatg  52980
tccaaatgac gcaatatttg ttccactgcc gtcctaaacg cgattctcat aaaaacgggc  53040
atatcctttt taactaacca acccttgtat acgattttat tctcactgtt gagatagcaa  53100
tattttttct tttttaatag tattaaaact ttcattaaat tttcaaatgc cattttgtaa  53160
ccgtccgtga atgagttatt aacgcgtgtc tcaacatgtg tgcatatttg ttttaatgtg  53220
```

-continued

```
tcggtttcgt tggatatttc gttatagtta aatgtgggca aaacaaatgt agaatctgtg  53280
tcgccgtaca caactttaaa agtgatgctg cccagattga atttttctaa aatctcaggg  53340
tcgttgctca aaccttcaat cagagaaatg gccagccgca actgattgcg accaactcta  53400
gtgatgtagt ttgcaagcac tttgtaaaaa atgccataat aaccgtatat gctattggcg  53460
gtgcgcttca cggaattttg tttttgatcg tacagatcgt acaagaatgc cgattcgctt  53520
tgattgtcgc gattcttttt aaatttgcac ctttcgctta acaattttaa tagcaattta  53580
acaactattg cacgcgaatt gtggttcaaa tacacgttgc cgtcttcgca taaaattaaa  53640
ttggacaaac aagcacaaat ggctatcatt atagtcaagt acaaagaatt aaaatcgaga  53700
gaaaacgcgt tcttgtaaat gcctgcacga ggttttaaca ctttgccgcc tttgtacttg  53760
accgtttgat tggcgggtcc caaattgatg gcatctttag gtatgttttt tagaggtatc  53820
aattttcttt tgagattaga aatacccgct gcggctttgt cggctttgaa ttggcccgat  53880
attattgaca gatcgttttt gttaaaaaaa tacgggtcag gctcctcttt gccggtgctc  53940
tcgttaatgc gcgtgtttgt gatggctgcg taaaagcacg ccacgctaat caaatgcgaa  54000
atattacata tcacgtcgtc tgtacacaaa cgatgcaata tacattgcga atatacagaa  54060
tcggccattt tcaatttgac aaacaatttt atcggcaaca tgcaatcctg cacgttgtac  54120
ttggcaatca cgtccagccg tcgagtgttg tacatcttga ccatttcggt ccaaggcaaa  54180
tcgattttgt tttcacccaa atagtaacta ctgattgtgt tcaattgaaa gttttcaact  54240
ttatgctgat tagaatcgct gctgaaaaat ttatacaaat caatgtgaat gtaatagtta  54300
aaataatacg tgtccacttt gttgcccaac ttgtttataa acagctttgt cgtcggcgcc  54360
gcagccggca aatcgtaacg ctttaatagc attttggttt tattcaatcg tccaagtata  54420
tagggcagat caaatacgtc tccgttaaaa tccaaaatca catcgggatt tgtaattttt  54480
atcatgtcaa aaaacgctgt aatcatgtcg atttcatttt gaaacatgac cacatacgtg  54540
tcatcgtcat aggtctctgg aatctgggtc ggcagcttgt gatacataaa acaaaatttt  54600
gcatactcgt cgtttttgta caccacaaat cctatagaca ttatgcaatc aaccgatgct  54660
ttcgacatgt tgtggccgtc cgaatgagtc tcaatgtcat agcacgacaa aacgggcatg  54720
atgccgctgg ttaaagtcat ttcatcgacc aactcaaagt cttcattaaa atgttgcaaa  54780
ttaaacatgc gcgtcgtcga tccaccgaca tagttatttt ggcagcgttg tgttttcttg  54840
aatcgcatat aggcgccttc cacaaacggc gtttgcatgt gtacgcgatt aacgttgtga  54900
agaaacttgt ccaaacacgc cgcgttgtcc gatggcgctg ctttgtttct ttcgtattta  54960
atcacgttta tcttgttcaa ataatttcct tccacgcccg gcgccacaaa cgtggtgtag  55020
ctgatgcact tgttgcggca agacggaaat atgtgcttgt cgtagcattg tttgtaagaa  55080
tacaaattta gttttacttt aaagtaaaac tgcagcactc gttctttgat atttgtatta  55140
caaaatgcaa acaagcaacc ttgtttttca tcgtaatgca aacgaatgat acgaaacgta  55200
tcggctgaag taatattgaa ttctcctggt tttgcatatt ctgcaaagcg cgttttgagt  55260
tcattgtaag gatatatttt catttttaaa tatgcagcga tggcccaaat atggaggcac  55320
agacgtcaac acgcgcactg tacacgattt gttaaacacc ataaacacca tgagtgctcg  55380
aatcaaaact ctggagcggt atgagcacgc tttgcgagag attcacaaag tcgttgtaat  55440
tttgaaaccg tccgcgaaca cacatagctt tgaacccgac gctctgccgg cgttgattat  55500
gcaattttta tcggatttcg ccggccgaga tatcaacacg ttgacgcaca acatcaacta  55560
caagtacgat tacaattatc cgccggcgcc cgtgcccgcg atgcaaccac cgccaccgcc  55620
```

```
tcctcaaccc cccgcgccac ctcaaccacc gtattacaac aattatccgt attatccgcc  55680
gtatccgttt tcgacaccgc cgccaacaca gccgccagaa tcgaacgtcg cgggcgtcgg  55740
cggctcgcaa agtttgaatc aaatcacgtt gactaacgag gaggagtctg aactggcggc  55800
tttatttaaa aacatgcaaa cgaacatgac ttgggaactt gttcaaaatt tcgttgaagt  55860
gttaatcagg atcgtacgcg tgcacgtagt aaacaacgtg accatgatta acgttatatc  55920
gtctataact tccgttcgaa cattaattga ttacaatttt acagaattta ttagatgcgt  55980
ataccaaaaa acaaacatac gttttgcaat agatcagtat ctgtgcacta acatagttac  56040
gtttatagat ttttttacta gagtctttta tttggtgatg cgaacaaatt ttcagttcac  56100
cacttttgac caattgaccc aatactctaa cgaactttac acaagaattc aaacgagcat  56160
acttcaaagc gcggctcctc tttctcctcc gaccgtggaa acggtcaaca gcgatatcgt  56220
catttcaaat ttgcaagaac aattaaaaag agaacgcgct ttgatgcaac aaatcagcga  56280
gcaacataga attgcaaacg aaagagtgga aactctgcaa tcgcaatacg acgagttgga  56340
tttaaagtat aaagagatat ttgaagacaa aagtgaattc gcacaacaaa aaagtgaaaa  56400
cgtgcgaaaa attaaacaat tagagagatc caacaaagaa ctcaacgaca ccgtacagaa  56460
attgagagat gaaaatgccg aaagattgtc tgaaatacaa ttgcaaaaag gcgatttgga  56520
cgaatataaa aacatgaatc gccagttgaa cgaggacatt tataaactca aaagaagaat  56580
agaatcgaca tttgataaag attacgtcga aaccttgaac gataaaattg aatcgttgga  56640
aaagcaattg gatgataaac aaaatttaaa ccgggaacta agaagcagca tttcaaaaat  56700
agacgaaact acacagaggt acaaacttga cgccaaagat attatggaac tcaaacagtc  56760
ggtatcgatt aaagatcaag aaattgccat gaaaaacgct caatatttag aattgagtgc  56820
tatatatcaa caaactgtaa atgaattaac tgcaactaaa aatgaattgt ctcaagtcgc  56880
gacaaccaat caaagtttat ttgcagaaaa tgaagaatct aaagtgcttt tagaaggcac  56940
gttggcgttt atagatagct tttatcaaat aattatgcag attgaaaaac ctgattacgt  57000
gccgatttct aaaccacagc ttacagcaca agaaagtata tatcaaacgg attatatcaa  57060
agattggttg caaaaattga ggtctaaact gtcaaacgcc gacgttgcca atttgcaatc  57120
agtttccgaa ttgagtgatt taaaaagtca aataatttct attgtaccac gaaatattgt  57180
aaatcgaatt ttaaaagaaa attataaagt aaaagtagaa aatgtcaatg cagaattact  57240
ggaaagtgtt gctgtcacaa gtgctgtaag cgctttagta cagcaatatg aacgatcaga  57300
aaagcaaaac gttaaactta gacaagaatt cgaaataaaa ttaaacgatt tacaaagatt  57360
attggagcaa aatcagactg attttgagtc aatatcagag tttatctcac gagatccggc  57420
tttcaacaga aatttaaatg acgagcgatt ccaaaacttg aggcaacaat acgacgaaat  57480
gtctagtaaa tattcagcct tggaaacgac taaaattaaa gagatggagt ctattgcaga  57540
tcaggctgtc aaatctgaaa tgagtaaatt aaacacacaa ctagatgaat taaactcttt  57600
atttgttaaa tataatcgta aagctcaaga catatttgag tggaaaacta gcatgcttaa  57660
aaggtacgaa acgttggcgc gaacaacagc ggccagcgtt caaccaaacg tcgaatagaa  57720
ttacaaaaat ttatattcat tttcatcttc gtcatacttc aacagtccca acacgttcat  57780
gttgtgattc tcgccgttct cgacagttac gtaaatagtt actttgatta aattatcttc  57840
cagcagcatt gagatttgat tgaaatccgc acatagcttt tgtagcgaat ccgcttcggt  57900
ttttttattt gtgttgacgt agaaaacaga tttgttccat ttgcccaagt cggaagaggt  57960
```

```
agaacagtca tccgaatcgg caatgttcaa ctcgtcgctt ttaaactgca caataaactt  58020
gttatcgccc atgtcatttt cttccaattc gctttttaac acatttacat tgtacgaagc  58080
aacgtgtttg ttcgatcgac taatgttgat ctttgcgttt gtgcaatttt gcaaatttga  58140
atatgcttcg ctttctttag cctcgcacaa ttcgatgcgc gtagagttga ccacgttcca  58200
attcatgtac acgtttgatc cattaaaaat ttgttgacac tttatactgt aaatggtaaa  58260
gatttggttt tcattgtctt ttaaatattt aaacacctca ttgatgtcgt cagacccctt  58320
tatattgttc ttgaatagat ttattagtgt tttcgcattg acagaacatt ccacttgaac  58380
cacgtcggga tcgtcgttga gatttttgta cacaacctca aaaacaactt tgtacaaacc  58440
gctgttgatt ttcttgtaga taaatttgta ctttacaata atattgacgc catcttcatt  58500
ttcaaaatgt ttgttagtca aatagtcgct catgggggtt gcagtttcaa tttccatttc  58560
acattctttg tattcgttga tctgaatcat ttgactaaac tttgttttca cataatttaa  58620
actaatgtca tagcacttgc cttcttccat gtctttgaaa gattgcgaat cgccgtagta  58680
ttcttgaatt ttgttgtcgg acattattcg aaaagtgtaa tggtattcat tatcgatact  58740
caacgtcatt ttgctcatca atttaccact aatccttttg taattttctc taatcttctt  58800
ggggctactg gccatagcca tgcgttttat aagcggctca ccgctacttt ctccagacaa  58860
agatcttttg gtcgccatat tgctgttgtc gatatgtggg aatctatccg atggcaaata  58920
ctgaatggcg acgaaatcga agtgtcgcca gagcaccgtt cgttagcgtg gagggagttg  58980
attataaacg tggccagcaa cacgccgctc gacaacacgt tcagaacaat gtttcaaaaa  59040
gccgattttg aaaatttcga ctacaacacg ccgattgtgt acaatttaaa aacaaaaact  59100
ttaacaatgt acaacgagag aataagagcg gctctgaaca gacccgtccg atttaacgat  59160
caaacggtca atgttaatat tgcgtacgta tttttgttct ttatttgtat agttttgctg  59220
agcgtgttgg ccgtcttttt cgacacaaac attgcgaccg acacgaagag taaaaatgtt  59280
gcagcaaaaa ttaaataaac tcaaagatgg tttgaacacg ttcagcagca agtcggtggt  59340
ttgcgctcgc tcaaaattat ttgacaaacg cccaacgcgc agacctagat gttggcgaaa  59400
actatcagag atcgacaaaa agtttcacgt ttgccgacac gttgacacgt ttttggattt  59460
gtgcggcgga ccgggcgagt ttgccaacta taccatgtcg ttgaacccgc tttgcaaagc  59520
gtatggcgtc acgttgacaa acaactcggt gtgcgtgtac aaaccgacag tgcgcaaacg  59580
caaaaatttc acaaccatta cggggcccga caagtcaggc gacgtgtttg ataaaaatgt  59640
tgtatttgag attagcatca agtgtggcaa cgcgtgcgat ctggtgttgg cagatggctc  59700
ggttgacgtt aatggacgcg aaaacgaaca agaacgtctc aactttgatt tgatcatgtg  59760
cgagacgcag ctaattttaa tttgcctgcg tcccggcggc aattgcgttt taaaagtttt  59820
cgacgcgttt gaacacgaaa cgatccaaat gctaaacaag tttgttaacc atttcgaaaa  59880
atgggtttta tacaaaccgc cttcttctcg gcctgccaat tccgaacgct atttaatttg  59940
tttcaataaa ttagttagac cgtattgtaa caattatgtc aacgagttgg aaaaacagtt  60000
tgaaaaatat tatcgcatac aattaaaaaa cttaaacaag ttgataaact tgttgaaaat  60060
ataacgtgtg tataaaaagc cagcggcttc aaatcaggca tcattcaaca tggattcgct  60120
agccaatttg tgcttgaaaa ccctgcctta caagtttgag ccgcctaagt tttacgaac   60180
aaaatattgc gacgcatgtc gctacagatt tttaccaaaa ttttctgatg aaaaattttg  60240
tggacaatgc atatgcaaca tatgcaacaa tccaaaaaat atagattgtc catcatcata  60300
tatatcgaaa attaaaccga agaaagaaaa caaagaaata tatattacca gcaacaagtt  60360
```

```
taataaaacg tgcaaaaacg aatgtaatca acaatcaaac cggagatgtt taatttccta  60420
ttttacaaat gaaagttgta aagagctcaa ttgttgttgg tttaataaaa actgttacat  60480
gtgtttggaa tataaaaaga atttatacaa tgtaaatttg tatacgattg atggtcattg  60540
tccttcgttt aaagccgttt gtttttcatg tataaaaaga atcaaaacgt gccaagtttg  60600
caatcaacct ttattgaaaa tgtacaaaga gaagcaagaa gagcgtttga agatgcagtc  60660
gctgtacgca acgttggccg atgtagattt aaaaatatta gacatttacg atgtcgacaa  60720
ttattctaga aaaatgatat tgtgtgctca atgtcatata tttgcacgct gtttttgtac  60780
caataccatg caatgttttt gtcctcgaca gggttataag tgtgaatgta tatgccgacg  60840
atctaaatat tttaaaaata atgtattgtg tgttaaaagt aaagcggctt gttttaataa  60900
aatgaaaata aaacgtgttc caaaatggaa gcatagtgta gattatactt tcaaaagtat  60960
atacaagtta ataaatgttt aattttaagg atattgttat ggaataaact ataaaatgaa  61020
tttgatgcaa tttaattttt tgatactttc cacagacggt agattcagaa cgatggcaaa  61080
catgtcgcta gacaatgagt acaaacttga attggccaaa acggggctgt tttctcacaa  61140
taacctgatt aaatgtatag gctgtcgcac gattttggac aagattaacg ccaagcaaat  61200
taaacgacac acgtattcga attattgcat atcgtcaacc aacgcgttga tgttcaatga  61260
atcgatgaga aaaaaatcat ttacgagttt taaaagctct cggcgtcagt ttgcatcaca  61320
atccgtggtc gttgacatgt tggctcgtcg cggcttctat tattttggca aagccggcca  61380
tttgcgttgt tccggatgcc atatagtttt taaatataaa agcgtagacg acgcccaacg  61440
ccggcacaaa caaaattgca agtttctcaa cgcaatagaa gactattccg tcaatgaaca  61500
atttggcaaa ctcgatgttg cggaaaaaga aatactggct gccgatttga ttcctccgcg  61560
gctaagcgtt aaaccttcgg cgccgcccgc cgaaccgcta actcaacagg tctccgaatg  61620
caaagtttgt tttgatagag aaaaatcggt gtgtttcatg ccgtgccgtc acctggctgt  61680
gtgcacggaa tgttcgcgtc ggtgcaagcg ttgttgtgtg tgcaacgcaa aaattatgca  61740
gcgcatcgaa acattacctc agtaaacatt gcaaacgact acgacattct ttaaaaataa  61800
gctatatata aatattgcat tgtatgacaa aaaaattatt aacctactgc aaagtaaaac  61860
ttgtaaaagg cttttcaaaa aaatttgcga gtttattttg tcgctgcgtc gtgtcgcatc  61920
taagcgacga agacgacagc gacggtgatc gctattatca gtataataac aattgtaatt  61980
tcatatacat aaatattgta aaataaaaga catattattg tacataatgt tttattgtaa  62040
ttaaattaat acaccaattt aaacacatgt tgatgttgtt gtgaataatt tttaaatttt  62100
tacttttttc gtcaaacact atggcgttgc tttcgattag ttttttcgtt agcatttcat  62160
ctaaaaaatc aaactgtttg cccggcgcgt ttagggattc tatggtgtag tcgggcgtgt  62220
cgctgtttag atattggtcc acttcgcgca ttatgtccaa gacgttgttc tgcaaatgaa  62280
tgagctttgt caccacgtcc acggacgtgt tcatgtttct tttttgaaaa ctaaattgca  62340
acaattgtac gtgtccacta tacaattcgg cttaatatac tcgtcggcgc aatcgtattt  62400
gcaatccaat ttcgtgttca acaaattggt gatgatatct ttgaacgtgc acgttttcaa  62460
tttgtcctta tcggccaacg caagtttcaa ttcgctctgt aaagtttcta aaattttgtc  62520
tttattgttg tcaaattcgt gcgtgttgcg ttccaaccac aatttgaacg gctcgtcgac  62580
aaaaatgctg cgcaacacct cgtacaactg tctgcctaac gtgtacactt gctcgtattc  62640
tttcatgctg acctctttgc taacgtacat tactaaaaaa tctacaagta ttttcaaaca  62700
```

```
tttgtaatag gcgacgtatt ttgatttaag ttttaaaccg tccaccgtgt attcgtccac  62760
gttcgcatcg accacttttc gattattatc gccgcttgtt gccggcgcgt cggcctgttc  62820
ggttttaact atatccggtt caatatttaa agtttcaaaa gatttaatgg cattcataaa  62880
atcatctttt tgctttggcg tggtcaatgg taaatctatc gaggagttgt cgtccgtgtg  62940
ctcttcgggc acgctgttca gacgtaacgt aatctttttg ggatcgtctt catcgggtat  63000
caaatcggct ttaattttat tagaattgag caacgacatg gtggtcgctt gtaaatttaa  63060
taaattaatt aaagactgaa attgtatatt gcacaaattt attttcattt ttattgatct  63120
tactattaat acgctggcag ttggtatgct tcatccattt ttgtgactag aaaatttgct  63180
aaaaaactga gctcgtcctg tgttaaaacg ttgtcgtcca cgaatctatg caatgtaaat  63240
gttacactga cattgtttaa caatgcatgt attaaaaaat caacctgtcg cctactgagt  63300
ttattagaag agtcgaccgt ttctactagt ttgtagattt tgttattttc aatttcattg  63360
tttaaaaaca tgttaactac tcgtttgagt ttaagcgaaa aatccttgtc cggatagact  63420
tgttcgcaca gccaattgct aagagtggtt ttgaccacgg acaccttggt ggtgaacgtc  63480
gtcgatttga ccagttcggt gaaaaagttt ttcattaaat tggacatttt aacaaacact  63540
tatcaatcta ttgagctggt atttttgttt agaatcgcat caagcgcttg ctcgatctcc  63600
aatttttttc ggacgctctt agctttatga ctcggtatgt cttctacggt agactcggtg  63660
ttcttactta taatggccgg gctgacgata ataaacacga gaaacaatat gagcagatac  63720
aaaaagatgc tgttttcctt tttgtcatac actaggctaa atatggccag tgcgcccaac  63780
aacaaatata aattcatttt tattccctta ctctattcgt tgcgatagta caacaacgat  63840
tctcccgacg aaccggacga attgcgatta tgctgcgcgt cgtcgtcgtc gttgttgttc  63900
tcctcttcgc tgctcgtttc gtctaaacct atattgtatt tgttcaagta atgtttggtg  63960
cttgcggagg attcgtggtt cattaatttg gccacttttt gtaaaggcac gccgctattg  64020
tataggttac tgctcaaata atgtcttatc atgttgctgc gcggccgttc catctcgacg  64080
cccgactctt caaggagtcg cctgaaatct ttgaagggcg tcgaggtgtt tttagatatt  64140
tgcaaaatgg tcgggtttcg tgaataaatc tcgcgtgcca attccaacgg tttcattttg  64200
atgttgttga gtgtgttatt acgactgcgt tttcgcttta aattaatcgt gtcgctgtgc  64260
agttttcctc ttttaattag cacgttgaga tcgtccacgc tgagttggcg cgcttcgttg  64320
attcgcatac ccgtccctaa catgatgcaa aacactatcg cgcccctaat tagaccgcgg  64380
tcgtgaacat aatcgctgtt gagcatttta attttatcat taataaaatt taatatggta  64440
tctattacgt ttttaagcat taaattcttt tccttttccc tgatattttt gagctccttg  64500
tcgcgcggca gcataaccat gcggggaatt ttgtattcgg gcaagttcat catgttggtg  64560
taaaagttta tagtcaactg tagtgtttct ttggtgaccg agcgaagttc gagcatgcgc  64620
ctgcacagtt cttggggatc aatgagaagt gtttggtttt ctatcgagtc aaactccttg  64680
tccaacgagt acgacatgtc ttccaggtga acatcgtcta ccgagcagta cacaatttta  64740
atgaatcgag acttgtaact ttttaaagtg gtgggcgcaa acggtttggg gaacatgtac  64800
ttgctccaca gactgttgtt tttcacctcg tcgggcgtgc atcgttgccg atcggtggcc  64860
aaatcgaaca cggactcgaa ccggggagcg gattgaattt ttattttcca agaattaaaa  64920
ttgttttcgt tgcgaacatt aaaaccgttc attgtggtta atcaaattta ttaaaaacaa  64980
aaggagaatc ggtgtcaata ctatccgaat attgttgttg ttctcttaat attacgaaat  65040
aatatattac atacagcagt aagaataaag ctataaaagc gactacacta attaaaatta  65100
```

```
taattcccgc cgacacgttg ctcgtcgtgt tgtcatagcc caccatgtcg tttattggca  65160
ttttgtgaac gggctcgcta aattgttgcg gttcgctggc agtatcgtcg ttgagcgcca  65220
atttcaacgg gatgtattcc accttttcgt ggttgcccaa ccgatagtag ggcacgtcca  65280
aattcatgtt tacaacttat ttgctaacag gaatttatgc aacaaaagtg gtttggcttt  65340
gatgagacgc aatttgaaat acttgctgca tttacgctta agattgtatt ccatgcgggc  65400
ggcggtgttg tagtcgtacg cgctcgcgct gtgatacacg agccgtaaat tggttgcgtt  65460
gcgcaaacac ttggcgcctt gtttgttcga atgctgtttt atgcgtctgt taagattgct  65520
cgtgatgccc gtgtacaatt ttccattgtc ttgccgcaga atgtacacgc accacacctt  65580
gttggtgtac agagtcgtcg ccatgattat gcagtgcgcc ctttcgtgtt cggccgagtg  65640
gcgttaggcg cagccgcggc aataatcgcg ttggcgtcct tgttgtaatt tatttgttga  65700
aaaataaaac gtcttagagt ttcgttttgg aacgccaatt cggtcaagct ctcctggcaa  65760
gcgcttttgg tcaaatgagc ggccggcgaa ttgaccgcgt tggcggccga cgttaagaag  65820
gtggcgttct ggaacatgct gggctgcttg ccggctcgcg tcgccagctc ggccatgtaa  65880
ttgaatatgt tggcagacgc agatagcggc gccaaaaacg caacgttctc ttttaaactc  65940
atgactcgcg ccctgttttt ttcgttcagc acgtagtggt agtaatcgcc gccgccggca  66000
aacagatcgt caatcacggc gttgatcaga tcgttgatca tgttgatgtg cggaaagcga  66060
cgcgactcga ctgcgctctg tatgtttggc ggcagagtgg cgtgcttgag caacagagtc  66120
atgtaattgt tggccagctg ctgattgaaa ggtaacggaa tgggaatgtt gcacgtcacc  66180
gcttccgcca ccatgtactg gacggccaga ctgagttgtt tggcggcctc ggccaaagcg  66240
tctttgccca acatatcagc gccaccgttg taaaactttt gcgcgtacgc cggcagcgaa  66300
tttagcacaa acgatggctg aaatatattt gaatcgctcg acagggactc ggccgcgttg  66360
ctctgtccca actctttttg caaccgaatc aggtggcgta tcatggtttc ctccgattca  66420
aaccgcttta ccacgtttac gctgattggg ttcgtgtcga tgcacatgtc acgaatagtg  66480
tttataaaaa gaatcatgag aggactaagt tctgacatgt cattgcacct gtaatatcta  66540
ataatctttt gaacaaaatc cacacatttg ttgtaccaaa tagattcacc ggcgtcgagc  66600
gtcggttctt tgctcttgtt gtacggtgca atcgctaccg agtttgtgct gttgctgcgg  66660
ctcgtgtaat ccatcctgtt gtcgcgcgtg gcgacggtcg taggcaccgt cgccggcggc  66720
acgtacccgg gcgcgttgta agtttgcgcg ctggtgaata tggccgttgc cggattagag  66780
ggatacctca gcggcggagg ggtgttgtaa taaaaattgc cacgttcatc tgtcatactt  66840
tttatttgta ctcttatgat tacaaaactc aatatacgga ttacttataa tatagttgtt  66900
gtgacaaaaa agcgataata aaattaacaa aattatcaac aagttaatca tggaaaattt  66960
ttcaacgttg aataacaaca acaaaatggc gcaggtcaac agcaccgttt gaaaactgac  67020
gcgccgacac aaaatgcttt cgcaatttct aaaagccaca ttaaacgaat tttcaccttt  67080
gatataatca cgcagttctt ttttacaaca ttcgtcgcac aaaattaaca cctttataat  67140
gaggccgtcg gtgtgtatcg tttgaaatgt ccgcggttga ctgcctggat gaaattcaaa  67200
cgagtaccca gtggacacgt gtatctgtgc aaaataatgg gctaatatcg aggcgcccgt  67260
ttttttaacc tttacttttg atattttaat aacattaatg ttgttatttg cgtaatcaga  67320
gtttttattg tggtgatcat cgtacaaata atgaagcaac agttcactat cgtatttaat  67380
cttgtttagc gttgtcaagt ttttgtttct taggcgttgg agcgtctccg tcgtcgatat  67440
```

-continued

```
tttcttcgaa atcgagtcca acaacgtcgg cgtttccttc ttgctcatcg atagcggcgg  67500
cggaggcggc ctctccgtcg tcgtcattcg cggtttctac agtgcgtttg ggcgacgacg  67560
tgtgtacagc agcgtccgtc ttactattat cggaccgcca aatttttgtt tgaaataaca  67620
tttggccctt gttcaacttt atttcggcgc agttaaacat tattgcatta agatcatatt  67680
cgccgttttg caccaaattg cacaaaacac catagttgcc gcacgacact gtagaatagg  67740
cgtttttgta caacaatctg agttgcggcg agctagccac cttgataata tgggcgccaa  67800
cgccccgttt ttttaagtaa tattcgtctt caattataaa atctagtacg ttttcatctt  67860
cactgttgat ttgggcgttc acgatgatgt ctggcgtaat gttgctcatg cttgccattt  67920
ttcttataat agcgtttact ttaatgtatt tggcaattta ttttgaattt gacgaaacga  67980
ctttcaccaa gcggctccaa gtgatgactg aatatgtgaa gcgcaccaac gcagacgaac  68040
ccacacccga cgtaataggc tacgtgtcgg atattatgca aaacacttat attgtaacgt  68100
ggttcaacac cgtcgacctt tccacctatc acgaaagcgt gcatgatgac cggattgaaa  68160
tttttgattt cttaaatcaa aaatttcaac ctgttgatcg aatcgtacac gatcgcgtta  68220
gagcaaatga tgaaaatccc aacgagttta ttttgagcgg cgacaaggcc gacgtgacca  68280
tgaaatgccc cgcatatttt aactttgatt acgcacaact aaaatgtgtt cccgtgccgc  68340
cgtgcgacaa caagtctgcc ggtctttatc ccatggacga gcgtttgctg gacacgttgg  68400
tgttgaacca acacttggac aaagattatt ctaccaacgc gcacttgtat catcccacgt  68460
tctatcttag gtgttttgca aacggagcgc acgcagtcga agaatgtcca gataattaca  68520
cgtttgacgc ggaaaccggc cagtgtaaag ttaacgaatt gtgtgaaaac aggccagacg  68580
gctatatact atcatacttt ccctccaatt tgctcgtcaa ccagtttatg cagtgcgtaa  68640
atgggcgcca cgtggtgggc gaatgccccg cgaataaaat atttgatcgc aacttaatgt  68700
cgtgcgtgga agcgcatccg tgcgcgttta acggcgccgg acacacgtac ataacggccg  68760
atatcggcga cacgcaatat ttcaaatgtt tgaataataa cgagtcacaa ctgataacgt  68820
gcatcaaccg gatcagaaac tctgacaacc agtacgagtg ttccggcgac tccagatgca  68880
tagatttacc caacggtacg ggccaacatg tattcaaaca cgttgacgac gatatttcgt  68940
acaacagtgg ccaattggtg tgcgataatt ttgaagttat ttccgacatc gaatgtgatc  69000
aatcaaacgt gtttgaaaac gcgttgttta tggacaaatt tagattaaac atgcaattcc  69060
caactgaggt gtttgacggc accgcgtgcg tgccagccac cgcggacaat gtcaactttt  69120
tacgttccac gtttgccatt gaaaatattc caaaccatta tggcatcgac atgcaaacct  69180
ccatgttggg cacgaccgaa atggttaaac agttggtttc caaagatttg tcgttaaaca  69240
acgacgccat ctttgctcaa tggcttttgt atgcgagaga caaagacgcc atcgggctta  69300
acccgttcac cggcgagcct atcgactgtt ttggagacaa cttgtacgat gtgtttgacg  69360
ctagacgcgc aaacatttgt aacgattcgg gaacgagcgt tttaaaaacg ctcaattttg  69420
gcgatggcga gtttttaaac gtattgagca gcacgctgac cggaaaagat gaggattatc  69480
gccaattttg tgctatatcc tacgaaaacg gccaaaaaat cgtagaaaac gaacattttc  69540
agcgacgtat attgacaaat atactacagt cggacgtttg tgccgaccta tatactacac  69600
tttaccaaaa atatactaca ctaaactcta aatatactac aactccactt caatataacc  69660
acactctcgt aaaacggccc aaaaatatcg aaatatatgg ggcaaataca cgtttaaaaa  69720
acgctacgat tccaaaaaac gctgcaacta ttccgcccgt gtttaatccc tttgaaaacc  69780
agccaaataa caggcaaaac gattctattc taccccctgtt taaccctttt caaacgaccg  69840
```

```
acgccgtatg gtacagcgaa ccaggtggcg acgacgacca ttgggtagtg gcgccgccaa  69900
ccgcaccacc tccaccgccc gagccagaac cagagccaga acccgagcca gaacccgagc  69960
cagagttacc gtcaccgcta atattagaca acaaagattt attttattca tgccactact  70020
cggttccgtt tttcaagcta accagttgtc atgcggaaaa tgacgtcatt attgatgctt  70080
taaacgagtt acgcaacaac gttaaagtgg acgctgattg cgaattggcc aaagacctat  70140
cgcacgtttt gaacgcgtac gcttatgtgg gcaatgggat tggttgtaga tccgcgtacg  70200
acggagatgc gatagtggta aaaaaagaag ccgtgcctag tcacgtgtac gccaacctga  70260
acacgcaatc caacgacggc gtcaaataca accgttggtt gcacgtcaaa aacggccaat  70320
acatggcgtg tcccgaagaa ttgtacgata acaacgaatt taaatgtaac atagaatcgg  70380
ataaattata ctatttggat aatttacaag aagattccat tgtataaaca ttttatgtcg  70440
aaaacaaatg acatcattcc ggatcatgat ttacgcgtag aattctactt gtaaagcaag  70500
ttaaaataag ccgtgtgcaa aaatgacatc agacaaatga catcatctac ctatcatgat  70560
catgttaata atcatgtttt aaaatgacat cagcttatga ctaataattg atcgtgcgtt  70620
acaagtagaa ttctactcgt aaagcgagtt tagttttgaa aaacaaatga gtcatcatta  70680
aacatgttaa taatcgtgta taaaggatga catcatccac taatcgtgcg ttacaagtag  70740
aattctactc gtaaagcgag ttcggttttg aaaaacaaat gacatcattt cttgattgtg  70800
ttttacacgt agaattctac tcgtaaagta tgttcagttt aaaaaacaaa tgacatcatt  70860
ttacagatga catcatttct tgattatgtt ttacaagtag aattctactc gtaaagcaag  70920
tttagtttta aaaaacaaat gacatcatct cttgattatg ttttacaagt agaattctac  70980
tcgtaaagcg agtttagttt tgaaaaacaa atgacatcat ctcttgatta tgttttacaa  71040
gtagaattct actcgtaaag cgagtttagt tttcaaaaac aaatgacatc atcccttgat  71100
catgcgttac aagtagaatt ctactcgtaa agcgagttga atttgatta caaatatttt  71160
gtttatgata gcaagtataa ataaccgcac aaagttaaat ttttttcatt tacttgtcac  71220
catgtttcga atataccta ataacacaac tgtgcccggt tgtttagtgg gtgacattat  71280
tcaagttcgt tataaagatg tatcacatat tcgctttttg tcagattatt tatctttgat  71340
gcctaacgtt gcgattgtaa acgaatatgg acctaacaac cagttagtaa taaaacgcaa  71400
aaacaaatcg ctgaaaagct tgcaagattt gtgtctggac aaaatagccg tttcgctcaa  71460
gaaacctttt cgtcagttaa aatcgttaaa tgctgtttgt ttgatgcgag acattatatt  71520
ttcgctgggt ttaccaatta tttttaatcc ggctttgcta caaagaaaag tgccgcagcg  71580
cagcgtggga tatttcatga attcaaaatt ggaaaggttt gccaattgtg atcggggtca  71640
tgtcgttgaa gagaaacaat tgcagagtaa tttgtatata gattattttt gtatgatttg  71700
tggtttaaat gtttttaaaa taaaagaata acaatttaca cattgtttta ttacatggat  71760
aatgttgttt gtttgacatt aaaggttatc atggtgcaat gattaataat aaaacaatat  71820
tatgacatta ttttcctgtt attttacaat ataaaatcac accaattgtg caaagtttta  71880
ttatttgttt gtcgacggtc gaggggtcag cggcgtgtgc aacaataaaa aacatgaagc  71940
tgttaacaat tttgatttta ttttattcat tttttatgaa tttgcaagcg ctaccagatt  72000
accatcaagc aaataggtgt gtgttgctgg gaactcgcat tggatggaac gatgacaata  72060
gccaagatcc caacgtatat tggaaatggt gttaaataaa agtgaatata tttttttataa  72120
aattttttat ttaaaattcc aagtaatccc tgcaaacatt aaacactgta ggtattttta  72180
```

```
aatcttgcca catgcgaaca acgcacggcc tgtcgtcgaa caccgctatt acattatatt  72240
ttcctctgat atagttgtta aacaatttta attttaataa ataatcttta caagtatcgt  72300
ctgaaggcct cataaacaat ttatatgatt taatatcaaa atacttttca atccagtttc  72360
gagtgggctg ttcacaaatt acgcttctcc cgctcataaa cacgataatt gcgtcgtggc  72420
aatttgccaa atacttaacg caagtaataa cgtctaagcg ggcttcatct tgagcaactc  72480
tattatcaaa atcataaaac gatctatttg tgggcaaagc tactgtaccg tctaaatcac  72540
ataatacagc gcggggaaat ttgtcgccga caggaacgta atattcgaaa ttatttacct  72600
ttagaaactt tttatattgc tttttaatag tttctggatt taatggaaat ttatcagagc  72660
gtttataatt gcgttcaaga gccgtttcca aagaaacgtc catcaaacgc gttaaaaaat  72720
ggtaattatg cgttgcggcc attttttgcc acatgtccac cgattgagtg ttcaaattag  72780
tgtcgctgac aaccacgttg gcaccacatt ttgcggcttt taaaaactgt tcaatgcaca  72840
ttttggtaat ttgttcttct ttagtttgtc tacatttccg cgattggtta tagaaagcgt  72900
tcagttttgt ataatcgccg tttaaaaaca acttaacgcg cacgtcgtct ctgttgattt  72960
ctgtatagcc ttttaaactt ttggcatacg tgcttttgcc cgaacccgaa atgcctatca  73020
acaccaacaa ttgttttgaa gaaggcaatt taattgttgg agcaagttta ttatttaatg  73080
cctgcttagt cgatacaaat tttataatat ttttgatcat tttaattttt tcaggctcgg  73140
ttaattttaa aaattcgctc tccacatcga tcgtttgtgc tttacgacat ctgtacgcta  73200
aacatttcca cggcaaagtt tgcaccagtt cgttgaaacg ctgttgattc aaagtcaaac  73260
ccgacaccat aatatttatt gtagactcgt tggtgaacgt gtttctagca tcaacgtacg  73320
gtttaatgac actttttaaa tgcgggaaaa gagctagaaa gtcatcgtgt tcgccattta  73380
taacaagctg cgccaattta gtaggatttt cagcacggct ctgatttttg tgcatgttca  73440
aatacacgtc gcttttaatc ttgcatagtg gcgcgttgtt tttatcgtaa actacaaatc  73500
cttcttccaa atttttcaac tgggccgcgt gttcgacaca ttcttgcaca gacgtaaact  73560
cgtaacattt ggggtatttg caaaacggca aattggaaca gtaaaaataa tcgcccgttt  73620
cgttgtttct gcttgccaaa taccacaacg ttggctgttc atcgtaaacg gttacaattc  73680
tgttgtgttt gcttgttaac tcaaacatgt gagtcgacgc gcagtctaaa tattcgttac  73740
acaacgcttg aaattgattg tgggcctcgt caagttgaag agcttgcaaa actaaacgtt  73800
taaacgtcac gtctgacacg caaaggtttt ctgcaaaagc acttcctcgg gtgctggcat  73860
gccattcgcc gttgtacttg tagattttaa ttaaacttcc gtcgattttt tcgtaaaact  73920
taaaattctc cttcgattgg aacagtttgt gatgagcatc ttcgccgccg atattttgta  73980
gcaattcttg aaaattaaag aaacgatcga aagaacgcga cacaacggcg tacgtgcggc  74040
tgttaagaat taaaccgcga cattccacga ccacaggatg atctcgatcg cgttcaaacg  74100
attcgtaatt aagaaccatc aaatcgtgtt cggtataatt tttaattttg actttaaact  74160
tgtcacaaag atttttcact ccgccgtttg caagtagacg cgaaacgtgc aacatgattg  74220
ctgtttaata atgcatacca atgctaaact gtctattata taaagtgcag tgataacttt  74280
gttatcaacg cgttcgatgc cgacatatat aaacgcaatg taacagtttt tgctagtacc  74340
atcgcataca acattatgaa tacaaggggt tgtgttaata ataataaaat gatatttatg  74400
aatgctttgg gcttgcaacc tcaaagtaaa ttgaaaatta ttgcacataa aatactagaa  74460
aaatgtaaac gtgacgcgta cacgcgtttc aagggcgtaa aggcgatcaa gaatgaacta  74520
aaaacataca atcttacgtt gcaacaatac aacgaggcgc tcaatcagtg cgctttaaac  74580
```

```
gatagccgat ggcgcgacac aaataattgg catcacgata ttgaagaagg tgtgaaaata  74640
aacaagagac atatatatag agttaatttt aattctaaaa cccaagaaat tgaagaatat  74700
tattacatta aagtagaatg ttatgtaaac agttaattaa tctacattta ttgtaacatt  74760
tgtggtaata gtggcgttgg ttatacattt atatgattgt aatgttgtgt actcgttttg  74820
taataaattt ttgtgtttaa tcaattcaat atttttattt gataaaacct tattttcgct  74880
actcaatttg gcgtttttag acgcaagttt tgcgtaatcg tcattgagcg attttagcgc  74940
cttttcagtt gtaattcgtt tcagttgcaa ttctttaaaa gatttatgca tgttgttgta  75000
gtcgctttta attttgtcta acttttcttg catagaaacg cttgtttgtt gtaatttgtc  75060
taaatctaat tgttgtttaa tgttgagctg cgtttgttcg gcaatgtcta cctgtagttt  75120
ttttagtatc gcttgtgctt cagacagcat agtgtcgtcg gcatttgcgt tgttgtcttc  75180
tgcgtcgtcc aacagacttt tttcaaacaa cacactggcc aaagaggccg catcaaaatt  75240
agcgtttatt ttattccatt gtgcgacact cgacgcgctg catttaatca catccacaac  75300
gtttcggttt acgctgtaaa cgttgaaatg caaactttca accctacaca agggacatgg  75360
tacttttttt cgttttctaa tcttgcgtat acacattgag cataattgat gtttgcacgt  75420
gtctagttct aatacgggta ttatagtcaa tctgtctatt ggttgcagaa aataattttt  75480
aatttctgca accgaaaaac aaatgttgca ttgcaattta acaaactcca tttttagacg  75540
gctattcctc cacctgcttc gcctgcaaca ccaggcgcag gacctgccac tgcgccgccg  75600
cccagagtag cgttaggatt tgctcttggt ataaagtcgt tgcgcaaaaa gttgttttct  75660
gaattgatta tttggtatcc caaaaacagc ggaacgtacg tcgggtattc ttcgtatccg  75720
ctaagcgttc tgtccagctc acgtgtgtcg ccttcaaatt tcaaaacgtt tctaatttgc  75780
aaacgattgg gttgacttct cataatgtca ctgcttctta tcgggttgta caactcgggg  75840
ccgtcgggca cagacgcgac cagacccgtt tcgtcaatta tacacgtggc gcaatttcta  75900
aacctcaatt cctccgtgtc gatttgcaag tactcgggcg ctactgcgcg tcgaatcaaa  75960
ttttgcaaaa atccactgta attgttaaat aattgatcgc cagcaccgcc tcgaagcgct  76020
cgggcgttgg tcacgtcaaa gaaacgcaat tcgtctcgcg acacccgcga acaaaacgtg  76080
ttcgggtttg tggtgtccag aatgcttttt gtagttgcgt aaacgctgtg tataacgcgt  76140
tgcgtgttgc ttgtgaaacc ttcggtatat tttagattgt cgcatatagt gttaactgcg  76200
ttttcgttgt tatatatcaa atgaaagatt agctgttcgg cttgcatcat actgtttaga  76260
ttaaacacgt cttggtaatt ggttgcgctt ggaattaaaa ttcgcttgat acctctttct  76320
ttatttccaa ctaaatgcct agcgatcgtc attttgaatt gattgtcgtc ttcgtcgaaa  76380
atgggcaaaa ccatttttga cattttaaaa cgttttatga ggtggttgtt gcaaataaac  76440
catccatcgt catgatacgc gtcgggcgaa cacggcgatt tgtatgttat gcacgcgtcg  76500
aacgacacga tggacgcgaa aatgcagcga ttaactctca tttgtcgcgg cgccataccc  76560
acgggcacta gcgccatatt gttgccgtta taaatatgga ctacggcgat tttgtgattg  76620
agaaagaaat ctcttattca ataaatttta gccaagattt gttgtataaa attttaaatt  76680
cttatattgt tcctaattat tcgctggcac aacaatattt cgatttgtac gacgaaaacg  76740
gctttcgcac tcgtatacct attcagagcg cttgcaataa cataatatca agcgtgaaaa  76800
agactaattc caaacacaaa aaatttgttt attggcctaa agataccaac gcgttggtgc  76860
cgttggtgtg gagagaaagc aaagaaatca aactgcctta caagactctt tcgcacaact  76920
```

```
tgagtaaaat aattaaagtg tacgtttacc aacacgataa aattgaaatc aaatttgaac  76980
atgtatattt ttcgaaaagt gacattgatc tatttgattc cacgatggcg aacaagatat  77040
ccaaactgct gactttgttg gaaaatgggg acgcttcaga gacgctgcaa aactcgcaag  77100
tgggcagcga tgaaattttg gcccgcatac gtctcgaata tgaatttgac gacgacgcgc  77160
ccgacgacgc gcagctaaac gtgatgtgca acataattgc ggacatggaa gcgttaaccg  77220
acgcgcaaaa catatcaccg ttcgtgccgt tgaccacgtt gattgacaag atggcccctc  77280
gaaaatttga acgggaacaa aaaatagtgt acggcgacga cgcgttcgac aacgcgtccg  77340
taaaaaaatg ggcgctcaaa ttggacggta tgcggggcag aggtctgttt atgcgcaatt  77400
tttgcattat tcaaaccgac gatatgcaat tctacaaaac caaaatggcc aatctgtttg  77460
cgctaaacaa cattgtggcc tttcaatgcg aggttatgga caaacaaaag atttacatta  77520
cagatttgct gcaagtgttt aaatacaaat acaacaatcg aacacagtac gaatgcggcg  77580
tgaacgcgtc atacgctata gatccggtga cggccatcga atgtataaac tacatgaaca  77640
acaacgtgca aagcgtcacg ttgaccgaca cttgccccgc aattgaattg cggtttcagc  77700
aattttttga tccaccgcta cagcagagca attacatgac cgtgtccgtg gacgggtatg  77760
tcgtgctcga caccgagttg agatacgtca aatataaatg gatgccaaca accgagttag  77820
agtatgacgc cgtgaataag tcgtttaaca cactcaatgg gccattgaac ggtctcatga  77880
ttttaaccga cttgccggag ttactgcacg aaaacattta cgaatgtgta atcacggaca  77940
cgacaataaa cgtgttgaaa catcgtcgcg accgaatcgt gccaaattaa agcacgttaa  78000
gcggatacaa cgggcagtcc gagctgttaa agtcaataca accatcgtta acaaacgaat  78060
acgcattgtt gtgacagctg aggatataaa aaggaataga gaagtaattg caatgaaata  78120
tcccgttaca attccacggc acagcgtatg ttgctcgagt tctatcagtt gcacacaacg  78180
gcctaagaaa atttattaat gcttcatttg tatctatatt agaaggataa tacataggtt  78240
cgcccaaagg actgggagaa ggcggcggcg aaggtgtagg tgtaggagga ataggagaag  78300
gcggcggcga aggtgtaggt gttggaggaa taggagaagg cggcggcgaa ggtgtaggtg  78360
taggaggaat aggagaaggt ggaggtgtag gtgtaggtgt tggaggtata ggtgttggag  78420
gaggtgtagg tgtaggtgtt ggaggtatag gtgttggagg aggtgtaggc gaaggtggag  78480
aaggtgtagg agtaggtgga ggtgtaggta acggtacaat tggtggagat gtaggtggtg  78540
gtacaattgg tggatttgga tacaattcct gaatgtcgtc taatattttt aaagttaata  78600
aaattattat aaataaattt aatattatta ttattattat tatcacaata atgtaccaca  78660
tgttgcttaa atataaaaat taaacaaaga atgttgtatt attgcaaatt taacaatttt  78720
ttgtattctc cccatgtcat gcgttcgtaa tgagcgggcg gttttttatt tctttgtatc  78780
cacttgtaat cgttaatgtg gttgtgaaaa gtcatactga cgtaggccat taaatttttc  78840
atgagcatat tatttgacac aactgcaaca tctgcgcctg ccgtttcttg ctggtacgaa  78900
tcgacaaacg taatgtctgt gccgtatttt tctttgtcaa gtgcaatttc tataagctca  78960
atgtggtaaa tgatgaaacc tttgacgttc atataatgat cgcggcacat ggcgcactgt  79020
agtatgaaaa atacgttgta aaatagcacc ttcattgttt tcaactgctg catgacaaaa  79080
tctaaactgc ttttgtctcg cgtatacacc atatcgtcga tgatgagact gagaaagtgc  79140
atggtgtccc atatggtagt aaacgtgtaa gtaaaactct tgggctggca cgaacgcaaa  79200
ttgagttctg tggttttgtc cataaattct atgcgaaact gttgcaagtc catgtcgggg  79260
gatgcgttaa tggcccattc gatcaactgc tgcacctcgt acttttgaat gtctttgtat  79320
```

```
ttcatcaaac acgcaaaatg gtataagtaa gttgcttgcg aagacaacag tttggtgagg  79380
tgcgtcgatt tagaggctcg caaaaggtct atgagacgaa acgaatacaa cagatagctg  79440
tctttgtaac gagaaaaaag cggcgtcagc ggtatcatgg cgactagcaa aacgatcgtg  79500
ctgtacttgt gtcaggcgcc ggccacagcg tcgttgtacg ttagcgcaga cacggacgcc  79560
gacgagccta ttatttattt cgaaaatatt acagaatgtc ttacggacga ccaatgcgac  79620
aagtttactt attttgctga actcaaacag gagcaagcct tatttatgaa aaaagtatac  79680
aaacacttgg tgcttaaaaa cgagggtgct tttaacaaac accacgtatt gttcgatgca  79740
atgattatgt ataagacata tgtgcatttg gtcgacgagt ctgcgttcgg aagcaacgtt  79800
atcaactatt gcgaacagtt tatcacggcc atttttgaaa tttttacgct cagcagtaaa  79860
atcgtcgtgg ccgtgcccgt caattgggaa aacgataatt taagtgtact tttgaaacat  79920
ttgcacaacc taaatctcat tggaattgaa attgtaaatt aaaacaaatc atgtggggaa  79980
tcgtgttact tatcgttttg ctcatactgt tttatcttta ttggacgaat gcattaaatt  80040
tcaattcctt aaccgagtcg tcgcccagtt tagggcagag cagcgactcg gtggaattag  80100
acgagaacaa acaattaaac gtaaagctga ataacggccg ggtggccaac ttgcgcatcg  80160
cacacggcga taataaattg agccaagtgt atattgccga aaaaccgcta tctatagacg  80220
acatagtcaa agagggctcc aacaaggtgg gcactaacag cgtttttctg ggcaccgtat  80280
acgactatgg aatcaaatca ccaaacgcgg ccagcacatc tagtaatgta accatgacgc  80340
gcggcgccgc aaactttgat atcaaggaat tcaagtccat gtttatcgta ttcaagggtg  80400
tgacgcccac taaaactgta gaggacaatg gcatgttgcg attcgaagtc gacaacatga  80460
ttgtgtgttt gatcgacccc aacacggcgc cgctgtccga acgagaggtg cgcgaattgc  80520
gcaaatctaa ttgcactttg gtgtacacaa gaaacgcggc agctcagcaa gttttattgg  80580
aaaataactt taccgtcatt aatgctgaac aaaccgccta tctcaaaaac tataaatcat  80640
acagagaaat gaattaataa aacaaaaagt ctatttatat aatatattat ttattaacat  80700
acaaaatttg gtacactagt gttcaaatcg tttctgttca acgccattgt catgttataa  80760
aacacatttg tagttttatt gtaattattt ttaaatttat ttttaatttg ctgtaataaa  80820
acttgttcat taaatacaaa agactttgaa ctacttgcgt ttatattctt tttataattg  80880
tactgaacaa acgaggggtg caaaaagttt ttgaaatgct gcacggcaat acctatcatc  80940
tcctccattt tgtcctctcc tattgtaata gtggcactgc gcaccgtttt aatgtttaga  81000
atgtaaatga gcgcatacag cggactattg ttggtgctca agcacattag gttgtgctta  81060
tgcatagggt cgttgctcag cagcgttttg tatactacaa agcccgtttt ggggtcgcgt  81120
ctgtacatta gtacgtgcga caaaaacaaa cgcaccggcg tcacaagcga ctcgtaatac  81180
atgctttcta tcggaaactg tttggacttg atgtgttcgt acacggagcc ggcaaacttg  81240
acgctgtcta caaacttatg gttcgtgtaa acaatcaaaa atctgtcttg tacaccgtcg  81300
tcataatcgt ccacgtacag cggcttgttg ttaacaatta acattttgta gttggcttca  81360
tactttagca gcccttggta ttttctgctc ttggaatcgc tcttgctcga atcggcatgc  81420
ttcttaaagt acgactcgct gcattgtttc aactcgttga tagtgtacaa ctgcgagttg  81480
agtttgctca cttccttgtc gctcgtttcc ttgttggact ctccgctgtg gttgtcatcg  81540
tcaaacttgt gcatcaacac caaatagtcc aacagctcaa aaaacgacga cttgcccgaa  81600
cccggttcgc cgggcatgta aatagccttc tttccgtaat ctacgggaat ggccaaacta  81660
```

```
gcggcgaaat gcatcaacat aatcgcgttc gcgtgattaa aattggtgaa gcgtttaaag  81720
tacaaatagc cttcgacaat ctttttcaaa taattgtacg agtactcctt caagtccact  81780
ttggacatga tgatgcgcat gtagaatcga gtcagccaag tgggcaaatc gtccgtgctg  81840
cgcgccaata tgattttgtc ccaccacaca ttgtacttct tcaagatcat taacgcgtcg  81900
gcgtggtgcg tgtaaaattt ggaaatgtta tccgattctt caaactgaac atcgggttca  81960
cgtgcaacat catcgcgcaa ttcggttaaa aacaaacgtt tatcattaaa cttgtccatc  82020
aacatgtcga catattcgat tttgtgaatt gttcgataca agtactgaat aattttgttg  82080
tgttctttgg aaaaaaactc tccgtgttgg ttaacaaatt cgctgttcgt gcgaatcaac  82140
gtggtcgaca cgtacgtttt gttagtaaaa attagcatcc aaatcaattc gctcaattct  82200
gcatcgttac cgaacatgtc cgccatcaag cagactttta gcgcttttct attgatcttt  82260
attttcttgt agcatttgca ttttggtcga gatcccgata ccgttgaccg acacggtttg  82320
cattttaggt tgtgcaacat gtcggaaacc ctgttcttgt ttacgtacag agcgagcgta  82380
atcagatttt catcgtccaa attccacaaa tcgcgaaaca ggttgtttaa cgcgactcgc  82440
atatcggctt ggcatgtgtt gcaattgccc atgtagttaa ctatggccgt gttagttttt  82500
agcattttta catctcggca cattttggcg atgtgataag ttctataaat gctgagctcg  82560
tcggcgctag tagatagcat gtaattaaac gcgtcctcgg gcaaatactt ttcgtcggtg  82620
ggcttcttga atgtctgcgg caacgtggtg cccaacaaaa atggacagct cgaatgaaag  82680
ctgttggtga acacgttgta cacaccgtgc gttgtcaagt acaagtattt ccaattgtta  82740
aattttatgt tgctcaactt gtaacaattg cttttggtca atttgaatag gtcatcctct  82800
ttctttacaa tttgataatg tttgccgttg aaaaccaaat tgactccggt cactacgttt  82860
tccaattttc taaagaatcc tttacacaca atgtcaggcg gcaagtttag cgccatcaca  82920
ttctcgtacg tgtacgccca caattcatcg tgatccaaaa tttcgttttt agccgactga  82980
gtcaaatata tcatgtagtg tatgccaaaa taatagccca acgatacgca caatttggta  83040
tcgtcaaagt caaaccaatg attgcaggcc ctattaaaca ctattttctc ttgttttttg  83100
taaggctcac atcgcttcaa agcttcattc aaagcttctt tgtcgcaggc aaataatgat  83160
tcacacaaaa gttccaaaaa cagtttgatg tcggtttctc tgtacgagaa attttcgttc  83220
ttggtcaata tcttccacag tacatagatt aaaaaatcaa aatttttaaa tttgcttttt  83280
tcaaagtatt gttgtagaag gtttggatcg ttggctcgtt cgtgggtcgc caaaacttta  83340
accatgttct cgtgaattgc tataagcccc aaattgattt gcgtttgaat gtagtctgca  83400
ttttcgctgc tcgccgatat aatgggtacg atgcgcggtt ttctggaacg cgtgtcgctc  83460
aagtccacgt cgtttttgtc aaaattgttg ttctcgaaca ctctgaggct tttgaggttg  83520
acgttgacga tatgcttgta cttgggcacc gtaatgcatt cctccaaatt aatgtcgtcc  83580
ctaatgtaat tgaaaaaatt tttatccgaa ttgaccagct cgccattaac tttgcacgtg  83640
gccacagtgc cgtcggccat tttgagtata aacaagtctt cgtgagaatc gtcaaacttg  83700
gtttttccat ttacaaacag cgtttgcggc ggatcgtgat tcgtgcgcag gctgagctcg  83760
acgttgagaa aacatttagg gtcaaacaca aacaaatcca cagggcctag ttttttgttg  83820
tgtatgattg gtatcgtggg ttcgatgaca attccaaatt ttatatttaa aaacagctgc  83880
catccgttaa aagagaaagc ttgctttttg ggccagttgg gccaataata gtaatcgccc  83940
gcttgcacgc atttgttaat gtatccaggg tcggtgctct tgaaaaaatc ttcaaaatta  84000
atatactttt gtatgatgtc atagtgcttc ttcaaaatga aaggttttac aaaaatgcaa  84060
```

```
aaatcgttac tttccaacac ccagtcgtgg ccgtctaatg tttgagctgc gtgtttctct  84120
gcaggttctt cggtgtcttc gcaagatgcg cccatgtcgt gtttcgcgca cggaccgtta  84180
aagttgtttc taattgtgtt taagaactgt tgaaagttgt tgacgtactc aaacaatcta  84240
cgtgttcctg ttcgcgtgtt tctaatgatt aaatgatttg catcttgcaa gttgttaatc  84300
tcgtacgttt tgtcttgagg cacgtttttc aaaaaaaatt gtaaaatgtt gtcaatcatg  84360
ttggctatcg tgtttgtact tttcgtgtta atttatttaa taatttcgat caaaaatcac  84420
catccattct tacatagaat agaaacgcta atacaagatt tcaacaacac attgttgttt  84480
ggcgcgtatg tacagattta cgatttaagc acgcccgccc gcaccgaacg attgtttatt  84540
attgcgcccg aaaatgtggt gttgtataat tttaacaaaa cgctctatta ttacttggac  84600
tcggcgaacg tgttttgtcc caacgagttt agcgtgacca cgttcacgca atccactatt  84660
aaaacgatca acgagacggg aatatatgcc accgcatgca cgccggtcag cagcttgacg  84720
ctaattgaac attttgcaac attaaaaaat aacgtgcccg atcacacgct cgttctcgat  84780
gtggtcgacc aacagattca gttttcaata ctcgacatta tcaattattt gatttacaat  84840
ggctacgtgg atttgttggc cgaataacgc gtatatagac gcttgtacgt tcatcgtagt  84900
aatcatttta atacatttga ttgaactaaa catacatctg caatgggtga aagagtcact  84960
aaattttgca atggaaaacg gcgataaaga agacagcgac aatgaataga gtttatattt  85020
ttatttaata aaatattgtt cgtaatccat aatgttttgt attatttcat tgtgataatg  85080
ttcccaatct tgcacggggg tggggcatcg tttgactttg acgtagaaat cgtacgcgta  85140
gttattagtt ggcagatcgt cgacaagtgt gatcgacttg aaaaagttta catttttatc  85200
gctcaaatat ttaattacaa tttttggcga tttgggtata ttgttgtcgg atcgatgatt  85260
gtgaatgtca aaaacaaatt tattttcaat gaaacgcttt tttaaattgt aatctacaat  85320
agcgttgtgt gaattttgaa ctaaatcaga gcgttcttct tgaacggtgg aaccttcgct  85380
gataatgata tcaaaatagc cttccaaatc gacgtctcgc atcgagtgtg ctacatgatc  85440
tctactgcca tacgaccaca agactaaaac gcaacccatc tcgtgcaact cctgcaagct  85500
gtcatacaca aacggatctc gaatctcaac ttgctcctct tcggttatga gagtgctgtc  85560
caaatcaaac acgaccacgt gcggaaatcc ccacgtcaaa gattcgcttt tgagagagac  85620
cactttgtag tgtggcaata gaaaccattc tttaagaaac gaatacattg gcggtttgtt  85680
gctaagcacg cacatgtggc ccaacactgg cgttttgaat gcgcgtttaa tattgtgcct  85740
gatgtcgcgc atgtcgtcgg cgggcgcttt gaatatttgc atacagtaat tgtaattgtt  85800
ttctatgatc ttgcacagct gcgggtcgtt gcaaaattga aatattacat attcaaaaaa  85860
tttatacttt tcaaagccaa ggtatttgag gtcggcgtac tcgcttaaaa cgagaacatg  85920
tcgtttgatg atggcgtcgt taaggcgcaa acagatccat ttgctttgaa gcgaggaggc  85980
cataatgtac aaaaatggac cagttacgcc ttatttaaac tgtttaaaga gtttcgtata  86040
aacaaaaact actctaaact aatagatttc ttaacagaaa attttcccaa caacgtcaaa  86100
aacaaaacgt tcaacttttc gtctaccggc catctgtttc actcgttgca cgcgtacgtg  86160
cccagcgtca gtgatttggt gaaagagcgc aaacaaattc gattgcagac agaatatttg  86220
gcaaagctgt tcaacaacac aataaacgat ttcaaactgt acactgagct gtacgagttt  86280
atcgaacgga ccgaaggcgt cgattgctgt tgtccgtgcc agctattgca caagagtcta  86340
ctcaacacca aaaattacgt ggaaaactta aattgcaaac tgtttgacat aaagccgccc  86400
```

```
aaatttaaaa aggaaccttt tgacaacatt ctttacaagt attccctaaa ttacaaaagt  86460
ttgttgttga aaaaaaagga aaaacatacc agcactgggt gtacacgcaa aaagaaaatc  86520
aaacacaggc aaatattgaa tgataaagtt atttatttac aaaacagtaa taaaaataaa  86580
ctatttgagc ttagcgggct tagtttaaaa tcttgcagac atgattttgt aacagtcgaa  86640
agccaaacga gggcaggcga cgaaatcgct tcgttcattc gctactgtcg gctgtgtgga  86700
atgtctggtt gttaatagta gcgtgttctg taacttcggc gacctgtcga tgaacggctc  86760
ctggatcttc tgtatgtgcg gggtctaccc gggcggcgtc tgtaacccga gcttctgcgc  86820
ctgcgtgtcg aaccatatgt ggtaccggtt gaagaacggc gacggcgacg ataaaccatg  86880
tttaaattgt gtaatttatg tagctgtaat ttttacctta ttaatatttt ttacgctttg  86940
cattcgacga ctgaactccc aaatatatgt ttaactcgtc ttggtcgttt gaatttttgt  87000
tgctgtgttt cctaatattt tccatcacct taaatatgtt attgtaatcc tcaatgttga  87060
acttgcaatt ggacacggca tagttttcca tagtcgtgta aaacatggta ttggctgcat  87120
tgtaatacat ccgactgagc gggtacggat ctatgtgttt gagcagcctg ttcaaaaact  87180
ctgcatcgtc gcaaaacgga atttcggtac cgctgttgat gtattgttgc ggctgcaaca  87240
tttgtatctt ttcgccgcgc tcgatcaaca attcttcaag agtggtgcgt ttgtcgcgct  87300
gtaaagccac gttttgtaac agcactattt tcgcatatct cataatcgga ctgttgaaac  87360
agcgtgcaaa cgacgaccgc ataatatcga cggtcgtcaa gtcgattgtg gtcgaaggca  87420
tctccaacag agatcgcacg gcgtccaaca gcgtgtccgt ttgaacctgc gtcatttgcg  87480
gtctgcacgt gtagtcgtca aacgtggttt cgagcagttt gaacaacgaa tgatactttt  87540
ccgatcgcag caaaaatatc atggtcatga ccacgtcgct gattttgtat tctgtagaac  87600
tggtgctgtt caacgaatag tgatggatta gtttgcgagc agcatttctg tatcggcgca  87660
tgttgatcaa ctcttcggaa ggctgcgcgg gcgcggcggc gttggctcgc gcaaacaaat  87720
ttattacggg acgcggcgta ggctgcgcgg acgctggcgc ggcgacgacg tccgcgtttc  87780
ccgccgcgta ctgagacgct atggcagcgt tgttatttaa aattgtgttt tgcgatttgc  87840
gagccacgtg catcataaaa tttatcaaca cgtcggtgtt caactgcacg ctttgatgtt  87900
cgtcgcagag caaaggaaat agctggggcc atatcgccaa ttgcataggc tcgtctattt  87960
ttaaccgcaa tttgtttatt tccaaataca acgcgatagc gctcatcgtg accgacgacg  88020
cacacttact ctgtaactat cacttggatc gtgttgtcgt aaacgcttcc caaaaagtct  88080
aacacgttga ccgtttcgat tctattcaac ttaattgtgg acgcgttggc ttgcatcggt  88140
tccaacagac tgcgcgctcc gacagattga gtagacaaaa tttttaaact ttccgtctta  88200
ttgggcgtaa tgtcgttgat taacaacgac gcagccgttt gagaggccgc agtgttgatg  88260
gtttgcaaca tgtcgacggc cgccatttgc gtttgcgccg aaggtcttgc tggcggcctg  88320
ttgcggcggt ttcttcgtgc ttgcgacatg ttgtcgtcag tgtccatatc ggtatcattt  88380
attgaagcaa tcatggttga gttcgataag cagagatatt tcgttgtcca attggtactt  88440
ggtaatgatg tgccttataa atgtttcggg cacaatcatt tctgtcatta gcacgttaca  88500
aatatctatt ttgatcaatt tcaatttatg aattaacaga ttaatgtttt cgtccgagta  88560
cttgctcatg atgaaacgac aaacgttgcg gagttccaac tccgctaccg gatacgcttt  88620
gttgggcaaa ctctctaaat agtgtctcaa ataaaagccg atcaatacgg tggacgctat  88680
tttgttaacc tttttcattt tagtattgcg gcccatttct atcatgaagt ttttaaacgg  88740
tagcaacagc ctgtctccgt tagcaacagt ggagcagccg ttgcattgcg cgctcaaaat  88800
```

```
actcaacacg cgctcgtgat cttcttggcg caatccgacg gttgcttttt tgcattcttt  88860
gacaaatggc acgcacatgt cgcgtttcgt gtacaaagaa tacgctttgt cgcaaatcaa  88920
gttatagaaa aattgcacaa atatctgcgt aatcaagttg ttttcgttaa taatgtcact  88980
ttcgtttttg taatcggttc gaagcaacac gtacaacatc agaggcatgc cgaacatggg  89040
tcttaaaaaa atgtcccaac cattttgcaa gcccgcgtcg agggtgctca gcgaggacgc  89100
caagtatttg catttgcact caaaacattg aattttgttt gcgggcttgc acgactgaca  89160
catgatcgca tccacgtcgg gtgccggcgt cggattgtaa tatttttgca agtattgcat  89220
aatggtccta aaatggggta cctgtttgat aaactcgtcg cgcaaaaata tcgaaaaaat  89280
gtttttttaca ttgtgtatgt tgtctgtgtt gttggcttga ttctcaaaac tactctttat  89340
ggaaacaata catttgttaa attctgtgaa aaaagtaaga cctttactgt ccacgatcaa  89400
gctttggttg aaatattttg aaaataaaaa acacaacgaa tcgatttcat cttgtaacaa  89460
ttgcgcttca aaacacacgt tttcaaagcg gtcgtaaatg ttaaacctta aactgtattg  89520
taatctgtaa gcgcacatgg tgcattcgat ataaccttat aatatgaacg attccaattc  89580
tctgttgatt acgcgtttgg cagcgcaaat actgtccaga aacatgcaaa cggtggatgt  89640
gattgttgac gacaaaacgc tcagtttgga agaaaaaaata gacacgttga ccagcatggt  89700
gttggctgta aatagcccgc cgcaatcgcc gccgcgggta acatccagcg acctggccgc  89760
atcgatcatt aaaaataaca gcaaaatggt gggcaacgat tttgaaatgc gatacaacgt  89820
gttgcgtatg gccgtcgttt ttgttaagca ttatcccaag tattacaacg agacgaccgc  89880
cggtttagtt gccgaaatag aaagtaatct gttgcaatat caaaattatg taaaccaagg  89940
caattatcag aacattgagg gttacgatag tttattaaat aaggcggaag agtgttatgt  90000
taaaattgat agactattta aagagagcat taaaaaaatc atggacgaca cggaagcgtt  90060
cgaaagagaa caggaagcgg agagattgag ggccgaacaa actgccgcaa acgctcttct  90120
ggagaggcga gcgcagacgt ccgcagacga tgtcgttaat cgtgccgacg ccaatattcc  90180
cacggcattt agcgatccgc ttccaggccc cagcgcgccg cggtacatgt acgaaagttc  90240
agagtcggac acgtacatgg aaaccgcccg acgtaccgcc gaacattaca ccgatcagga  90300
caaagactac aacgcggcgt acactgccga cgagtacaat tccctggtca agacggttct  90360
tttgcgttta atcgaaaagg cgctggccac tctaaaaaat cggttgcaca taacaactat  90420
tgatcaattg aaaaagttta gagattatct gaatagcgat gctgatgctg gagaatttca  90480
aatattttta aaccaggaag attgtgtgat actgaaaaat ttgtcaaatt tagcgtcaaa  90540
gtttttcaac gttcgttgcg tggccgacac gttagaggta atgttggaag cgcttcgcaa  90600
taatattgag ttggtgcagc ctgaaagcga tgccgtacgg cgaatagtca taaaaatgac  90660
gcaagaaatt aaagattcga gcacgccgct gtacaacatt gccatgtaca aaagcgatta  90720
tgacgccata aaaaacaaaa acattaaaac cttgttcgac ttgtacaacg acaggctgcc  90780
aatcaatttc ttggacacgt ccgcaaccag tccagttcgc aaaacttccg gcaagagatc  90840
tgcggaagac gacttgttgc cgactcgcag cagcaaacgt gccaatagac ccgaaattaa  90900
tgtaatatcg tcagaagacg agcaggaaga tgatgacgtt gaagatgtcg actacgaaaa  90960
agaaagtaaa cgcagaaaat tagaagacga agattttctc aaattaaaag cattagaatt  91020
tagcaaggac attgtcaacg aaaagcttca aaaaattatt gtggtcaccg acggtatgaa  91080
acggctgtac gaatactgca actgcaaaaa ttctttagag actttaccga gcgccgctaa  91140
```

```
ctatggcagc ttgctcaaaa ggctaaacct gtacaatctc gatcatatcg aaatgaatgt  91200
aaatttttac gagttgctgt ttccattgac actgtacaat gacaatgata acagtgacaa  91260
aacgctttct catcaattgg taaattacat atttttggcc agtaactatt ttcaaaactg  91320
cgctaaaaac ttcaactata tgcgcgaaac ttttaacgtg tttggcccgt ttaaacaaat  91380
cgactttatg gtcatgtttg ttataaaatt taacttttta tgcgacatgc gtaattttgc  91440
caaattaatc gacgagctgg tgcccaacaa acagcccaac atgagaattc acagcgtgtt  91500
ggtcatgcgg gataaaattg ttaaactagc ttttagtaat ttacaatttc aaaccttttc  91560
aaagaaagac aagtcgcgca acacaaaaca tttgcaaaga ctaataatgt tgatgaacgc  91620
aaactacaat gttatataat aaaaaattat aaaatatttt taatttttat ttatattcag  91680
tacatttaca catattaaca tattgtttat acaaattctt ataatcatta tgatttaaat  91740
tgaattgttg tctaaacaaa ttaaacactt tattaaacaa taacttttcg ttgtaatttt  91800
ttactttgca catgttataa caaaaaatta aaattttcat catgtctgat ttgtctatgg  91860
cgtcacagtt gcttttaatg taatcgcaag ttaaccactc aaaaggaccc ttttctattt  91920
ttaatttgtt taaatcttta taatcagact tcagtttgta aattagattt ccacatcgaa  91980
taataaatcc ttccagcggg ctttggggaa acattaaaga cttgaaattt aacctttcta  92040
caaaatcgtt gtacaaatat ttgtgacacg gaatagtatt aaaccccacg ttagtcaaca  92100
actcttgcgc ctccacaaag ggcacaaact ccccgccgta taattgaatt tcgtaagcgt  92160
agtatttcaa actctctttc tggtccacgt agttaattac gttaatgggt gtcgtttttg  92220
cgtcgtcttt ccaacccatt aattcgccgt agacaataaa accgtcattg aaccgcgcct  92280
gaagcgatcg catgcacgtt tctaaatctt ttcgaatgcg gtaataattc ataaaattgc  92340
cgtccggtct gtaagtgttt cttgacccgt acgtaatttt attttggttg caaatgattc  92400
tgaaattaca accgtccaac ttttcttgaa caataatttc tttgtcggcc aacgtacctt  92460
ttttaccttg atctagatgc gacacagatg gataaatttg atacacaatt ttattctcat  92520
cttcgggcat tacgggtccg cgttcattta acgcgtacat gacaatgttg tggcgaatgt  92580
cggtgcgctc cggcggttct ggcacgtggt gcagtctgtc ctgcaattgt tgcttccatt  92640
gttgaaaata ttcggtccat tcttgttgat actcgccgcg ttgcatgagt tttacgtaca  92700
gttttaaaag tttgacattc tttacaaata acgttagagt ttcgtcgatt ttgtatcctc  92760
cattattttt gtttaaatcc aatacattta aatcgttcac taccagttga ttgtttttat  92820
ccatcgtaat ttttatctca tcgcccacgt tgaacaacat gtttaaaatt ttggtggatt  92880
tcggcgcacg tttataatct aaataatatt caacgtacac gtaattgaac atgagctgca  92940
acaatccttt ggcattgttc aaaattttgt atctcatcaa agtataaata attttcacca  93000
tcgacaccgt catcaacttg gttacaaact cgtacaattg caagttttca ataccgtatt  93060
tgtctttaaa atcttcacgt ttactgaaca tgcttaattc gggagatttt ccagtcaaaa  93120
tgccaattaa tcccgtgtac aagtcaacgt atttgacatc gttgcccgat tcatcttttg  93180
catgtcgatt tttcaaaagc tctttattgt cgataaattt ttcaaaggtc tctcgatcac  93240
atttagtgta aatatggtag tcagtgtcgc tgctttcgac cgcgtatccc ttggcatggc  93300
tgcccgtatc aatgcaaatg tacaccatgt tagaatgtgc tgcttactgt gcctgtatca  93360
agccttatat acctcaaaat atttcacatt tttgcatcat cgtaaaatat acatgcatat  93420
aattgtgtac aaaatatgac tcattaatcg atcgtgcgtt acaagtagaa ttctactggt  93480
aaagcaagtt cggttgtgag ccgtgtgcaa aacatgacat cataactaat catgtttata  93540
```

```
atcatgtgca aaatatgaca tcatccgacg attgtgtttt acaagtagaa ttctactcgt  93600
aaagcgagtt taaaaatttt gtgacgtcaa tgaaacaacg tgtaatattt tttacaatat  93660
ttaagtgaaa cattatgact tccaataatt ttgtggatgt ggatacgttt gcaagacaat  93720
tgattacaga taaatgtagt gctctaatca aagtgcggat ctgttgccgg caaacatttt  93780
agagattgta gagaaggcca gagacaagta ttttgagggc caactcaaaa aaactatgaa  93840
tacattaaaa aattattttt acgaaaaaat atatggacga ttcgatagat tataaagatt  93900
ttaacagacg catcctattg atagttttta aattcgcttt aaacaagagc acaatacttt  93960
ccatcgtaca aagagatcat cgagtggcca ttaaacgttt aaacaaaatt aaccccgatt  94020
taaagagttc tccgcgcaat gcttcagcat tacaatgaat gtttggaaaa tctagacaat  94080
ccagtcacgg acgaacatca tttgttgaca aaagagttgc tacaaaaata tttatcgaag  94140
cgtttgaata cagttacacc aacactaatg ccatcagcat ggacaaaaca gatgaatttg  94200
attttattaa accggcattg aaacctttgc cagatgcaag accgccatcg cttttggcca  94260
acgtgatgaa cgaacgtaaa agaaaattac aaaacaccaa ctcaacggca aaatgtttgc  94320
taccagcacc accgccacaa ttgcgtaaac ttgaaaaaaa gaatcattta ttgcctttgt  94380
tttctttgta attatattgt tgcatttcta tttctaatat catagttttc taataaagta  94440
gtttcatatt tttgtttttg tacagtaatt gtttcttggt ttaacaagat cacaaccaat  94500
aacataaaga ataacacaat cataacaaaa attaaaaagc cgcatactac tagaacaaat  94560
tctttaatta gcgatcggtt tctatttaca aattggccga gctgatcgcc ttcagtcggc  94620
gagttgtggg cttggatgat gtcgacgata ttgttgccgg cgcgaccgcc tgtcgctctc  94680
gatataatgt cggccgccgt cggtttcatg atgtgcttaa ctacaaataa tagttgtact  94740
tgacgggcgt caccgtgatg ccgctgctaa aacctccgtc cgttaagacg cgttgcgtta  94800
caaaattaat gtttgtccga ttagcgtagt cggaataatc aaacgtgttg ggcggactaa  94860
aatcgggcat gttgatgggc acaatgccgc tggagctgat agcaatgctg tcgttcttgc  94920
aaaacagccg aatttttttg tagggctctg ctttattcgg cgcagacgac accatctggt  94980
caaagttgtt caattttatg attacgttgg gtaccaattg ataggggaaa attattttct  95040
ggaacatttt gacaaagtcc acaaccgttt ggctatagtc gggaatgccg agcaaagact  95100
gcgcctgttt aatgtatttg agactggagc ggtttactgt agcgcaattg gatggcacgt  95160
cgcccttcat aagccggcgc gttctctccc aattcaattt gttgtacaaa ttatcaatct  95220
cctcgtgcgg cagattgatt acatagcgcg cgggctgttt gcgatattga aagatgcaaa  95280
aaatgcgttt caacgacaat atcttcacca tggtggacgt ttccagattg aaacataaca  95340
aaaagtcatt gctttccacc aattctttaa aatgagacag cggaatttca caagcgatcg  95400
gtcgcaaatt gctttttatt ggaggcggaa cgctttgacc gttgcggttt tttagtaacg  95460
cgctgcacgc agattgcatg tccgtttcgg gatacgtaaa ctcgatggga catttggggt  95520
tttcatggtg aacgatcata gtgttgcaat aaaacaagtt gttggtcagg agcacgctaa  95580
aaacacgcgt ttcgcccgca ccgatttcgg tgatgggtac caacgggttc cagtagacta  95640
tggtggcgga cgctgttttt tttggcgatc gactgtctat gttaacatca tgctcgtgcc  95700
tgtacactag cacagaattg aattttggaa attgtttttt gtcaatgtac aaccggtcgt  95760
cgtctgtggg cacgtacacg atcaagtttt cgattaattt gttgcctacg tcgctttgcg  95820
gttccaccaa attgtgaggg aacgcaaaaa agcgatcgct aatacaaact tgaatctgaa  95880
```

-continued

```
acgggcactc catcgtgatg tatatgtctt acttcattag actttagatt attttaattt  95940
gtgaactcgt accgtattca atagggtgtc gggcacgtaa ttgtaatggt aaaacagatc  96000
ctgttgaaca cgtgcgttgt tcactacgat tgaaatgcaa aaatacatca agtacataaa  96060
cactatgatt agaaaggtag cagacagaaa atatttcatc tttaaatctt atgctagttg  96120
aataaaatac atagtacttt tatacgttta tttatatttg ttttctttgt tataaccgta  96180
attgtaaaac ttgtgatcgt gctcgccagg cataatttct ttgcacatca gcttgcgaat  96240
atatgtgaca tcttcgtaca ccgatttctt gatgttacca tcgtgaagcg ttgtcggctt  96300
gagaggtttg cggtcgttgt tgtaaaaatt ttgcaccgaa taattatcca tagtgcagca  96360
caggcaatgt cactgatgca tatgctttaa tttttttattg cattcagtta ttatatgatt  96420
taataaacgt acacaatagc acgtttatcg gttaaagata actttcaata tataaaagtg  96480
tttgaattgc gagaccgtca acataacgtt tatcaacgcg atgactaaac gacaatttgc  96540
tttgctgttt gtgtggcacc acgacaacca atttgtttgc aacacggacg aatacccgtt  96600
ttggcacaac attgaatacc atgcacggcg ctataaatgc atcgttttgt actgtgtgga  96660
aaacgacgga tcgctacaac tgcccgtttg caaaaacata aatctcataa attataaaaa  96720
agcgtatcct cattattatg gaaactgtgt tgacagtata gtgaaacgtg ctggcaaaaa  96780
ttgattatat gaaagtaact gcaatgttaa acccccacct gttggacgtc gcgtacaatt  96840
atttgctgtt gatggacatg gattgtgtgg tgcaaagcgt gcaatggaaa caattgtcaa  96900
ccgacacgta ttgttttgag ccgttttacg actctcaaat taaatggttg tacgcgccca  96960
aaagcggaca aagttttgat agttatcttg aaaactatgc aactctaatt cgagtcaaac  97020
aagtgcagca acatcgaaaa gaattaatac tgcattgtgt ggatttttctt acaatgaaag  97080
caaatgacaa ttttatggtg ttcaaaaatt atattaacat gattataaaa gtgtatttgc  97140
aattttacaa ttacagattt cccatcaatt ttgaggacaa cacgatgaaa ccttgtgtaa  97200
atttaacttt tagacgtggc ggcagttgga aaactcaact gcaacccgta tgcaattatg  97260
tttacaaaag taaaaatatg ccaaaattta ttaaataaaa caaattaatt taaacaagcg  97320
tttttattga caatactcac atttgatatt atttataatc aagaaatgat gtcatttgtt  97380
ttcaaaattg aactggcttt acgagtagaa ttttacttgt aaaacacaat caagaaatga  97440
tgtcattttt gtacgtgatt ataaacatgt ttaaacatgg tacattgaac ttaatttttg  97500
caagttgata aacatgatta atgtacgact catttgtttg tgcaagttga taaacgtgat  97560
taatatatga ctcatatgtt tgtgcaaaaa tgatgtcatc gtacaaactc gctttacgag  97620
tagaattcta cttgtaacgc atgatcaagg gatgatgtca tttgtttttt taaaattcaa  97680
ctcgctttac gagtagaatt ctacttgtaa aacacaatcg agggatgatg tcatttgtag  97740
aatgatgtca tttgtttttc aaaaccgaac tcgctttacg agtagaattc tacttgtaac  97800
gcaagatcgg tggatgatgt cattttaaaa atgatgtcat cgtacaaact cgctttacga  97860
gtagaattct acgtgtaaaa cacgattaca gcacttcgta gttgtatcga aaattgttca  97920
atggctcttt gttaatgtcg taattgatta atatgtcgta caatttggcg gcgttgtgtt  97980
tgcacacgac cgtttttagt tcttgaaaca ttttttcgtg tatgtttagc atgttgtatt  98040
tcagagtgcg atgtgtaatg ctggtgacga gcatcaaaat gataaaatct aaagcggcta  98100
atttgtaatc ccgttcatac gctctgtaat cgccaacaac tctgtggcca gatcttttta  98160
gattttgaca ggcgttatgg tacgaattga taatatttac tatagtttct cttgttatcg  98220
gtttgtcgat taaactgtta acaaacatca cgttgcccaa gcgcgacggt ttagacaccg  98280
```

```
acttgttttt tgtctgttca aatttgtaca aattaaaaac gctcatagac tggtcgtcag  98340
gcagtgtgtc gttatacaaa caaaatggta aaacgtttaa ttcgacaaac gacgagcaca  98400
ttaaagtttg ttggctgtta acgtcctggg gatgtaaact gttattcata acgtaacaca  98460
cttcaatgtc ggaatgcttg ttttcaaatt tgtccttgtc tacagtttca atggtgattg  98520
agcgaggttt gagtttattt tctaaattca tttggatatt ttcaatatgg tataccaccg  98580
acacgttgtg agccagcgat ccttgattgg ttttaatcat attcaaaata ttcatgatat  98640
ggttgaaaaa agagtctgtc aaaacgtttg tgtcgttgtt aaatatcgct ttccagggtt  98700
tactgttgcg tgactcaacg acggccgtgt aacataacaa gcgcgccagt tgcatgtgcg  98760
acaacttaat gttatcaatg tcggtgatgt ttggcaccag attttcattg ccgtcttcca  98820
gtagcgtgct cagttcggtc gagtagttat tcaacgatcg attgtgcgat tcaaacaagt  98880
ttactatcgc aggttgtaca tagtttttta tgtcgtcaaa ttgaattata tcgatcttgt  98940
ccttgttctc cagcataaac gacaaatttt ttaggtcgaa tttaatattt ggcgcgtttt  99000
cgttggactt tttgtaattt aacaacatcg ccaacagttt gtgtaactcg ccgttagctt  99060
gatctttgct aaacagttta ttggtagcgt aattcacgtt gtcgttcaaa aacagcaact  99120
cgttgatgat catttttttgt aaaagcgcgt acttgctcat gttgacagaa tctcttacat  99180
ttcagttgta aacgcgtctg tacaaattgg ccatgcgatt cggaatgcac acggggatcg  99240
tgcgagccag tgccgtttgg cgaaatagca ttttttcata gccgctcgaa caatcgcacg  99300
cgtccggcga aaattgcacc gtgttcaaat tcatattcaa ccggccgtcg ttgcatagat  99360
aaggcctcgg tgttcccgta tcgtccacca agtctctgta cgtgctcacg catgtttgag  99420
acacgacaaa atctccgccg gcggagaaaa cgtgaaccaa gcccagtgcg ggatcgcatt  99480
ctatcaagtc cggagcctgc gcgtttacca aagcgtcgga ggcgttgcaa aagccatcct  99540
ggcaggtcaa ctcgtttgca gcgctggaga tcacgcagtt gtctctacac tgctgatccg  99600
tcacgcacgg taaccggttc aatgaacaat ctacgcctcg attgcgctga aacgtaaaat  99660
ttaacggcgg cgcttccaac tcgttaatgt gcatgtatgc atcttgcaaa ataaattttt  99720
gaacaaattt aaacgtgtac atgtacacga ttagtataat taccagtaga ataagtattt  99780
gccaaaagtt caacatgatc gtcttaactg agtgtgaaaa gcgtggtgtg acgcacgaaa  99840
tgactggttg cgcaaaaaat aaaccggggt ctatataact cggcgtcgac cgcgttcatt  99900
tttaccgtca tgcatctgac ggctaatgta ttgctcgttc ctaacgcgct caaaaagcgg  99960
gacgtgaaat acatttataa tacctatttg aaaaattaca gtgtaattga aggtgtgatg 100020
tgttgcaatg gcgattgttt ggccgtggtg gtgttggacc gaaatcagct gcaaaacacg 100080
gacatggaag tgttggagag tttagaatac actagtgaca acattgaact gttatgcgaa 100140
aaaatatgtg tgatagttga taattacgac aagtattacc aaaaaaattg tgtataaata 100200
aaataccaaa ttttattata tcattttgtt ttatttaata attaaagaat acaacgccac 100260
atctattcct agtacaacaa ataatttgat tattattttt gagtgcacat taaaaaataa 100320
caaacagtgt aaaaatacta cagaataata caatacataa atattatagt aaatagctgc 100380
aattttgata gcgtaattta tactttgata tttttcaacg tacaacgtta aatgttgata 100440
cgcattattc acaaataaca aaatttttct aatatgccat ttgtccgcaa ttgtttttgc 100500
gatatcaaag ccttttttcaa acaattgaaa aattgcaaac aaaaccacgt acatgacgtt 100560
atacatagtg ttaaagtttt tacataacaa ttctataatg aagaaaattg ctaaacacgg 100620
```

catgagcgcg cacataatcg cgttggccgc aaatatctcg tacgtacaaa aatactcgga 100680
cattctccaa taagtaaaat gcattttgct attatactgt tgtttcttct agtgattatt 100740
gcaatagtgt acacgtatgt agacttgata gatgtgcacc atgaagaggt gcgttatcct 100800
attacggttt ttgacaacac acgcgcgccg cttattgaac cgccgtccga aatagtaatc 100860
gaaggcaatg cacacgaatg tcacaaaact ttgacgccgt gcttcacaca cggcgattgc 100920
gatctgtgcc gcgaaggatt agccaactgc cagttgtttg acgaagatac aatagtcaag 100980
atgcgtggag atgacggcca agaacacgag acgcttattc gagcgggaga agcgtactgc 101040
ttggctttgg atcgagaacg cgcccgatcg tgtaacccca acacgggtgt gtggttgttg 101100
gccgaaactg aaactggttt cgctcttttg tgcaactgct tacggcccgg acttgttacg 101160
cagctcaaca tgtacgaaga ctgcaacgtg cccgtgggct gcgcgcctca cggccgtatc 101220
gacaatatca acagcgcttc gatccggtgc gtgtgcgacg acgggtacgt gagcgactat 101280
aacgccgaca ccgaaactcc gtattgccgt ccgcgcaccg tgcgcgacgt aatgtacgac 101340
gagagttttt ttccgcgggc gccatgcgca gacggccaag ttcgtctgga tcatccggcg 101400
ctcaatgatt tttaccgcag acactttaga ctcgaagaca tttgcgtgat cgacccttgc 101460
tcggtggacc cgattagcgg gcaacgcaca tcgggacgct tatttcacca accaaccgta 101520
aatggtgtgg gaatcaacgg atgcaattgt ccggccgatg acgggttact gcccgtgttt 101580
aatcgacaca ccgccgacac gggcatggtt agacaaagcg accgcaccgt cgcgaacgct 101640
tgcttgcagc cgtttaacgt gcacatgtta tcgttgcgtc atgtggatta caaatttttc 101700
tggggccgca gcgaccacac cgagtttgcc gacgcggaca tggtgtttca agcgaatgtc 101760
aaccaactca gtcacgaacg gtatcgagcg attttgtact cgttgctcga gtcgcacccg 101820
gacgtaacag aaatcgtaac agtcaacatg ggtgtcatga aaatttccgt gtcatacgat 101880
accacattga aaaatatact attaccatct tctgttttta ggctatttag atttaaagaa 101940
agtggcactg ctcagccggt atgcttcttt ccaggcgtag gacggtgcat aaccgtcaat 102000
tccgattcgt gcatcaggcg acacgctggt ggtcaagtgt ggaccgcaga aacgttcacc 102060
aactcgtggt gtgtactgag tcgtgaaggt acgcatataa aagtttggag tcgcgcgtca 102120
cgatatccac gcggagacgc gcctgcagcg ttaagattgc gcggcttctt tctgaacaac 102180
gatcgcgaac gaaacacaat aagagcggtc actacaggcg acatgaccca agggcaacaa 102240
atagacgcat taacccaaat acttgaaact taccccaact actctgtata acaacatgag 102300
cattttaaaa gttgtagaag cgtgcaattt ggcacacact tttttaaaat tgggttattt 102360
atttagggcc aagacttgtt tggatatcgc tttagataat ttggaactat tgcgtcgaaa 102420
gactaacata aaagaagtgg cagtcatgtt aaacaagaaa actacagagt gtttgcaatt 102480
gaaacgaaaa atagataaaa aaattgcaca acgtgtttta ataaaaattt acactatcaa 102540
atgatgacat cataacgggt tcaatattct gtgtgcaaaa ataaatgaca tcatatttca 102600
aacttgtttt acgcgtaaaa ttctactggt aaaacaagtt tgagatatga tgtcatcatc 102660
acaaataata gtatgtaata aaataaacat atttgtgtgt aaatataatt tattacaaat 102720
aaattttaca ttgaatcaat ctgtcttcgt gtttgttgta aggtcttcga atcttgtgtt 102780
tcagcccctc gggatggtca aaatgcgccg tagtaattgt taatggatct ttcaacgatt 102840
ttttgcccat ggcgagtgtg acaaacgcgg ccacgacaaa cagcaggata atcagtttca 102900
tggtgttcta tattcgacaa tatatgggtc gcttctaaat caccttgtcc ccaaaagcct 102960
cttttatagt tttttagaac acgttgtgta ttccaacagt aattgttcca tctctttcaa 103020

```
cagccattca gcatccggtc gttgactgta atcatgctga attaatttac aaacaatttc 103080
ggtcaattta ggatggcctt gggataaact tgccggcatt tgctgtacat tgtttctaaa 103140
gttagttagc gtagtttcgc gttccaaagc agtcttgaag ggcattatca attcgaataa 103200
aacaatgccc aaactataca tgtcattttt gggggtgtac acttttttga tttgttctgg 103260
tgcagcgtac aaagttatat tttgagggtt gtttttgata aacgttttgt atagactgcc 103320
aaacatgccg cccacataca aatcaaagtc gggcccagtc atgaaaatat cttcgggatt 103380
aatattgtgg tgcacgatat ttacggaatg aatcgctttc acggcgctca ccaaatcaac 103440
aaacttgcta atataaaagc caaaatccgc cggaacttta atgttggtct ttgcaaaagt 103500
ttgcaaattg cgttgtttca aatagtcgct caacatgtac tcgtttagag gcgacgcaat 103560
atatatgcgg tgctgccgcg gattcaaata aaccaattgt tcgggtttca tggtatacag 103620
ttaagtgtta acgcgtcact aaattcagac acgagcgcac gccctatata catacaattt 103680
atcgcacaag atgcttaacg cgatctgttt ataaactaaa acgcactgca ataaatttta 103740
gcaagcattt gtatttaatc aatcgaaccg tgcactgata taagaattaa aaatgggttt 103800
gtttgcgtgt tgcacaaaat acacaaggct gtcgaccgac acaaaaatga agtttcccta 103860
tgttgcgttg tcgtacatca acgtgacgct gtgcacctac accgccatgt tggtgggata 103920
catggtaaca ttcaatgact ccagcgaatt gaaatattta caatactggt tgctgttgtc 103980
gtttttgatg tccgtggtgc taaacgctcc gactctgtgg acgatgctca aaaccacaga 104040
agcccatgaa gtaatttacg aaatgaagct gttccacgcc atgtacttta gtaacgtgct 104100
gttgaattat gtggtgtttt tggacaatca aatgggtaca aattttgttt ttgttaacaa 104160
tttaattcac tgttgtgtac tttttatgat atttgttgaa ttgcttatcc tgttgggcca 104220
cacaatgggc acgtacacgg attatcaata tgtcaaatcg tgttatatgg ttatattgtt 104280
tgtttcagtt atgagtgtta ctattgttat gggtttagag tgtttgaaaa cgaaactaat 104340
tgataacagt ttgatgttta acgcgtttgt gtgcgctttg tacattgtga ttgcaataat 104400
gtggtcttta aaaaataatt tgactagtta ttacgtttca aatttacaaa gtattcaagt 104460
tgttccgttt tcatacaacg atccgccgcc accgttctct aacattgtaa tggatgacat 104520
aaaaaataaa aaataattta taaaaatgtt ttttattctt tcacaattct gtaaattcta 104580
aacaaaaaat ataaatacaa acttattatg ttgtcgtcta aataaacatc aatttgtaaa 104640
tctggacacc tattcatatc attgatatta cagtctacta tacaacaatt aaaactaacc 104700
aaattatctt tacaacaatt aaagcaatta aaacaattta aataatcttc attgtcgtcg 104760
tataagttta tttgcactgt agacggtgtt acacagcgat ccattcgacg ttcgtgttcg 104820
atcaactttc tcgccaactt gtaccataaa aattgtttgg acaaaaagtt ttccaacaat 104880
ggtaacggcc aattcaacgt gacgatgcgc acgtcctcgg gtatgcattt gttaaaaaac 104940
acacagctcg ctttaccaaa cgaaagcaaa ggtactaaat atggcgccat tggctgattt 105000
gttattccaa gataattaca aataaactga tccgtcgtgg ggtgataact ggcaggtgtc 105060
agctttaaat aatcttcaac gttgttgtcg cgcaaaagtc tgcattttac acgcgttgtt 105120
aatcccacga cttttgcatg taaaatcgga tccaaatact gcagaatcgt gtctataatt 105180
tctaatggta aacgtatgcg ttttgctcgt gggcgctttg taacgctcga catcctaata 105240
acaactaaca caaaactaaa atgatactca atatattgct tttacagttc atctttaggt 105300
ttaaactgtg cgtttatcgc gttgagcaag tcgccgttat cggcatcaat ctcccaagca 105360
```

-continued

```
aacaggccgc ccaatttatt tcggtcgaca tatttaactt ttcctaacac agagtcgacg 105420
ctgtcaaacg aaatcaaatc acctttactt ttatcgaaaa cgtacgacgc ttgagcggcg 105480
ctgtcaaacg tgtacacata attgttgaga tctttttgaa tttgacgata atctacaaca 105540
ccgtcctccc acgtgcccga ccccggcccg ttgccagtgc cggaaaaata gttgtcattc 105600
gtataatttg ttacgccggt ccagccgcgg ccgtacatgg cgacgcccac aattattttg 105660
ttgggatcga cgccttgttt cagtaacgca tcgacagcgt agtgtgtagt gtatagctct 105720
tccgagttcc aacttggcgc gtagactgtt gtttggtagc ccaaatccgt gtttgaccaa 105780
gccccttaa aatcgtaact catgagaaat attttgccta atgacttttg cgcttcggcg 105840
tagtttacca cggcaatctt gtcgtaaccc gcgcttatag cgcttgttaa ttcgtaaacc 105900
ctgccggttt gcgcttcgag gtcgtctagc attgcgcgca gctcctccaa caacaaaatg 105960
tatgttttgg cgtcaccgtc cgcatcgccc aacgacgggt tagcccttt gccgcccgga 106020
aactcccaat cgatgtctac accgtcaaag aatttccaca cttgcagaaa ttccttaacc 106080
gaatctacaa aaacgtttct tttttcaaca tcgtgcataa aataaaatgg gtctgataga 106140
gtccagcctc ctattgaagg aagaattttt aaatgggggt ttgctaattt tgccgccatc 106200
aactgtccaa aattgccttt atacggctcg ttccaagcgg acacaccttt ttggggtttt 106260
tgtacggcgg cccacggatc gtgaatggca actttgaaat cttcgcgtcc cttgcacgat 106320
ctttgcaaag attcaaagct tccgggtatc gttttgaggg cgtcgtttat tccatcgccg 106380
ccgcagatgg gtatgaaacc atacaacaag tgtgataaat ttggcaaggg aactttgtct 106440
acgggaaagt tgcgcccgta cacaccccac tcaacaaagt acgcagcgac aattttatcc 106500
tctctcctgc caggtttgtt gttttccagc catgtgtatt cgagcggtgc cagatggccg 106560
ccgtcggtgt ctgcgacttt gaccaacacg ggatcgctca cggaacagcc gtcctcattg 106620
caaagtttga cacgcatgtt aaattgcccg ctcacaagaa ctttaatggt agccctttta 106680
ctttcggcgt cgcctttcca tacctgctgc tcgtcaaaca acacgtacgc tatgtcgcca 106740
atgtcgccgt tccagacgtt ccaactgact tgaacgtcga cttgttcttt aggctttatt 106800
aaattttcgt aagcggtggc ctcgtaattt atttctacga gcgcataatt gcgatcggcc 106860
caatcgatca ccggcgtgcc gggaatcgcg ttagaaacgg cgaccaacca caaaacgttt 106920
aacaatttgt acaacatttt aatttatctt aattttaagt tgtaattatt ttatgtaaaa 106980
aaatgaacaa aattttgttt tatttgtttg tgtacggcgt tgtaaacagc gcggcgtacg 107040
accttttgaa agcgcctaat tattttgaag aatttgttca tcgattcaac aaagattatg 107100
gtagcgaagt tgaaaaattg cgaagattca aaattttcca acacaattta aatgaaatta 107160
ttaataaaaa ccaaaacgat tcggccaaat atgaaataaa caaattctcg gatttgtcca 107220
aagacgaaac tatcgcaaaa tacacaggtt tgtctttgcc tattcagact caaaattttt 107280
gcaaagtaat agtcctagac cagccaccgg gcaaagggcc ccttgaattc gactggcgtc 107340
gtctcaacaa agtcactagc gtaaaaaatc agggcatgtg tggcgcctgc tgggcgtttg 107400
ccactctggc tagtttggaa agtcaatttg caatcaaaca taaccagttg attaatctgt 107460
cggagcagca aatgatcgat tgtgattttg tcgacgctgg ctgtaacggc ggcttgttgc 107520
acacagcgtt cgaagccatc attaaaatgg gcggcgtaca gctggaaagc gactatccat 107580
acgaagcaga caataacaat tgccgtatga actccaataa gtttctagtt caagtaaaag 107640
attgttatag atacattacc gtgtacgagg aaaaacttaa agatttgtta cgccttgtcg 107700
gccctattcc tatggccata gacgctgccg acattgttaa ctataaacag ggtattataa 107760
```

aatattgttt caacagcggt ctaaaccatg cggttctttt agtgggttat ggtgttgaaa 107820
acaacattcc atattggacc tttaaaaaca cttggggcac ggattgggga gaggacggat 107880
ttttcagggt acaacaaaac ataaacgcct gtggtatgag aaacgaactt gcgtctactg 107940
cagtcattta ttaatctcaa cacactcgct atttggaaca taatcatatc gtctcagtag 108000
ctcaaggtag agcgtagcgc tctggatcgt atagatcttg ctaaggttgt gagttcaagt 108060
ctcgcctgag atattaaaaa actttgtaat tttaaaaatt ttattttata atatacaatt 108120
aaaaactata caatttttta ttattacatt aataatgata caatttttat tattacattt 108180
aatattgtct attacggttt ctaatcatac agtacaaaaa taaaatcaca attaatataa 108240
ttacaaagtt aactacatga ccaaacatga acgaagtcaa tttagcggcc aattcgcctt 108300
cagccatgga agtgatgtcg ctcagactgg tgccgacgcc gccaaacttg gtgttctcca 108360
tggtggttat gaggttgctt ttttgttggg caataaacga ccagccgctg gcatctttcc 108420
aactgtcgtg ataggtcgtg ttgccgatgg tcgggatcca aaactcgacg tcgtcgtcaa 108480
ttgctagttc cttgtagttg ctaaaatcta tgcattgcga cgagtccgtg ttggccaccc 108540
aacgcccttc tttgtagatg ctgttgttgt agcaattact ggtgtgtgcc ggcggattgg 108600
tgcacggcat cagcaaaaac gtgtcgtccg acaaaaatgt tgaagaaaca gagttgttca 108660
tgagattgcc aatcaaacgc tcgtccacct tggccacgga gactatcagg tcgtgcagca 108720
tattgtttag cttgttgatg tgcgcatgca tcagctcaat gttcattttc agcaaatcgt 108780
tttcgtacat cagctcctct tgaatatgca tcaggtcgcc tttggtggca gtgtctccct 108840
ctgtgtactt ggctctaacg ttgtggcgcc aagtgggcgg ccgcttcttg actcggtgct 108900
cgactttgcg tttaatgcat ctgttaaact tgcagttcca cgtgttttta gaaagatcat 108960
atatatcatt gtcaatcaaa cagtgttcgc gtgtcaccga ctcggggtta tttttgtcat 109020
ctttaatgag cagacacgca gcttttattt ggcgcgtggt gaacgtagac ttttgtttga 109080
gaatcatact cacgccgtct cgatgaagca cagtgtccac ggtcacgttg atggggttgc 109140
cctcagcgtc caaaatgtat acctggcact cgtccgtgtc gtcctggcac tcgagcctgc 109200
tgtacatttt cgaagtggaa atgccgcatc gccacgattt gttgcacgtg tggtgcgcaa 109260
agtgattgtt attctgccgc ttcaccaact ctttgccttt gacccactgg ccgcggccct 109320
cgttgtcgcg aaaacagtcg tcgctgtcac tgccccaacg gtcgatcagc tcttcgccca 109380
cctcgcactg ctgcctgatg ctccacataa gcaaatcctc tttgcccaca ttcagcgttt 109440
tcatggtttc ttcgacgcgt gtgttgggat ccagcgagcc gccgttgtac gcatacgcct 109500
ggtagtaccc cttgtagccg ataatcacgt tttcgttgta gtccgtctcc acgatggtga 109560
tttccacgtc cttttgcagc gtttccttgg gcggggtaat gtccaagttt ttaatcttgt 109620
acggacccgt cttcatttgc gcgttgcagt gctccgccgc aaaggcagaa tgcgccgccg 109680
ccgccaaaag cacatataaa acaatagcgc ttaccatctt gcttgtgtgt tccttattga 109740
agccttggtg tgactgattt actagtagca ttgaggcatc ttatataccc gaccgttatc 109800
tggcctacgt gacacaaggc acgttgttag attaataatc ttatcttttt atcttaattg 109860
ataagattat ttttatctgg ctgttataaa aacgggatca tgaacacgga cgctcagtcg 109920
acatcgaaca cgcgcaactt catgtactct cccgacagca gtctggaggt ggtcatcatt 109980
accaattcgg acggcgatca cgatggctat ctggaactaa ccgccgccgc caaagtcatg 110040
tcaccttttc ttagcaacgg cagttcggcc gtgtggacca acgcggcgcc ctcgcacaaa 110100

```
ttgattaaaa acaataaaaa ttatattcat gtgtttggtt tatttaaata tctgtcaaat 110160
tacaatttaa ataataaaaa gcgtcctaaa gagtattaca cccttaaatc gattattagc 110220
gacttgctta tgggcgctca aggcaaagta tttgatccgc tttgcgaagt aaaaacgcaa 110280
ctgtgtgcga ttcaggagag tctcaacgag gctatttcga ttttgaacgt tcatagcaac 110340
gatgcggccg ccaacccgcc tgcgccagac attaacaagt tgcaagaact gatacaagat 110400
ttgcagtctg aatacaataa aaaaattacc tttaccactg atacaatttt ggagaattta 110460
aaaaatataa aggatttaat gtgcctgaat aaataataat aagggttttg tacgatttca 110520
acaatgaact tttgggccac gtttagcatt tgtctggtgg gttatttggt gtacgcggga 110580
cacttgaata acgagctaca agaaataaaa tcaatattag tggtcatgta cgaatctatg 110640
gaaaagcatt tttccaatgt ggtagacgaa attgattctc ttaaaacgga cacgtttatg 110700
atgttgagca acttgcaaaa taacacgatt cgaacgtggg acgcagttgt aaaaaatggc 110760
aaaaaaatat ccaatctcga cgaaaaaatt aacgtgttat taacaaaaaa cggggtagtt 110820
aacaacgtgc taaacgttca ataaacgctt atcactaagt taatatacta aaaatcacat 110880
agtcactaca atatttcaaa atatgaagcc gacgaataac gttatgttcg acgacgcgtc 110940
ggtcctttgg atcgacacgg actacattta tcaaaattta aaaatgcctt tgcaggcgtt 111000
tcaacaactt ttgttcacca ttccatctaa acatagaaaa atgatcaacg atgcgggcgg 111060
atcgtgtcat aacacggtca aatacatggt ggacatttac ggagcggccg ttctggtttt 111120
gcgaacgcct tgctcgttcg ccgaccagtt gttgagcaca tttattgcaa acaattattt 111180
gtgctacttt taccgtcgtc gccgatcacg atcacgctca cgatcacgct cgcgatcacg 111240
ttctcctcat tgcagacctc gttcgcgctc tcctcattgc agacctcgtt cgcgatctcg 111300
gtcccggtct agatcgcggt cacgttcatc gtctcccagg cgagggcgtc gacaaatatt 111360
cgacgcgctg gaaaagattc gtcatcaaaa cgacatgttg atgagcaacg tcaaccaaat 111420
aaatctcaac caaactaatc aatttttaga attgtccaac atgatgacgg gcgtgcgcaa 111480
tcaaaacgtg cagctcctcg cggcgttgga aaccgctaaa gatgttattt tgaccagatt 111540
aaacacattg cttgccgaga ttacagactc gttacccgac ttgacgtcca tgttagataa 111600
attagctgaa caattgttgg acgccatcaa cacggtgcag caaacctgcg caacgagttg 111660
aacaacacca actctatttt gaccaattta gcgtcaagcg tcacaaacat caacggtacg 111720
ctcaacaatt tgctagccgc tatcgaaaac ttagtaggcg gcggcggcgg tggcaatttt 111780
aacgaagccg acagacaaaa actggacctc gtgtacactt tggttaacga aatcaaaaat 111840
atactcacgg gaacgctgac aaaaaaataa gcatgtccga caaaacacca acaaaaaagg 111900
gtggcagcca tgccatgacg ttgcgagagc gcggcgtaac aaaacccccca aaaaagtctg 111960
aaaagttgca gcaatacaag aaagccatcg ctgccgagca aacgctgcgc accacagcag 112020
atgtttcttc tttgcagaac cccggggaga gtgccgtttt tcaagagttg gaaagattag 112080
agaatgcagt tgtagtatta gaaaatgaac aaaaacgatt gtatcccata ttagatacgc 112140
ctcttgataa ttttattgtc gcattcgtga atccgacgta tcccatggcc tattttgtca 112200
ataccgatta caaattaaaa ctagaatgtg ccagaatcag aagcgattta ctttacaaaa 112260
acaaaaacga agtcgctatc aacaggccta agatatcgtc ttttaaattg caattgaaca 112320
acgtaatttt agacactata gaaactattg aatacgattt acaaaataaa gttctcacaa 112380
ttactgcacc tgttcaagat caagaactaa gaaaatccat tatttatttt aatattttaa 112440
atagtgacag ttgggaagta ccaaagtata tgaaaaaatt gtttgatgaa atgcaattgg 112500
```

aacctcccgt cattttacca ttaggtcttt agatttggta aggctagcac gtcgacatca 112560
tgtttgcgtc gttgacctca gagcaaaagc tgttattaaa aaaatataaa tttaacaatt 112620
atgtgaaaac gatcgagttg agtcaagcgc agttggctca ttggcgttca aacaaagata 112680
ttcagccaaa acctttggat cgtgcagaaa ttttacgtgt cgaaaaggcc accaggggac 112740
aaagcaaaaa tgagctgtgg acgctattgc gtttggatcg caacacagcg tctgcatcgt 112800
ccaactcgtc cggcaacatg ttacaacgac cagcgctttt gtttggaaac gcgcaagaaa 112860
gtcacgtcaa agaaaccaac ggcatcatgt tagaccacat gcgcgaaatc atagaaagta 112920
aaattatgag cgcggtcgtt gaaacggttt tggattgcgg catgttcttt agccccttgg 112980
gtttgcacgc cgcttcgccc gatgcgtatt tttctctcgc cgacggaacg tggatcccag 113040
tggaaataaa atgtccgtac aattaccgag acacgaccgt ggagcagatg cgtgtcgagt 113100
tggggaacgg caatcgcaag tatcgcgtga aacacaccgc gctgttggtt aacaagaaag 113160
gcacgcccca gttcgaaatg gtcaaaacgg atgcgcatta caagcaaatg caacggcaga 113220
tgtatgtgat gaacgcgcct atgggctttt acgtggtcaa attcaaacaa aatttggtgg 113280
tggtttctgt gccgcgcgac gaaacgttct gcaacaaaga actgtctacg gaaaacaacg 113340
cgtacgtggc gtttgccgtg gaaaactcca actgcgcgcg ctaccaatgc gccgacaagc 113400
gacggctttc attcaaaacg cacagctgca atcacaacta tagtggtcaa gaaatcgatg 113460
ctatggtcga tcgcggaata tatttagatt atggacattt aaaatgtgcg tactgtgatt 113520
ttagctcaga cagtcgggaa acgtgcgatt ctgttttaaa acgcgagcac accaactgca 113580
aaagttttaa cttgaaacat aaaaactttg acaatcctac atactttgat tatgttaaaa 113640
gattgcaaag tttgctaaag agtcaccact ttagaaacga cgctaaaaca cttgcctatt 113700
ttggttacta tttaactcat acaggaaccc tgaagacctt ttgctgcgga tcgcaaaact 113760
cgtcgcccac caaacacgat catttaaacg actgtgtata ttatttggaa ataaaataaa 113820
cctttatatt atatataatt cttttattta tacatttgtt tatacaattt tatttacgac 113880
aaatattgac tcgttgttca gaaagtttaa taagcttgtc aatttcttcg gcttgcaaag 113940
ggctgccaac gcgttcgttt tgaatgcgcg taatccggtt tacggtattg ttggcgcgaa 114000
caataaactc ctcaactggc aaattaacaa ttttgtttgc gtactcattg tgcactgcgg 114060
ccaggttttg tagaatgttt tcgggaaaaa tggcaattct attaaatttg acatgttttt 114120
gattgtatac atagttttga tattcttcca gcgtaggata tttgtttaaa ctcttgacgc 114180
attcaatgta caatttgtgc agtgacaaaa ttctgttaaa atccaaacga gaacatttct 114240
caaaagttat ttcttgaccg ttgaaatgta cactttgcaa ttgtttcaat aaactgtcgt 114300
aaaaagtttt tccttcttca agcacaaacg cggggcgcat cgtgttatct acaacgctta 114360
tgtacttgtc aaaatcttca attatatgat agaaatacaa atatctctcc gcgtttatgg 114420
acgtgtcgtt taaaacatgt tcgtcaacaa ctccgttatg atttactttc aaaaatttca 114480
aatcttgcaa agcgtccgcg ttggtcaact tgttgataat aaatttgtct ttgcattcaa 114540
acgctctgtt tgcaatccac tccacagcgt ccaaaacgga catgcgttta aacatgttga 114600
tacgttttag acaatacgct cgttttttta ccgcctcaac gttcacgtcc gtgtagtcgc 114660
accattgcag gatttgcaac atgtcctcgg caaaatgcgc gaactgccgc agcttttcct 114720
ttccaaaatg ttgattgtcg tgtttaaaaa gcaacgttga aatttccgag acataccaca 114780
aagccgtggg caattttact ttgatcagcg gctccatagc caggttgctg aacccgatca 114840

```
tgcattccgt gttgttaatg cggtaaatga catagcgttt aaagtagtcc tttacattat 114900
cgtcaatgta ttctgcgtcg tttatgtgct tgtacagcaa atagtacata aggcccgcgt 114960
taaacgcgac ctttttagcg tcaaaatacg tgcacgccaa cacgtaatcg ttgtattcgt 115020
cgaattgctc gttgggcact atggcgcccg taaaagggcg tctgctgcgc ggtgacaaac 115080
gcgttccatg ctgaatcaac tgcttcaaac tttccaaatt ataacaatat tcaattgaat 115140
ttttaatctc tttattttgg ctccataaaa gaggaaactc gagtcggctt ttaaacttgg 115200
tcaaactgcc ctgaattgtt tcaaacaagt tgtaatgtgt taacaatatg gccggcacac 115260
cgctatcgtt ggctaaaata caatcgggga atcgaatatt ttctacgttg ctgtaatcgt 115320
acgcttcgtc gtcgtcgttg gcaacaacat cgtcggtttc ggcgttaacg ctcgctaact 115380
tgttctgata gtgtaaattt ttcattacat caaaagcgta tgacttgttg cgattgtgca 115440
aataatttat ggccgtgcta atggtgctgt cgataatttt atcaaaattg agaacatcgg 115500
cgttatacaa cgttttataa aattctgttg acttgaacgt gtttacaaac tcatttttat 115560
ttttaatctg gtcaaaattc atactagaat tgttagtttg tttgatttcg ctgaatagcc 115620
gctggcggag acgcttcagc ttgtccacct cgtttaacac gttggcgtcc gtcggcatgg 115680
aattgataaa tttgaaccga acaaaagaca gcagttcatc ttttttcgat ataaaatttt 115740
cggttgtaat gatatcgtag ttaaattctt tggttaaatt gacccattcg accatttcat 115800
cgttgcgata aatcttgcag tccgagttgt tgacaaacgc cgaggcaacg gacaaatcaa 115860
tctgttccgt gttattattg atggcataaa acacaatgcg ttcgaaacta aacggttttt 115920
cgtttagcaa atttttgcaa acgtttgcct catttttgga aatttggccg tcggtcacca 115980
tgtacaaaag tttcaacttg ccgtcgagca agtttatatt cttgtgaatc cactttatga 116040
attcgctggg cctggtgtca gtaccctcgc cattgcggcg caaataacga ctcttgacgt 116100
ctccgatttc tttttggcgg caataagcac tccaatgcaa atacaaaact ttgtcgcaac 116160
tactgatgtt ttcgatttca ttctgaaatt gttctaaagt ttgtaacgcg ttcttgttaa 116220
agtaatagtc cgagtttgtc gacaaggaat cgtcggtggc gtacacgtag tagttaatca 116280
tcttgttgat tgatatttaa ttttggcgac ggatttttat atacacgagc ggagcggtca 116340
cgttctgtaa catgagtgat cgtgtgtgtg ttatctctgg cagcgcgata gtggtcgcga 116400
aaattacacg cgcgtcgtaa cgtgaacgtt tatattataa atattcaacg ttgcttgtat 116460
taagtgagca tttgagcttt accattgcaa aatgtgtgta atttttccgg tagaaatcga 116520
cgtgtcccag acgattattc gagattgtca ggtggacaaa caaaccagag agttggtgta 116580
cattaacaag attatgaaca cgcaattgac aaaacccgtt ctcatgatgt ttaacatttc 116640
gggtcctata cgaagcgtta cgcgcaagaa caacaatttg cgcgacagaa taaaatcaaa 116700
agtcgatgaa caatttgatc aactagaacg cgattacagc gatcaaatgg atggattcca 116760
cgatagcatc aagtatttta aagatgaaca ctattcggta agttgccaaa atggcagcgt 116820
gttgaaaagc aagtttgcta aaattttaaa gagtcatgat tataccgata aaaagtctat 116880
tgaagcttac gagaaatact gtttgcccaa attggtcgac gaacgcaacg actactacgt 116940
ggcggtatgc gtgttgaagc cgggatttga gaacggcagc aaccaagtgc tatctttcga 117000
gtacaacccg attggtaaca aagttattgt gccgtttgct cacgaaatta acgacacggg 117060
actttacgag tacgacgtcg tagcttacgt ggacagtgtg cagtttgatg gcgaacaatt 117120
tgaagagttt gtgcagagtt taatattgcc gtcgtcgttc aaaaattcgg aaaaggtttt 117180
atattacaac gaagcgtcga aaaacaaaag catgatctac aaggctttag agtttactac 117240
```

agaatcgagc tggggcaaat ccgaaaagta taattggaaa attttttgta acggttttat 117300
ttatgataaa aaatcaaaag tgttgtatgt taaattgcac aatgtaacta gtgcactcaa 117360
caaaaatgta atattaaaca caattaaata aatgttaaaa tttattgcct aatattattt 117420
tgtcattgct tgtcatttat taatttggat gatgtcattt gtttttaaaa ttgaactggc 117480
tttacgagta gaattctacg cgtaaaacac aatcaagtat gagtcataat ctgatgtcat 117540
gttttgtaca cggctcataa ccgaactggc tttacgagta gaattctact tgtaatgcac 117600
gatcagtgga tgatgtcatt tgtttttcaa atcgagatga tgtcatgttt tgcacacggc 117660
tcataaactc gctttacgag tagaattcta cgtgtaacgc acgatcgatt gatgagtcat 117720
ttgttttgca atatgatatc atacaatatg actcatttgt ttttcaaaac cgaacttgat 117780
ttacgggtag aattctactt gtaaagcaca atcaaaaaga tgatgtcatt tgtttttcaa 117840
aactgaactc gctttacgag tagaattcta cgtgtaaaac acaatcaaga aatgatgtca 117900
tttgttataa aaataaaagc tgatgtcatg ttttgcacat ggctcataac taaactcgct 117960
ttacgggtag aattctacgc gtaaaacatg attgataatt aaataattca tttgcaagct 118020
atacgttaaa tcaaacggac gttatggaat tgtataatat taaatatgca attgatccaa 118080
caaataaaat tgtaatagag caagtcgaca atgtggacgc gtttgtgcat attttagaac 118140
cgggtcaaga agtgttcgac gaaacgctaa gccagtacca ccaatttcct ggcgtcgtta 118200
gttcgattat tttcccgcaa ctcgtgttaa acacaataat tagcgttttg agcgaagacg 118260
gcagtttgct cacgttgaaa ctcgaaaaca cttgttttaa ttttcacgtg tgcaataaac 118320
gctttgtgtt tggcaatttg ccagcggcgg tcgtgaataa tgaaacgaag caaaaactgc 118380
gcattggagc tccaattttt gccggcaaaa agctggtttc ggtcgtgacg gcgtttcatc 118440
gtgttggcga aaacgaatgg ctgttaccgg tgacgggaat tcgagaggcg tcccagctgt 118500
cgggacatat gaaggtgctg aacggcgtcc gtgttgaaaa atggcgaccc aacatgtccg 118560
tctacgggac tgtgcaattg ccgtacgata aaattaaaca gcatgcgctc gagcaagaaa 118620
ataaaacgcc aaacgcgttg gagtcttgtg tgctatttta caaagattca gaaatacgca 118680
tcacttacaa caagggggac tatgaaatta tgcatttgag gatgccggga cctttaattc 118740
aacccaacac aatatattat agttaaataa gaattattat caaatcattt gtatattaat 118800
taaaatacta tactgtaaat tacattttat ttacaatcat gtcaaagcct aacgttttga 118860
cgcaaatttt agacgccgtt acggaaacta acacaaaggt tgacagtgtt caaactcagt 118920
taaacgggct ggaagaatca ttccagcttt tggacggttt gcccgctcaa ttgaccgatc 118980
ttaacactaa gatctcagaa attcaatcca tattgaccgg cgacattgtt ccggatcttc 119040
cagactcact aaagcctaag ctgaaaaccc aagcttttga actcgattca gacgctcgtc 119100
gtggtaaacg cagttccaag taaatgaatc gtttttaaaa taacaaatca attgttttat 119160
aatattcgta cgattctttg attatgtaat aaaatgtgat cattaggaag attacgaaaa 119220
atataaaaaa tatgagttct gtgtgtataa caaatgctgt aaacgccaca attgtgtttg 119280
ttgcaaataa acccagtatt atttgattaa aattgttgtt ttctttgttc atagacaata 119340
gtgtgttttg cctaaacgtg tactgcataa actccatgcg agtgtatagc gagctagtgg 119400
ctaacgcttg ccccaccaaa gtagattcgt caaaatcctc aatttcatca ccctcctcca 119460
agtttaacat ttggccgtcg gaattaactt ctaaagatgc cacataatct aataaatgaa 119520
atagagattc aaacgtggcg tcatcgtccg tttcgaccat ttccgaaaag aactcgggca 119580
taaactctat gatttctctg gacgtggtgt tgtcgaaact ctcaaagtac gcagtcagga 119640
acgtgcgcga catgtcgtcg ggaaactcgc gcggaaacat gttgttgtaa ccgaacgggt 119700
cccatagcgc caaaaccaaa tctgccagcg tcaatagaat gagcacgatg ccgacaatgg 119760
agctggcttg gatagcgatt cgagttaacg ctttggcagt cacggtcagc gttttgatgg 119820
cgatcacgtt gagcgagtgc actaacgcgg ctttgtaagt ctctcccaac atgcgcacgg 119880
tcacgcgccg agtcgtgcta agcaacatgt gtttcatggc cggaatgaga gaagtgttaa 119940
ttttttcaa catgctttta aacccggaca ttagcatatc aaagccaatg tccgtagcaa 120000
taccgaaaac gagcgcgtaa tcttccaaaa acgatgttat aattgactcc aagtcttggt 120060
cgctgattga acggtcgagc gcctcgaaat gttcgacacg tgcacgttcg ttaccgcggt 120120
aattgtatgc gatcggagtt ttagtaaagc cggtttcggc cgtgtacgtg atctggacgg 120180
gcgacccgtt gacgatcatg cccaaatcgt ttagtgttgg atttttgtta aaaagttttt 120240
caaattccaa gtctgtggcg ttatcgcgca cgctgcgcca ttgcgctagt attgcgttgg 120300
agtccacgtt gggtcgtggc ggtagtatgc tggaaggcgc tttgtaatca aaatcgcgca 120360
gttcgctaaa aatgttgttg gccagcattt tgaaagtgac aaagatcgtg tcgcccagca 120420
cgaatccgat gagcgattcc caccatctaa acgaacaacc gccgttgaat agctctctgc 120480
cgaaacgtcg acagtaggct tcgttgaatt cgcctttaaa gcgttcggga aacaaggggt 120540
cgggatcggg ccgaacgtta aaagccggca catcgtccac gcccatgatc gtgtgttctt 120600
cggtgcgcaa gtatgggctg ttaaagtaca ttttggacag cgagtccact aagatgcatt 120660
tgttgtcgag cgtgtatcta aactcggcag actgaacttg ggtttcggcg ccttcacgca 120720
tggccgccgc cctgtccagg tggtagcacg cgggctgcgc gtaacccacg ctagtctcgg 120780
aggtctgcat gtacatgaac ggcgtcgtgt tggacacgac gccggtttcg tgaaacggat 120840
agcagctcat gcttacacac ccgcgcttgc tgaaagccag tttgacggcc agcgctttgt 120900
cggccaattt cggcggcaca taataatcgt cgtcacttga cgcgggacgc agcgtgtagt 120960
cgattagtat atgcggaaac ctggtgcgcc atctcgaaat aaactcgaga cgatgcatat 121020
gtatggcata cctactggca ttagttaaat cgacggctgt taaaaccgcc atgttatata 121080
ggacttaaaa taaacaacaa tatataatga aatatttatt agattatatt atagcaatac 121140
atttacattt attataacaa tactttttat ttaatctgat tatattataa cgatacattt 121200
ttatttagac attgttattt acaatattaa ttaacttttt atacattttt aaatcataat 121260
atataatcat ttcgttgtgc atttcaaagc ttttgatagc ttcaaagtaa tacatgaatt 121320
tagagtattc aggaaaatga taaacgttgg taaacccgca tttggtacaa tataacacgg 121380
gatttttata atacagttta gttttttac acaatttgca atagttgtta gttgtaggtt 121440
tcaaaggaaa cgtgattgcg ccgtccaata cctgggtaaa ctttttgact ttaacagtgg 121500
caaacacggt tcctttgata cccgaaaatc ggttgtcttg cagagcggcc atcatttcgc 121560
ttggctcttg aagtataaaa cagttgacgt catccaccac gtcgggtctg gtgcacatgc 121620
ttcggtagcg ctgcaacact atattggtgt atgtttccct gagaacgaga ccgccggtgg 121680
tgctaagatc gattgtttga atgcgctcgt tgggctcttt gtgatttcga attatgcgcc 121740
gaattatttc aaacactttg cagttgtgat cgtcaattct caattcttta acttccgtcg 121800
tgtgctctaa acttacaggg aaaatgtatt ggtaaaaaaa cctctctctg gctaaatagc 121860
tgaggtcgac caaattgata gaaggatata tttcgtacga ggtttttgga acgttgtgat 121920
atagatagca tttttgacag cagatgtcta tgcggtcagg atcgtccaac ggcttttcga 121980

```
tgtgaaccac aacatacaaa aaccattcgc gcgtgttgtc tttgaatcta taattgcaag 122040
tggtgcatcg cgaatcgctc atgtgctcca tagtcttctt gtatttcaca ggcctgcttg 122100
caaatttgcc cgtcatgcgc atatctttgc tgtttatgta gcccataatg taattggtgg 122160
aaaattttag cgtggctttc atgatgtcgc gttctaaatc gctcatgaaa tgcatacgta 122220
gatcgcgctc ttgtttgaaa tccagtttgt cgctgtacgc gggcaaacct tcaaacttgt 122280
tcccaaactc gggcggcaca aaatatccat cttttctgtt gacgactggt tttttactta 122340
caatgctgct gtgctccaac ggcttggccg gagaggtgca cataggctgt ttaggcggag 122400
agatgcgcgt aggtggtttg atgttagatt ttggcggcgg acgaacaggc gacggcggcg 122460
agttggcggc aggcgctggc aaagatttgg cacgaccctt gcccccggtc cttggcgcgt 122520
caaaaatgtt attctctcga aaaaaacggt tcattgtaac tgttagttag cactcagaaa 122580
tcaacacgat actgtgcacg ttcagccatc gagaggcttt atatatggaa accttatcta 122640
tagagataag attgtatatg cgtaggagag cctggtcacg taggcacttt gcgcacggca 122700
ctagggctgt ggaggggaca ggctatataa agcccgtttg cccaactcgt aaatcagtat 122760
caattgtgct ccggcgcaca cgctcgcttg cgcgccggat agtataagta attgataacg 122820
ggcaacgcaa catgataaga accagcagtc acgtgctgaa cgtccaggaa aatataatga 122880
cgtcaaactg tgcgtcatcg ccatattcgt gcgaggcaac gtccgcttgc gcagaagctc 122940
agcaggtaat gatcgataac tttgttttct ttcacatgta caacgccgac atacaaattg 123000
acgcaaagct gcaatgcggc gtgcgctcgg ccgcgtttgc aatgatcgac gataaacatt 123060
tggaaatgta caagcataga atagagaata aattttttta ttactatgat caatgtgccg 123120
acattgccaa acccgaccgt ctgcccgatg acgacggcgc gtgctgtcac cattttattt 123180
ttgatgccca acgtattatt caatgtatta aagagattga aagcgcgtac ggcgtgcgtg 123240
atcgcggcaa tgtaatagtg ttttatccgt acttgaaaca gttgcgagac gcgttgaagc 123300
taattaaaaa ctcttttgcg tgttgtttta aaattataaa ttctatgcaa atgtacgtga 123360
acgagttaat atcaaattgc ctgttgttta ttgaaaagct ggaaactatt aataaaactg 123420
ttaaagttat gaatttgttt gtagacaatt tggttttgta cgaatgcaat gtttgtaaag 123480
aaatatctac ggatgaaaga tttttaaagc caaaagaatg ttgcgaatac gctatatgca 123540
acgcgtgctg cgttaacatg tggaagacgg ccaccacgca cgcaaaatgt ccagcgtgca 123600
ggacatcgta taaataagca cgcaacgcaa aatgagtggt ggcggcaact tgttgactct 123660
ggaaagagat cattttaaat atttattttt gaccagctat tttgatttaa aagataatga 123720
acatgttcct tcagagccta tggcatttat tcgcaattac ttgaattgca cgtttgattt 123780
gctagacgat gccgtgctca tgaactattt caattacttg caaagcatgc aattgaaaca 123840
tttggtgggc agcacgtcga caaacatttt caagtttgta aagccacaat ttagatttgt 123900
gtgcgatcgc acaactgtgg acattttaga atttgacacg cgcatgtaca taaaacccgg 123960
cacgcccgtg tacgccacga acctgttcac gtccaatccc cgcaagatga tggctttcct 124020
gtacgctgaa tttggcaagg tgtttaaaaa taaaatattc gtaaacatca acaactacgg 124080
ctgcgtgttg gcgggcagtg ccggtttctt gttcgacgat gcgtacgtgg attggaatgg 124140
tgtgcgaatg tgtgcggcgc cgcgattaga taacaacatg catccgttcc gactgtatct 124200
actgggcgag gacatggcta agcactttgt cgataataat atactaccgc cgcacccttc 124260
taacgcaaag actcgcaaaa tcaacaattc aatgtttatg ctgaaaaact tttacaaagg 124320
```

```
tctgccgctg ttcaaatcaa agtacacggt ggtgaacagc actaaaatcg tgacccgaaa 124380
acccaacgat atatttaatg agatagataa agaattaaat ggcaactgtc cgtttatcaa 124440
gtttattcag cgcgactaca tattcgacgc ccagtttccg ccagatttgc ttgatttgct 124500
aaacgaatac atgaccaaaa gctcgatcat gaaaataatt accaagtttg tgattgaaga 124560
aaaccccgct atgagcggtg aaatgtctcg cgagattatt cttgatcgct actcagtaga 124620
caattatcgc aagctgtaca taaaaatgga aataaccaac cagtttcctg tcatgtacga 124680
tcatgaatcg tcgtacattt ttgtgagcaa agactttttg caattgaaag gcactatgaa 124740
cgcgttctac gcgcccaagc agcgtatatt aagtattttg gcggtgaatc gtttgtttgg 124800
cgccacggaa acgatcgact ttcatcccaa cctgctcgtg taccggcaga gttcgccgcc 124860
ggtccgtttg acgggcgacg tgtatgttgt tgataagaac gaaaaagttt ttttggtcaa 124920
acacgtgttc tcaaacacgg tgcctgcata tcttttaata agaggtgatt acgaaagttc 124980
gtctgacttg aaatcccttc gcgatttgaa tccgtgggtt cagaacacgc ttctcaaatt 125040
attaatcccc gactcggtac aataatatga tttacactga tcccactact ggcgctacga 125100
ctagcacaga cgtcgtccgt ccacaaacta tttaaacagg ctaactccaa acatgttctt 125160
gaccatcttg gctgtagtag taattattgc tttaataatt atatttgttc aatctagcag 125220
taatggaaac agctcggggg gtaatgtacc tccaaacgcc ctgggggggtt ttgtaaatcc 125280
tttaaacgct accatgcgag ctaatccctt tatgaacacg cctcaaaggc aaatgttgta 125340
gataagtgta taaaaaatga aacgtatcaa atgcaacaaa gttcgaacgg tcaccgagat 125400
tgtaaacagc gatgaaaaaa tccaaaagac ctacgaattg gctgaatttg atttaaaaaa 125460
tctaagcagt ttagaaagct atgaaactct aaaaattaaa ttggcgctca gcaaatacat 125520
ggctatgctc agcaccctgg aaatgactca accgctgttg gaaatattta gaaacaaagc 125580
agacactcgg cagattgccg ccgtggtgtt tagcacatta gcttttatac acaatagatt 125640
ccatcccctt gttactaatt ttactaacaa aatggagttt gtggtcactg aaaccaacga 125700
cacaagcatt cccggagaac ccattttgtt tacggaaaac gaaggtgtgc tgctgtgttc 125760
cgtggacaga ccgtctatcg ttaaaatgct aagccgcgag tttgacaccg aggctttagt 125820
aaactttgaa aacgacaact gcaacgtgcg gatagccaag acgtttggcg cctctaagcg 125880
caaaaacacg acgcgcagcg atgattacga gtcaaataaa caacccaatt acgatatgga 125940
tttgagcgat tttagcataa ctgaggttga agccactcaa tatttaactc tgttgctgac 126000
cgtcgaacat gcctatttac attattatat ttttaaaaat tacggggtgt ttgaatattg 126060
caaatcgcta acggaccatt cgctttttac caacaaattg cgatcgacaa tgagcacaaa 126120
aacgtctaat ttactgttaa gcaaattcaa atttaccatt gaagattttg acaaaataaa 126180
ctcaaattct gtaacatcag ggtttaatat atataatttt aataaataat taaataatat 126240
acaatgtttt tattaattat atttttaata ttaattaaaa gtattaatat ttaaaaaaat 126300
gaatcaaatt catctaaagt gtcacagcga taaaatttgt cctaaagggt attttggcct 126360
caacgccgat ccctatgatt gcacggcgta ttatctgtgt ccgcataaag tgcaaatgtt 126420
ttgcgaatta aatcacgaat ttgacttgga ctccgccagc tgcaagccta tcgtgtacga 126480
tcacacgggc agcgggtgta cggctcgcat gtatagaaac ttgttactat gaagagcggg 126540
tttccagttg cacaacacta ttatcgattt gcagttcggg acataaatgt ttaaatatat 126600
cgatgtcttt gtgatgcgcg cgacattttt gtaggttatt gataaaatga acggatacgt 126660
tgcccgacat tatcattaaa tccttggcgt agaatttgtc gggtccattg tccgtgtgcg 126720
```

ctagcatgcc cgtaacggac ctcgtacttt tggcttcaaa ggttttgcgc acagacaaaa 126780
tgtgccacac ttgcagctct gcatgtgtgc gcgttaccac aaatcccaac ggcgcagtgt 126840
acttgttgta tgcaaataaa tctcgataaa ggcgcggcgc gcgaatgcag ctgatcacgt 126900
acgctcctcg tgttccgttc aaggacggtg ttatcgacct cagattaatg tttatcggcc 126960
gactgttttc gtatccgctc accaaacgcg tttttgcatt aacattgtat gtcggcggat 127020
gttctatatc taatttgaat aaataaacga taaccgcgtt ggttttagag ggcataataa 127080
aagaaatatt gttatcgtgt tcgccattag ggcagtataa attgacgttc atgttggata 127140
ttgtttcagt tgcaagttga cactggcggc gacaagatcg tgaacaacca agtgactatg 127200
acgcaaatta attttaacgc gtcgtacacc agcgcttcga cgccgtcccg agcgtcgttc 127260
gacaacagct attcagagtt ttgtgataaa caacccaacg actatttaag ttattataac 127320
catcccaccc cggatggagc cgacacggtg atatctgaca gcgagactgc ggcagcttca 127380
aactttttgg caagcgtcaa ctcgttaact gataatgatt tagtggaatg tttgctcaag 127440
accactgata atctcgaaga agcagttagt tctgcttatt attcggaatc ccttgagcag 127500
cctgttgtgg agcaaccatc gcccagttct gcttatcatg cggaatcttt tgagcattct 127560
gctggtgtga accaaccatc ggcaactgga actaaacgga agctggacga atacttggac 127620
aattcacaag gtgtggtggg ccagtttaac aaaattaaat tgaggcctaa atacaagaaa 127680
agcacaattc aaagctgtgc aacccttgaa cagacaatta atcacaacac gaacatttgc 127740
acggtcgctt caactcaaga aattacgcat tattttacta atgattttgc gccgtattta 127800
atgcgtttcg acgacaacga ctacaattcc aacaggttct ccgaccatat gtccgaaact 127860
ggttattaca tgtttgtggt taaaaaaagt gaagtgaagc cgtttgaaat tatatttgcc 127920
aagtacgtga gcaatgtggt ttacgaatat acaaacaatt attacatggt agataatcgc 127980
gtgtttgtgg taacttttga taaaattagg tttatgattt cgtacaattt ggttaaagaa 128040
accggcatag aaattcctca ttctcaagat gtgtgcaacg acgagacggc tgcacaaaat 128100
tgtaaaaaat gccatttcgt cgatgtgcac cacacgttta aagctgctct gacttcatat 128160
tttaatttag atatgtatta cgcgcaaacc acatttgtga ctttgttaca atcgttgggc 128220
gaaagaaaat gtgggtttct tttgagcaag ttgtacgaaa tgtatcaaga taaaaattta 128280
tttactttgc ctattatgct tagtcgtaaa gagagtaatg aaattgagac tgcatctaat 128340
aatttctttg tatcgccgta tgtgagtcaa atattaaagt attcggaaag tgtgcagttt 128400
cccgacaatc ccccaaacaa atatgtggtg gacaatttaa atttaattgt taacaaaaaa 128460
agtacgctca cgtacaaata cagcagcgtc gctaatcttt tgtttaataa ttataaatat 128520
catgacaata ttgcgagtaa taataacgca gaaaatttaa aaaaggttaa gaaggaggac 128580
ggcagcatgc acattgtcga acagtatttg actcagaatg tagataatgt aaagggtcac 128640
aattttatag tattgtcttt caaaaacgag gagcgattga ctatagctaa gaaaaacaaa 128700
gagttttatt ggatttctgg cgaaattaaa gatgtagacg ttagtcaagt aattcaaaaa 128760
tataatagat ttaagcatca catgtttgta atcggtaaag tgaaccgaag agagagcact 128820
acattgcaca ataatttgtt aaaattgtta gctttaatat tacagggtct ggttccgttg 128880
tccgacgcta taacgtttgc ggaacaaaaa ctaaattgta aatataaaaa attcgaattt 128940
aattaattat acatatattt tgaatttaat taattataca tatattttat attatttttg 129000
tcttttatta tcgaggggcc gttgttggtg tggggttttg catagaaata acaatgggag 129060
ttggcgacgt tgctgcgcca acaccacctc ctcctcctcc tttcatcatg tatctgtaga 129120
taaaataaaa tattaaacct aaaaacaaga ccgcgcctat caacaaaatg ataggcatta 129180
acttgccgct gacgctgtca ctaacgttgg acgatttgcc gactaaacct tcatcgccca 129240
gtaaccaatc tagacccaag tcgccaacta aatcaccaaa cgagtaaggt tcgatgcaca 129300
tgagtgtttg gcccgcagga agatcgctaa tatctacgta ttgaggcgaa tctgggtcgg 129360
cggacggatc gctgccgcga caaactgttt tttctacttc atagttgaat ccttggcaca 129420
tgttggttag ttcgggcgga ttgttaggca acaaggggtc gaatgggcaa atggtaacat 129480
ccgactgatt tagattgggg tcttgacgac aagtgcgctg caataacaag caggcctcgg 129540
cgatttctcc ggcgtcttta ccttgcacat aataacttcc gccggtgtta ttgatggcgt 129600
tgattatatc ttgtactagt gtggcggcgc taaacaagaa atagccgccg gtggccaaga 129660
gtatgcccgt tcctcctact tttaagcttt gcatgtaact atgtagacgg gggttttgct 129720
gcagtgcgtt ttgaacacct tcgggcgtgc gcacgttggt ttccgggaag ttttgtttga 129780
ctgcattgga tcgcgtctgc ttggtgtggt aattaaagtc tggcacgttg tccacgcgcc 129840
gcaattggct caatgagttt atttgagggt ctgaaatgcc ctgaaatact ccgcgtatgt 129900
tggggacatc attgttacga gtaattctgt ttatgtctga agtgctcaca aactggttgt 129960
tagatagttg atagcccggc tgaaatctgt tgtttccaat gttgcgtaca ctgggcgcgt 130020
tgagcacatt tgtgaaaccg gcgggagtgc ttgttaaaag acgcgtatta tcagtaataa 130080
aactggcctg attaggatac aatttattga ctgcgcgaag atttgaaaaa aaactcattt 130140
taaagcaaac ttatttaata aatatatcac agtaaaggtt ttgcaaaact gccgtcgtca 130200
atacaacacg gcagcggcgt catgttggta aaatctaatc ttctccttgc tttagattct 130260
gggcgagaag gcgcatttgt tgtgtaagtt atttcgacgt ctgcattatt tgttgtgtaa 130320
ggtatctcga cgtatgaagc aactttaaca ttgttataat ttttttaaa tattgatgcg 130380 ctccacggcg cgcgttgata cggatgatat ctctccattg tatgatcgct aaatttatat 130440
accgtttcaa taaatatgtt aaaacccaac atgttaatta taatattcat aatagtttgt 130500
ttgttttcaa taattatttt tactgttttg aaatctaaaa gaggtgacga tgacgaatca 130560
gacgacgggt tcagttgcta taacaaacca attggagtaa attttccgca tcctactaga 130620
tgtgacgctt tctacatgtg tgtcggttta aatcaaaaat tagagttaat ctgccctgaa 130680
ggatttgaat ttgatccaga tgttaaaaat tgtgttccta tatcagatta tggatgtacc 130740
gctaaccaaa actaaaaata aaataaaatt tatatagatt aatgaaataa aatttatata 130800
gattaataaa ataaaattta tttaatatat tatactattt atattattta caacacttaa 130860
cgtctagaca taacagtttg taacttagaa actaaatcag agttactgcg ctcaaactct 130920
gaaaatttgg cttgagactc ggccacctgc ttacgcaatt gttcttgcag attattcaca 130980
gtcgattgca actcttctga tttcttggta gattcttgca agtcatagtt tgccttttgt 131040
aaatctaatt cggcgacagc atgcttgtgt ttaagcataa tgtagtcgct gtttaacatg 131100
gtcattttat gttcaacttg gctggtcttg gctcgcagct cggacagttc tttttgcaat 131160
tgctccacat agttcaagtc cgtggtgtga ttgttgaccg tgttattttc taaaagctcg 131220
cgccaatgct gtttgatgga atcctggtta cgagtgacgt taatgggcat aaattctaca 131280
tacccgtgct tattgtacac gcgacaatct gatgaagtag cgctgcaaaa acatttgtac 131340
acagaattgt ccataattat cttgacataa cacttgaaac acacagcatg gttacaatga 131400
atcgaagtca caaacgagga atttacgttt ttagtgtctt taaaagtagt aaaacaaata 131460

```
ttacacgaaa cctctacttc ttcttcgggt tctgattgct gctgctgctg ctgctgcggc 131520
tgcggagact gcggcgaggc aaacaaatct ggcgactgtg gtattacgta attcggcgaa 131580
taagatggac tataagtggg agaccttggg gcaatctcat tcatcagctg agcctcaaga 131640
tctaaacctc gttgcagagc cctctgcgca gctgtctccg acgcaatgtt atcctggtac 131700
tgctgggcag tgatgtcggg aaaccgttca cgatccacat tttcactatt aattagtatg 131760
acgtcatcct cttgacttaa tagcggatcg tcattgctaa tgttaacctg accgtgcacg 131820
taatacgtga caccctgacg atggtaggtg cgcgtcaacg gctcgttgac gttcccgata 131880
atctgcacgt tttcttcgct gacacgctgc tcctgacgcc gctcctgacg gcgatggctg 131940
cgactgcttg aagacggctg gctgcgactg cttgaagacg gctgggcttc gggagatgtt 132000
gtaaagttga tgcggcgacg gctgagagac agcctgtggc ggcggctgct gctgggagtg 132060
gcggcgttga tttggcgact catggctggg ctggtaggat actgttcact aggctgtgag 132120
gcttgaactg tgcttacgag tagaacggca gctgtattta tactgtttat cagtactgca 132180
cgactgataa gacaatagtg gtgggggaac ttgccaggca aaaatgaact tttttgtaat 132240
gcaaaaaagt tgatagtgta gtagtatatt gggagcgtat cgtacagtgt agactattct 132300
aataaaatag tctacgattt gtagagattg tactgtatat ggagtgtcag gcaaaagtga 132360
actttttgc attgcaaaaa aattcatttt aaatttatca tatcacaggc tgcagtttct 132420
gttatctgtc ccccactcag gcgtgcagct ataaaagcag gcactcacca actcgtaagc 132480
acagttcgtt gtgaagtgaa cacggagagc ctgccaataa gcaaaatgcc aagggacacc 132540
aacaatcgcc accggtctac gccatatgaa cgtcctacgc ttgaagatct ccgcagacag 132600
ttgcaagaca atttggacag cataaaccgc cgagacagaa tgcaagaaga acaagaagaa 132660
aacctgcgct atcaagtgcg tagaaggcag cgtcaaaacc agctccgctc catacaaatg 132720
gaacagcagc gaatgatggc ggaattaaac aacgagccgg tgattaattt taaatttgag 132780
tgtagtgtgt gtttagaaac atattcccaa caatctaacg atacttgtcc tttttgatt 132840
ccgactacgt gcgaccacgg tttttgtttc aaatgcgtca tcaatctgca aagcaacgcg 132900
atgaatattc cgcattccac tgtgtgctgt ccattgtgca atacccaggt aaaaatgtgg 132960
cgttccttaa agcctaacgc tgttgtgacg tgtaagtttt acaagaaaac tcaagaaaga 133020
gttccgcccg tgcagcagta taaaaacatt attaaagtgc tacaagaacg gagcgtgatt 133080
agtgtcgaag acaacgacaa taattgtgac ataaatatgg agaatcaggc aaagatagct 133140
gctttggaag ctgaattgga agaagaaaaa aatcacagtg atcaagtagc ttctgaaaac 133200
cgacagctga tagaagaaaa tactcgtctc aatgaacaga ttcaagagtt gcagcatcag 133260
gtgaggacat tggtgccgca acgtggcatt acggttaatc agcaaattgg ccgtgacgac 133320
agtgcgccag ccgagctgaa cgagcgtttt cgctcacttg tctattcgac tatttcagag 133380
ctgtttattg aaaatggcgt tcatagtatt caaaattatg tttatgccgg aacttctgct 133440
gctagttcat gtgatgtaaa tgttactgtt aattttgggt ttgaaaatta atgtgatatg 133500
aaatgtatat ataaaaatga tggaataaat aataaacatt tttatacttt ttatgttttt 133560
tttatttcat gtgattaaga aacttttaag atggatagta gtaattgtat taaaatagat 133620
gtaaaatacg atatgccgtt acattatcaa tgtgacaata acgcagataa agacgttgta 133680
aatgcgtatg acactatcga tgttgacccc aacaaaagat ttataattaa tcataatcac 133740
gaacaacaac aagtcaatga aacaaataaa caagttgtcg ataaaacatt cataaatgac 133800
```

acagcaacat acaattcttg cataataaaa atttaaatga catcatattt gagaataaca 133860
aatgacatta tccctcgatt gtgttttaca agta 133894

<210> SEQ ID NO 2
<211> LENGTH: 45
<212> TYPE: DNA
<213> ORGANISM: artificial
<220> FEATURE:
<223> OTHER INFORMATION: vp39-F forward primer

<400> SEQUENCE: 2
gcttctaata cgactcacta tagggtcgta tccgctaagc gttct 45

<210> SEQ ID NO 3
<211> LENGTH: 45
<212> TYPE: DNA
<213> ORGANISM: artificial
<220> FEATURE:
<223> OTHER INFORMATION: vp39-R reverse primer

<400> SEQUENCE: 3
gcttctaata cgactcacta tagggacgca acgcgttata cacag 45

<210> SEQ ID NO 4
<211> LENGTH: 43
<212> TYPE: DNA
<213> ORGANISM: artificial
<220> FEATURE:
<223> OTHER INFORMATION: 45510 forward primer

<400> SEQUENCE: 4
cttctaatac gactcactat agggacagcg tgtacgagtg cat 43

<210> SEQ ID NO 5
<211> LENGTH: 45
<212> TYPE: DNA
<213> ORGANISM: artificial
<220> FEATURE:
<223> OTHER INFORMATION: 46235 reverse primer

<400> SEQUENCE: 5
gcttctaata cgactcacta tagggatctc gagcgtgtag ctggt 45

<210> SEQ ID NO 6
<211> LENGTH: 44
<212> TYPE: DNA
<213> ORGANISM: artificial
<220> FEATURE:
<223> OTHER INFORMATION: 90292 forward primer

<400> SEQUENCE: 6
gcttctaata cgactcacta tagggtaccg ccgaacatta cacc 44

<210> SEQ ID NO 7
<211> LENGTH: 43
<212> TYPE: DNA
<213> ORGANISM: artificial
<220> FEATURE:
<223> OTHER INFORMATION: 90889 reverse primer

<400> SEQUENCE: 7
gcttctaata cgactcacta tagggtctat tggcacgttt gct 43

<210> SEQ ID NO 8
<211> LENGTH: 45

<212> TYPE: DNA
<213> ORGANISM: artificial
<220> FEATURE:
<223> OTHER INFORMATION: ec-27-F forward primer

<400> SEQUENCE: 8
gcttctaata cgactcacta tagggaaagc agacactcgg cagat 45

<210> SEQ ID NO 9
<211> LENGTH: 45
<212> TYPE: DNA
<213> ORGANISM: artificial
<220> FEATURE:
<223> OTHER INFORMATION: ec-27-R reverse primer

<400> SEQUENCE: 9
gcttctaata cgactcacta tagggttgag tggcttcaac ctcag 45

<210> SEQ ID NO 10
<211> LENGTH: 44
<212> TYPE: DNA
<213> ORGANISM: artificial
<220> FEATURE:
<223> OTHER INFORMATION: dbp-F forward primer

<400> SEQUENCE: 10
gcttctaata cgactcacta tagggcgctc gctagttttg ttct 44

<210> SEQ ID NO 11
<211> LENGTH: 44
<212> TYPE: DNA
<213> ORGANISM: artificial
<220> FEATURE:
<223> OTHER INFORMATION: dbp-R reverse primer

<400> SEQUENCE: 11
gcttctaata cgactcacta tagggaaaga tcggaaggtg gtga 44

<210> SEQ ID NO 12
<211> LENGTH: 45
<212> TYPE: DNA
<213> ORGANISM: artificial
<220> FEATURE:
<223> OTHER INFORMATION: gfp-F forward primer

<400> SEQUENCE: 12
gcttctaata cgactcacta tagggctgac cctgaagttc atctg 45

<210> SEQ ID NO 13
<211> LENGTH: 44
<212> TYPE: DNA
<213> ORGANISM: artificial
<220> FEATURE:
<223> OTHER INFORMATION: gfp-R reverse primer

<400> SEQUENCE: 13
gcttctaata cgactcacta tagggaactc cagcaggacc atgt 44

<210> SEQ ID NO 14
<211> LENGTH: 45
<212> TYPE: DNA
<213> ORGANISM: artificial
<220> FEATURE:
<223> OTHER INFORMATION: cat-F forward primer

<400> SEQUENCE: 14
gcttctaata cgactcacta tagggacggc atgatgaacc tgaat 45

<210> SEQ ID NO 15
<211> LENGTH: 45
<212> TYPE: DNA
<213> ORGANISM: artificial
<220> FEATURE:
<223> OTHER INFORMATION: cat-R reverse primer

<400> SEQUENCE: 15
gcttctaata cgactcacta tagggatccc aatggcatcg taaag 45

<210> SEQ ID NO 16
<211> LENGTH: 68
<212> TYPE: DNA
<213> ORGANISM: artificial
<220> FEATURE:
<223> OTHER INFORMATION: vp80-KO-F forward primer

<400> SEQUENCE: 16
ctgtattgta atctgtaagc gcacatggtg cattcgatat aaccttataa tgtgtgctgg 60
aatgccct 68

<210> SEQ ID NO 17
<211> LENGTH: 71
<212> TYPE: DNA
<213> ORGANISM: artificial
<220> FEATURE:
<223> OTHER INFORMATION: vp80-KO-R reverse primer

<400> SEQUENCE: 17
aaatgtactg aatataaata aaaattaaaa atattttata attttttatt taccgttcgt 60
atagcataca t 71

<210> SEQ ID NO 18
<211> LENGTH: 21
<212> TYPE: DNA
<213> ORGANISM: artificial
<220> FEATURE:
<223> OTHER INFORMATION: 89507 forward primer

<400> SEQUENCE: 18
agcggtcgta aatgttaaac c 21

<210> SEQ ID NO 19
<211> LENGTH: 25
<212> TYPE: DNA
<213> ORGANISM: artificial
<220> FEATURE:
<223> OTHER INFORMATION: 91713 reverse primer

<400> SEQUENCE: 19
tgtataaaca atatgttaat atgtg 25

<210> SEQ ID NO 20
<211> LENGTH: 34
<212> TYPE: DNA
<213> ORGANISM: artificial
<220> FEATURE:
<223> OTHER INFORMATION: gfp-NheI-F forward primer

<400> SEQUENCE: 20
ccaaaccgct agcaacatgg tgagcaaggg cgag 34

<210> SEQ ID NO 21
<211> LENGTH: 49
<212> TYPE: DNA
<213> ORGANISM: artificial
<220> FEATURE:
<223> OTHER INFORMATION: gfp-SphI reverse primer

<400> SEQUENCE: 21
aggaaagggc atgcttaacg cgtaccggtc ttgtacagct cgtccatgc 49

<210> SEQ ID NO 22
<211> LENGTH: 40
<212> TYPE: DNA
<213> ORGANISM: artificial
<220> FEATURE:
<223> OTHER INFORMATION: pvp80-StuI-F forward primer

<400> SEQUENCE: 22
ggaacaaagg cctgagctca aagtaagacc tttactgtcc 40

<210> SEQ ID NO 23
<211> LENGTH: 35
<212> TYPE: DNA
<213> ORGANISM: artificial
<220> FEATURE:
<223> OTHER INFORMATION: vp80-XbaI-R reverse primer

<400> SEQUENCE: 23
ccttctatct agattatata acattgtagt ttgcg 35

<210> SEQ ID NO 24
<211> LENGTH: 35
<212> TYPE: DNA
<213> ORGANISM: artificial
<220> FEATURE:
<223> OTHER INFORMATION: vp80-SacI-F forward primer

<400> SEQUENCE: 24
ttatcttgag ctcaatatga acgattccaa ttctc 35

<210> SEQ ID NO 25
<211> LENGTH: 69
<212> TYPE: DNA
<213> ORGANISM: artificial
<220> FEATURE:
<223> OTHER INFORMATION: vp80-FLAG-R1 reverse primer

<400> SEQUENCE: 25
caacagagaa ttggaatcgt tcttatcgtc gtcatccttg taatccatat tataaggtta 60
tatcgaatg 69

<210> SEQ ID NO 26
<211> LENGTH: 62
<212> TYPE: DNA
<213> ORGANISM: artificial
<220> FEATURE:
<223> OTHER INFORMATION: vp80-FLAG-R reverse primer

<400> SEQUENCE: 26
ccttctatct agattactta tcgtcgtcat ccttgtaatc tataacattg tagtttgcgt 60
tc 62

<210> SEQ ID NO 27
<211> LENGTH: 23
<212> TYPE: DNA

<213> ORGANISM: artificial
<220> FEATURE:
<223> OTHER INFORMATION: M13-F forward primer

<400> SEQUENCE: 27
cccagtcacg acgttgtaaa acg 23

<210> SEQ ID NO 28
<211> LENGTH: 23
<212> TYPE: DNA
<213> ORGANISM: artificial
<220> FEATURE:
<223> OTHER INFORMATION: M13-R reverse primer

<400> SEQUENCE: 28
agcggataac aatttcacac agg 23

<210> SEQ ID NO 29
<211> LENGTH: 20
<212> TYPE: DNA
<213> ORGANISM: artificial
<220> FEATURE:
<223> OTHER INFORMATION: GenR reverse primer

<400> SEQUENCE: 29
agccacctac tcccaacatc 20

<210> SEQ ID NO 30
<211> LENGTH: 71
<212> TYPE: DNA
<213> ORGANISM: artificial
<220> FEATURE:
<223> OTHER INFORMATION: vp39-KO-F forward primer

<400> SEQUENCE: 30
tcgggcacag acgcgaccag acccgtttcg tcaattatac acgtggcgca taccgttcgt 60
ataatgtatg c 71

<210> SEQ ID NO 31
<211> LENGTH: 70
<212> TYPE: DNA
<213> ORGANISM: artificial
<220> FEATURE:
<223> OTHER INFORMATION: vp39-KO-R reverse primer

<400> SEQUENCE: 31
gtttatttgc aacaaccacc tcataaaacg ttttaaaatg tcaaaaatgt accgttcgta 60
tagcatacat 70

<210> SEQ ID NO 32
<211> LENGTH: 33
<212> TYPE: DNA
<213> ORGANISM: artificial
<220> FEATURE:
<223> OTHER INFORMATION: vp39-SacI-F forward primer

<400> SEQUENCE: 32
aaggttctct agattagacg gctattcctc cac 33

<210> SEQ ID NO 33
<211> LENGTH: 32
<212> TYPE: DNA
<213> ORGANISM: artificial
<220> FEATURE:
<223> OTHER INFORMATION: vp39-XbaI-R reverse primer

<400> SEQUENCE: 33
ttatcttgag ctcaatatgg cgctagtgcc cg 32

<210> SEQ ID NO 34
<211> LENGTH: 39
<212> TYPE: DNA
<213> ORGANISM: artificial
<220> FEATURE:
<223> OTHER INFORMATION: vp39-StuI-F forward primer

<400> SEQUENCE: 34
ggaacaaagg cctgagctct tagacggcta ttcctccac 39

<210> SEQ ID NO 35
<211> LENGTH: 34
<212> TYPE: DNA
<213> ORGANISM: artificial
<220> FEATURE:
<223> OTHER INFORMATION: lef-4-XbaI-R reverse primer

<400> SEQUENCE: 35
ccttctatct agattaattt ggcacgattc ggtc 34

<210> SEQ ID NO 36
<211> LENGTH: 39
<212> TYPE: DNA
<213> ORGANISM: artificial
<220> FEATURE:
<223> OTHER INFORMATION: cg-30-XbaI-F forward primer

<400> SEQUENCE: 36
aaggttctct agattaatct acatttattg taacatttg 39

<210> SEQ ID NO 37
<211> LENGTH: 61
<212> TYPE: DNA
<213> ORGANISM: artificial
<220> FEATURE:
<223> OTHER INFORMATION: vp39-FLAG-SacI-R reverse primer

<400> SEQUENCE: 37
ttatcttgag ctcaatatgg attacaagga tgacgacgat aaggcgctag tgcccgtggg 60
t 61

<210> SEQ ID NO 38
<211> LENGTH: 72
<212> TYPE: DNA
<213> ORGANISM: artificial
<220> FEATURE:
<223> OTHER INFORMATION: vp1054-KO-F forward primer

<400> SEQUENCE: 38
gtactgaaag ataatttatt tttgatagat aataattaca ttattttaaa cgtgttcgac 60
caagaaaccg at 72

<210> SEQ ID NO 39
<211> LENGTH: 45
<212> TYPE: DNA
<213> ORGANISM: artificial
<220> FEATURE:
<223> OTHER INFORMATION: vp1054-KO-R1 reverse primer

<400> SEQUENCE: 39
agggcgaatt ccagcacact ttattacgtg gacgcgttac tttgc 45

<210> SEQ ID NO 40
<211> LENGTH: 71
<212> TYPE: DNA
<213> ORGANISM: artificial
<220> FEATURE:
<223> OTHER INFORMATION: vp1054-KO-R2 reverse primer

<400> SEQUENCE: 40
gataagaatg cttgtttaac aaataggtca gctgttaaat actggcgatg taccgttcgt 60
atagcataca t 71

<210> SEQ ID NO 41
<211> LENGTH: 41
<212> TYPE: DNA
<213> ORGANISM: artificial
<220> FEATURE:
<223> OTHER INFORMATION: vp1054-Rep-F forward primer

<400> SEQUENCE: 41
ggttgtttag gcctgagctc ctttggtacg tgttagagtg t 41

<210> SEQ ID NO 42
<211> LENGTH: 36
<212> TYPE: DNA
<213> ORGANISM: artificial
<220> FEATURE:
<223> OTHER INFORMATION: vp1054-Rep-R reverse primer

<400> SEQUENCE: 42
tcctttcctc tagattacac gttgtgtgcg tgcaga 36

<210> SEQ ID NO 43
<211> LENGTH: 67
<212> TYPE: DNA
<213> ORGANISM: artificial
<220> FEATURE:
<223> OTHER INFORMATION: p6.9-KO-F forward primer

<400> SEQUENCE: 43
gcttcgttca ttcgctactg tcggctgtgt ggaatgtctg gttgttaagt gtgctggaat 60
tcgccct 67

<210> SEQ ID NO 44
<211> LENGTH: 70
<212> TYPE: DNA
<213> ORGANISM: artificial
<220> FEATURE:
<223> OTHER INFORMATION: p6.9-KO-R reverse primer

<400> SEQUENCE: 44
aatattaata aggtaaaaat tacagctaca taaattacac aatttaaact accgttcgta 60
tagcatacat 70

<210> SEQ ID NO 45
<211> LENGTH: 32
<212> TYPE: DNA
<213> ORGANISM: artificial
<220> FEATURE:
<223> OTHER INFORMATION: Ac-p6.9-F forward primer

<400> SEQUENCE: 45
tttgaattca tggttgcccg aagctccaag ac 32

<210> SEQ ID NO 46
<211> LENGTH: 34
<212> TYPE: DNA
<213> ORGANISM: artificial
<220> FEATURE:
<223> OTHER INFORMATION: Ac-p6.9-R reverse primer

<400> SEQUENCE: 46
tttgcggccg cttaatagta gcgtgttctg taac 34

<210> SEQ ID NO 47
<211> LENGTH: 29
<212> TYPE: DNA
<213> ORGANISM: artificial
<220> FEATURE:
<223> OTHER INFORMATION: Se-p6.9-F forward primer

<400> SEQUENCE: 47
tttgaattca tgtatcgtcg tcgttcatc 29

<210> SEQ ID NO 48
<211> LENGTH: 34
<212> TYPE: DNA
<213> ORGANISM: artificial
<220> FEATURE:
<223> OTHER INFORMATION: Se-p6.9-R reverse primer

<400> SEQUENCE: 48
tttgcggccg cttaatagtg gcgacgtctg tatc 34

<210> SEQ ID NO 49
<211> LENGTH: 22
<212> TYPE: DNA
<213> ORGANISM: artificial
<220> FEATURE:
<223> OTHER INFORMATION: 86596 forward primer

<400> SEQUENCE: 49
gggcttagtt taaaatcttg ca 22

<210> SEQ ID NO 50
<211> LENGTH: 21
<212> TYPE: DNA
<213> ORGANISM: artificial
<220> FEATURE:
<223> OTHER INFORMATION: 86995 reverse primer

<400> SEQUENCE: 50
aattcaaacg accaagacga g 21

<210> SEQ ID NO 51
<211> LENGTH: 21
<212> TYPE: DNA
<213> ORGANISM: artificial
<220> FEATURE:
<223> OTHER INFORMATION: 45122 forward primer

<400> SEQUENCE: 51
gcaatcatga cgaacgtatg g 21

<210> SEQ ID NO 52
<211> LENGTH: 22
<212> TYPE: DNA
<213> ORGANISM: artificial
<220> FEATURE:
<223> OTHER INFORMATION: 46441 reverse primer

<400> SEQUENCE: 52
cgataatttt tccaagcgct ac 22

<210> SEQ ID NO 53
<211> LENGTH: 30
<212> TYPE: DNA
<213> ORGANISM: artificial
<220> FEATURE:
<223> OTHER INFORMATION: pp6.9-F forward primer

<400> SEQUENCE: 53
ggtcgacgta ccaaattccg ttttgcgacg 30

<210> SEQ ID NO 54
<211> LENGTH: 34
<212> TYPE: DNA
<213> ORGANISM: artificial
<220> FEATURE:
<223> OTHER INFORMATION: pp6.9-R reverse primer

<400> SEQUENCE: 54
ggtcgacgga tccgtttaaa ttgtgtaatt tatg 34

<210> SEQ ID NO 55
<211> LENGTH: 21
<212> TYPE: DNA
<213> ORGANISM: artificial
<220> FEATURE:
<223> OTHER INFORMATION: 75834 forward primer

<400> SEQUENCE: 55
cttcttatcg ggttgtacaa c 21

<210> SEQ ID NO 56
<211> LENGTH: 20
<212> TYPE: DNA
<213> ORGANISM: artificial
<220> FEATURE:
<223> OTHER INFORMATION: 76420 reverse primer

<400> SEQUENCE: 56
gcgtatcatg acgatggatg 20

BACULOVIRUS-BASED PRODUCTION OF BIOPHARMACEUTICALS FREE OF CONTAMINATING BACULOVIRAL VIRIONS

CROSS-REFERENCE TO RELATED APPLICATION

This application is the U.S. national stage application of International Patent Application No. PCT/EP2010/061456, filed Aug. 5, 2010, the disclosure of which is hereby incorporated by reference in its entirety, including all figures, tables and amino acid or nucleic acid sequences.

The present invention relates to methods for the production of biopharmaceuticals implementing a baculovirus-based system. These methods advantageously allow the production of biopharmaceuticals with reduced or no contaminating baculoviral virions.

Over the past two decades the baculovirus-insect cell technology has become a very frequently used eukaryotic expression system for the production of recombinant proteins, not only for scientific purposes, but more and more for human and veterinary medicine (Condreay and Kost, 2007, van Oers, 2006). In particular, recombinant baculoviruses derived from *Autographa californica* multicapsid nucleopolyhedrovirus (AcMNPV) are widely employed for large-scale production of heterologous proteins in cultured insect cells. The main reasons for the frequent application of this system are: (1) high levels of expression of foreign proteins, (2) insect cells are able to grow in a suspension culture and thus are easy to scale up, (3) the proteins synthesized in insect cells are processed and modified post-translationally, (4) well-developed manipulation techniques for the viral vectors resulting in a flexible expression system, and 5) non-pathogenic to humans, as the baculovirus host range is restricted to insects and invertebrates. Recombinant baculovirus vectors are being used for the production of individual proteins, as for sub-unit vaccine purposes, but also for higher order structures containing one or more proteins, such as enzyme complexes, viruses or virus-like particles.

Virus-like particles (VLPs) are highly organised structures that self-assemble from virus-derived structural proteins. These stable and versatile nano-particles possess excellent adjuvant properties capable of inducing innate and acquired immune responses (Ludwig & Wagner, 2007). During the past years, VLPs have been applied in other branches of biotechnology taking advantage of their structural stability and tolerance towards manipulation to carry and display heterologous molecules or serve as building blocks for novel nanomaterials. For immuno-therapeutic and prophylactic applications, many types of virus-like particles (VLP) have been successfully produced in baculovirus-infected insect cells (Noad & Roy, 2003, van Oers et al., 2006, Ramqvist et al., 2007). The first commercial achievement of baculovirus VLP technology for use in humans is the human papillomavirus (HPV) vaccine recently marketed by GlaxoSmithKline, prophylactic against HPV strains 16 and 18. The L1 protein of each of these types of HPV was expressed via a recombinant baculovirus vector and the resulting VLPs were combined to produce the vaccine Cervarix™ (Harper et al., 2006).

Today, there is a huge effort to develop baculovirus-derived influenza virus-like particles as well as influenza subunit-vaccines as a new generation of non-egg and non-mammalian cell culture-based candidate vaccine. Non-replicating influenza virus-like particles are effective in eliciting a broadened, cross-clade protective immune response to proteins from emerging H5N1 influenza isolates giving rise to a potential pandemic influenza vaccine candidate for humans that can be stockpiled for use in the event of an outbreak of H5N1 influenza (Bright et al., 2008). An influenza subunit vaccine produced in insect cells is close to FDA approval (Cox and Hollister, 2009). Similar strategies could in principle be applied for vaccines against the pandemic influenza such as the recent outbreak of Swine flu.

For gene therapy purposes, baculovirus-insect cell technology is also being applied for the production of infectious adeno-associated virus vectors (e.g. Urabe et al., 2002) and lentiviral vectors (Lesch et al., 2008). For the production of AAV vectors insect cells are co-infected with three recombinant baculoviruses—One producing the AAV replicase (REP) proteins, one carrying the cap functions for producing the AAV viral structural proteins (VP1, VP2. VP3), and a third baculovirus comprising an AAV-ITR vector with the ability to carry and transfer transgenes. Recently an improved version of this production had been published which is based on the use of only recombinant baculoviruses, one of them carrying the rep and cap functions of AAV (Smith et al. 2009). The produced AAV vector is indistinguishable from that produced in mammalian cells in its physical and biological properties. The yield of the AAV-ITR vector particles approached $5\times10^4$ per Sf9 insect cell demonstrating that the system is able to produce high quantities of AAV vectors in a simple manner. Currently, clinical trials with baculovirus-derived AAV vectors are underway for instance for lipoprotein lipase deficiency (Amsterdam Molecular Therapeutics B.V.). As an alternative, scalable approach to produce lentiviral vectors (Lesch et al., 2008) mammalian 293T cells were transduced simultaneously by four recombinant baculoviruses produced in insect cells to express all elements required for generation of a safe lentivirus vector. The unconcentrated lentiviral titers in mammalian cell culture media were on average $2.5\times10^6$ TU $ml^{-1}$, comparable to titers of the lentiviruses produced by conventional four-plasmid transfection methods. In addition, there is a general effort to convert lentiviral vector production methods into better scalable insect cell-based technologies.

Tjia et al., 1983 discovered that BVs can be internalized by mammalian cells and even some of the viral DNA reached the cell nucleus. Further studies showed that baculoviruses can enter mammalian cells and mediate expression of *Escherichia coli* chloramphenicol acetyl-transferase under the Rous sarcoma virus promoter (Carbonell et al., 1985). These findings led to the development of novel baculovirus-based gene delivery vehicles for mammalian cells (Boyce & Bucher, 1996, Hofmann et al., 1995, Condreay and Kost, 2007, Kaikkonen et al., 2008). Today, there is strong evidence that baculovirus-derived gene delivery vectors can mediate transient and stable expression of foreign genes in mammalian cells following antibiotic selection (Lackner et al., 2008).

There is still poor knowledge about transcriptional activities of baculovirus promoters in mammalian cells. It has been demonstrated that the transactivator protein IE1 of AcMNPV is functional in mammalian cells (Murges et al., 1997) as well as the early-to-late (ETL) promoter (Liu et al., 2006a,b). Among the other imperfectly explored areas is the interaction of baculoviruses with components of the mammalian immune system. AcMNPV virus is able to induce antiviral cytokine production, which protects cells from infection with vesicular stomatitis virus and influenza virus (Abe et al., 2003, Gronowski et al., 1999). AcMNPV is also recognized by Toll-like receptor 9 on dendritic cells and macrophages, and AcMNPV induces antitumor acquired immunity (Kitajima & Takaku, 2008). These results suggest that AcMNPV has the potential to be an efficient virus or tumor therapy agent which induces innate and acquired immunity. In spite of universally positive effects of AcMNPV on components of the humoral and adaptive cell-mediated immunity in mice, the interaction of baculoviruses with the human immune system can be slightly different. Additionally, immunoadjuvant properties of AcMNPV should be fully separated from immune response against target vaccine/biopharmaceuticals produced in insect cells.

These features of baculoviruses are strongly disadvantageous in cases where baculoviruses are utilized for the production of vaccines or viral vectors for therapeutical purposes (e.g. AAV, lentivirus). Contamination of the produced biopharmaceuticals with both types of baculovirus virions—budded virions (BVs) and occlusion-derived virions (ODVs) should, therefore, be avoided. In general, the recombinant proteins can be produced in insect cells as cytosolic, membrane-bound, or extra-cellularly secreted proteins. The latter secreted proteins are highly "contaminated" with baculoviral BVs present in the culture medium. It can be very difficult to separate undesirable baculovirus virions from produced recombinant biopharmaceuticals in some production and purification configurations. It has been shown for instance that these BVs can cause problems during the purification process of AAV vectors produced with baculovirus-insect cell technology (personal communication O. Merten, Genethon). On the other hand, there are also ODVs, always formed inside the nuclei of infected cells, in all conventional baculovirus-insect cell expression systems, even if occlusion bodies are not formed, due to replacement of the polyhedrin open reading frame by a desired gene. Analogously, these virions can co-purify with intracellularly produced recombinant proteins or VLPs during purification process.

In summary, the separation of recombinant proteins and, especially, VLPs from baculovirus particles, requires a lot of effort and occurs at high costs. In addition, it results in reduced efficiency of recombinant protein production. Therefore, the development of an improved baculovirus-insect cell technology allowing high expression of heterologous proteins while eliminating baculovirus BV and ODV production is highly desirable, and is the topic of this patent application. Such a baculovirus virion-free production system would represent a significant improvement over existing systems for the production of all kinds of biopharmaceuticals in insect cells.

The present invention is based on the identification of efficient baculovirus-insect cell based methods for producing biopharmaceuticals with reduced amounts or absence of baculovirus virions.

An object of the present invention thus provides a method for the production of a biopharmaceutical product, comprising:

(a) infecting a biopharmaceutical-producing insect cell with at least one baculovirus, said at least one baculovirus comprising a genome coding for said biopharmaceutical product, and (b) maintaining the biopharmaceutical-producing insect cell under conditions such that the biopharmaceutical product is produced, wherein each genome of said at least one baculovirus is deficient for at least one gene essential for proper baculovirus virion assembly or wherein said biopharmaceutical-producing insect cell comprises an expression control system allowing the inactivation of at least one gene essential for proper baculovirus virion assembly.

In an embodiment, the invention relates to the above method, wherein said at least one gene essential for proper baculovirus virion assembly is made deficient in said genome by mutation, for example by way of nucleotide substitution, insertion or deletion.

In another embodiment, the invention relates to the above method, wherein the biopharmaceutical-producing insect cell is a recombinant insect cell comprising a construct expressing a dsRNA specific for the at least one gene essential for proper baculovirus virion assembly, the dsRNA being optionally expressed under the control of an inducible promoter.

In a further embodiment, the invention relates to the above method, wherein the at least one baculovirus is produced before step (a) in a baculovirus-producing cell expressing a complementing copy of the at least one gene essential for proper baculovirus virion assembly.

In yet another embodiment, the invention relates to the above method, wherein the at least one gene essential for proper baculovirus virion assembly is selected from vp80, vp39, vp1054 and p6.9.

In another embodiment, the invention relates to the above method, wherein the deficiency or inactivation of the at least one gene essential for proper baculovirus virion assembly does not affect very late gene expression from said baculovirus in comparison to very late gene expression from the wild-type baculovirus vector.

In yet another embodiment, the invention relates to the above method, wherein the at least one baculovirus is preferably derived from AcMNPV or *Bombyx mori* (Bm) NPV.

In a further embodiment, the invention relates to the above method, wherein the biopharmaceutical product is a recombinant protein, a recombinant virus, a virus-derived vector, or a virus-like particle.

In another embodiment, the invention relates to the above method, wherein the biopharmaceutical product is a recombinant AAV vector. Furthermore, the invention relates to the above method, wherein the biopharmaceutical product is a vaccine. Representative examples of vaccines than can be produced with the method of the present invention include, but are not limited to, influenza virus-like particles or influenza subunit vaccines, and vaccines against Human papillomavirus.

In a further embodiment, the invention relates to the above method, wherein the biopharmaceutical product is coded by at least one gene introduced in the recombinant baculovirus genome under the control of a baculovirus promoter, preferably the p10 or polyhedrin promoter.

Another object of the invention provides the use of a baculovirus-insect cell system for the production of a biopharmaceutical product wherein the baculovirus-insect cell system comprises a biopharmaceutical-producing insect cell infected with at least one recombinant baculovirus, wherein:

the, or each, recombinant baculovirus comprises a recombinant baculovirus genome that encodes the biopharmaceutical product, or at least one component of the biopharmaceutical product, and the recombinant baculovirus genome is deficient for at least one gene essential for proper assembly of said baculovirus, or the biopharmaceutical-producing insect cell comprises an expression control system allowing the inactivation of the at least one gene essential for proper baculovirus virion assembly.

Yet another object of the invention relates to a bacmid comprising a baculovirus genome, wherein said genome is deficient for a gene essential for proper baculovirus virion assembly, preferably wherein the genome of said baculovirus is deficient for vp80, vp39, p6.9 or vp1054. In a particular aspect, said bacmid is derived from AcMNPV and is lacking the vp80 ORF.

A further object of the invention relates to a recombinant AcMNPV baculovirus vector, wherein the genome of said baculovirus is deficient for a gene essential for proper baculovirus virion assembly, preferably wherein the genome of said baculovirus is deficient for vp80, vp39, vp1054 or p6.9. In a particular aspect, the invention relates to a recombinant AcMNPV baculovirus lacking the vp80 ORF.

The invention has also as an object an insect cell infected with the above mentioned recombinant AcMNPV baculovirus.

Another object of the invention relates to an insect cell, comprising a construct expressing a dsRNA specific for a gene essential for proper baculovirus virion assembly, preferably directed against vp80, vp39, vp1054 and/or p6.9, said construct being preferably integrated in the genome of the insect cell.

A further object of the invention relates to an insect cell comprising an expression cassette coding for a gene essential for proper baculovirus virion assembly. In particular, the invention relates to said insect cell, wherein the gene coded by the expression cassette is vp80, vp39, vp1054 and/or p6.9.

Another object of the invention relates to a method for the production of a baculovirus deficient for at least one gene essential for proper baculovirus virion assembly, comprising the step of transfecting an insect cell comprising an expression cassette coding for a gene essential for proper baculovirus virion assembly, with a bacmid comprising a baculoviral genome, wherein said genome is deficient for a gene essential for proper baculovirus virion assembly, preferably wherein the genome of said baculovirus is deficient for vp80, vp39, p6.9 and/or vp1054, wherein the gene essential for proper baculovirus virion assembly deficient in said bacmid is the gene coded by the expression cassette comprised in said insect cell.

The present invention relates to the production of biopharmaceuticals in insect cells by implementing a baculoviral system, but without coproduction of contaminating baculovirus virions. The methods of the invention simplify the downstream processing of biopharmaceuticals produced in insect cells to a large extent.

Thus, the invention relates to methods for the production of a biopharmaceutical product implementing a baculoviral system designed to avoid the production of contaminating baculoviral virions. The method of the present invention comprises the infection of biopharmaceutical-producing insect cells with at least one baculovirus coding for said biopharmaceutical product.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm)NPV (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

According to the present invention, any genome derived from a baculovirus commonly used for the recombinant expression of proteins and biopharmaceutical products may be used. For example, the baculovirus genome may be derived from for instance AcMNPV, BmNPV, *Helicoverpa armigera* (HearNPV) or *Spodoptera exigua* MNPV, preferably from AcMNPV or BmNPV. In particular, the baculovirus genome may be derived from the AcMNPV clone C6 (genomic sequence: Genbank accession no. NC_001623.1—SEQ ID NO:1).

The terms "Biopharmaceutical", "Biopharmaceuticals" and "Biopharmaceutical Product" are intended to define medical drugs produced using biotechnology. As such, biopharmaceuticals may correspond to recombinantly produced drugs such as recombinant proteins, notably recombinant hormones or recombinant proteins for use as vaccines, viruses, for example therapeutic recombinant AAV or other viral vectors for use in gene therapy, as well as virus-like-particles (or VLPs). Such biopharmaceuticals are intended to be administered to a subject in need thereof for the prophylactic or curative treatment of a disease condition in said subject which may be of either human or animal origin.

A biopharmaceutical product may correspond to a single chain protein or peptide, for example in the case of a therapeutic recombinant protein, or may be a complex structure such as a virus or a virus-like particle. In the latter two cases, the components of the complex may be expressed from several recombinant baculoviruses, each carrying at least one component of the complex structure, or from a single baculovirus whose genome has been genetically modified by the insertion of sequences encoding all the components of the complex. For example, for the production of a recombinant AAV, a system comprising three baculoviruses may be used: a baculovirus coding for the AAV Rep proteins, a baculovirus coding the AAV Cap proteins and a baculovirus coding the AAV-ITR genome comprising a therapeutic gene between the two AAV ITRs. A system comprising two baculoviruses is also available now, for which the DNA sequences coding for the AAV Rep proteins and the AAV Cap proteins are provided by one baculovirus.

In a preferred embodiment of the invention, the heterologous gene(s) encoding the biopharmaceuticals are placed under the control of a baculoviral promoter. For example, the heterologous gene(s) is (are) placed under the control of the polyhedrin or p10 promoter, or of any other baculoviral promoter commonly used for expression in an insect cell (e.g. ie-1, p6.9, gp64 or the *Orchyia pseudotsugata* (Op) MNPV ie-2 promoter). In a preferred embodiment of the invention, the baculoviral promoter is selected from very late expression promoters, for example from the p10 and polyhedrin promoters, preferably under the control of the polyhedrin promoter.

In the method of the present invention, at least one gene essential for proper baculovirus virion assembly is either absent from the genome of the recombinant baculovirus(es) implemented in the above described method, or its expression is prevented. The inventors have shown that the deletion or inactivation of such genes results in the reduction, or even the complete absence, of budded virions and/or occlusion derived virions, the two forms of a baculovirus.

A "gene essential for proper baculovirus virion assembly" is a gene whose deficiency or inactivation in a baculovirus-producing cell negatively impacts the number of BVs and ODVs produced from said cell. Such a gene may be identified as provided in the herein below examples. In particular, one can use double stranded RNAs specific for a particular baculoviral gene to assess the impact of the absence of said particular gene on the production of BVs and ODVs, for example by detecting the expression of a reporter gene present in the baculoviral genome in the cell culture, and thus determine the spreading or absence of spreading of the baculovirus (single-infection phenotype). Alternatively baculovirus virions may be detected by the presence of baculoviral structural proteins or genome sequences in the culture medium when sampling for BV production. Both virion types may be detected by electron microscopy.

In a preferred embodiment of the invention, the gene essential for proper baculovirus virion assembly is selected from vp80, vp39, vp1054 and p6.9. More preferably, the gene is selected from vp80 and vp39, said gene being preferably vp80.

The invention provides the inactivation of genes essential for proper baculovirus virion assembly. Several strategies may be implemented for this purpose, and in particular: the mutation, for example by deletion, of the selected gene(s) in the recombinant baculovirus genome; or the reduction of the expression of the selected gene by an expression control system provided in the biopharmaceutical-producing insect cell intended to be infected by the baculovirus. Preferably, the expression control system involves the down-regulation by RNA interference of the expression of the protein(s) encoded by the selected gene(s).

In one embodiment of the invention, the genome of the at least one baculovirus implemented in the method of the invention is deficient for at least one gene essential for proper baculovirus virion assembly, in particular for a gene coding for vp80, vp39, vp1054 and/or p6.9, preferably for vp80 and/or vp39, and even more preferably for vp80. More particularly, said genome is derived from AcMNPV, more particularly from AcMNPV clone C6 genome sequence (Genbank accession no. NC_001623.1-SEQ ID NO: 1). Accordingly, in one aspect the invention provides the method as defined above, wherein the baculoviral genome is an AcMNPV genome, in particular an AcMNPV clone C6 genome, deficient for the gene coding for vp80, vp39, vp1054 and/or p6.9, preferably for vp80 and/or vp39, and even more preferably for vp80. As is well known in the art and specified in Genbank accession no. NC_001623.1, these genes are positioned as follows in AcMNPV clone C6 genome (i.e. in SEQ ID NO:1): positions 89564-91639 for vp80; positions 75534-76577 for vp39 (complementary sequence); positions 45222-46319 for vp1054; positions 86712-86879 for p6.9 (complementary sequence).

It should be noted that in case the biopharmaceutical product is a complex product comprising various subunits each encoded by different baculoviruses, the genomes of all the implemented recombinant baculoviruses are deficient for the selected essential gene, so as to avoid complementation of one genome by another. In other words, when several baculoviruses are used to infect the same biopharmaceutical-producing insect cell, each of these baculoviruses are deficient for the same gene(s) essential for proper baculovirus virion assembly.

According to the present invention, a gene may be made deficient by mutating said gene. A mutation of a gene essential for proper baculovirus virion assembly is a modification of said gene that results in the complete absence of a functional essential gene product. Accordingly, said mutation may result in the introduction of one or several stop codon in the open reading frame of the mRNA transcribed from the gene essential for proper baculoviral virion assembly or may correspond to the deletion, either total or partial, of the gene essential for proper baculovirus virion assembly. A gene essential for the proper baculoviral virion assembly may be mutated by way of nucleotide substitution, insertion or deletion in the sequence of all or a part of the wild type gene (for example in the sequence provided in Genbank Accession No. NC_001623.1, for a genome derived from AcMNPV). The mutation may correspond to the complete deletion of the gene, or to only a part of said gene. For example, one may delete at least 50%, more preferably at least 60%, more preferably at least 70%, more preferably at least 80% and even preferably more at least 90% of the gene essential for proper baculoviral virion assembly.

The mutant baculoviral genome may be produced using standard methods well known in the art, such as site-directed mutagenesis (see, e.g., Sambrook et al. (1989)) and Lambda red recombination (Datsenko & Wanner, 2000). The gene essential for proper baculovirus virion assembly may in particular be deleted as provided in the below examples. In summary, one can make use of the mutant loxP sites described by Suzuki at al. (2005), by replacing either totally or in part the gene essential for proper baculovirus virion assembly with a reporter gene flanked by mutant LoxP sites by recombination. The reporter gene (for example the gene coding for chloramphenicol acetyl transferase (cat) is then excised by implementing a recombination with Cre recombinase.

This embodiment is illustrated in the below examples and is detailed for baculoviruses whose genome has been modified by deleting a 2074-bp fragment of the vp80 ORF in the AcMNPV genome. This particular genome is part of the present invention, but is given as a non limiting example of what is a mutant baculoviral genome according to the invention.

It should be noted that recombinant engineering of the baculovirus genome may result in the insertion of several sequences like cloning sites or recombination sites (for example one remaining LoxP site after recombination with Cre recombinase). This is irrelevant as long as the resulting genome is made deficient for the selected gene essential for proper baculovirus virion assembly.

In this embodiment, wherein the genome of the at least one baculovirus is deficient for at least one gene essential for proper assembly of baculovirus virion, the production of recombinant budded baculovirus particles needed for the initial infection of the cells producing the bio-pharmaceuticals requires the implementation of special cells rescuing the deficient gene, i.e. these baculovirus-producing cells express the selected gene. In other terms, the baculovirus-producing cell expresses a complementing copy of the at least one gene essential for proper baculoviral virion assembly which is deficient in the baculovirus genome. For example, a Sf9-derived cell line constitutively producing the product of the gene essential for proper assembly of the baculovirus virion may be established. This recombinant cell line is used for production of baculovirus seed stock while conventional insect cell lines like Sf9, Sf21 or High-five cell lines can be infected with the produced baculovirus for heterologous expression of the biopharmaceutical product. Accordingly, the invention also relates to an insect cell modified so as to express a gene essential for proper baculovirus assembly, said gene being mutated in a baculovirus used for the production of biopharmaceuticals, as defined above. Such a cell line used for the production of the mutant baculovirus vector implemented in the method of the present invention is referred to as a "baculovirus-producing cell". When the baculovirus genome is deficient for a gene essential for proper baculovirus virion assembly, the baculovirus-producing insect cell must provide and express said gene in order to complement the deficiency and to produce an infectious baculovirus. In a particular embodiment, the insect cell used for the production of the baculovirus is modified by transfection with an expression cassette coding for at least one gene essential for proper baculovirus virion assembly. In an embodiment, said expression cassette is integrated in the genome of said cell. One may also use insect cells transiently transfected with at least one plasmid comprising the expression cassette. The terms "expression cassette" denote a construct comprising the coding sequence of a gene of interest functionally linked to expression control sequences. Such an expression cassette may be a plasmid comprising the ORF of a gene essential for proper baculovirus virion assembly placed under the control of a promoter functional in the selected insect cell, and does not contain baculoviral genome sequences other than the gene essential for proper baculovirus virion assembly to be complemented and optionally the promoter sequence allowing the expression of said gene (in particular, an expression cassette is not a bacmid or any other baculoviral entire genome). Exemplary expression control sequences may be chosen among promoters, enhancers, insulators, etc. In one embodiment, the complementing gene is derived from the genome of the baculovirus in which the gene essential for proper baculovirus virion assembly has been made deficient. In another embodiment, the complementing gene originates from the genome of a different baculovirus species than the baculovirus genome used for the production of biopharmaceuticals. For example, the baculovirus used for the production of biopharmaceuticals may be derived from the AcMNPV genome, and the complementing gene introduced in the baculovirus-producing cell is derived from BmNPV or SeMNPV. More specifically, the baculovirus genome may be made deficient for vp80, vp39, vp1054 and/or p6.9 and the baculovirus-producing cell may comprise a copy of a gene from BmNPV or SeMNPV able to complement these genes (e.g. as provided in the examples, p6.9 is deleted in the AcMNPV genome and the baculovirus-producing cell provides a rescuing copy of SeMNPV p6.9 gene).

The invention thus also provides a method for the production of a baculovirus deficient for at least one gene essential for proper baculovirus virion assembly, comprising the step of transfecting an insect cell comprising an expression cassette coding for a gene essential for proper baculovirus virion assembly, with a bacmid comprising a baculoviral genome, wherein said genome is deficient for a gene essential for proper baculovirus virion assembly, preferably wherein the genome of said baculovirus is deficient for vp80 or vp39, p6.9 and/or vp1054, wherein the gene essential for proper baculovirus virion assembly deficient in said bacmid is the gene coded by the expression cassette comprised in said insect cell. According to this method, the gene deficient in the baculoviral genome is complemented by the gene expressed in the insect cell. The cells transfected with the bacmid are maintained in conditions such that baculovirus virions are produced. These produced baculovirus virions, which comprise a genome where at least one gene essential for proper baculovirus virion assembly is lacking, are then collected for their subsequent use for infecting biopharmaceutical-producing insect cells for the production of the biopharmaceutical.

In the embodiment where the genome of the baculovirus is deficient for at least one gene essential for baculovirus virion assembly, the biopharmaceutical-producing insect cell must be unable to complement the deficiency of said gene. Otherwise, the deficiency would be rescued by the biopharmaceutical-producing cell and BVs and ODVs might be produced. The presence or absence of a gene essential for proper baculovirus assembly may be monitored for example by checking said cell by a PCR specific to said gene or by detection of the protein product of this gene (for example by western-blot with an antibody specific to said gene product). Cells expressing a functional product of the gene essential for proper baculovirus virion assembly which has been made deficient in the genome of the implemented baculovirus intended to infect said cell must be disregarded as bio-pharmaceutical producing cells.

In another embodiment of the invention, the expression of the gene essential for proper assembly of baculovirus virions is controlled by an expression control system. The term "expression control system" defines a modification of the baculovirus-producing insect cell system/the biopharmaceutical-producing cell system and/or yet another adaptation of the viral genome, resulting in the specific regulation of the gene essential for proper baculovirus virion assembly. This system may be an inducible expression system (for example Tet-On, Tet-Off, ecdysone-based systems (Dai et al., 2005) or baculovirus homologous region (hr) containing elements, such as the hr2 system described by Aslanidi et al., (2009) allowing the desired triggering or shutdown of the essential gene, an RNA interference expressing construct or a combination of these.

In a particular embodiment, the expression of the gene essential for proper assembly of baculovirus is inactivated by RNA mediated silencing, or RNA interference (Salem & Maruniak, 2007, Kanginakudru et al., 2007). Preferably, an insect-cell derived cell line, in particular a Sf9-derived cell line, is established by stably transforming such a cell with a construct coding for a gene-specific double stranded RNA (dsRNA) to silence the expression of the gene essential for proper baculovirus virion assembly. This dsRNA expressing cell line is used for the expression of the biopharmaceutical product after infection with the recombinant baculovirus(es) carrying the gene coding for said biopharmaceutical product. In this embodiment, seed stock recombinant baculovirus(es) may be produced with conventional Sf9, Sf21 or High-Five cell lines (i.e. without the need of a complementing copy of the gene in the cell), since in this case the baculovirus genome comprises the wild-type gene essential for proper baculovirus virion assembly.

In yet another embodiment of the invention, the gene essential for proper baculovirus virion assembly is placed under the control of an inducible promoter, allowing either the expression or repression of said gene under controlled conditions.

In a preferred embodiment, the number of baculovirus virions produced in the method of the present invention is reduced by at least 50% in comparison to the number of baculovirus otherwise produced by the biopharmaceutical-producing cell using a baculovirus genome comprising all the genes essential for proper baculovirus virion assembly. More preferably, the number of baculovirus virions is reduced by at least 60%, at least 70%, at least 80%, at least 90% and most preferably by at least 95% in comparison to a wild type baculovirus genome.

As discussed above, the use of insect cell/baculovirus systems for the production of biopharmaceuticals in the prior art is characterized by the co-production of huge quantities of recombinant baculoviruses (and may be over $10^8$ pfu/ml) in parallel to the biopharmaceutical product, needing carefully developed and optimized downstream processing protocols to inactivate and eliminate this baculovirus contamination. Inactivation can be performed by the addition of a detergent step leading to disintegration of the lipid layer of the contaminating baculovirus, such as used for the purification of virus like particles for vaccine purposes (porcine parvovirus-VLPs (Maranga et al. (2002)) or rotavirus-VLPs (Mellado et al. (2008)) or the purification of different serotypes of AAV (Smith et al. 2009).

Further efficient separation steps have been used: centrifugation (Wang et al. (2000); Maranga et al. (2002); Mellado et al. (2008)), microfiltration (Tellez. (2005)) negative elimination of baculovirus proteins (e.g. Mellado et al. (2008)) or positive affinity chromatography (retention/capture of a biopharmaceutical—flow through of the contaminating proteins, such as capture of the vp7 protein of rotavirus by Concanavalin A chromatography (Mellado et al. (2008), capture of the immunogenic chimeric rVP2H infectious bursal disease virus particles by immobilized metal-ion affinity chromatography (Wang et al. (2000)) or capture of different AAV serotypes by immunoaffinity chromatography using camelid antibodies (Smith et al. 2009). In particular, due to the use of highly specific immunoligands, the use of immunoaffinity allows the complete separation of the to be purified biopharmaceutical (e.g. specific AAV) from any contaminant, and in the case of the baculovirus system, from the huge contamination by baculovirus due to the concomitant production of baculovirus in parallel to the biopharmaceutical.

These references present very clearly the need of these different process steps for inactivating and eliminating residual baculovirus contaminants, because without these steps, the biopharmaceutical product is still considerably contaminated by various baculovirus proteins and cannot be used for clinical purposes.

The method of the present invention allows a significant reduction of the number of contaminating baculovirus virions, or even a complete absence. As a consequence, a reduced number of purification steps will be necessary for getting a biopharmaceutical for clinical purposes (or even no purification step if no baculoviral virion is produced). Thus, the biopharmaceutical production and purification protocol is simplified because by using the method of the present invention, the need for eliminating residual baculovirus virion is greatly reduced. In case a simplified purification protocol is still to be applied, the skilled artisan may select at least one of the above identified methods and protocols to obtain a purified biopharmaceutical product.

Preferably, the selected essential gene is a gene whose inactivation does not affect baculoviral very late gene expression, compared to the original baculovirus vector. In the AcMNPV genome (and other alpha-baculoviruses), the p10 and polyhedrin promoters are the very late expression promoters and it should be noted that in baculovirus/insect cell production systems, the heterologous gene is most commonly inserted under the control of these very strong promoters allowing expression of very large amounts of recombinant proteins. The inactivation of a gene essential for proper baculovirus virion assembly, which does not affect very late gene expression is thus preferred. The terms “does not affect very late gene expression” denotes the fact that the level of recombinant protein expression from very late baculovirus promoter comprised in the genome of a baculovirus modified according to the invention is at least 70% in comparison to the levels obtained from a non-modified genome, more preferably greater than 80%, more preferably greater than 90%. It should be mentioned that the level of expression of a biopharmaceutical product from a very late baculoviral promoter may even be greater than 100% of the level obtained with the non-modified vector in the method of the present invention.

Among the genes tested by the inventors, the vp80 gene is particularly preferred since its deletion does not affect very late expression, while it totally prevents production of BVs and results in a significant reduction in the number of intracellular nucleocapsids, the precursors of ODVs.

Very late expression may be evaluated by placing a reporter gene, for example a gene coding for a GFP, in particular egfp, or a luciferase gene, under the control of the polyhedrin or p10 promoter in a wild type AcMNPV vector and in a mutant AcMNPV genome from which the essential gene has been inactivated, and by comparing the expression of the product of the reporter gene from both genomes. Preferably, very late expression from the vector with a mutated baculovirus backbone is at least 60% of the expression level obtained with the wild type AcMNPV vector and preferably higher than 80%, more preferably higher than 90%, as measured from a reporter gene under the control of either p10 or polyhedrin gene promoters.

The invention also relates to a method for screening baculoviral genes, the inactivation of which could be useful for producing biopharmaceuticals without contaminating baculovirus virions in an insect cell—baculovirus system as defined above, comprising:

a) providing a cell culture of cells containing a baculoviral genome;
b) contacting said cell culture with means for inactivating at least one test baculoviral gene of said baculoviral genome, for example with RNA interference; and
c) testing virion formation from said cell culture in comparison to virion formation from a cell culture not contacted with said means;

wherein a test gene is selected as potentially useful for producing biopharmaceuticals if its inactivation results in a reduction of baculoviral virion formation.

In a particular embodiment, the method for screening of the invention further comprise step d) of testing very late gene expression from the cell culture contacted with said means in comparison to very late gene expression from a cell culture not contacted with said means;

wherein a test gene is selected as potentially useful for producing biopharmaceuticals if its inactivation results in a reduction of baculoviral virion formation and if it does not affect very late gene expression from said baculoviral genome.

The invention also relates to a method for screening baculoviral genes, the inactivation of which could be useful for producing biopharmaceuticals without contaminating baculovirus virions in an insect cell—baculovirus system as defined above, comprising:

- inactivating at least one test gene of a baculoviral genome (for example by deletion of said test gene in said genome);
- evaluating baculoviral very late gene expression from said baculoviral genome as defined above;
- determining production of baculoviral virions from cells containing said baculoviral genome;

wherein a gene is selected as potentially useful for the production of biopharmaceuticals if its inactivation

- results in a reduction in the production of baculoviral virions, and
- does not affect very late gene expression from said baculoviral genome, as defined above.

In a particular embodiment of the method for screening a baculoviral gene, the inactivation of which could be useful for producing biopharmaceuticals, the inactivation of the test gene is carried out with dsRNA specific for said test gene.

In particular, the candidate baculovirus gene can be identified by knocking down its expression by RNA interference to test its role in virion formation.

The invention will now be illustrated with the following examples, which are provided as non limiting exemplary embodiments of the invention.

LEGENDS TO THE FIGURES

Figure 1:
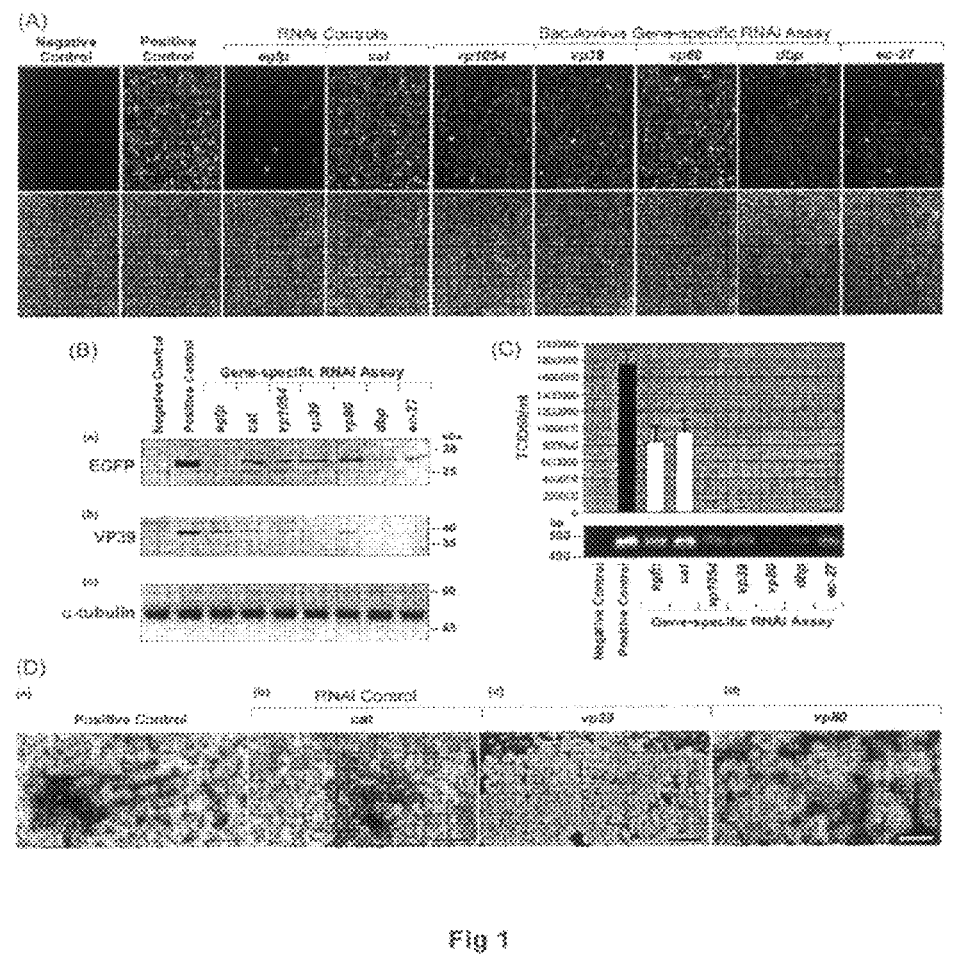

FIG. 1. dsRNA-mediated gene silencing screening. Insect Sf9 cells were seeded in 24-well tissue culture plates ($2\times10^5$ cells/well) in 1 ml Sf-900 II SFM culture medium at 28° C. After two hours, the culture medium was removed, and the cells were infected with recombinant baculovirus carrying the egfp gene under control of the polyhedrin promoter (AcMNPV-EGFP) under standard conditions. (A) Determination of very late gene expression level using fluorescent microscopy. Cells were infected at MOI=10 $TCID_{50}$ units/cell and transfection with gene-specific dsRNA for vp1054, vp39, vp80, dbp and ec-27 was performed at 1 h post infection (p.i.). The level of very late gene expression was checked by EGFP-specific fluorescence at 48 h p.i. dsRNAs specific for egfp and cat sequences were used as RNAi controls. (B) Measurement of very late gene expression levels by an immunoblotting-based assay. The cells were infected with AcMNPV-EGFP at MOI=1 and transfection with gene-specific dsRNA was also performed at 1 h p.i. The level of very late gene expression was analyzed by using an rabbit anti-EGFP polyclonal antiserum at 48 h p.i. Anti-vp39 and anti-α-tubulin antibodies were used as internal controls. (C) Titration and detection of produced budded virions in dsRNA-treated cells. Budded virions were harvested at 36 hours p.i., and used either for end-point dilution assays to measure titers of infectious virions, or for PCR-based detection to check the presence of virus particles. (D) Presence of occlusion-derived virions and rod-shaped structures in vp39- and vp80-down-regulated cells. The cells were harvested 36 hours p.i., lysed, and the cell lysates were ultracentrifuged through a cushion of 40% sucrose solution (45,000 rpm for 1 hour, Beckman SW55). Pellets were resuspended in demi-water and analyzed by negative staining electron microscopy. The bars represent 100 nm.

FIG. 2. Construction of the AcMNPV vp80-null bacmid. (A) Strategy for construction of a vp80-null bacmid containing a complete deletion of the AcMNPV vp80 open-reading frame via homologous recombination in *E. coli*. At the first step, a 2074-bp fragment encompassing the vp80 ORF was deleted and replaced with a sequence cassette containing the chloramphenicol (cat) resistance gene flanked by modified loxP (LE and RE) sites. Subsequently, the antibiotic resistance gene (cat) was eliminated from the bacmid sequence using the Cre/loxP recombination system. The promoter sequence of the p48 gene and the polyadenylation signal of the he65 gene were remained intact. Oligonucleotide pairs were used in PCR analysis of the wild-type locus and two vp80 knock-out genotypes to confirm the deletion of the vp80 ORF and the correct insertion/deletion of the chloramphenicol resistance gene cassette, as indicated by unilateral arrows. Their names are designated according to nucleotide sequence coordinates. Primers for cat gene cassette amplification are named cat-F and cat-R. (B) PCR-based detection of the presence or absence of sequence modifications in the vp80 locus in the original AcMNPV bacmid (Ac-wt), Ac-vp80null(+cat), and Ac-vp80null(−cat) bacmids. The top figure confirms the vp80 gene deletion and the insertion of the cat cassette into the vp80 locus with primer pairs 90292/90889 and cat-F/cat-R. The bottom figure is showing PCR-based verification of the correct recombination processes in the vp80 locus using the 89507/91713 primer pair.

Figure 3:
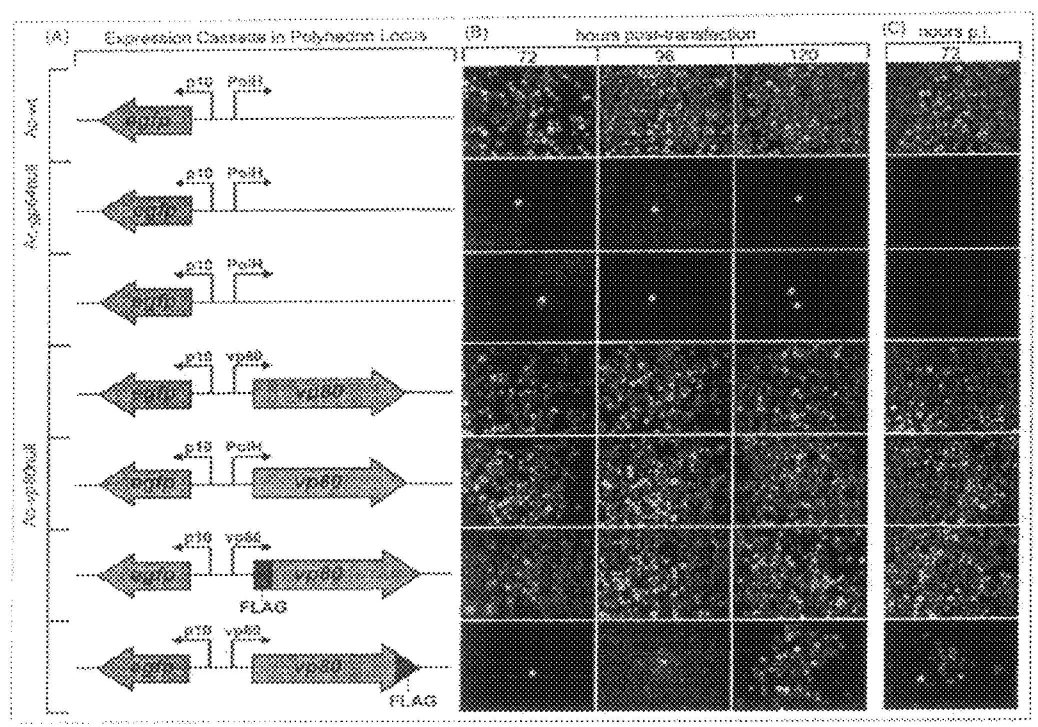

FIG. 3. Viral replication capacity of AcMNPV-vp80 knockout and repaired bacmid constructs using transfection-infection assays (A) Schematic representation of expression cassettes transposed into the polyhedrin locus. Four repair constructs were made (vp80 driven by its native promoter, vp80 driven by the polyhedrin promoter, N-terminally FLAG-tagged vp80 and C-terminally FLAG-tagged vp80, both expressed from its native promoter). The bacmid genome backbones used for transfection assays are indicated on the left. As positive control of viral replication the wild type AcMNPV (bMON14272) bacmid was used. The Ac-gp64null bacmid was used as negative control representing a prototype bacmid with a "single-cell infection" phenotype. (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection.

Figure 4:
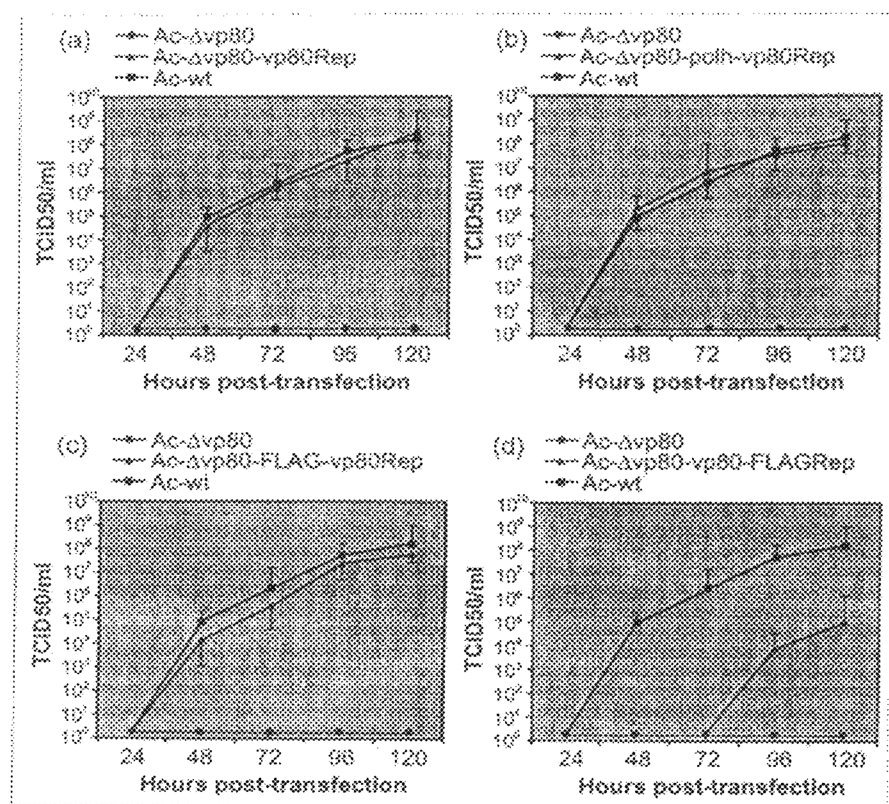

FIG. 4. Growth curves of AcMNPV-vp80null repaired bacmid constructs generated from a transfection time-course assays. Sf9 cells were transfected with 5.0 μg of DNA from each repair bacmid. (a) vp80 driven by its native promoter, (b) vp80 driven by the polyhedrin promoter, (c) N-terminally FLAG-tagged vp80, and (d) C-terminally FLAG-tagged vp80, both expressed from the vp80 promoter. Cell culture supernatants were harvested at the indicated time points post-transfection and analysed for the production of infectious budded virus by an $TCID_{50}$ end-point dilution assay. Infectivity was determined by monitoring EGFP expression. The points indicate the averages of titers derived from three independent transfections, and the error bars represent the standard deviation.

Figure 5:
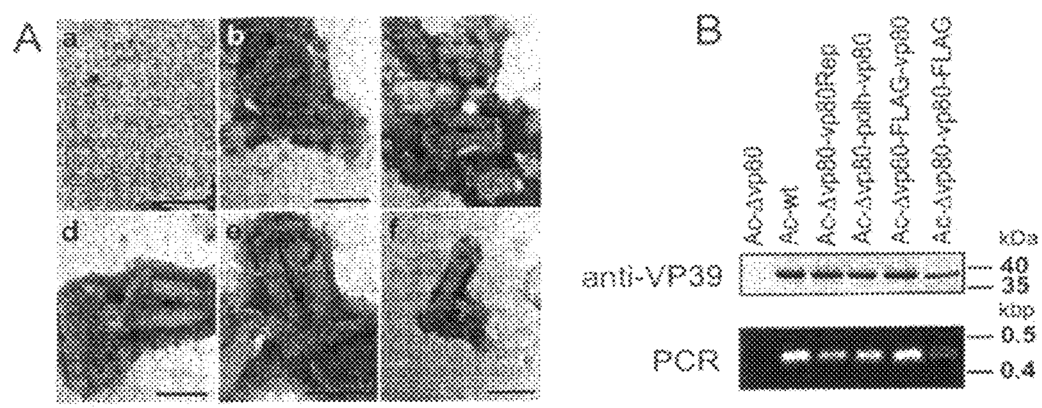

FIG. 5. The AcMNPV-vp80null mutant is unable to produce any infectious/non-infectious budded virions. The Sf9 cells were independently transfected with 20 μg of bacmid DNA of Ac-Δvp80 (a), Ac-wt (b), Ac-Δvp80-vp80 (c), Ac-Δvp80-pH-vp80 (d), Ac-Δvp80-FLAG-vp80 (e), or Ac-Δvp80-vp80-FLAG (f). Five days p.t., the budded virus-enriched cell culture supernatants were ultracentrifuged and budded viruses were observed by negative staining electron microscopy (A). The bars represent 200 nm. Parallelly, harvested budded virions were also either separated on SDS-PAGE, blotted and immuno-detected using anti-VP39 antibody or used for PCR-based detection to detect the presence of viral particles (B).

Figure 6:
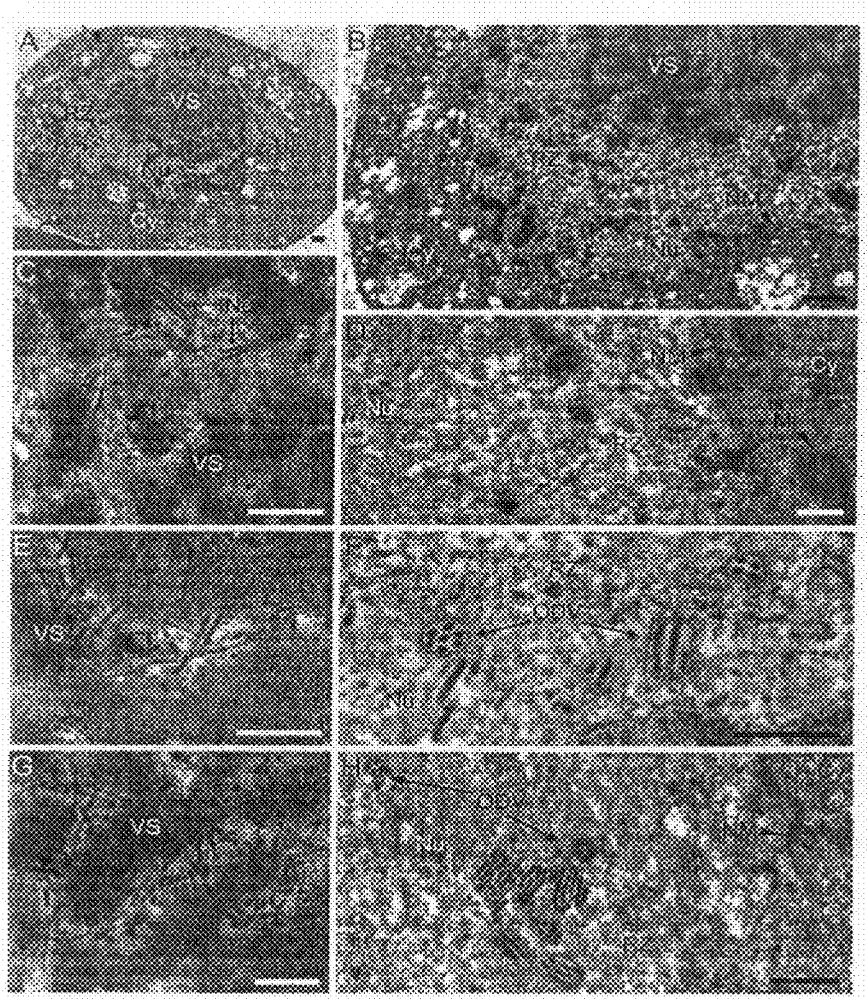

FIG. 6. The null bacmid mutant in the vp80gene forms small number of nucleocapsids, and is deficient in production of occlusion-derived virions. The Sf9 cells transfected either with Ac-Δvp80 (A to D), Ac-Δvp80-vp80 (E, F), or Ac-wt (G, H) were fixed, stained, embedded and thin-sectioned as described in Materials and Methods. (A) Representative overview of Sf9 cell transfected with Ac-vp80null bacmid mutant. (B) The Ac-vp80null mutant does form less number of nucleocapsids in the virogenic stroma (C), and no occlusion-derived virions in the ring zone of transfected cells (D). On the other hand, repair bacmid construct Ac-Δvp80-vp80 fully regenerates formation of plenty nucleocapsids in the virogenic stroma (E), as well as normally-appearing occlusion-derived virions in the ring zone of transfected cells (F). Representative images of the virogenic stroma (G) and the ring zone (H) of cells transfected with Ac-wt bacmid. Bars represent 500 nm. Abbreviations: Nc, nucleocapsid; NM, nuclear membrane; Nu, nucleus; RZ, ring zone; Mi, mitochondrion; ODV, occlusion-derived virions; VS, virogenic stroma.

Figure 7:
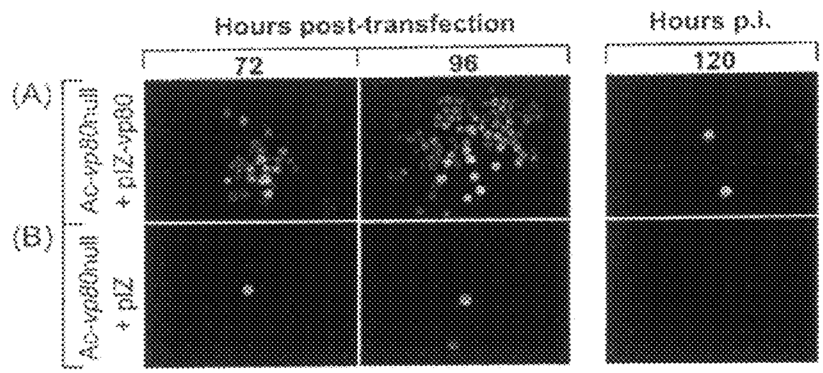

FIG. 7. Functional complementation of the Ac-vp80null bacmid mutant using the trans-acting vp80 gene. The Sf9 cells were transfected with either pIZ-flag-vp80 (A) or pIZ (B) vector, and subjected to Zeocin-based selection. Three weeks post-transfection, a polyclonal Zeocin resistant populations of cells were seeded to new 6-well plate and transfected with the Ac-vp80null bacmid mutant to check complementation activity. Virus propagation was monitored by EGFP-specific fluorescence at 72 h and 96 h p.t. At 120 hours p.t., the cell culture supernatants were collected to initiate a secondary infection in untreated (wild-type) Sf9 cells (right panel). EGFP was detected at 72 hours p.i. to signal the progress of infection. EGFP was detected at 120 hours p.i. to signal the progress of infection.

Figure 8:
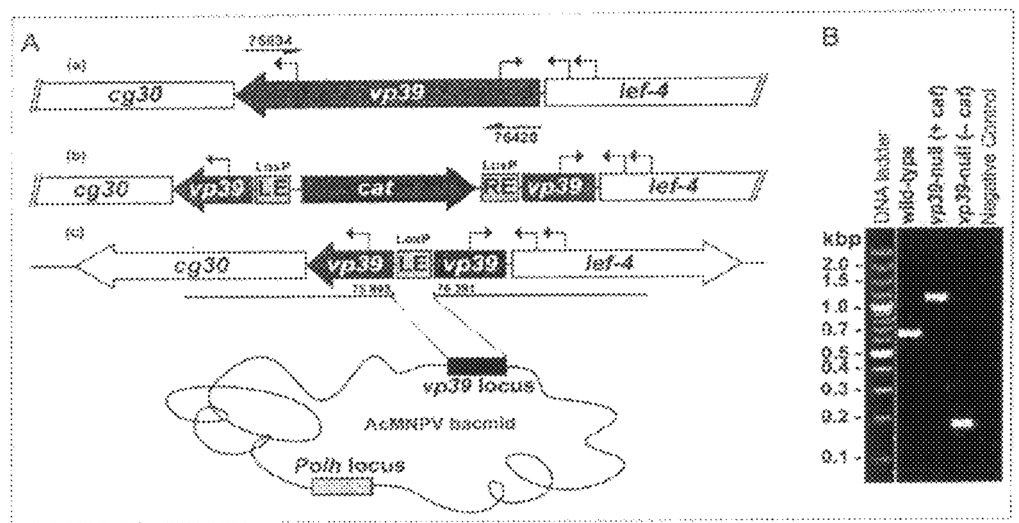

FIG. 8. Construction of an AcMNPV vp39-null bacmid. (A) Strategy for construction of a vp39-null bacmid containing a partial deletion of the AcMNPV vp39 open-reading frame via homologous recombination in *E. coli*. At the first step, an internal 498-bp fragment of the vp39 ORF was deleted and replaced with a sequence cassette containing the chloramphenicol (cat) resistance gene flanked by modified loxP (LE and RE) sites. Subsequently, the cat gene was eliminated from the bacmid sequence using the Cre/loxP recombination system. The promoter sequences of the lef-4 and cg-30 genes were not affected. Arrows indicate the positions of oligonucleotide pairs used in PCR analysis of the wild-type locus and two vp39 knock-out genotypes to confirm the partial deletion of the vp39 ORF and the correct insertion/deletion of the cat gene cassette. Primers names are designated according to the nucleotide sequence coordinates. (B) PCR-based detection of the presence or absence of sequence modifications in the vp39 locus of Ac-wt, Ac-vp39null(+cat), and Ac-vp39null(−cat) bacmids. The figure is showing the PCR-based verification of the correct recombination processes in the vp39 locus using the 75834/76420 primer pair.

Figure 9:
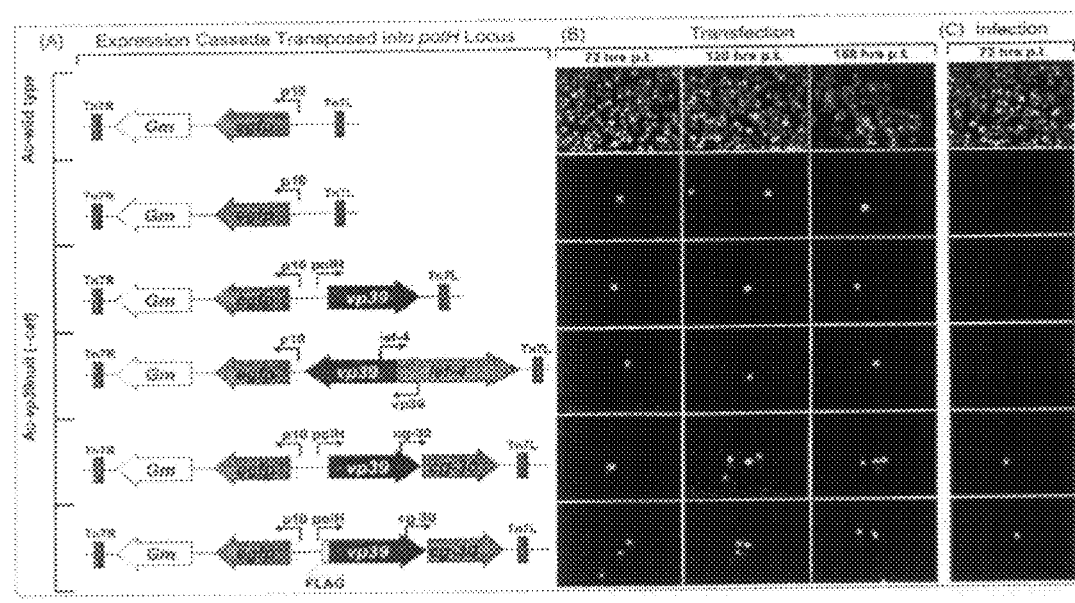

FIG. 9. Determination of viral replication capacity of AcMNPV-vp39 knockout and repaired bacmid constructs using transfection-infection assays (A) Schematic representation of expression cassettes, Tn7-based transposed into the polyhedrin locus. (1) vp39 expressed form the polyhedrin promoter, (2) a double gene vp39 and lef-4, both driven by their native promoters, (3) a double gene vp39 and cg-30 both driven by the polyhedrin promoter, and finally (4) a double gene construct of N-terminally FLAG-tagged vp39 driven by the polyhedrin promoter and the cg-30 ORF expressed from both its native and also the more upstream polyhedrin promoter. The parental bacmid genome backbones used for transfection assays are indicated on the left. The wild type AcMNPV (bMON14272) bacmid was used as positive control of viral replication. (B) Time course fluorescence microscopy showing the propagation of the infection in Sf9 cells transfected with indicated bacmid constructs. Viral progressions were checked by EGFP detection at indicated times post transfection. At 168 hours p.t., the cell culture supernatants were collected to initiate a secondary infection. (C) Secondary infection assay. EGFP detection was performed at 72 hours p.i. to measure progress of the infection.

Figure 10:
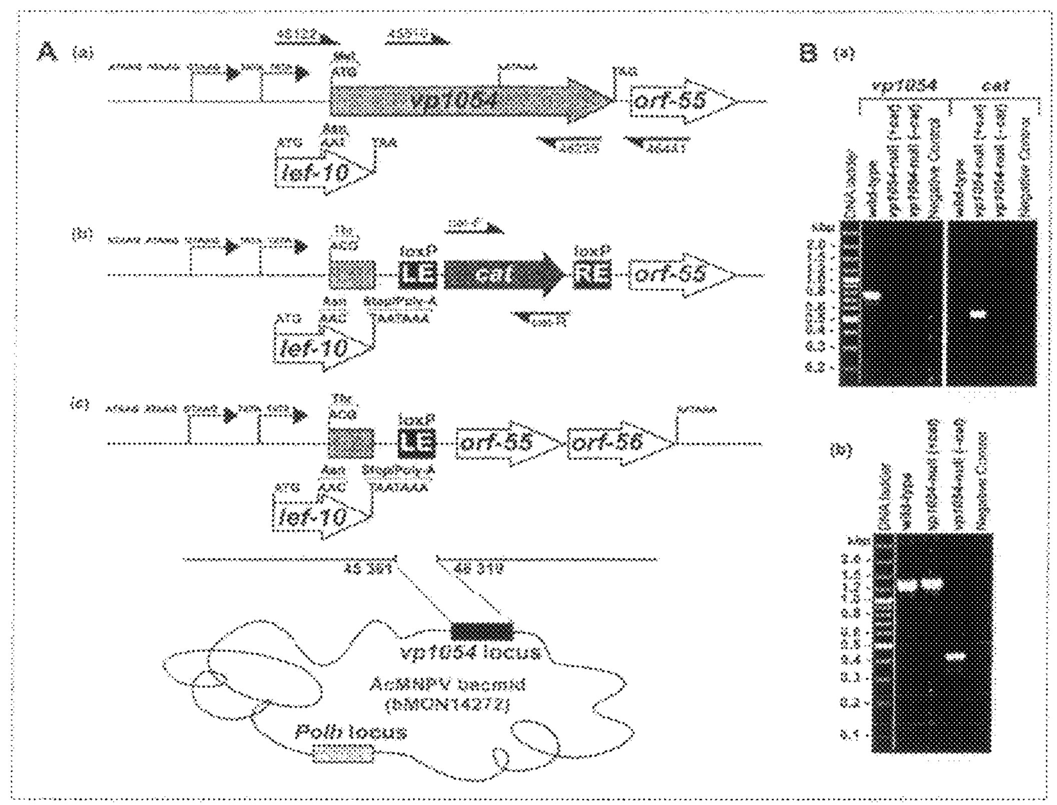

FIG. 10. Construction of an AcMNPV vp1054-null bacmid. (A) Strategy for the construction of a vp1054-null bacmid containing a deletion of the AcMNPV vp1054 open-reading frame via homologous recombination in *E. coli*. A 955-bp sequence from the 3'-end of the vp1054 ORF was deleted and replaced with a cat sequence cassette flanked by modified loxP (LE and RE) sites. At the same time, a single point mutation was introduced to change the first translation codon ATG→Met to ACG→Thr, to prevent translation into a C-truncated VP1054 protein. It also meant that the internal AAT codon no. 32 of lef-10 was mutated to AAC, both encoding Asn. Subsequently, the cat gene was eliminated using the Cre/loxP recombination system. The promoter sequence of vp1054/lef-10 was not affected in the bacmid construct. Since the polyadenylation signal of the lef-10 gene was removed, a novel synthetic poly-A signal combined with stop codon (TAATAAA) was introduced at the 3'-end of the lef-10 ORF. Arrows represent locations of oligonucleotide pairs used in the PCR analysis of the wild-type locus and two vp1054 knock-out genotypes to confirm the deletion of the vp1054 ORF and correct insertion/deletion of the cat cassette. (B) PCR-based detection of the presence or absence of sequence modifications in the vp1054 locus of Ac-wt, Ac-vp1054null (+cat), and Ac-vp1054null(−cat) bacmids. The top figure is showing confirmation of the vp1054 gene deletion and insertion of the cat cassette into vp1054 locus using primer pairs 90292/90889 and cat-F/cat-R. The bottom figure shows CR-based verification of the correct recombination processes in the vp1054 locus using the 89507/91713 primer pair.

Figure 11:
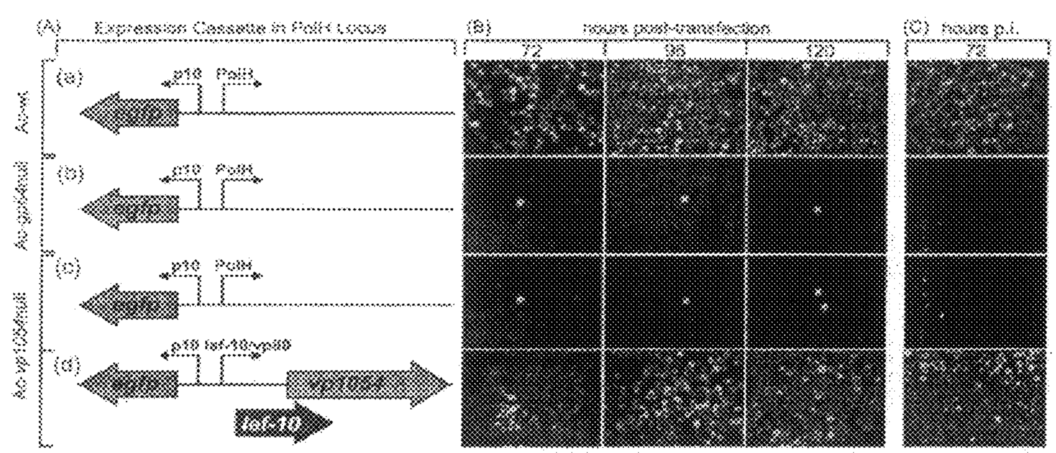

FIG. 11. Viral replication capacity of AcMNPV-vp1054 knockout and repaired bacmid constructs using transfection-infection assays (A) Schematic representation of expression cassettes transposed into the polyhedrin locus. The bacmid genome backbones used for transfection assays are indicated on the left. Two Ac-vp1054null-derived constructs were made: first construct carrying only egfp marker gene under control of p10 promoter, and second construct carrying both egfp marker and over-lapping lef-10/vp1054 locus directed from their natural promoter sequences (d). As positive control of viral replication the wild type AcMNPV (bMON14272) bacmid was used (a). The Ac-gp64null bacmid was used as negative control representing a prototype bacmid with a "single-cell infection" phenotype (b). (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection.

Figure 12:
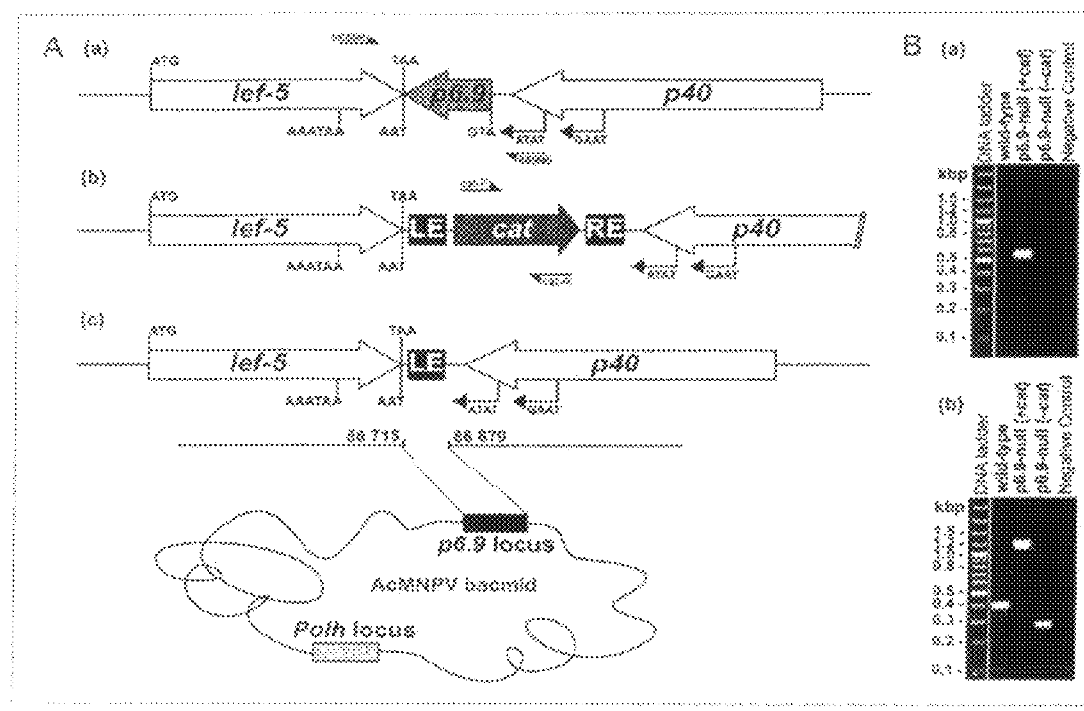

FIG. 12. Construction of an AcMNPV p6.9-null bacmid. (A) Strategy for construction of a p6.9-null bacmid containing a complete deletion of the AcMNPV p6.9 open-reading frame via homologous recombination in *E. coli*. A 164-bp fragment of the p6.9 ORF was deleted and replaced with a cat resistance gene flanked by modified loxP (LE and RE) sites. Subsequently, the cat gene was eliminated from the bacmid sequence using Cre/loxP recombination. The promoter sequence of p6.9 gene was left unaffected, since its sequence is overlapping with the p40 ORF. Arrows represent locations of primer pairs used in the PCR analysis of the wild-type locus and two p6.9 knock-out genotypes. (B) PCR-based detection of the presence or absence of sequence modifications in the p6.9 locus of Ac-wt, Ac-vp6.9null(+cat), and Ac-vp6.9null(−cat) bacmids. The top figure shows the insertion of the cat cassette into the p6.9 locus using primer pairs cat-F/cat-R. The bottom figure shows PCR-based verification of the correct recombination processes in the p6.9 locus using the 86596/86995 primer pair.

Figure 13:
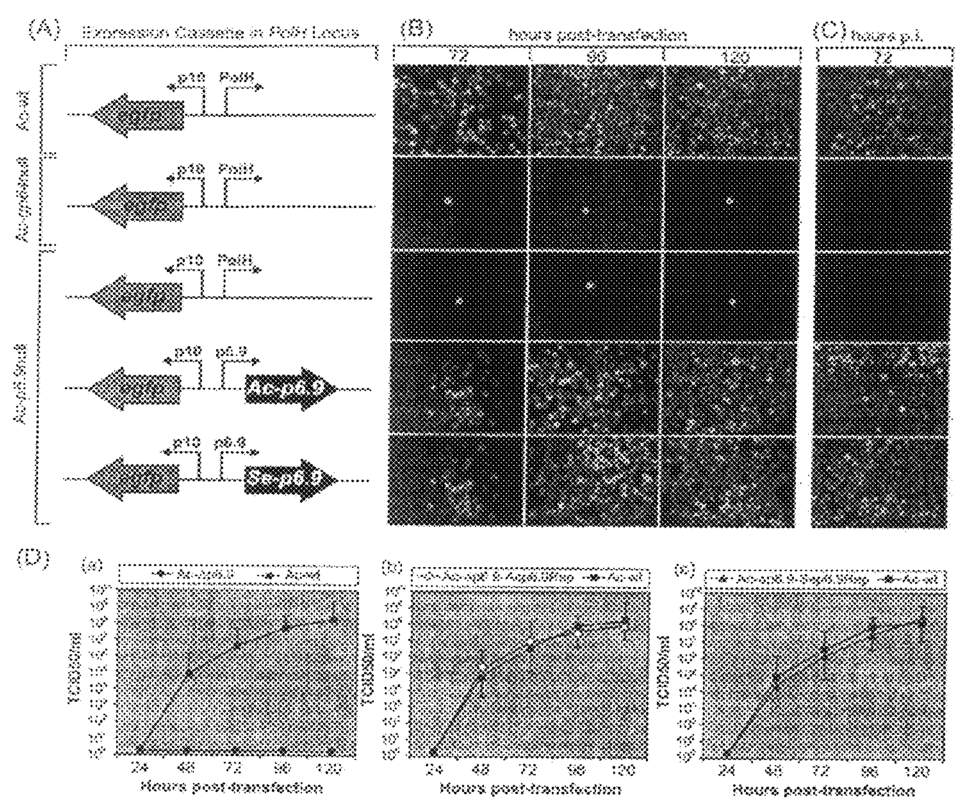

FIG. 13. Viral replication capacity of AcMNPV-p6.9 knockout and repaired bacmid constructs using transfection-infection assays (A) Schematic representation of expression cassettes transposed into the polyhedrin locus. Two repair constructs were made (AcMNPV p6.9 and SeMNPV p6.9 genes, both driven by the AcMNPV p6.9 promoter). The bacmid genome backbones used for transfection assays are indicated on the left. As positive control of viral replication the wild type AcMNPV (bMON14272) bacmid was used. The Ac-gp64null bacmid was used as negative control representing a prototype bacmid with a "single-cell infection" phenotype. (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection. (D) Comparisons of growth curves of AcMNPV-p6.9null (a), AcMNPV-p6.9null rescued with AcMNPV p6.9 (b), and AcMNPV-p6.9null rescued with SeMNPV p6.9 (c) constructs with wild-type (Ac-wt) bacmid. Sf9 cells were transfected with 5.0 μg of DNA from each bacmid, cell culture supernatants were harvested at the indicated time points post-transfection and analysed for the production of infectious budded virus by an $TCID_{50}$ end-point dilution assay. Infectivity was determined by monitoring EGFP expression. The points indicate the averages of titers derived from three independent transfections, and the error bars represent the standard deviation.

Figure 14:
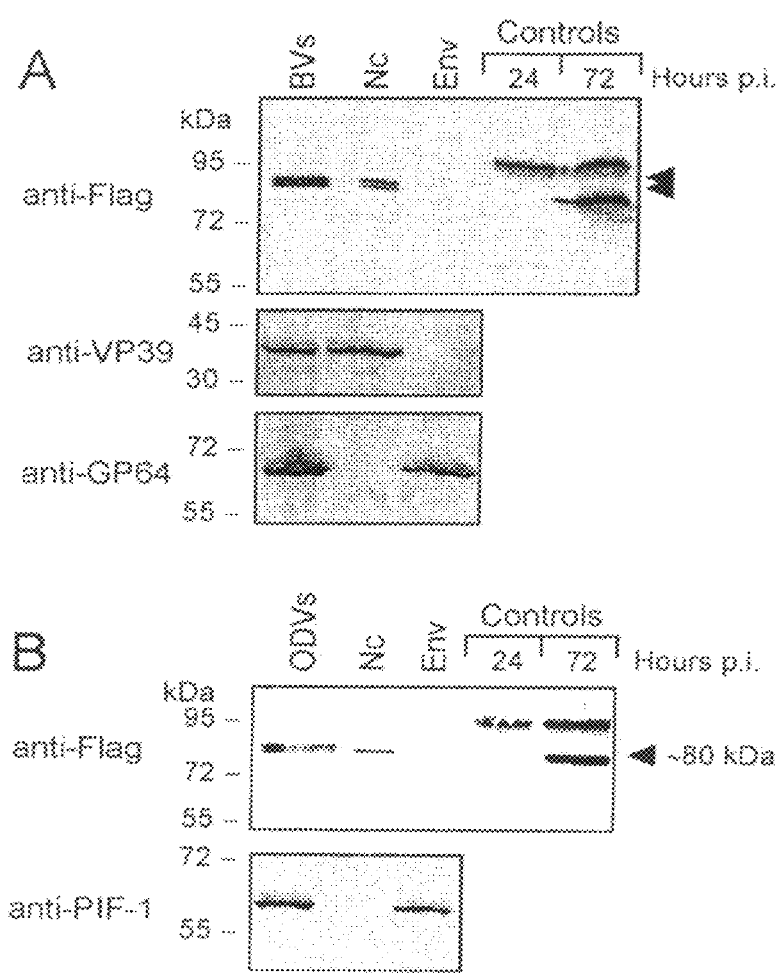

FIG. 14: Western blot analysis of Flag:vpp80 in cells, BV and ODC Time course of vp80 expression in infected insect cells. Sf9 cells were infected with the Ac-Δvp80-Flag·vp80 repair virus, and harvested at an indicated time points. Flag·VP80 was detectable by western blot analysis from 12 h to 72 h p.i. as a band of approximately 95 kDa. In addition, a second Flag·VP80-specific band of ~80 kDa accumulated from 48 h till 72 h p.i. Tubulin was used as an internal loading control. (B) The VP80 associates with the nucleocapsid fraction of BV. Two days p.i., BVs were purified by isokinetic ultracentrifugation in a sucrose gradient and separated into nucleocapsid (Nc) and envelope (Env) fractions by Nonidet-P40-based extraction. Flag·VP80 was detected in the Nc fraction as a double-band with molecular weights between the two variants (80-kDa and 95-kDa) detected in infected Sf9 cells (upper panel). Correct separation into Nc and Env fractions was controlled by anti-VP39 and anti-GP64 antibodies (bottom panels). (C) VP80 is also a structural component of ODV- nucleocapsids. Sf9 cells were co-infected with Ac-Δvp80-Flag·vp80 (MOI=25) and AcMNPV strain E2 (MOI=5) viruses. Five days p.i., ODVs were released from occlusion bodies and subsequently separated into nucleocapsid (Nc) and envelope (Env) fractions. Western blot analysis showed that VP80 is present in the DV Nc fraction as a single band of ~80 kDa. Proper fractionation into Nc and Env fractions was controlled using anti-PIF-1 antiserum (bottom panel).

Figure 15:
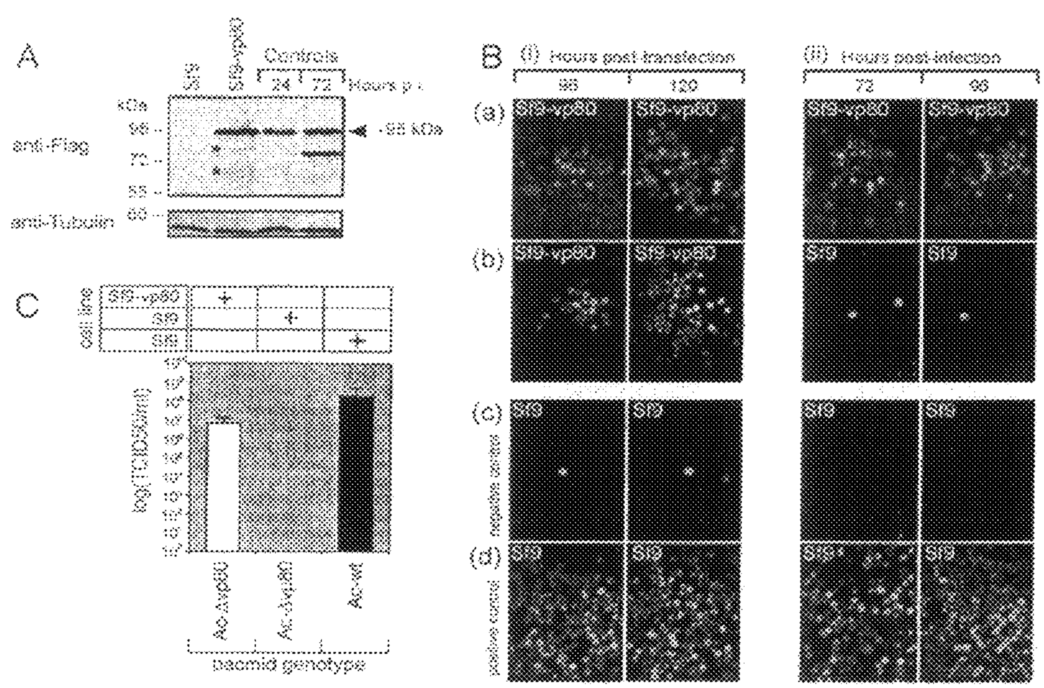

FIG. 15. Functional complementation of the Ac-vp80null bacmid defective in BV production by trans-complementation. (A) Detection of FLAG:VP80 in a transgenic Sf9-derived cell line (Sf9-vp80) by Western analysis. Tubulin was used as an internal loading control. (B) Time-course fluorescence microscopy (EGFP) to follow the infection in Sf9-vp80 cells transfected (i) or infected (ii) with the Ac-Δvp80 bacmid (a,b). At 120 h p.t., the cell culture supernatants were collected to initiate a secondary infection in either Sf9-vp80 (a) or Sf9 (b) cells (panels on the right side). As negative control Ac-Δvp80 was propagated in Sf9 cells (c), Ac-wt propagated in Sf9 cells (d) was used as positive control. (C) Comparative release of infectious BV virions. Sf9-vp80 cells were transfected with the Ac-Δvp80 bacmid and Sf9 cells with either the Ac-Δvp80 (negative control) or the Ac-wt (positive control) bacmid. BVs were quantified in cell culture supernatants at 6 days p.t. by end point dilution. Representative results of three independent assays with error bars giving the SD are shown.

Figure 16:
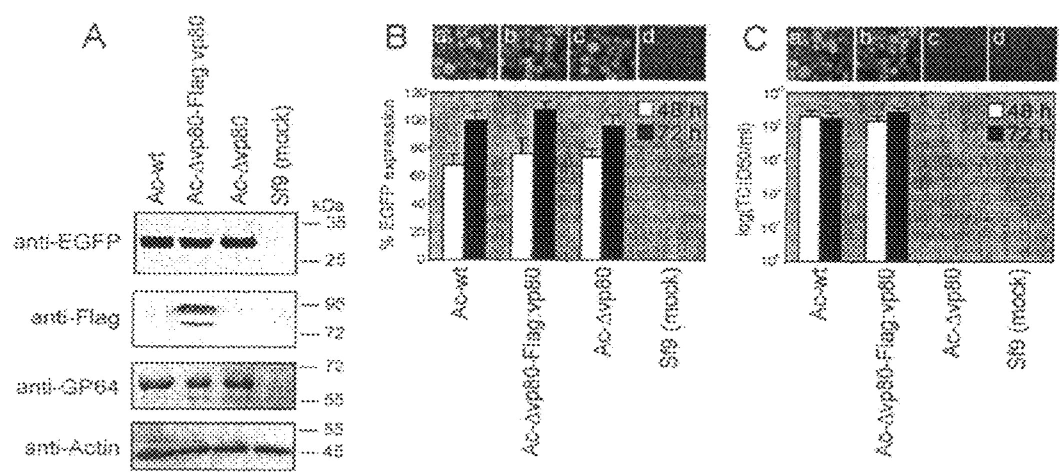

FIG. 16. Analysis of foreign gene expression by trans-complemented, replication-deficient baculovirus seed. Sf9 cells were infected with Ac-wt, Ac-Δvp80-Flag:vp80 or Ac-Δvp80 virus seed (MOI=10 $TCID_{50}$ units per cell), all expressing egfp from the very late p10 promoter. (A) At 48 h p.i. the presence of EGFP, Flag:VP80 and GP64 was analyzed by Western blotting. Actin was used as an internal loading control. (B) Photomicrographs of cells expressing EGFP 72 h p.i. (top), and relative amount of EGFP measured by ELISA at 48 and 72 h p.i. (bottom) (C) Photomicrographs of cells expressing EGFP 72 h p.i. (top), and analysis of BV release to test for revertant genotypes by $TCID_{50}$ titration (bottom). The results of three independent assays are shown with error bars (SD) (B and C).

Figure 17:
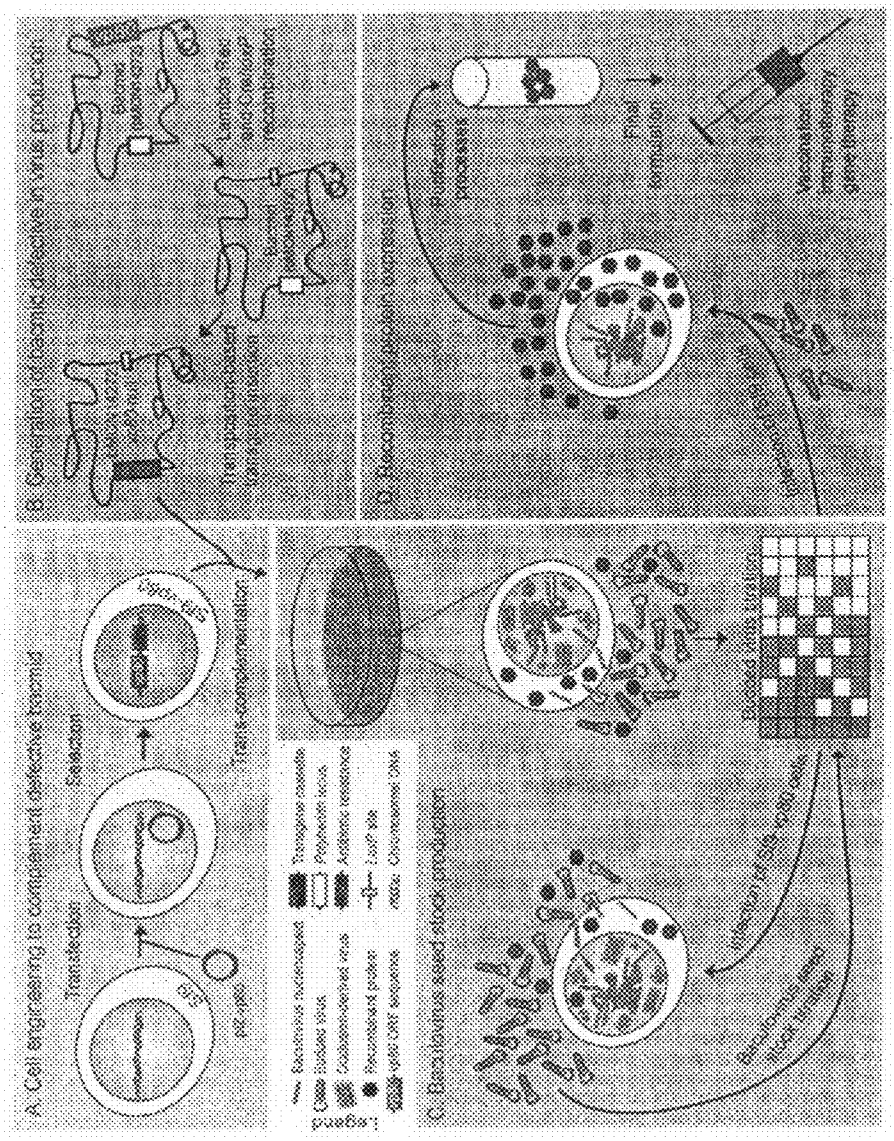

FIG. 17. The novel baculovirus-insect cell technology approach designated for the production of biopharmaceuticals free of contaminating baculoviral virions. (A) Insect cell engineering to express an essential viral factor (vp80) to complement a vp80 mutation in the virus. The transgenic Sf9 cells encode the vp80 ORF and a resistance gene allowing antibiotics-based selection of the transgenic cells. (B) Generation of an Ac-Δvp80 bacmid defective in production of BV and ODV virions. The bacmid lacks the entire vp80 ORF. (C) Production of a baculovirus seed stock by trans-complementation in the engineered Sf-vp80 cells. The Sf9-vp80 cells are transfected with the Ac-Δvp80 bacmid to produce trans-complemented virus progeny. After budded virus propagation, high-titer virus stocks are produced in the Sf9-vp80 packaging cells (D) Baculovirus-based recombinant protein expression. Conventional Sf9 cells are infected with the trans-complemented budded virus progeny. Recombinant protein is expressed from very late baculovirus promoters (p10 or polh) allowing high levels of expression, while no contaminating baculovirus virions (BV/ODV) are produced.

EXAMPLES

Example I

Materials and Methods

Insect Cells and Viruses

*Spodoptera frugiperda* (Sf9) cells were maintained in SF900-II serum-free medium (Invitrogen) under standard conditions. Recombinant bacmid-derived AcMNPV virus (AcMNPV-EGFP) carrying an egfp reporter gene under control of the very late polyhedrin promoter transposed into the polyhedrin locus was obtained from Pijlman et al. (2006). The virus was propagated and its titers were determined by an end-point dilution assay in Sf9 cells.

In Vitro Synthesis of dsRNA

The method used to synthesize dsRNA is similar to that described by Ramadan et al. (2007) with minor modifications. All DNA templates were PCR amplified using primers with twenty-five nucleotide overhangs homologous to the T7 RNA polymerase promoter sequence 5'-gcttctaatacgactcactataggg-3'. The sequences of the primers indicated below are given in Table 1. The following primers were used for amplifying these genes: primers vp39-F and vp39-R for vp39; primers 45510 and 46235 for vp1054, primers 90292 and 90889 for vp80; primers ec-27-F and ec-27-R for odv-ec27; and primers dbp-F and dbp- for dbp. To test the efficiency of the RNAi studies we made dsRNA against egfp with primers gfp-F and gfp-R, and to have a negative control we made dsRNA with primers cat-F and cat-R for the chloramphenicol acetyl transferase (cat) gene.

The PCR products were purified using the Illustra GFX PCR DNA and Gel Band Purification Kit (GE Healthcare, Buckinghamshire, UK) and were used as templates for dsRNA in vitro synthesis using the T7 RiboMAX™ Express RNAi System (Promega, Madison, Wis., USA) according to manufacturer's protocol. Briefly, approximately 1 μg of purified DNA templates were used for RNA synthesis at 37° C. for 4 h. After synthesis, DNA templates were removed by digestion with DNase. Complementary RNA strands were annealed by incubation at 70° C. for 10 min followed by slow cooling to room temperature (~30 min). Non-annealed (single-stranded) RNA molecules were degraded by RNase A treatment (30 min, 37° C.). Finally, the dsRNA was isopropanol precipitated, resuspended in DEPC-treated sterile water to a final concentration of 0.5-1 mg/ml, and its purity and integrity were checked by agarose gel electrophoresis. The dsRNA was kept at −80° C. in aliquots of 40 μl. Immediately before transfection, the dsRNA was thawed on ice.

RNAi Procedure in Baculovirus-Infected Insect Cells

Sf9 cells were seeded in 24-well tissue culture plates ($2\times10^5$ cells/well) in 1 ml Sf900-II culture medium without serum at 28° C. After two hours, the culture medium was removed, and the cells were infected with recombinant baculovirus AcMNPV-EGFP at a multiplicity of infection (MOI) of 10 $TCID_{50}$ units/cell for 1 h, under standard conditions. One hour post infection (p.i.), dsRNA (20 μg/well) was introduced into the cells by Cellfectin™-based (Invitrogen) transfection in Grace's serum-free medium. After 4 h, the transfection mixture was replaced with Sf900-II serum-free medium. The cells were incubated for a total of 48 h p.i. at 28° C. and then harvested by centrifuging at 1000×g for 5 min for Western blot and electron microscopy analysis. However, one fifth of the culture medium was harvested at 36 h p.i., and used for titration of budded virions by end-point dilution assays or for PCR-based detection of viral DNA. In all the experiments, dsRNA corresponding to the cat gene was taken as negative control. On the other hand, egfp gene-specific dsRNA was used as positive control for the RNAi procedure.

SDS-Polyacrylamide Electrophoresis and Western Blotting

For immuno-detection, the Sf9 cells were disrupted in 125 mM Tris-HCl, 2% sodium dodecyl sulfate (SDS), 5% 2-mercapthoethanol, 10% glycerol, 0.001% bromophenol blue, pH 6.8 at 95° C. for 10 min. Proteins were separated in 10% SDS-polyacrylamide gels, and subsequently transferred to Immobilon-P membranes (Millipore) by semi-dry electroblotting. Membranes were blocked for 30 min in 1×PBS containing 2% fat-extracted milk powder, followed by incubation for 1 h at room temperature with either rabbit polyclonal anti-GFP antiserum (Molecular Probes), rabbit polyclonal anti-VP39 antiserum, or monoclonal anti-α-tubulin antibody (Sigma-Aldrich), all diluted 1/2000 in 1×PBS containing 0.2% milk power. After washing (3×10 min) in 1×PBS, the membranes were incubated with 1/4000 dilution of either goat anti-rabbit IgG or rabbit anti-mouse IgG antibodies conjugated with alkaline phosphatase (Sigma). After final washing (3×10 min) in AP buffer (100 mM Tris-Cl [pH 9.5], 100 mM NaCl, 5 mM $MgCl_2$), the blots were developed with 5-bromo-4-chloro-3-indolyl phosphate nitroblue tetrazolium (NBT)/5-bromo-4-chloro-3-indolylphosphate (BCIP) (Bio-Rad) according to the manufacturer's instructions.

Preparation of Viral Genomic DNA and its PCR-Based Detection

Two-hundred microliters of cell culture medium were collected at 36 h p.i. and used for preparation of viral DNA. The cells and cell debris were removed from samples by centrifuging at 1000×g for 5 min. Supernatants containing budded virions were quantitatively transferred to new sterile tubes and centrifuged again at 12000×g for 90 min. Pelleted BVs were re-suspended in 200 μl TE buffer (10 mM Tris-HCl [pH 7.5], 1mM EDTA) containing Proteinase K (540 μg/ml), and incubated at 55° C. for 2 h. A phenol:chloroform:isoamyl alcohol (25:24:1) and a chloroform extraction were subsequently performed. The DNA was precipitated by adding an equal amount of isopropanol and the pellet was washed with 70% ethanol. The DNA pellet was dissolved in 15 μl sterile water, and 2 μl of the final DNA solution was applied to PCR-based detection of the vp39 gene sequence using primers mentioned above. All PCR reactions were performed in 25 μl volumes including: 2 μl DNA, 200 μM dNTPs, 10 pmol of each primer, 1.5 mM $MgCl_2$ and 1.5 U GoTaq DNA polymerase (Promega). Amplification conditions were as follows: an initial denaturation at 94° C. for 2 min, after which 30 cycles of denaturation (30 s at 94° C.), primer annealing (20 s at 60° C.) and primer extension (25 s at 72° C.). The termination cycle was 7 min at 72° C. Negative controls were included in all PCR amplifications to test for contaminants in the reagents. Aliquots (3.0 μl) of the PCR products were analysed by electrophoresis in 1.2% (w:v) agarose gels, with 1×TAE buffer, stained with ethidium bromide (0.5 μg/ml).

Generation of an Antibiotic Resistance Gene-Free AcMNPV vp80-Null Bacmid

To determine whether the VP80 protein has an essential role in the context of viral progeny production, we constructed an AcMNPV bacmid (derived from bMON14272 (from Invitrogene)) with a deletion of the vp80 ORF by homologous recombination in *E. coli*. To accomplish this, a cat gene flanked by mutant LoxP sites (Suzuki et al., 2005) was amplified using PCR primers vp80-KO-F and vp80-KO-R (see Table 1) from a plasmid comprising a cat gene flanked by mutant LoxP sites. The resulting PCR fragment, which contained the cat gene flanked by mutant LoxP sites and AcMNPV ~50-bp homology sequences to the 5' or 3' proximal region of the vp80 ORF, was treated with DpnI and gel-purified to eliminate the template plasmid. The PCR product was then transformed into DH10β *E. coli* cells containing bMON14272 (Invitrogen) and the Lambda RED recombinase-producing plasmid pKD46 (Datsenko & Wanner, 2000), which had been prepared in the following manner. Transformed DH10β-bMON14272/pKD46 *E. coli* cells were grown in 50-ml LB (2.0% peptone, 0.5% yeast extract, 85.5 mM NaCl, [pH 7.0]) cultures with kanamycin (50 μg/ml), ampicillin (100 μg/ml) and L-arabinose (1.5 mg/ml) at 30° C. to an $OD_{600}$ of ≈0.6 and then made electrocompetent by a standard procedure. The electroporated cells were incubated at 37° C. for 3 h in 3 ml LB medium and plated on LB-agar containing chloramphenicol at a concentration of 6.5 μg/ml. After 48-h incubation at 37° C., the chloramphenicol-resistant colonies were streaked to fresh LB-agar medium with 34 μg/ml chloramphenicol. The plates were incubated at 37° C. overnight, and colonies resistant to chloramphenicol were selected for further confirmation of the relevant genotype by PCR. Primers 90292 and 90889 were used to confirm the absence of the vp80 ORF, and primers cat-F and cat-R were employed to verify the presence of cat cassette into bacmid (detailed sequences in Table 1).

To eliminate the introduced antibiotic resistance gene (cat) from the bacmid backbone, a Cre/LoxP recombinase system was employed. A Cre recombinase-carrying plasmid pCRE obtained from Jeanine Louwerse (LUMC Leiden, The Netherlands) was introduced into DH10b-bMON14272-vp80null *E. coli* cells, and CRE expression was subsequently induced by the addition of isopropyl thiogalactoside (IPTG). Briefly, the electroporated cells were incubated at 37° C. for 3 h in 3 ml of LB medium (2.0% peptone, 0.5% yeast extract, 85.5 mM NaCl, [pH 7.0]) and plated on LB-agar medium containing 50 μg/ml kanamycin, 100 μg/ml ampicillin and 2 mM IPTG. After 24-h incubation, colonies resistant to kanamycin and ampicillin were selected for further verification of the desired genotype by PCR. In PCR-based analysis, primers 89507 and 91713 (Table 1) were used to verify elimination of cat gene from bacmid backbone. Positive clones were also confirmed by DNA-sequencing.

To recover transposition competence, the helper transposase-encoding plasmid pMON7124 (Invitrogen) was re-introduced into DH10β-bMON14272-vp80null *E. coli* cells.

Finally, the egfp reporter gene was introduced into the vp80-null bacmid to facilitate observation of its behaviour in insect cells. Briefly, the egfp reporter gene was amplified using PCR oligonucleotides gfp-NheI-F and gfp-SphI-R (Table 1) from plasmid pEGFP-N3 (Clontech). The PCR product was cloned into plasmid pJet1.2/Blunt using CloneJETT™ PCR Cloning Kit (Fermentas) according to manufacturer's protocol. Subsequently, the egfp ORF was excised from error-free pJet1.2-egfp with NheI and SphI and subcloned into NheI/SphI-digested pFastBacDUAL (Invitrogen), to generate plasmid pFB-egfp. An expression cassette containing the egfp reporter gene under transcriptional control of the very late p10 promoter was transposed from pFB-egfp into polyhedrin locus of vp80-null bacmid as described in the Bac-to-Bac manual (Invitrogen). In the resulting genome, the complete vp80 ORF has been removed (see FIG. 2). This corresponds to the deletion of 2074 bp from nucleotide positions 89564 to 91637 in the AcMNPV clone C6 genome provided in SEQ ID NO: 1.

Construction of Repaired vp80-Null Bacmids

To prepare vp80 repair donor vectors, we modified plasmid pFB-egfp (noted above) by removing the polyhedrin promoter and replacing it with a fragment containing the vp80 promoter region and the vp80 ORF. First, a 2300-bp fragment containing both the vp80 promoter and ORF sequence was amplified using primers pvp80-StuI-F and vp80-XbaI-R (Table 1) from bacmid bMON14272 template, and cloned into vector pJet1.2/Blunt (Fermentas) to form pJet1.2-pvp80-vp80. After DNA sequence verification, the vp80 cassette was excised from pJet1.2-pvp80-vp80 by StuI/XbaI double digestion, and then subcloned into Bst1107I/XbaI-digested and gel-purified pFB-egfp to generate donor plasmid pFB-egfp-pvp80-vp80. Parallelly, a donor plasmid pFB-egfp-polh-vp80, where vp80 ORF is driven by the very late polyhedrin promoter (polh) was constructed. To this aim, a 2105-bp fragment carrying the vp80 ORF was amplified using primers vp80-SacI-F and vp80-XbaI-R (Table 1) and cloned into pJet1.2/Blunt, to generate pJet1.2-vp80. In the final step, the vp80 ORF was cut out (SacI/XbaI) from pJetol.2p-vpo80p, and subcloned into SacI/Xba/-digested pFB-egfp, to create pFB-egfp-polH-vp80.

To overcome a problem associated with the unavailability of anti-VP80 antibody, FLAG tag decoration (N— and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

To overcome a problem associated with the inavailability of anti-VP80 antibody, FLAG tag decoration (N- and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst11071/XbaI-digested and gel-purified pFB-egfp to generate donor plasmid pFB-egfp-pvp 80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

The inserts of all developed donor plasmids were transposed into the vp80-null bacmid following the Bac-to-Bac protocol (Invitrogen). Screening of transposition-positive constructs into the polh locus was done by a the triplex PCR-based assay employing a M13 forward and reverse primers and a gentamicin resistance gene-specific primer GenR (Table 1).

Transfection-Infection Assay

Bacmid DNAs were prepared from 1.5-ml over-night bacterial cultures of 2 to 3 independent colonies carrying the bacmid with the inserted heterologous gene according to the Bac-to-Bac manual (Invitrogen) and were analyzed in parallel. For transfections, 1 μg of each bacmid DNA preparation was used to transfect $1\times10^6$ Sf9 cells in a 6-well plate by the Cellfectin™-based transfection protocol as described in the Bac-to-Bac (Invitrogen) manual. From 72 h to 120 h post transfection (p.t.), viral propagation was checked by fluorescence microscopy. At 120 h p.t., the cell culture medium was centrifuged for 5 min at 2000×g to remove cell debris, and this clarified supernatant was used to infect $1.5\times10^6$ Sf9 cells in 6-well plates. After 72 h p.i., the spread of virus infection was again monitored by fluorescence microscopy. In all experiments, a wild-type bMON14272 bacmid carrying the egfp reporter gene under control of the p10 promoter was used as positive control. A bMON14272-gp64null bacmid also carrying the egfp reporter gene under control p10 promoter served as negative control, since it has lost the ability of cell-to-cell movement of the infection (Lung et al., 2002).

Time-Course Characterization of Viral Propagation in Cell Culture

Time course analyses were performed to compare budded virus production of the AcMNPV-vp80null virus and the various repair constructs in comparison to the wild type AcMNPV bacmid (Ac-wt) all containing egfp. Briefly, the Sf9 cells were seeded in 6-well tissue culture plates ($1\times10^6$ cells/well in 1 ml Sf900-II culture medium without serum at 28° C. After two hours, the culture medium was removed, and the cells were transfected with 5 μg bacmid DNA, under standard conditions as recommended in Bac-to-Bac manual (Invitrogen). Cell culture supernatants were harvested at 24, 48, 72, 96 and 120 h p.t., and analysed for the production of infectious budded virus by an end-point dilution assay to determine the tissue culture infective dose 50 ($TCID_{50}$). Infection was determined by monitoring egfp expression (from the p10 promoter). The average values of infectious titers derived from three independent transfections were calculated and plotted into graphs.

Transmission Electron Microscopy

Insect Sf9 cells were seeded in 25T flask ($3.5\times10^6$ cells/flask), and transfected with 20 μg either the Ac-Δvp80, rescue Ac-Δvp80-vp80 or Ac-wt bacmid construct. After 48 h p.t., the cells were harvested and prepared for transmission electron microscopy as described previously (van Lent et al., 1990). Samples were examined and photographed with a Philips CM12 electron microscope.

Budded Virus Production Assay

Insect Sf9 cells were seeded in two 25T flasks ($3.5\times10^6$ cells/flask), and transfected with 20 μg either Ac-Δvp80, Ac-Δvp80-vp80, Ac-Δvp80-pH-vp80, Ac-Δvp80-FLAG-vp80, Ac-Δvp80-vp80-FLAG, or Ac-wt bacmid construct. Five days p.t., the BV-enriched cell culture supernatants were harvested, and ultracentrifuged through a cushion of 10% sucrose solution (25,000 rpm for 1.5 hour, Beckman SW32). Pelleted budded virions were resuspended in sterile demi-water, and prepared for either negative staining electron microscopy, SDS-polyacrylamide electrophoresis, or PCR-based detection (as mentioned the above Purification of ODVs and Rod-Shaped Structures from Infected Cells The presence of ODVs and rod-like structures in infected/transfected insect cells was analyzed by electron microscopy (EM). For this purpose, insect cells were harvested 48 h p.i., lysed and the cell lysates were ultracentrifuged through a 40% sucrose cushion in TE (1 mM Tris-HCl pH 7.4, 0.1 mM EDTA) buffer (45,000 rpm for 1 hour, Beckman SW55). Pellets were resuspended in sterile demi-water and analyzed by negative staining EM as described previously (van Lent et al., 1990).

Development of Transgenic Sf9-Derived Cell Line Expressing vp80

To develop a cell line, which produces the VP80 protein, a 2105-bp fragment carrying the vp80 ORF was amplified using primers vp80-SacI-F and vp80-XbaI-R (Table 1) and cloned into pJet1.2/Blunt, to generate pJet1.2-vp80. In the next step, the vp80 ORF was cut out (SacIlXbaI) from pJet1.2-vp80, and subcloned into SacI/Xba/-digested pIZ (Invitrogen), to create pIZ-vp80. The resulting plasmid vector pIZ-vp80 was linearized with Eco57I, and gel-purified. Sf9 cells were seeded in six-well plate ($1\times10^6$ cells/well), and transfected with 10 μg of the linearized vector. After 24 hours post-transfection, cells were selected by cell culture medium containing Zeocin™(300 μg/ml) for 2 to 3 weeks, until no control Sf9 cells survived under the same conditions. Cells were then propagated as an uncloned cell line.

Generation and Characterization of a AcMNPV vp39-Null Bacmid

To study the role of vp39 gene in the context of viral progeny production and the nucleocapsid assembly process, we constructed an AcMNPV bacmid (bMON14272) with a deletion of vp39 by homologous recombination in *E. coli* according to the same procedure as noted above for the AcMNPV vp80null bacmid construct. Since the sequence of the vp39 ORF is overlapping with promoter sequences of both flanking ORFs (cg-30 and lef-4), only an internal part of the vp39 ORF could be deleted, to avoid de-regulations of cg-30 and lef-4 expression. To reach this, a cat gene flanked by mutant LoxP sites was amplified using PCR primers vp39-KO- and vp39-KO-R (Table 1) from a plasmid comprising a cat gene flanked by mutant LoxP sites. The resulting PCR fragment, which contained the cat gene flanked by mutant LoxP sites and ~50-bp sequences homologous to an internal region of the vp39 ORF, was treated with DpnI and gel-purified to eliminate the template plasmid. The PCR product was then transformed into DH10β *E. coli* cells containing bacmid bMON14272 (Invitrogen) and Lambda RED recombinase-producing plasmid pKD46 (Datsenko & Wanner, 2000) prepared in the above mentioned manner. In the final step, colonies resistant to kanamycin were subjected to PCR-based analysis using primers 75834 and 76420(Table I) to verify insertion/elimination of the cat gene from the bacmid backbone. Positive clones were further verified by DNA-sequencing of the obtained PCR products. According to this protocol, an internal part (498 nt=166 aa) of the vp39 ORF was removed, coordinates: 75894-76391 as indicated in FIG. 9.

Construction and Analysis of Repaired vp39-Null Bacmids

To prepare a vp39 repair donor vector, we modified plasmid pFB-egfp (noted above) by introduction of the vp39 ORF under control of the polyhedrin promoter. Initially, a 1073-bp fragment was amplified using primers vp39-SacI-F and vp39-XbaI-R (see Table I for primer sequences) from the bMON14272 template, and cloned into vector pJet1.2/Blunt (Fermentas) to form pJet1.2-vp39. After DNA sequence verification, the vp39 ORF was excised from pJet1.2-vp39 by SacI/XbaI double digestion, and then subcloned into SacI/XbaI-digested and gel-purified pFB-egfp to generate donor plasmid pFB-egfp-vp39. After an unsuccessful attempt to rescue AcMNPV vp39null with pFB-egfp-vp39, a set of novel donor plasmids was prepared. First, a 2498-bp fragment containing vp39 and lef-4 ORFs was PCR-generated using primers vp39-StuI-F and lef-4-XbaI-R from bacmid bMON14272 template, and cloned into vector pJet1.2/Blunt (Fermentas) to form pJet1.2-vp39-lef-4. After DNA sequence confirmation, the fragment containing vp39 and lef-4 ORFs was excised from pJet1.2-vp39-lef-4 by StuI/XbaI double digestion, and then subcloned into StuI/XbaI-digested and gel-purified pFB-egfp to generate donor plasmid pFB-egfp-vp39-lef-4.

Parallelly, donor plasmid pFB-egfp-vp39-cg30 was constructed, where both vp39 and cg-30 ORFs are driven from the very late polyhedrin promoter, and the cg-30 ORF can also use its native promoter situated inside the 3'-end of the vp9 ORF. Briefly, a 1868-bp fragment carrying both vp39 and cg-30 ORFs was amplified using primers cg30-XbaI-F and vp39-XbaI-R (noted above) and cloned into pJet1.2/Blunt, to generate pJet1.2-vp39-cg30. The vp39/cg-30 cassette was subcloned as SacI/Xba into pFB-egfp, to create pFB-egfp-vp39-cg30. Additionally, a similar donor vector pFB-egfp-FLAG-vp39-cg30 was constructed, where vp39 ORF is N-terminally FLAG-tagged. The same strategy was employed to develop this vector, only the reverse primer vp39-FLAG-SacI-R was used to amplified vp39/cg-30 cassette instead of the vp39-XbaI-R primer.

All developed donor plasmids were transposed into vp39-null bacmid following the Bac-to-Bac kit protocol (Invitrogen) and screened as detailed above for vp80 repair bacmids. The functional analysis was performed as described above for the vp80 constructs.

Generation and Analysis of AcMNPV vp1054-Null Bacmid

To verify the essential role of the vp1054 gene in the context of viral progeny production and nucleocapsid assembly, we constructed an AcMNPV bacmid (bMON14272) with a deletion of vp1054 by homologous recombination in *E. coli* according to the same procedure as for the vp80null bacmid construct with minor alternations. Since the vp1054 ORF is overlapping with the essential lef-10 ORF, we could not remove the whole vp1054 ORF, but only a 955-bp nucleotide 3'-end part of the ORF. To prevent translation of the C-truncated VP1054 mutant in insect cells, we decide to mutate the first translation codon ATG→Met to ACG→Thr. This single nucleotide substitution did also change an internal codon no.

32 (AAT) to AAC of lef-10 ORF, however, both are encoding the same amino acid (Asn). To accomplish this, we first amplified the 5'-end of the vp1054 ORF using primers vp1054-KO-F and vp1054-KO-R1 from bacmid bMON14272 (Invitrogen). The 214-bp PCR product contained a mutation of the ATG start codon of the vp1054 ORF, introduced a synthetic stop/poly-A signal sequence for the lef-10 ORF, and has a 3'-end sequence homology overhang to the cat cassette to facilitate the second PCR, and a 49-bp homology sequence to the 5'-end of vp1054 ORF to mediate Lambda RED-directed homologous recombination in *E. coli*. After gel-purification and DNA quantification, the 214-bp fragment was used as forward primer in a second step PCR with reverse primer vp1054-KO-R2 with a plasmid comprising a cat gene flanked with mutant LoxP sites as template. The resulting 1230-bp PCR fragment, which contained the cat gene flanked by mutant LoxP sites, a mutated 5'-end of the vp1054 ORF and ~50-bp sequences homologous to the 5' or 3' proximal region of the vp1054 ORF, was treated with DpnI and gel-purified to eliminate the template plasmid. Recombination of this PCR product with the bMON14272 bacmid was performed as described above for the vp80 mutant. Kanamycin resistant colonies were verified by PCR with primer pairs cat-F/cat-R, 45510/46235, and 45122 and 46441 to check the insertion/elimination of the cat gene from the bacmid backbone. Insertion sites were also confirmed by DNA-sequencing. This method resulted in the deletion of 955 bp from nucleotide positions 45365 to 46319 in the AcMNPV clone C6 genome provided in SEQ ID NO: 1. All primers sequences are given in Table 1.

Construction of a Repaired vp1054-Null Bacmid Construct

To prepare vp1054 repair donor vector, we modified plasmid pFB-egfp (noted above) by removing the polyhedrin promoter and replacing it with a fragment containing the vp1054 promoter region and the vp1054 ORF. First, a 1714-bp fragment containing both the vp1054 promoter and ORF sequence was amplified using primers vp1054-Rep-F and vp1054-Rep-R from bacmid bMON14272 template, and cloned into vector pJet1.2/Blunt (Fermentas) to form pJet1.2-pvp1054-vp1054. After DNA sequence verification, the vp1054 cassette was excised from pJet1.2-pvp1054-vp1054 by StuI/XbaI double digestion, and then subcloned into Bst11071/XbaI-digested and gel-purified pFB-egfp to generate donor plasmid pFB-egfp-pvp1054-vp1054. The developed donor plasmids were transposed into the vp1054-null bacmid following the Bac-to-Bac protocol (Invitrogen) and screened. Recombinant bacmids were analyzed as detailed above for vp80 bacmids.

Generation and Analysis of AcMNPV p6.9-Null Bacmid

To verify the essential role of p6.9 in the context of viral progeny production, we constructed an AcMNPV bacmid (bMON14272) with a deletion of p6.9 by homologous recombination in *E. coli*. To accomplish this, a chloramphenicol resistance gene (cat) flanked by mutant LoxP sites was amplified using PCR primers p6.9-KO-F and p6.9-KO-R from a plasmid comprising a this cat gene flanked by mutant LoxP sites. Mutant viruses were obtained following the same procedure as for the other mutants. For the PCR-based analysis of the finally obtained mutant clones the primer pairs cat-F and cat-R and 86596 and 86995 were used to check insertion/elimination of cat gene from bacmid backbone. Positive clones were also confirmed by DNA-sequencing. This method results in the deletion of 164 bp from nucleotide positions 86716 to 86879 in the AcMNPV clone C6 genome provided in SEQ ID NO: 1. Table 1 for primer sequences.

Construction and Functional Analysis of Repaired p6.9-Null Bacmids

To prepare p6.9 repair donor vectors, the pFB-GFP-p6.9 vector was used, which was constructed by Marcel Westenberg (Wageningen University). To make this vector, the AcMNPV p6.9 promoter sequence was amplified from the plasmid pAcMP1 (Hill-Perkins & Possee, 1990) with primers pp 6.9-F and pp 6.9-R using the high-fidelity Expand long-template PCR system (Roche). The PCR product was cloned as SalI fragment into pFastBac1 (Invitrogen), from which the polyhedrin promoter was deleted in advance by fusing the Bst1107I to the StuI site, to obtain pFB1-p6.9. The p6.9 promoter from pFB1-p6.9 was recloned as SnaBI/BamHI fragment into the Bst1107I and BamHI sites of pFastBacDUAL (Invitrogen), thereby deleting the polyhedrin promoter. Subsequently, the egfp reporter gene was cloned downstream of the p10 promoter into the XmaI site to obtain pFB-GFP-p6.9. Finally, the p6.9 genes of AcMNPV and *Spodoptera exigua* (Se)MNPV were PCR amplified from either the AcMNPV bacmid (bMON14272) or SeMNPV genomic DNA by using the high-fidelity Expand long-template PCR system and primers generating EcoRI and NotI at the 5' and 3' ends, respectively (Table 1). The PCR products were cloned downstream of the p6.9 promoter in the EcoRI/NotI sites of pFB-GFP-p6.9. All generated clones were sequenced to verify the incorporated p6.9 sequences.

The expression cassettes of both developed donor plasmids were transposed into the p6.9-null bacmid following the Bac-to-Bac protocol (Invitrogen). Screening of transposition-positive constructs into the polh locus was done by the triplex PCR-based assay as described above for the vp80 constructs. The analysis was performed as for the vp80 constructs Results Silencing of AcMNPV vp80 does not Affect Baculovirus Very Late Gene Expression We explored the effect of transfecting Sf9 cells with different dsRNAs during infection with AcMNPV-GFP. To trigger dsRNA-induced silencing of selected baculoviral genes (vp1054, vp39, vp80, dbp and odv-ec27), we generated gene-specific dsRNAs using in vitro T7 RNA polymerase-based synthesis. However, when we began these studies it was not clear what amount and time point of dsRNA transfection is the most effective to silence baculoviral genes. To determine an optimal amount of dsRNA for RNAi assay purpose in baculovirus-infected cells, we first attempted to silence reporter egfp gene with different amounts of dsRNA. These pilot assays showed that the most potent RNAi effect is achieved using 100 pg dsRNA per cell (data not shown). At the same time, it was also proved that RNAi treatment has no negative effect on the production of infectious budded virions progeny. We also tried to transfect dsRNA into the cells at two different time points, 24 h prior to infection or 1 h p.i. The results proved that transfection performed at 1 h p.i. is more efficient in silencing of genes expressed at late/very late phases of baculoviral infection in contrast to transfection carried out at 24 h prior to infection (data not shown). In addition, to ensure that knock-down was gene-specific, dsRNA corresponding to the cat gene was transfected as an RNAi negative control. Herein, we could observe a moderate inhibition of baculovirus infection propagation in comparison to untransfected insect cells. However, the same phenomenon was also observed when insect cells were treated only with transfection reagents. Therefore, we could conclude that the effect can be explained by a negative impact (cytotoxicity) of the presence of transfection reagents on cell viability.

Silencing screening of baculovirus genes revealed that down-regulation of vp1054, vp39, dbp and odv/ec-27 is also associated with a reduction or inhibition of very late gene expression measured by EGFP detection (FIGS. 1A and 1B). The highest levels of this inhibition were observed in dbp- and odv/ec-27-targeted cells. The cause of this effect can be explained by the presence of bi-cistronic and overlapping mRNA transcripts, which are produced during a baculovirus replication cycle. Eventually, a cross-reaction with targets of limited sequence similarities can also be involved in the process. Only cells treated with vp80 dsRNA showed a similar level of EGFP expression as untransfected cells or particularly with cat dsRNA-treated cells. Importantly, very few EGFP-producing cells were observed in insect cells where egfp-specific dsRNA was introduced (positive RNAi control), showing that the transfection efficiency was high. Based on our RNAi screening achievements, the vp80 gene (locus) seems to be a suitable candidate for RNAi-based targeting in context of interference with baculoviral very late gene expression.

Knock-Down of vp80 Totally Prevents Production of BVs and Normally Appearing ODVs To determine the roles of selected candidate genes (vp1054, vp39, vp80, dbp and odv/ec-27) in production of budded virions progeny, cell culture medium (36 h p.i.) from dsRNA-treated cells was examined for the presence of BVs. End-point dilution-based titrations confirmed that all tested genes are essential for infectious budded virus progeny production (FIG. 1C). We were not able to detect any infectious BVs in vp80- and dbp-targeted cells. In addition, PCR-based assay indicated that defective or non-infectious viral particles are also not produced in vp80-targeted cells. It is important to point out that the results also showed a significant decrease in the production of infectious BVs in the RNAi controls (egfp- and cat-specific dsRNA-treated cells) compared to untransfected cells. The cytotoxicity of transfection reagents is again the assumed cause of this negative effect. Electron microscopy analysis of cell lysates showed that formation of ODVs and rod-like structures was totally inhibited in cells treated with dsRNA-vp39 as expected (FIG. 1D). Production of ODVs and rod-like structures was also significantly reduced in insect cells treated with dsRNA-vp80 (FIG. 1D). However, in vp80-targeted cells we could mostly find nucleocapsids of aberrant phenotypes (pointed shape). On the other hand, introduction of dsRNA-cat into insect cells did not cause any changes in the production of ODVs.

The AcMNPV vp80 Gene is Essential for Viral Replication

An AcMNPV deletion virus was constructed as detailed in FIG. 2. Repair constructs were designed such that the wild-type vp80 ORF or N- and C-terminally FLAG-tagged vp80 genes along with its native or polyhedrin promoter regions were inserted into the polyhedrin locus along with the egfp gene under the p10 promoter (FIG. 3A). To investigate the function of the vp80 gene, Sf9 cells were transfected with either the knock-out or repair bacmid constructs and monitored for EGFP expression by fluorescence microscopy. When Ac-vp80 null was introduced into Sf9 cells, no viral propagation was observed in cell culture at 72 h to 120 h p.t. We could observe only a “single-cell infection” phenotype similar to the phenotype of Ac-gp64null bacmid (FIG. 3B). The results indicate that Ac-vp80null is able to reach the very late phase of infection as confirmed by p10 promoter-driven EGFP expression. From 72 h to 120 hours p.t., widespread EGFP expression could be seen in insect cell monolayers that were transfected with the three repair (vp80 driven from its native promoter, vp80 driven from polyhedrin promoter and N-terminally FLAG-tagged vp80 driven from its native promoter) constructs indicating that these bacmids were able to produce levels of infectious budded virions sufficient to initiate secondary infection at similar level as the wild-type bacmid (FIG. 3B). In contrast, in insect cells transfected with C-terminally FLAG-tagged vp80 repair constructs, by 72 h p.t. EGFP expression was only observed in isolated cells that were initially transfected indicating that this bacmid construct is defective in viral replication (FIG. 3B). However, by 96 h p.t. formation of tiny plaques was observed and by 120 h p.t. very few plaques of normal size were developed. The results show that the C-terminal flagged mutant is strongly delayed in producing budded virus and showed that an unmodified C-terminus is very important for the function of VP80. At 5 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with repair constructs showed numerous EGFP expressing cells (FIG. 3C). Nevertheless, cells incubated with supernatant from C-terminally FLAG-tagged constructs showed a significant reduction in the number of EGFP-positive cells. On the other hand, in insect cells incubated with supernatant from the transfection with the vp80 knockout, no EGFP expression was detected at any time-point analyzed up to 72 h (FIG. 3C).

Moreover, to characterize the exact effect of deletion of the vp80 gene on AcMNPV infection, the viral propagation in transfected Sf9 cells was compared between Ac-wt, Ac-Δvp80, Ac-Δvp80-vp80Rep, Ac-Δvp80-polh-vp80Rep, Ac-Δvp80-FLAG-vp80Rep and Ac-Δvp80-vp80-FLAGRep. Cell culture supernatants of all the above bacmid constructs were analysed at indicated time points for BV production (FIG. 4). As expected, the repaired Ac-Δvp80-vp80Rep, Ac-Δvp80-polh-vp80Rep, Ac-Δvp80-FLAG-vp80Rep viruses showed kinetics of viral replication consistent with wild-type virus (Ac-wt) propagation. Budded virion production by the C-terminal flagged Ac-Δvp80-vp80-FLAGRep virus was reduced to approximately 0.06% compared to the Ac-wt virus or the other repaired viruses.

These results indicate that the vp80 gene is essential for infectious BV production. It has clearly been proven that the whole sequence of vp80 ORF can completely be deleted from the bacmid backbone and adequately rescued by introduction of the vp80 ORF into a heterologous site (polyhedrin locus) of the genome. We also showed that vp80 gene expression can be driven by the heterologous polyhedrin promoter sequence with no negative effect on viral replication in cell culture. Additionally, we observed that the N-terminus in contrast to the C-terminus of VP80 is permissive to gene modifications (epitope tag-labeling). We noted that the kinetics of the C-terminally FLAG-tagged VP80 virus was significantly delayed when compared with all other rescue or wild-type viruses, indicating the functional importance of the VP80 C-terminus.

VP80 is Required for Production of Both BV and ODV

The results described above indicated that the Ac-vp80null mutant is completely defective in production of infectious budded virus. However, there was also a possibility that the mutant can still produce non-infectious budded particles. To investigate the ability, Sf9 cells were transfected with either the knock-out, repair or wild-type bacmid constructs and 7 days p.t. cell culture mediums were ultracentrifuged to pellet budded viruses. The formed pellets were either analyzed by negative staining electron microscopy or by Western blot- and PCR-based detection to confirm the presence of the budded viruses. No intact budded virus, virus-like particles, nor its structures (such as major capsid protein VP39 and viral genome sequence) were revealed in the pellet from the cells transfected with the Ac-vp80null mutant (FIGS. 5A and 5B). On the other hand, all analyzed repair constructs produced normally-appearing budded virus as compared with budded virus-derived from the wild-type virus (FIG. 5A). Nevertheless, it was very difficult to find representative budded virions in the pellet derived from C-terminally FLAG-tagged vp80 gene repair construct-transfected cells.

To further characterize deletion of the vp80 gene on baculovirus life cycle, electron microscopy was performed with ultra-thin sections generated from bacmid-transfected cells. The Ac-vp80null-transfected cells developed typically phenotype of baculovirus-infected cell with an enlarged nucleus, a fragmented host chromatin, an electron-dense virogenic stroma, etc. (FIG. 6A). The absence of VP80 did not prevent formation of normally-appearing nucleocapsids inside the virogenic stroma (FIG. 6C). The formed nucleocapsids were phenotypically undistinguishable from those produced by either the Ac-vp80null repair or Ac-wt bacmids. However, an abundance of assembled nucleocapsids was rather less as compared with cells-transfected with the Ac-vp80null repair or Ac-wt bacmids (FIGS. 6E and 6G). In addition, no occlusion-derived virions nor bundles of nucleocapsids prior to an envelopment could be observed in the peristromal compartment of a nucleoplasm (so called the ring zone) of Ac-vp80null bacmid-transfected cells (FIGS. 6B and 6D). It seems that VP80 plays a role during maturation of nucleocapsids and/or their release/transport from the virogenic stroma. Eventually, VP80 can somehow contribute to an efficient nucleocapsid assembly which could be explained by small number of nucleocapsids present in the virogenic stroma of Ac-vp80null transfected cells. When the vp80 gene was re-introduced back into the bacmid mutant, a lot of nucleocapsids and occlusion-derived virions could be seen in the ring zones of transfected cells (FIG. 6F). An abundance and morphology of occlusion-derived virions produced in Ac-Δvp80-vp80 repair bacmid-transfected cells were similar to those produced by wild-type bacmid (FIGS. 6F and 6H).

VP80 Function can be Complemented by the Trans-Acting vp80 Gene

To prove that VP80 function can be complemented by the trans-acting vp80 ORF, a complementation assay was performed with a transgenic cell line, Sf9-vp80, that was stably transformed with the vp80 gene expressed under control of an early baculovirus *Orgyia pseudotsugata* ie-2 promoter. In the assay, both Sf9 and Sf9-vp80 cells were transfected with the Ac-vp80null bacmid mutant (FIG. 7). Virus infection spread was monitored by EGFP-specific fluorescence at 72 h and 96 h p.t. In Sf9-vp80 cells we could observe viral plaques demonstrating the virus spread. On the other hand, in Sf9 cells only "single-cell infection" phenotype could be seen as previously described above. After six days, the cell culture supernatants were harvested and used as a inoculum to infect fresh groups of Sf9 cells. After 5 days, EGFP-positive cells were monitored by fluorescence microscopy. Only "single-cell infection" phenotype was observed in Sf9 cells receiving the supernatant from Sf9-vp80 cells. As assumed, no EGFP signal was detected in Sf9 cells receiving the supernatant from Sf9 cells. These results show that the Ac-vp80null can be rescued by VP80-expressing cells (Sf9-vp80) and demonstrate that the observed complementation is due to VP80 protein expressed from the host cell line and not from acquisition of the vp80 gene from the cell line. In other words, the results match requirements asked to produce biopharmaceuticals (EGFP protein in our model assay) without contaminating baculovirus virions.

Generation and Characterization of vp39-Null Bacmid

To study the functionality of the AcMNPV vp39 gene during virus infection, an vp39-null AcMNPV bacmid was constructed by partial deletion of the vp39 gene. The deletion construct was selected by its resistance to chloramphenicol indicating that site-specific deletion of the vp39 gene had occurred. In the resulting vp39-null AcMNPV bacmid, the internal part of vp39 gene was correctly replaced by the cat gene. Subsequently, the cat was eliminated by Cre/LoxP recombination (FIG. 8A). The vp39 sequence was removed from nucleotides 75894 to 76391 according to the AcMNPV clone C6 genome sequence (SEQ ID NO:1). The structure of the vp39 deletion constructs was confirmed by PCR using primers 75834 and 76420 (FIG. 8B). A 647-bp DNA fragment was amplified when wild-type AcMNPV bacmid was used as a template, whereas a 1113-bp DNA fragment could be amplified on AcMNPV vp39-null(+cat) template (FIG. 8B). When the final construct AcMNPV-vp80null(−cat) with eliminated cat cassette was used in PCR analysis, only a short 183-bp DNA fragment could be detected (FIG. 8B). The results were confirmed by DNA sequencing.

Functional Mapping of vp39 ORF Indicates a Presumable Functional Relationship Between vp39 and cg-30 ORFs The repair constructs were designed in such a way that the wild-type vp39 ORF under control of the polyhedrin promoter sequence was inserted into the polyhedrin locus along with the egfp gene controlled by the p10 promoter (FIG. 9A). To investigate the function of the vp39 gene, Sf9 cells were transfected with either the knock-out or repair bacmid constructs and monitored for EGFP expression by fluorescence microscopy. When Ac-vp39 null was introduced into Sf9 cells, no viral propagation was observed from 72 h to 168 h p.t. We could observe only a "single-cell infection" phenotype similar to the phenotype of the Ac-gp64null bacmid (FIG. 9B).

These results indicate that the Ac-vp39null construct is able to reach the very late phase of infection as shown by the p10 promoter-driven EGFP expression. Unexpectedly, no viral propagation could be seen in insect cell monolayers that were transfected with the vp39 repair (vp39 driven from polyhedrin, Ac-Δvp39-polh-vp39Rep) constructs (FIG. 3B). For this reason, we decided to prepare three extra repair bacmids carrying both vp39 and lef-4 ORFs under controls of their native promoters. When the insect cells were transfected with these repair constructs again viral replication did not occur (FIG. 9B) and a "single-cell infection" phenotype was observed from 72 h to 168 h p.t. Interestingly, in insect cell monolayers that were transfected with the repair constructs carrying both vp39 (or FLAG-tagged vp39) and cg-30 we could observe tiny clusters of EGFP-positive cells (3-5 cells) (FIG. 9B). However, we did not see a full-value viral replication as that of the wild-type vector (Ac-wt), At 7 days p.t., cell culture supernatants were collected and added to freshly plated Sf9 cells, which were then incubated for 3 days to detect infection by virus generated from cells transfected with all bacmids mentioned here (FIG. 9C). As expected, Sf9 cells incubated with the supernatant from Ac-wt transfections, showed numerous EGFP expressing cells. On the other hand, cells incubated with supernatants from Ac-Δvp39-polh-vp39Rep and Ac-Δvp39-vp39-lef-4Rep constructs did not show any EGFP-positive cells. However, in insect cells incubated with supernatants from Ac-Δvp39-vp39-cg30Rep and Ac-Δvp39-FLAG-vp39-Rep, a number of EGFP-expressing cells was detected (FIG. 9C). These results indicated that a possible functional relationship between the vp39 and cg-30 ORFs is required for baculovirus replication.

Since the vp39 ORF sequence overlaps with the promoter sequences of the two flanking ORFs (lef-4 and cg-30), we could not delete the whole vp39 ORF in our vp39null bacmid construct. It may therefore also be that C- and/or N-truncated mutant(s) of vp39 may be expressed which may interfere as a competitive inhibitor with the normal VP39 protein.

Construction and Analysis of vp1054-Null Bacmid

To study the functionality of the AcMNPV vp1054 gene during virus infection, an vp1054-null AcMNPV bacmid was constructed by partially deleting the vp1054 gene from AcMNPV bacmid (bMON14272) by homologous recombination in *E. coli*. The deletion construct was selected by its resistance to chloramphenicol that indicated that site-specific deletion of the vp1054 gene had occurred. In the resulting vp1054-null AcMNPV bacmid, the 955-bp 3'-end part of the vp1054 gene was correctly replaced by the cat gene. Subsequently, the antibiotic resistance cassette (cat) was eliminated from bacmid backbone using Cre/LoxP recombination system (FIG. 10A). The deleted sequence was removed from the nucleotide coordinates 45365 to 46319 according to the AcMNPV clone C6 genome sequence (SEQ ID NO:1). The structure of all the deletion constructs was confirmed by PCR (FIG. 10B). When the vp1054 gene is present, as in the parental wild-type AcMNPV bacmid, a 775-bp PCR product can be amplified using primers 45510 and 46235, whereas a 596-bp PCR fragment amplified with cat-F and cat-R primers is produced only when cat gene was introduced into bacmid sequence in case of AcMNPV vp1054null(+cat) construct (FIG. 10B). Correct recombination process was also confirmed by PCR mapping of vp1054 locus using primers 45122 and 46441. A 1320-bp DNA fragment was amplified when wild-type AcMNPV bacmid was used as a template, whereas a 1353-bp DNA fragment could be amplified on AcMNPV vp1054-null(+cat) template (FIG. 10B). When final construct AcMNPV-vp 1054null(−cat) with eliminated cat cassette was used in PCR analysis, only a 423-bp DNA fragment could be detected (FIG. 10B). Positive clones were successfully verified by DNA sequencing.

AcMNPV vp1054 Gene is Essential for Viral Replication

The repair construct was designed such that the AcMNPV vp1054 ORF with its native promoter region was inserted into the polyhedrin locus along with the egfp gene under the control of the p10 promoter (FIG. 11A). Since the vp1054 promoter and ORF sequences are overlapping with lef-10 ORF, the repair construct is also capable to express LEF-10. To investigate the function of the vp1054 gene, Sf9 cells were transfected with either the vp1054 knock-out or repair bacmid construct and monitored for EGFP expression by fluorescence microscopy. When Ac-vp1054 null construct was introduced into Sf9 cells, no viral propagation was observed in cell culture at 72 h to 120 h p.t. We could observe only a "single-cell infection" phenotype similar to the phenotype of Ac-gp64null bacmid (FIG. 11B). The results indicate that Ac-vp1054null is able to reach the very late phase of infection as confirmed by p10 promoter-driven EGFP expression. In other word, the results suggest that the expression of late expression factor 10, LEF-10, was not affected in vp1054-null bacmid mutant. From 72 h to 120 hours p.t., widespread EGFP expression could be seen in insect cell monolayers that were transfected with the repair constructs (Ac-Δvp1054-vp1054). The results are indicating that the repair bacmid is able to produce levels of infectious budded virions sufficient to initiate secondary infection at similar level as the wild-type bacmid (FIG. 11B). At 6 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with the repair constructs showed numerous EGFP expressing cells (FIG. 11C). On the other hand, in insect cells incubated with supernatant from the transfection with the Ac-vp1054null knockout, no EGFP expression was detected at any time-point analyzed up to 72 h (FIG. 11C).

These results indicate that the vp1054 gene is essential for infectious BV production. It has clearly been proven that the 955-bp 3'-end sequence part of the vp1054 ORF can completely be deleted from the bacmid backbone and adequately rescued by introduction of the AcMNPV vp1054 ORF into a heterologous site (polyhedrin locus) of the genome. In addition, the results proved that deletion of the vp1054 gene does not affect very late gene expression, as demonstrated by EGFP-positive cells in cells transfected with Ac-vp1054null bacmid mutant (FIG. 11B).

Generation and Characterization of p6.9-Null Bacmid

To study the functionality of the AcMNPV p6.9 gene during virus infection, an vp80-null AcMNPV bacmid was constructed by deleting the p6.9 gene from AcMNPV bacmid (bMON14272) by homologous recombination in *E. coli*. The deletion construct was selected by its resistance to chloramphenicol that indicated that site-specific deletion of the p6.9 gene had occurred. In the resulting p6.9-null AcMNPV bacmid, the p6.9 gene was correctly replaced by the cat gene. Subsequently, the antibiotic resistance cassette (cat) was eliminated from bacmid backbone using Cre/LoxP recombination system (FIG. 12A). The deleted sequence was removed from the translational start codon (ATG→Met) to the stop codon (TAT→Tyr), nucleotide coordinates 86716 to 86879 according to the AcMNPV clone C6 genome sequence (SEQ ID NO:1). The stop codon of the p6.9 orf was not removed since its sequence is overlapping with the stop codon of flanked lef-5 orf. The structure of all the deletion constructs was confirmed by PCR (FIG. 12 B). When the p6.9 gene is present, as in the parental wild-type AcMNPV bacmid, a 596-bp PCR fragment could be only amplified with cat-F and cat-R primers when cat gene was introduced into bacmid sequence in case of AcMNPV p6.9null(+cat) construct (FIG. 12B). Correct recombination process was also confirmed by PCR mapping of p6.9 locus using primers 86596 and 86995. A 400-bp DNA fragment was amplified when wild-type AcMNPV bacmid was used as a template, whereas a 1220-bp DNA fragment could be amplified on AcMNPV vp80-null(+cat) template (FIG. 12B). When final construct AcMNPV-vp80null(−cat) with eliminated cat cassette was used in PCR analysis, only a short 290-bp DNA fragment could be detected (FIG. 12B). Positive clones were successfully verified by DNA sequencing.

AcMNPV p6.9 Gene is Essential for Viral Replication

The repair constructs were designed such that the wild-type AcMNPV or SeMNPV p6.9 ORFs with AcMNPV p6.9 promoter region were inserted into the polyhedrin locus along with the egfp gene under the p10 promoter (FIG. 13A). To investigate the function of the p6.9 gene, Sf9 cells were transfected with either the p6.9 knock-out or repair bacmid constructs and monitored for EGFP expression by fluorescence microscopy. When Ac-p6.9 null was introduced into Sf9 cells, no viral propagation was observed in cell culture at 72 h to 120 h p.t. We could observe only a "single-cell infection" phenotype similar to the phenotype of Ac-gp64null bacmid (FIG. 13B). The results indicate that Ac-p6.9null is able to reach the very late phase of infection as confirmed by p10 promoter-driven EGFP expression. From 72 h to 120 hours p.t., widespread EGFP expression could be seen in insect cell monolayers that were transfected with the two repair constructs (Ac-Δp6.9-Acp6.9 and Ac-Δp6.9-Sep6.9). The results are indicating that these two repair bacmids are able to produce levels of infectious budded virions sufficient to initiate secondary infection at similar level as the wild-type bacmid (FIG. 13B). At 6 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with the repair constructs showed numerous EGFP expressing cells (FIG. 13C). On the other hand, in insect cells incubated with supernatant from the transfection with the Ac-p6.9null knockout, no EGFP expression was detected at any time-point analyzed up to 72 h (FIG. 3C). Moreover, to characterize the exact effect of deletion of the p6.9 gene on AcMNPV infection, the viral propagation in transfected Sf9 cells was compared between Ac-wt, Ac-Δp6.9, Ac-Δp6.9-Acp6.9Rep, Ac-Δp6.9-Sep6.9Rep). Cell culture supernatants of all the above bacmid constructs were analysed at indicated time points for BV production (FIG. 13D). As expected, the repaired Ac-Δp6.9-Acp6.9Rep and Ac-Δp6.9-Sep6.9Rep viruses showed kinetics of viral replication consistent with wild-type virus (Ac-wt) propagation.

These results indicate that the p6.9 gene is essential for infectious BV production. It has clearly been proven that the whole sequence of p6.9 ORF can completely be deleted from the bacmid backbone and adequately rescued by introduction of the AcMNPV vp80 ORF into a heterologous site (polyhedrin locus) of the genome. We also showed that p6.9 gene can be complemented efficiently by the SeMNPV-derived p6.9 ORF (M. Westenberg). In addition, the results proved that deletion of the p6.9 gene does not affect very late gene expression, as demonstrated by EGFP-positive cells in cells transfected with Ac-p6.9null bacmid mutant (FIG. 15B).

Example II

The inventors have amended the best mode of the present invention in the following example.

Materials and Methods

Generation of an Antibiotic Resistance Gene-Free AcMNPV vp80-Null Bacmid

To determine whether the VP80 protein has an essential role in the context of viral progeny production, we constructed an AcMNPV bacmid (derived from bMON14272 (from Invitrogene)) with a deletion of the vp80 ORF by homologous recombination in *E. coli*. To accomplish this, a cat gene flanked by mutant LoxP sites (Suzuki et al., 2005) was amplified using PCR primers vp80-KO-F and vp80-KO-R (see Table 1) from a plasmid comprising a cat gene flanked by mutant LoxP sites. The resulting PCR fragment, which contained the cat gene flanked by mutant LoxP sites and AcMNPV ~50-bp homology sequences to the 5' or 3' proximal region of the vp80 ORF, was treated with DpnI and gel-purified to eliminate the template plasmid. The PCR product was then transformed into DH10β *E. coli* cells containing bMON14272 (Invitrogen) and the Lambda RED recombinase-producing plasmid pKD46 (Datsenko & Wanner, 2000), which had been prepared in the following manner. Transformed DH10β-bMON14272/pKD46 *E. coli* cells were grown in 50-ml LB (2.0% peptone, 0.5% yeast extract, 85.5 mM NaCl, [pH 7.0]) cultures with kanamycin (50 μg/ml), ampicillin (100 μg/ml) and L-arabinose (1.5 mg/ml) at 30° C. to an $OD_{600}$ of ≈0.6 and then made electrocompetent by a standard procedure. The electroporated cells were incubated at 37° C. for 3 h in 3 ml LB medium and plated on LB-agar containing chloramphenicol at a concentration of 6.5 μg/ml. After 48-h incubation at 37° C., the chloramphenicol-resistant colonies were streaked to fresh LB-agar medium with 34 μg/ml chloramphenicol. The plates were incubated at 37° C. overnight, and colonies resistant to chloramphenicol were selected for further confirmation of the relevant genotype by PCR. Primers 90292 and 90889 were used to confirm the absence of the vp80 ORF, and primers cat-F and cat-R were employed to verify the presence of cat cassette into bacmid (detailed sequences in Table 1).

To eliminate the introduced antibiotic resistance gene (cat) from the bacmid backbone, a Cre/LoxP recombinase system was employed. A Cre recombinase-carrying plasmid pCRE obtained from Jeanine Louwerse (LUMC Leiden, The Netherlands) was introduced into DH10b-bMON14272-vp80null *E. coli* cells, and CRE expression was subsequently induced by the addition of isopropyl thiogalactoside (IPTG). Briefly, the electroporated cells were incubated at 37° C. for 3 h in 3 ml of LB medium (2.0% peptone, 0.5% yeast extract, 85.5 mM NaCl, [pH 7.0]) and plated on LB-agar medium containing 50 μg/ml kanamycin, 100 μg/ml ampicillin and 2 mM IPTG. After 24-h incubation, colonies resistant to kanamycin and ampicillin were selected for further verification of the desired genotype by PCR. In PCR-based analysis, primers 89507 and 91713 (Table 1) were used to verify elimination of cat gene from bacmid backbone. Positive clones were also confirmed by DNA-sequencing.

To recover transposition competence, the helper transposase-encoding plasmid pMON7124 (Invitrogen) was re-introduced into DH10β-bMON14272-vp80null *E. coli* cells. Finally, the egfp reporter gene was introduced into the vp80-null bacmid to facilitate observation of its behaviour in insect cells. Briefly, the egfp reporter gene was amplified using PCR oligonucleotides gfp-NheI-F and gfp-SphI-R (Table 1) from plasmid pEGFP-N3 (Clontech). The PCR product was cloned into plasmid pJet1.2/Blunt using CloneJET™ PCR Cloning Kit (Fermentas) according to manufacturer's protocol. Subsequently, the egfp ORF was excised from error-free pJet1.2-egfp with NheI and SphI and subcloned into NheI/SphI-digested pFastBacDUAL (Invitrogen), to generate plasmid pFB-egfp. An expression cassette containing the egfp reporter gene under transcriptional control of the very late p10 promoter was transposed from pFB-egfp into polyhedrin locus of vp80-null bacmid as described in the Bac-to-Bac manual (Invitrogen). In the resulting genome, the complete vp80 ORF has been removed (see FIG. 2). This corresponds to the deletion of 2074 bp from nucleotide positions 89564 to 91637 in the AcMNPV clone C6 genome provided in SEQ ID NO: 1.

Construction of Repaired vp80-Null Bacmids

To prepare vp80 repair donor vectors, we modified plasmid pFB-egfp (noted above) by removing the polyhedrin promoter and replacing it with a fragment containing the vp80 promoter region and the vp80 ORF. First, a 2300-bp fragment containing both the vp80 promoter and ORF sequence was amplified using primers pvp80-StuI-F and vp80-XbaI-R (Table 1) from bacmid bMON14272 template, and cloned into vector pJet1.2/Blunt (Fermentas) to form pJet1.2-pvp80-vp80. After DNA sequence verification, the vp80 cassette was excised from pJet1.2-pvp80-vp80 by StuI/XbaI double digestion, and then subcloned into Bst1107I/XbaI-digested and gel-purified pFB-egfp to generate donor plasmid pFB-egfp-pvp80-vp80. Parallelly, a donor plasmid pFB-egfp-polh-vp80, where vp80 ORF is driven by the very late polyhedrin promoter (polh) was constructed. To this aim, a 2105-bp fragment carrying the vp80 ORF was amplified using primers vp80-SacI-F and vp80-XbaI-R (Table 1) and cloned into pJet1.2/Blunt, to generate pJet1.2-vp80. In the final step, the vp80 ORF was cut out (SacI/XbaI) from pJet1.2-vp80, and subcloned into SacI/Xba/-digested pFB-egfp, to create pFB-egfp-polH-vp80.

To overcome a problem associated with the unavailability of anti-VP80 antibody, FLAG tag decoration (N— and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XabaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

The inserts of all developed donor plasmids were transposed into the vp80-null bacmid following the Bac-to-Bac protocol (Invitrogen). Screening of transposition-positive constructs into the polh locus was done by a the triplex PCR-based assay employing a M13 forward and reverse primers and a gentamicin resistance gene-specific primer GenR (Table 1).

Transfection-Infection Assay

Bacmid DNAs were prepared from 1.5-ml over-night bacterial cultures of 2 to 3 independent colonies carrying the bacmid with the inserted heterologous gene according to the Bac-to-Bac manual (Invitrogen) and were analyzed in parallel. For transfections, 1 μg of each bacmid DNA preparation was used to transfect $1\times10^6$ Sf9 cells in a 6-well plate by the Cellfectin™-based transfection protocol as described in the Bac-to-Bac (Invitrogen) manual. From 72 h to 120 h post transfection (p.t.), viral propagation was checked by fluorescence microscopy. At 120 h p.t., the cell culture medium was centrifuged for 5 min at 2000×g to remove cell debris, and this clarified supernatant was used to infect $1.5\times10^6$ Sf9 cells in 6-well plates. After 72 h p.i., the spread of virus infection was again monitored by fluorescence microscopy. In all experiments, a wild-type bMON14272 bacmid carrying the egfp reporter gene under control of the p10 promoter was used as positive control. A bMON14272-gp64null bacmid also carrying the egfp reporter gene under control p10 promoter served as negative control, since it has lost the ability of cell-to-cell movement of the infection (Lung et al., 2002).

Time-Course Characterization of Viral Propagation in Cell Culture

Time course analyses were performed to compare budded virus production of the AcMNPV-vp80null virus and the various repair constructs in comparison to the wild type AcMNPV bacmid (Ac-wt) all containing egfp. Briefly, the Sf9 cells were seeded in 6-well tissue culture plates ($1\times10^6$ cells/well in 1 ml Sf900-II culture medium without serum at 28° C. After two hours, the culture medium was removed, and the cells were transfected with 5 μg bacmid DNA, under standard conditions as recommended in Bac-to-Bac manual (Invitrogen). Cell culture supernatants were harvested at 24, 48, 72, 96 and 120 h p.t., and analysed for the production of infectious budded virus by an end-point dilution assay to determine the tissue culture infective dose 50 ($TCID_{50}$). Infection was determined by monitoring egfp expression (from the p10 promoter). The average values of infectious titers derived from three independent transfections were calculated and plotted into graphs.

Transmission Electron Microscopy

Insect Sf9 cells were seeded in 25T flask ($3.5\times10^6$ cells/flask), and transfected with 20 μg either the Ac-Δvp80, rescue Ac-Δvp80-vp80 or Ac-wt bacmid construct. After 48 h p.t., the cells were harvested and prepared for transmission electron microscopy as described previously (van Lent et al., 1990). Samples were examined and photographed with a Philips CM12 electron microscope.

Budded Virus Production Assay

Insect Sf9 cells were seeded in two 25T flasks ($3.5\times10^6$ cells/flask), and transfected with 20 μg either Ac-Δvp80, Ac-Δvp80-vp80, Ac-Δvp80-pH-vp80, Ac-Δvp80-FLAG-vp80, Ac-Δvp80-vp80-FLAG, or Ac-wt bacmid construct. Five days p.t., the BV-enriched cell culture supernatants were harvested, and ultracentrifuged through a cushion of 10% sucrose solution (25,000 rpm for 1.5 hour, Beckman SW32). Pelleted budded virions were resuspended in sterile demi-water, and prepared for either negative staining electron microscopy, SDS-polyacrylamide electrophoresis, or PCR-based detection (as mentioned the above Purification of ODVs and Rod-Shaped Structures from Infected Cells The presence of ODVs and rod-like structures in infected/transfected insect cells was analyzed by electron microscopy (EM). For this purpose, insect cells were harvested 48 h p.i., lysed and the cell lysates were ultracentrifuged through a 40% sucrose cushion in TE (1 mM Tris-HCl pH 7.4, 0.1 mM EDTA) buffer (45,000 rpm for 1 hour, Beckman SW55). Pellets were resuspended in sterile demi-water and analyzed by negative staining EM as described previously (van Lent et al., 1990).

Purification and Fractionation of BV and ODV Virions

To produce BVs, $3.0\times10^7$ Sf9 cells were infected with Ac-Δvp80-Flag·vp80 or control Ac-wt virus at an MOI=1. Six days p.i., 72 ml of BV-enriched medium was collected and centrifuged at 1,500×g for 10 min. The supernatant was then ultracentrifuged at 80,000×g (Beckman SW28 rotor) for 60 min at 4° C. The BV pellet was resuspended in 350 μl 0.1×TE buffer, and loaded onto a linear sucrose gradient (25 to 56% (w/v), and ultracentrifuged at 80,000×g (Beckman SW55 rotor) for 90 min at 4° C. The formed BV band was collected and diluted in 12 ml 0.1×TE. The BV preparation was concentrated at 80,000×g for 60 min at 4° C. The final virus pellet was resuspended in 150 μl of 0.1×TE.

To produce ODVs, $6.0\times10^7$ Sf9 cells were co-infected with Ac-Δvp80-Flag·vp80 (MOI=25) and AcMNPV (MOI=5) viruses (strain E2, Smith & Summers, 1979). Five days p.i., the infected cells were harvested, and ODVs were purified from viral occlusion bodies as described previously (Braunagel et al., 1994). The final ODV pellet was resuspended in 0.5 ml of 0.1×TE (10 mM Tris, 1 mM EDTA, pH=7.5). The purified BV and ODV virions were fractionated into envelope and nucleocapsid fractions as described previously (Braunagel et al., 1994). Final fractions were processed for SDS-PAGE and immunoblotted against either mouse monoclonal anti-Flag antibody (Stratagene), rabbit polyclonal anti-VP39 antiserum (kindly provided by Lorena Passarelli, Kansas State University, USA), rabbit polyclonal anti-GP64 antiserum (kindly provided by Hualin Wang and Feifei Yin, Wuhan Institute of Virology, China (Yin et al., 2008), or rabbit polyclonal antiserum against per os infectivity factor 1 (PIF-1) (kindly provided by Ke Peng, Wageningen University, The Netherlands (Peng et al., 2010).

Development of Transgenic Sf9-Derived Cell Line Expressing vp80

To develop a cell line, which produces the VP80 protein, a 2105-bp fragment carrying the vp80 ORF was amplified using primers vp80-SacI-F and vp80-XbaI-R (Table 1) and cloned into pJet1.2/Blunt, to generate pJet1.2-vp80. In the next step, the vp80 ORF was cut out (SacI/XbaI) from pJet1.2-vp80, and subcloned into SacI/Xba/-digested pIZ (Invitrogen), to create pIZ-vp80. The resulting plasmid vector pIZ-vp80 was linearized with Eco57I, and gel-purified. Sf9 cells were seeded in six-well plate ($1\times10^6$ cells/well), and transfected with 10 μg of the linearized vector. After 24 hours post-transfection, cells were selected by cell culture medium containing Zeocin™(300 μg/ml) for 2 to 3 weeks, until no control Sf9 cells survived under the same conditions. Cells were then propagated as an uncloned cell line.

Recombinant Protein Expression with the vp80Null Virus

To measure the capacity to express recombinant protein with the Ac-Δvp80 (trans-complemented) virus seed, $3.0\times10^7$ non-transformed Sf9 cells were infected (independent triplicate assay) with Ac-wt, Ac-Δvp80-Flag·vp80 (both produced in non-transformed cell line) or Ac-Δvp80 virus (produced in the Sf9-vp80 cell line) at a MOI=10. All of these virus seeds are expressing egfp as a model heterologous gene from the baculovirus very late p10 promoter. At 48 h and 72 h p.i. cells and culture medium were harvested and used for Western blotting, enzyme-linked immunosorbent assay (ELISA) or BV titration (see above). For Western blotting the same antibodies as mentioned above were used to detect the Flag-tag, EGFP, and GP64, as well as a monoclonal mouse anti-actin antibody (ImmunO).

For relative quantification, Maxisorp 96-well plates (Nunc) were coated overnight at 4° C. with 100 ng of rabbit polyclonal anti-GFP antibody (Molecular Probes) in a volume of 100 μl per well, which was followed standard ELISA procedures as previously described (Fric et al., 2008). The percentage of EGFP production was calculated (independent triplicate assay) according to the formula: % EGFP expression=(test absorbance$_{nh}$−background absorbance)/(Ac-wt EGFP$_{72h}$−background absorbance)×100%, where nh represents the time point p.i. The statistical significance of the observed differences between the control Ac-wt and the experimental Ac-Δvp80-Flag·vp80 and Ac-Δvp80 genotypes was analyzed with the Student's t-test.

Results

The AcMNPV vp80 Gene is Essential for Viral Replication

An AcMNPV deletion virus was constructed as detailed in FIG. 2. Repair constructs were designed such that the wild-type vp80 ORF or N- and C-terminally FLAG-tagged vp80 genes along with its native or polyhedrin promoter regions were inserted into the polyhedrin locus along with the egfp gene under the p10 promoter (FIG. 3A). To investigate the function of the vp80 gene, Sf9 cells were transfected with either the knock-out or repair bacmid constructs and monitored for EGFP expression by fluorescence microscopy. When Ac-vp80 null was introduced into Sf9 cells, no viral propagation was observed in cell culture at 72 h to 120 h p.t. We could observe only a "single-cell infection" phenotype similar to the phenotype of Ac-gp64null bacmid (FIG. 3B). The results indicate that Ac-vp80null is able to reach the very late phase of infection as confirmed by p10 promoter-driven EGFP expression. From 72 h to 120 hours p.t., widespread EGFP expression could be seen in insect cell monolayers that were transfected with the three repair (vp80 driven from its native promoter, vp80 driven from polyhedrin promoter and N-terminally FLAG-tagged vp80 driven from its native promoter) constructs indicating that these bacmids were able to produce levels of infectious budded virions sufficient to initiate secondary infection at similar level as the wild-type bacmid (FIG. 3B). In contrast, in insect cells transfected with C-terminally FLAG-tagged vp80 repair constructs, by 72 h p.t. EGFP expression was only observed in isolated cells that were initially transfected indicating that this bacmid construct is defective in viral replication (FIG. 3B). However, by 96 h p.t. formation of tiny plaques was observed and by 120 h p.t. very few plaques of normal size were developed. The results show that the C-terminal flagged mutant is strongly delayed in producing budded virus and showed that an unmodified C-terminus is very important for the function of VP80. At 5 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with repair constructs showed numerous EGFP expressing cells (FIG. 3C). Nevertheless, cells incubated with supernatant from C-terminally FLAG-tagged constructs showed a significant reduction in the number of EGFP-positive cells. On the other hand, in insect cells incubated with supernatant from the transfection with the vp80 knockout, no EGFP expression was detected at any time-point analyzed up to 72 h (FIG. 3C).

Moreover, to characterize the exact effect of deletion of the vp80 gene on AcMNPV infection, the viral propagation in transfected Sf9 cells was compared between Ac-wt, Ac-Δvp80, Ac-Δvp80-vp80Rep, Ac-Δvp80-polh-vp80Rep, Ac-Δvp80-FLAG-vp80Rep and Ac-Δvp80-vp80-FLAGRep. Cell culture supernatants of all the above bacmid constructs were analysed at indicated time points for BV production (FIG. 4). As expected, the repaired Ac-Δvp80-vp80Rep, Ac-Δvp80-polh-vp80Rep, Ac-Δvp80-FLAG-vp80Rep viruses showed kinetics of viral replication consistent with wild-type virus (Ac-wt) propagation. Budded virion production by the C-terminal flagged Ac-Δvp80-vp80-FLAGRep virus was reduced to approximately 0.06% compared to the Ac-wt virus or the other repaired viruses.

These results indicate that the vp80 gene is essential for infectious BV production. It has clearly been proven that the whole sequence of vp80 ORF can completely be deleted from the bacmid backbone and adequately rescued by introduction of the vp80 ORF into a heterologous site (polyhedrin locus) of the genome. We also showed that vp80 gene expression can be driven by the heterologous polyhedrin promoter sequence with no negative effect on viral replication in cell culture. Additionally, we observed that the N-terminus in contrast to the C-terminus of VP80 is permissive to gene modifications (epitope tag-labeling). We noted that the kinetics of the C-terminally FLAG-tagged VP80 virus was significantly delayed when compared with all other rescue or wild-type viruses, indicating the functional importance of the VP80 C-terminus.

VP80 is Required for Production of Both BV and ODV

The results described above indicated that the Ac-vp80null mutant is completely defective in production of infectious budded virus. However, there was also a possibility that the mutant can still produce non-infectious budded particles. To investigate the ability, Sf9 cells were transfected with either the knock-out, repair or wild-type bacmid constructs and 7 days p.t. cell culture mediums were ultracentrifuged to pellet budded viruses. The formed pellets were either analyzed by negative staining electron microscopy or by Western blot- and PCR-based detection to confirm the presence of the budded viruses. No intact budded virus, virus-like particles, nor its structures (such as major capsid protein VP39 and viral genome sequence) were revealed in the pellet from the cells transfected with the Ac-vp80null mutant (FIGS. 5A and 5B).

On the other hand, all analyzed repair constructs produced normally-appearing budded virus as compared with budded virus-derived from the wild-type virus (FIG. 5A). Nevertheless, it was very difficult to find representative budded virions in the pellet derived from C-terminally FLAG-tagged vp80 gene repair construct-transfected cells.

To further characterize deletion of the vp80 gene on baculovirus life cycle, electron microscopy was performed with ultra-thin sections generated from bacmid-transfected cells. The Ac-vp80null-transfected cells developed typically phenotype of baculovirus-infected cell with an enlarged nucleus, a fragmented host chromatin, an electron-dense virogenic stroma, etc. (FIG. 6A). The absence of VP80 did not prevent formation of normally-appearing nucleocapsids inside the virogenic stroma (FIG. 6C). The formed nucleocapsids were phenotypically undistinguishable from those produced by either the Ac-vp80null repair or Ac-wt bacmids. However, an abundance of assembled nucleocapsids was rather less as compared with cells-transfected with the Ac-vp80null repair or Ac-wt bacmids (FIGS. 6E and 6G). In addition, no occlusion-derived virions nor bundles of nucleocapsids prior to an envelopment could be observed in the peristromal compartment of a nucleoplasm (so called the ring zone) of Ac-vp80null bacmid-transfected cells (FIGS. 6B and 6D). It seems that VP80 plays a role during maturation of nucleocapsids and/or their release/transport from the virogenic stroma. Eventually, VP80 can somehow contribute to an efficient nucleocapsid assembly which could be explained by small number of nucleocapsids present in the virogenic stroma of Ac-vp80null transfected cells. When the vp80 gene was re-introduced back into the bacmid mutant, a lot of nucleocapsids and occlusion-derived virions could be seen in the ring zones of transfected cells (FIG. 6F). An abundance and morphology of occlusion-derived virions produced in Ac-Δvp80-vp80 repair bacmid-transfected cells were similar to those produced by wild-type bacmid (FIGS. 6F and 6H).

VP80 is Associated with Nucleocapsids of Both BV and ODV

To investigate the association of VP80 with BV preparations, BVs were collected at 48 h p.i. and nucleocapsid and envelope fractions were separated. The Flag·VP80 protein was only detected in the nucleocapsid fraction as a double-band of molecular masses ranging between 80-kDa and 95-kDa that were observed in infected Sf9 cells (FIG. 14A, upper panel). Correct separation into nucleocapsid and envelope fractions was confirmed with antibodies against VP39 (nucleocapsid only) and GP64 (envelope only) (FIG. 14A, lower panels).

To examine whether VP80 is also associated with ODVs, Sf9 cells were co-infected with the Ac-Δvp80-Flag·vp80 and occlusion body (OB)-producing wt AcMNPV viruses to provide the POLH protein. Western blot analysis showed that VP80 associates with the nucleocapsid fraction of ODVs and in this case migrates as a single band of ~80 kDa, corresponding to the 80-kDa form produced in the very late phase of infection (FIG. 14B, upper panel). Proper fractionation into nucleocapsid and envelope fractions was controlled with antiserum against PIF-1, an ODV envelope protein (FIG. 14B, lower panel).

The Function of vp80 can be Rescued by Genetic Trans-Complementation

To verify whether a vp80 deletion in the viral genome can be complemented by a vp80 ORF offered in trans under control of a constitutive promoter, a transgenic cell line expressing Flag-tagged vp80 was constructed. In these cells VP80 was mainly produced as a protein of approximately 95-kDa as was shown by Western blot analysis with anti-Flag antibody (FIG. 15A). Two minor bands, one of ~80-kDa and second of ~65-kDa were also observed.

In trans-complementation assays, Sf9-vp80 cells were transfected with the Ac-Δvp80 bacmid, and the spread of virus infection was monitored by EGFP-specific fluorescence at 96 h and 120 h p.t. (FIG. 15Ba-c). Viral plaques were seen in the transfected Sf9-vp80 cells demonstrating that the virus was transmitted from cell to cell. Nevertheless, we noted that the number and size of the developed plaques was significantly smaller than observed in Sf9 cells transfected with the Ac-wt bacmid (FIG. 15Bd). As a control, non-transgenic Sf9 cells showed only single-cell infections when transfected with the Ac-Δvp80 bacmid (FIG. 15Bc).

When the culture medium of the Ac-Δvp80 transfected Sf9-vp80 cells was used to infect freshly seeded non-transgenic Sf9 cells a "single-cell infection" phenotype was observed (FIG. 15Bb, right panel). Hence, the BV particles resulting from trans-complementation were able to enter cells but were defective in producing new BV. This also shows that the Ac-Δvp80 did not revert to Ac-wt in the Sf9-vp80 cells, by picking up the transgene from the host cells. As predicted, no EGFP signal was detected in Sf9 cells receiving the supernatant from Ac-Δvp80-transfected, non-transgenic Sf9 cells (FIG. 15Bc, right panel). The numbers of infectious BVs released from the Sf9-vp80 cells transfected with the Ac-Δvp80 bacmid were compared with those produced in Sf9 cells transfected with Ac-wt at 6 days p.i. This experiment showed that the current trans-complementation system is approximately 25 fold less effective in BV production than the classical Sf9-based production system (FIG. 15C).

Trans-Complemented, Replication-Deficient Ac-vp80Null Virus is Competent to Express High Levels of Recombinant Protein To assess the effect of the vp80 gene deletion on the level of recombinant protein expression, a bench-scale comparative production assay has been performed. Herein, the Sf9 cells were in parallel infected with three types of baculovirus seeds at an MOI=10, namely (i) Ac-wt, (ii) Ac-Δvp80-Flag·vp80 (both produced in Sf9 cells), and (iii) Ac-Δvp80 (produced in Sf9-vp80 cells) all encoding EGFP. Western blotting profiles showed that the EGFP protein was expressed at identical levels for all three tested baculovirus genotypes as was the GP64 glycoprotein which served here for control purposes (FIG. 16A, upper panel). The relative amount of EGFP was quantified by ELISA at 48 and 72 h p.i in infected cell lysates (FIG. 16B) and did not reveal any statistically significant difference in EGFP levels between the three tested baculovirus genotypes. The results thus demonstrate that the trans-complemented Ac-Δvp80 virus seed, although defective in viral replication, is as capable to produce recombinant protein as conventional baculovirus expression vectors as long as the initial multiplicity of infection is high enough to infect all cells.

Also during the production culture, revertant virus genotypes carrying the vp80 gene were not detected, as no de novo expressed Flag·VP80 protein (FIG. 16A) was detected in immunoblots. Theoretically, a certain quantity of Flag·VP80 protein associated with the trans-complemented virus seed is entering the insect cells, but this was no longer detected at very late times post-infection and is probably degraded by either lysosome- or proteasome-mediated activity. In the same experiment, no BV release was recorded in cell culture supernatants originated from Sf9 cells inoculated with the Ac-Δvp80 virus seed (FIG. 16C), demonstrating that neither revertant virus generation nor wild-type virus contamination had occurred.

Summary

In this study we focused on the improvement of conventional baculovirus-based expression tools with the goal to eliminate contaminating baculovirus progeny from manufactured recombinant protein(s). This effort is strongly driven by pharmaceutical perspectives, since recombinant baculovirus-expressed therapeutics are being more and more used in human and veterinary medicine. Hence, we aimed to identify baculovirus gene(s), whose targeting results in a deficiency of baculovirus virion production, but does not or, only mildly affect very late gene expression. In this way high level expression of heterologous genes will be safeguarded.

A summarizing overview of the new technology with the vp80 gene as example is presented in FIG. 17. Using bacmid-based engineering the inventors constructed an AcMNPV genome lacking the vp80 gene (FIG. 17B). Functional genomics and electron microscopy analyses revealed that vp80 deficiency prevents production of both BVs and ODVs. In parallel, Sf9 cells were engineered to produce VP80 to trans-complement the Ac-Δvp80 knock-out bacmid (FIGS. 17A,C). Finally, we proved that trans-complemented, replication-deficient baculovirus seed is capable to produce an amount of recombinant protein similar to that produced by conventional baculovirus vectors.

TABLE 1

List of PCR primers in order of appearance in the text.

| SEQ ID # | Primer name | Sequence | Orientation |
|---|---|---|---|
| 2 | vp39-F | 5'-gcttctaatacgactcactatagggtcgtatccgctaagcttct-3' | Forward |
| 3 | vp39-R | 5'-gcttctaatacgactcactatagggacgcaacgcgttatacacag-3' | Reverse |
| 4 | 45510 | 5'-gcttctaatacgactcactatagggacagcgtgtacgagtgcat-'3 | Forward |
| 5 | 46235 | 5'-gcttctaatacgactcactatagggatctcgagcgtgtagctggt-3' | Reverse |
| 6 | 90292 | 5'-gcttctaatacgactcactatagggtaccgccgaacattacacc-3' | Forward |
| 7 | 90889 | 5'-gcttctaatacgactcactatagggtctattggcacgtttgct-3' | Reverse |
| 8 | ec-27-F | 5'-gcttctaatacgactcactatagggaaagcagacactcggcagat-3' | Forward |
| 9 | ec-27-R | 5'-gcttctaatacgactcactatagggttgagtggcttcaacctcag-3' | Reverse |
| 10 | dbp-F | 5'-gcttctaatacgactcactatagggcgctcgctagttttgttct-3' | Forward |
| 11 | dbp-R | 5'-gcttctaatacgactcactatagggaaagatcggaaggtggtga-3' | Reverse |
| 12 | gfp-F | 5'-gcttctaatacgactcactatagggctgaccctgaagttcatctg-3' | Forward |
| 13 | gfp-R | 5'-gcttctaatacgactcactatagggaactccagcaggaccatgt-3' | Reverse |
| 14 | cat-F | 5'-gcttctaatacgactcactatagggacggcatgatgaacctgaat-3' | Forward |
| 15 | cat-R | 5'-gcttctaatacgactcactatagggatcccaatggcatcgtaaag-3' | Reverse |
| 16 | vp80-ko-F | 5'-ctgtattgtaatctgtaagcgcacatggtgcattcgatataaccttataatgtgt-gctggaatgccct-3' | Forward |
| 17 | vp80-ko-R | 5'-aaatgtactgaatataaataaaaattaaaaatatttataatttttatttaccg-ttcgtatagcatacat-3' | Reverse |
| 18 | 89507 | 5'-agcggtcgtaaatgttaaacc-3' | Forward |
| 19 | 91713 | 5'-tgtataaacaatatgttaatatgtg-3' | Reverse |
| 20 | gfp-NheI-F | 5'-ccaaaccgctagcaacatggtgagcaagggcgag-3' | Forward |
| 21 | gfp-SphI | 5'-aggaaagggcatgcttaacgcgtaccggtcttgtacagctcgtccatgc-3' | Reverse |
| 22 | pvp80-StuI-F | 5'-ggaacaaaggcctgagctcaaagtaagacctttactgtcc-3' | Forward |
| 23 | vp80-XbaI-R | 5'-ccttctatctagattatataacattgtagtttgcg-3' | Reverse |
| 24 | vp80-SacI-F | 5'-ttatcttgagctcaatatgaacgattccaattctc-3' | Forward |
| 25 | vp80-FLAG-R1 | 5'-caacagagaattggaatcgttcttatcgtcgtcatccttgtaatc-catattataaggttatatcgaatg-3' | Reverse |
| 26 | vp80-FLAG-R | 5'-ccttctatctagattacttatcgtcgtcatccttgtaatctataacat-tgtagtttgcgttc-3' | Reverse |
| 27 | M13-F | 5'-cccagtcacgacgttgtaaaacg-3' | Forward |
| 28 | M13-R | 5'-agcggataacaatttcacacagg-3' | Reverse |
| 29 | GenR | 5'-agccacctactcccaacatc-3' | Reverse |

TABLE 1-continued

List of PCR primers in order of appearance in the text.

| SEQ ID # | Primer name | Sequence | Orientation |
|---|---|---|---|
| 30 | vp39-ko-F | 5'-cttcttatcgggttgtacaac-3' | Forward |
| 31 | vp39-ko-R | 5'-gcgtatcatgacgatggatg-3' | Reverse |
| 32 | vp39-SacI-F | 5'-aaggttctctagattagacggctattcctccac-3' | Forward |
| 33 | vp39-XbaI-R | 5'-ttatcttgagctcaatatggcgctagtgcccg-3' | Reverse |
| 34 | vp39-StuI-F | 5'-ggaacaaaggcctgagctcttagacggctattcctccac-3' | Forward |
| 35 | lef-4-XbaI-R | 5'-ccttctatctagattaatttggcacgattcggtc-3' | Reverse |
| 36 | cg-30-XbaI-F | 5'-aaggttctctagattaatctacatttattgtaacatttg-3' | Forward |
| 37 | vP39-FLAG-SacI-R | 5'-ttatcttgagctcaatatggattacaaggatgacgacgataaggc-gctagtgcccgtgggt-3' | Reverse |
| 38 | vp1054-ko-F | 5'-gtactgaaagataatttattttgatagataataattacattattttaa-acgtgttcgaccaagaaaccgat-3' | Forward |
| 39 | vp1054-ko-R1 | 5'-agggcgaattccagcacactttattacgtggacgcgttactttgc-3' | Reverse |
| 40 | vp1054-ko-R2 | 5'-gataagaatgcttgtttaacaaataggtcagctgttaaatact-ggcgatgtaccgttcgtatagcatacat-3' | Reverse |
| 41 | vp1054-Rep-F | 5'-ggttgtttaggcctgagctcctttggtacgtgttagagtgt-3' | Forward |
| 42 | vp1054-Rep-R | 5'-tcctttcctctagattacacgttgtgtgcgtgcaga-3' | Reverse |
| 43 | p6.9-ko-F | 5'-gcttcgttcattcgctactgtcggctgtgtggaatgtctggttgtt-aagtgtgctggaattcgccct-3' | Forward |
| 44 | p6.9-ko-R | 5'-aatattaataaggtaaaaattacagctacataaattacacaattta-aactaccgttcgtatagcatacat-3' | Reverse |
| 45 | Ac-p6.9-F | 5'-tttgaattcatggttgcccgaagctccaagac-3' | Forward |
| 46 | Ac-p6.9-R | 5'-tttgcggccgcttaatagtagcgtgttctgtaac-3' | Reverse |
| 47 | Se-p6.9-F | 5'-tttgaattcatgtatcgtcgtcgttcatc-3' | Forward |
| 48 | Se-p6.9-R | 5'-tttgcggccgcttaatagtggcgacgtctgtatc-3' | Reverse |
| 49 | 86596 | 5'-gggcttagtttaaaatcttgca-3' | Forward |
| 50 | 86995 | 5'-aattcaaacgaccaagacgag-3' | Reverse |
| 51 | 45122 | 5'-gcaatcatgacgaacgtatgg-3' | Forward |
| 52 | 46441 | 5'-cgataatttttccaagcgctac-3' | Reverse |
| 53 | pp6.9-F | 5'-ggtcgacgtaccaaattccgttttgcgacg-3' | Forward |
| 54 | pp6.9-R | 5'-ggtcgacggatccgtttaaattgtgtaatttatg-3' | Reverse |
| 55 | 75834 | 5'-cttcttatcgggttgtacaac-3' | Forward |
| 56 | 76420 | 5'-gcgtatcatgacgatggatg-3' | Reverse |

REFERENCES

Abe, T., Takahashi, H., Hamazaki, H., Miyano-Kurosaki, N., Matsuura, Y. & Takaku, H. (2003). Baculovirus induces an innate immune response and confers protection from lethal influenza virus infection in mice. *Journal of Immunology* 171, 1133-1139.

Aslanidi, G., Lamb, K. & Zolotukhin, S. (2009). An inducible system for highly efficient production of recombinant adeno-associated virus (rAAV) vectors in insect Sf9 cells. *Proceedings of the National Academy of Sciences U S A* 106, 5059-5064.

Boyce, F. M. & Bucher, N. L. R. (1996). Baculovirus-mediated gene transfer into mammalian cells. *Proceedings of the National Academy USA* 93, 2348-2352.

Braunagel, S. C. & Summers, M. D. *Autographa californica* nuclear polyhedrosis virus, PDV, and ECV viral envelopes and nucleocapsids: Structural proteins, antigens, lipid and fatty acid profiles. Virology 202, 315 (1994).

Bright, R. A., Carter, D. M., Crevar, C. J., Toapanta, F. R., Steckbeck, J. D., Cole, K. S., Kumar, N. M., Pushko, P., Smith, G., Tumpey, T. M. & Ross, T. M. (2008). Cross-clade protective immune responses to influenza viruses with H5N1 HA and NA elicited by an influenza virus-like particle. *PLoS ONE* 3.

Carbonell, L. F., Klowden, M. J. & Miller, L. K. (1985). Baculovirus-mediated expression of bacterial genes in dipteran and mammalian cells. *Journal of Virology* 56, 153-160.

Carbonell L. F., Hodge M. R., Tomalski, M. D., Miller, L. K. (1988). Synthesis of a gene coding for an insect-specific scorpion neurotoxin and attempts to express it using baculovirus vectors. *Gene* 73, 409-18.

Charlton, C. A. & Volkman, L. E. (1991). Sequential rearrangement and nuclear polymerization of actin in baculovirus-infected *Spodoptera frugiperda* cells. *Journal of Virology* 65, 1219-27.

Charlton, C. A. & Volkman, L. E. (1993). Penetration of *Autographa californica* nuclear polyhedrosis virus nucleocapsids into IPLB Sf 21 cells induces actin cable formation. *Virology* 197, 245-54.

Cohen, D. P. A., Marek, M., Davies, B. G., Vlak, J. M. & van Oers, M. M. (2009). Encyclopedia of *Autographa californica* nucleopolyhedrovirus genes. *Virologica Sinica* 24, 359

Condreay, J. P.& Kost, T. A. (2007). Baculovirus expression vectors for insect and mammalian cells. *Curr Drug Targets* 8, 1126-31.

Cox, M. M. J. & Hollister, J. (2009). FluBlok, A next generation influenza vaccine manufactured in insect cells. Biologicals 37, 182-189.

Dai, X., Willis, L. G., Palli, S. R. & Theilmann, D. A. (2005). Tight transcriptional regulation of foreign genes in insect cells using an ecdysone receptor-based inducible system. *Protein Expression and Purification* 42, 236-245.

Datsenko, K. A. & Wanner, B. L. (2000). One-step inactivation of chromosomal genes in *Escherichia coli* K-12 using PCR products. *Proceedings of the National Academy of Sciences USA* 97, 6640-6645.

Fric, J., Marek, M., Hrusková, V., Holán, V. & Forstová J. (2008). Cellular and humoral immune responses to chimeric EGFP-pseudocapsids derived from the mouse polyomavirus after their intranasal administration. *Vaccine* 26, 3242

Friesen. P. D. & Miller, L. K. (1986). The regulation of baculovirus gene expression in: "The Molecular Biology of Baculoviruses" (W. Doerfler and P. Boehm, eds.) Springer-Verlag, Berlin, pp. 31-49.

Funk, C. J. & Consigli, R. A. (1993). Phosphate cycling on the basic protein of *Plodia interpunctella* granulosis virus. *Virology* 193, 396-402.

Gheysen, D., Jacobs, E., De Foresta, F., Thiriart, C., Francotte, M., Thines, D. & De Wilde, M. (1989). Assembly and release of HIV-1 precursor pr55(gag) virus-like particles from recombinant baculovirus-infected insect cells. *Cell* 59, 103-112.

Gronowski, A. M., Hilbert, D. M., Sheehan, K. C. F., Garotta, G. & Schreiber, R. D. (1999). Baculovirus stimulates antiviral effects in mammalian cells. Journal of Virology 73, 9944-9951.

Harper, D. M., Franco, E. L., Wheeler, C. M., Moscicki, A.-B., Romanowski, B., Roteli-Martins, C. M., Jenkins, D., Schuind, A., Costa Clemens, S. A. & Dubin, G. (2006). Sustained efficacy up to 4.5 years of a bivalent L1 virus-like particle vaccine against human papillomavirus types 16 and 18: follow-up from a randomised control trial. *The Lancet* 367, 1247-1255.

Hill-Perkins, M. S., &, Possee, R. D. (1990). A baculovirus expression vector derived from the basic protein promoter of *Autographa californica* nuclear polyhedrosis virus. *Journal of General Virology* 71: 971-976.

Hofmann, C., Sandig, V., Jennings, G., Rudolph, M., Schlag, P. & Strauss, M. (1995). Efficient gene transfer into human hepatocytes by baculovirus vectors. *Proceedings of the National Academy of Sciences USA* 92, 10099-10103.

Jeong, S. H., Qiao, M., Nascimbeni, M., Hu, Z., Rehermann, B., Murthy, K. & Liang, T. J. (2004). Immunization with hepatitis C virus-like particles induces humoral and cellular immune responses in nonhuman primates. *Journal of Virology* 78, 6995-7003.

Jing Chen, S., Er Hui, Z., Lun Guang, Y., Hong Ling, Z. & Peng Fei, J. (2009). A high efficient method of constructing recombinant *Bombyx mori* (silkworm) multiple nucleopolyhedrovirus based on zero-background Tn7-mediated transposition in *Escherichia coli. Biotechnology Progress* 25, 524-529.

Kaikkonen, M. U., Viholainen, J. I., Narvanen, A., Yla-Herttuala, S. & Airenne, K. J. (2008). Targeting and purification of metabolically biotinylated baculovirus. *Human Gene Therapy* 19, 589-600.

Kanginakudru, S. S., Royer C., Edupalli S. V., Jalabert A., Mauchamp B., Chandrashekaraiah, Prasad S. V., Chavancy G., Couble P., Nagaraju J. (2007). Targeting ie-1 gene by RNAi induces baculoviral resistance in lepidopteran cell lines and in transgenic silkworms. *Insect molecular biology* 16, 635-644.

Kato, T., Kajikawa, M., Maenaka, K. & Park, E. Y. (2010). Silkworm expression system as a platform technology in life science. *Applied Microbiology and Biotechnology* 85, 459-470.

Kelly, D.C., Brown, D. A., Ayres, M. D., Allen, C. J. & Walker, I. O. (1983). Properties of the major nucleocapsid protein of *Heliothis zea* singly enveloped nuclear polyhedrosis virus. *Journal of General Virology* 64, 399-408

Kitajima, M. & Takaku, H. (2008). Induction of antitumor acquired immunity by baculovirus *Autographa californica* multiple nuclear polyhedrosis virus infection in mice. *Clinical and Vaccine Immunology* 15, 376-378.

Kost, T. A., Condreay, J. P. & Jarvis, D. L. (2005). Baculovirus as versatile vectors for protein expression in insect and mammalian cells. *Nature Biotechnology* 23, 567-575.

Lackner, A., Genta, K., Koppensteiner, H., Herbacek, I., Holzmann, K., Spiegl-Kreinecker, S., Berger, W. & Grusch, M. (2008). A bicistronic baculovirus vector for transient and stable protein expression in mammalian cells. *Analytical Biochemistry* 380, 146-148.

Lebacq-Verheyden A M, Kasprzyk P G, Raum M G, Van Wyke Coelingh K, Lebacq J A, Battey J F. (1988) Post-translational processing of endogenous and of baculovirus-expressed human gastrin-releasing peptide precursor. *Molecular and Cell Biology* 8, 3129-35.

Lesch, H. P., Turpeinen, S., Niskanen, E. A., Mähönen, A. J., Airenne, K. J. & Ylä-Herttuala, S. (2008). Generation of lentivirus vectors using recombinant baculoviruses. *Gene Therapy* 15, 1280-1286.

Li, X., Pang, A., Lauzon, H. A. M., Sohi, S. S. & Arif, B. M. (1997). The gene encoding the capsid protein P82 of the *Choristoneura fumiferana* multicapsid nucleopolyhedrovirus: Sequencing, transcription and characterization by immunoblot analysis. *Journal of General Virology* 78, 2665-2673.

Liu, X., Li, K., Song, J., Liang, C., Wang, X. & Chen, X. (2006a). Efficient and stable gene expression in rabbit intervertebral disc cells transduced with a recombinant baculovirus vector. *Spine* 31, 732-735.

Liu, Y. K., Chu, C. C. & Wu, T. Y. (2006b). Baculovirus ETL promoter acts as a shuttle promoter between insect cells and mammalian cells. *Acta Pharmacologica Sinica* 27, 321-327.

Lopez, M. G., Alfonso, V., Carrillo, E. & Taboga, O. (2009). Trans-complementation of polyhedrin by a stably transformed Sf9 insect cell line allows occ-baculovirus occlusion and larval per os infectivity. Journal of Biotechnology 145, 199-205.

Lu, A. & Carstens, E. B. (1992). Nucleotide sequence and transcriptional analysis of the p80 gene of *Autographa californica* nuclear polyhedrosis virus: a homologue of the *Orgyia pseudotsugata* nuclear polyhedrosis virus capsid-associated gene. *Virology* 190, 201-209.

Luckow, V. A. & Summers, M. D. (1988). Trends in the development of baculovirus expression vectors. Bio/Technology 6, 47-55.

Luckow, V. A., Lee, S. C., Barry, G. F. & Olins, P. O. (1993). Efficient generation of infectious recombinant baculoviruses by site-specific transposon-mediated insertion of foreign genes into a baculovirus genome propagated in *Escherichia coli*. *Journal of Virology* 67, 4566-79

Ludwig, C. & Wagner, R. (2007). Virus-like particles-universal molecular toolboxes. *Current Opinion in Biotechnology* 18, 537-545.

Lung, O., Westenberg, M., Vlak, J. M., Zuidema, D. & Blissard, G. W. (2002). Pseudotyping *Autographa californica* multicapsid nucleopolyhedrovirus (AcMNPV): F proteins from group II NPVs are functionally analogous to AcMNPV GP64. *Journal of Virology.* 76, 5729-5736.

Maeda, S., Kawai, T., Obinata, M., Fujiwara, H., Horiuchi, T., Saeki, Y., Sato, Y. & Furusawa M. (1985). Production of human alpha-interferon in silkworm using a baculovirus vector. *Nature* 315, 592-4.

Maranga, L., Rueda, P., Antonis, A. F., Vela, C., Langeveld, J. P., Casal, J. I, & Carrondo, M. J. (2002). Large scale production and downstream processing of a recombinant porcine parvovirus vaccine. *Applied Microbiology Biotechnology* 59, 45-50.

Martin, B. M., Tsuji, S., LaMarca, M. E., Maysak, K., Eliason, W., Ginns, E. I. (1988). Glycosylation and processing of high levels of active human glucocerebrosidase in invertebrate cells using a baculovirus expression vector. DNA 7, 99-106.

McKenna, K. A., Hong, H., van Nunen & Granados, R. R. (1989). Establishment of new *Trichoplusia ni* cell lines in serum-free medium for baculovirus and recombinant protein production. *Journal of Invertebrate Pathology* 71, 82-90

Mellado, M. C., Peixoto, C., Cruz, P. E., Carrondo, M. J. & Alves, P. M. (2008) Purification of recombinant rotavirus VP7 glycoprotein for the study of in vitro rotavirus-like particles assembly. *Journal of Chromatography B Analyicalt Technology Biomedical Life Science.* 874, 89-94

Miller, D. W., Safer, P. & Miller, L. K. (1986). in *Genetic Engineering: Principles and Methods* Vol. 8 (eds Setlow, J. & Hollaender, A.) Plenum Publishing, New York, pp. 277-298.

Miller, L. K. (1988). Baculoviruses as gene expression vectors. *Annual Review Microbiology.* 42, 177-99.

Miyajima, A, Schreurs, J., Otsu, K., Kondo, A., Arai, K. & Maeda, S. (1987). Use of the silkworm, *Bombyx mori*, and an insect baculovirus vector for high-level expression and secretion of biologically active mouse interleukin-3. *Gene* 58, 273-81.

Mortola, E. & Roy, P. (2004). Efficient assembly and release of SARS coronavirus-like particles by a heterologous expression system. *FEBS Letters* 576, 174-178

Muller, R., Pearson, M. N., Russell, R. L. Q. & Rohrmann, G. F. (1990). A capsid-associated protein of the multicapsid nuclear polyhedrosis virus of *Orgyia* pseudotsugata: Genetic location, sequence, transcriptional mapping, and immunocytochemical characterization. Virology 176, 133-144.

Murges, D., Kremer, A. & Knebel-Morsdorf, D. (1997). Baculovirus transactivator IE1 is functional in mammalian cells. *Journal of General Virology* 78, 1507-1510.

Noad, R. & Roy, P. (2003). Virus-like particles as immunogens. *Trends in Microbiology* 11, 438-444.

Olszewski, J. & Miller, L. K. (1997). Identification and characterization of a baculovirus structural protein, VP1054, required for nucleocapsid formation. *Journal of Virology* 71, 5040-50.

Peng, K., van Oers, M. M., Hu, Z. H., van Lent, J. W. M., Vlak, J. M. (2010). Baculovirus per os infectivity factors form a complex on the surface of occlusion derived virus. *Journal of Virology* (in press).

Pijlman, G. P., Roode, E. C., Fan, X., Roberts, L. O., Belsham, G. J., Vlak, J. M. & van Oers, M. M. (2006). Stabilized baculovirus vector expressing a heterologous gene and GP64 from a single bicistronic transcript. *Journal of Biotechnology* 123, 13-21.

Ramadan, N., Flockhart, I., Booker, M., Perrimon, N. & Mathey-Prevot, B. (2007). Design and implementation of high-throughput RNAi screens in cultured *Drosophila* cells. *Nature Protocols* 2, 2245-2264.

Ramqvist, T., Andreasson, K. & Dalianis, T. (2007). Vaccination, immune and gene therapy based on virus-like particles against viral infections and cancer. *Expert Opinion on Biological Therapy* 7, 997-1007.

Salem, T. Z. & Maruniak, J. E. (2007). A universal transgene silencing approach in baculovirus-insect cell system. *Journal of Virological Methods* 145, 1-8.

Sambrook, J., Fritsch, E. F. & Maniatis. (1989). Molecular Cloning. A Laboratory Manual, Cold Spring Harbor, N.Y.

Slack, J. & Arif, B. M. (2006). The baculoviruses occlusion-derived virus: virion structure and function. *Advances in virus research* 69, 99-165.

Smith, G. E, Ju, G., Ericson, B. L, Moschera, J., Lahm, H. W, Chizzonite, R. & Summers, M.D. (1985). Modification and secretion of human interleukin 2 produced in insect cells by a baculovirus expression vector. *Proceedings National Academy of Sciences USA* 82, 8404-8.

Smith, R. H, Levy, J. R. & Kotin, R. M. (2009). A simplified baculovirus-AAV expression vector system coupled with one-step affinity purification yields high-titer rAAV stocks from insect cells. *Molecular Therapy* 17, 1888-1896.

Smith, G. E. & Summers, M.D. (1979). Restriction maps of five *Autographa californica* MNPV variants, *Trichoplusia ni* MNPV, and *Galleria mellonella* MNPV DNAs with endonucleases SmaI, KpnI, BamHI, SacI, XhoI, and EcoRI. *Journal of Virology* 30, 828-838.

Suzuki, N., Nonaka, H., Tsuge, Y., Okayama, S., Inui, M. & Yukawa, H. (2005). Multiple large segment deletion method for *Corynebacterium glutamicum. Applied Microbiology and Biotechnology* 69, 151-161.

Tang, X.-D., Xu, Y.-P., Yu, L.-I., Lang, G.-J., Tian, C.-H., Zhao, J.-F. & Zhang, C.-X. (2008). Characterization of a *Bombyx mori* nucleopolyhedrovirus with Bmvp80 disruption. *Virus Research* 138, 81-88.

Tellez, M. (2005). Process optimization protocol for tangential flow filtration of insect cells and baculovirus. Presented at WilBio Conference on Baculovirus & Insect Cell Culture—Process Development and Production Issues, Savannah/Georgia, 21st-24th Feb., 2005.

Thiem, S. M. & Miller, L. K. (1989a). A baculovirus gene with a novel transcription pattern encodes a polypeptide with a zinc finger and a leucine zipper. *Journal of Virology* 63, 4489-4497.

Thiem, S. M. & Miller, L. K. (1989b). A baculovirus gene with a novel transcription pattern encodes a polypeptide with a zinc finger and a leucine zipper. *Journal of Virology* 63, 4489-97.

Thiem, S. M. & Miller, L. K. (1989c). Identification, sequence, and transcriptional mapping of the major capsid protein gene of the baculovirus *Autographa californica* nuclear polyhedrosis virus. *Journal of Virology* 63, 2008-2018.

Tjia, S. T., Meyer zu Altenschildesche, G. & Doerfler, W. (1983). *Autographa californica* nuclear polyhedrosis virus (AcNPV) DNA does not persist in mass cultures of mammalian cells. *Virology* 125, 107-117.

Urabe, M., Ding, C. & Kotin, R. M. (2002). Insect cells as a factory to produce adeno-associated virus type 2 vectors. *Human Gene Therapy* 13, 1935-1943.

van Lent, J. W. M., Groenen, J. T. M., Klinge-Roode, E. C., Rohrmann, G. F., Zuidema, D. & Vlak, J. M. (1990). Localization of the 34 kDa polyhedron envelope protein in *Spodoptera frugiperda* cells infected with *Autographa california* nuclear polyhedrosis virus. *Archives of Virology* 111, 103-114.

van Oers, M. M. (2006). Vaccines for Viral and Parasitic Diseases Produced with Baculovirus Vectors. In *Advances in Virus Research* 68. 193-253.

Vlak J. M., Klinkenberg, F. A, Zaal, K. J., Usmany, M., Klinge-Roode, E. C., Geervliet, J. B, Roosien. J, & van Lent, J. W. (1988). Functional studies on the p10 gene of *Autographa californica* nuclear polyhedrosis virus using a recombinant expressing a p10-beta-galactosidase fusion gene. *Journal of General Virology* 69, 765-76.

Wang, M. Y, Kuo, Y. Y., Lee, M. S, Doong, S. R, Ho, J. Y, Lee, L. H. (2000). Self-assembly of the infectious bursal disease virus capsid protein, rVP2, expressed in insect cells and purification of immunogenic chimeric rVP2H particles by immobilized metal-ion affinity chromatography. *Biotechnology and Bioeneneering* 67, 104-11.

Wu, W., Liang, H., Kan, J., Liu, C., Yuan, M., Liang, C., Yang, K. & Pang, Y. (2008). *Autographa californica* multiple nucleopolyhedrovirus 38K is a novel nucleocapsid protein that interacts with VP1054, VP39, VP80, and itself. *Journal of Virology* 82, 12356-12364.

Yin, F., M. Wang, Y. Tan, F. Deng, J. M. Vlak, Z. Hu, and H. Wang. 2008. A functional F analogue of AcMNPV GP64 from the *Agrotis segetum* granulovirus. *Journal of Virology* 82, 8922-8926.

The invention claimed is:

1. A method for the production of a biopharmaceutical product, comprising:

(a) infecting a biopharmaceutical-producing insect cell with at least one baculovirus, said at least one baculovirus comprising a genome coding for said biopharmaceutical product, and (b) maintaining the biopharmaceutical-producing insect cell under conditions such that the biopharmaceutical product is produced, wherein the genome of said at least one baculovirus is deficient for the vp80 gene or wherein said biopharmaceutical-producing insect cell comprises an expression control system allowing the inactivation of the vp80 gene.

2. The method according to claim 1, wherein said vp80 gene is made deficient in said genome by way of nucleotide substitution, insertion or deletion.

3. The method according to claim 1, wherein the biopharmaceutical-producing insect cell is a recombinant insect cell comprising a construct expressing a dsRNA specific for said vp80 gene, the dsRNA being optionally expressed under an inducible promoter.

4. The method according to claim 1, wherein the at least one baculovirus is produced before step (a) in a baculovirus-producing cell expressing a complementing copy of the vp80 gene.

5. The method according to claim 1, wherein the deficiency or inactivation of said vp80 gene does not affect very late expression from said baculovirus in comparison to very late expression from wild-type baculovirus.

6. The method according to claim 1, wherein the at least one baculovirus is derived from AcMNPV or BmNPV.

7. The method according to claim 1, wherein the biopharmaceutical product is a recombinant protein, a recombinant virus or a virus-like particle.

8. The method according to claim 7, wherein the biopharmaceutical product is a recombinant AAV.

9. The method according to claim 1, wherein the biopharmaceutical product is coded by at least one gene introduced in the recombinant baculovirus genome under the control of the polyhedrin or p10 promoter.

* * * * *

UNITED STATES PATENT AND TRADEMARK OFFICE

CERTIFICATE OF CORRECTION

PATENT NO. : 8,993,317 B2
APPLICATION NO. : 13/390806
DATED : March 31, 2015
INVENTOR(S) : Otto-Wilhelm Merten, Martin Marek and Monique Van Oers It is certified that error appears in the above-identified patent and that said Letters Patent is hereby corrected as shown below:

In the Specification

Column 14,
Line 40, "vp80gene" should read --vp80 gene--.

Column 21,
Line 6, "CloneJETT™" should read --CloneJET™--.
Line 43, "(N— and" should read --(N- and--.

Column 21 - 22,
Lines 41-21,
"pFB-egfp-polH-vp80.

To overcome a problem associated with the unavailability of anti-VP80 antibody, FLAG tag decoration (N— and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

To overcome a problem associated with the inavailability of anti-VP80 antibody, FLAG tag decoration (N- and C-terminus fusion) of VP80 was performed to facilitate immunodetection. The N-terminally fused FLAG-vp80 sequence was generated by a double-step PCR strategy, a so-called Signed and Sealed this
Fifteenth Day of December, 2015

Michelle K. Lee
*Director of the United States Patent and Trademark Office* fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst11071/XbaI-digested and gel-purified pFB-egfp to generate donor plasmid pFB-egfp-pvp 80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

The inserts"

should read

--pFB-egfp-polH-vp80.

To overcome a problem associated with the unavailability of anti-VP80 antibody, FLAG tag decoration (N- and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transfer into pFB-egfp in a similar way as previous constructs.

The inserts--.

Column 23,
Line 38, "(SacI1XbaI)" should read --(SacI/XbaI)--.

Column 41,
Table 1, SEQ ID #2, "5'-gcttctaatacgactcactatagggtcgtatccgctaagcttct-3'" should read --5'-gcttctaatacgactcactatagggtcgtatccgctaagcgttct-3'--.

Column 47,
Line 7, "occ-baculoviras" should read --occ- baculovirus--.

Column 48,
Line 39, "Maniatis." should read --Maniatis, T.--.